(12) United States Patent
Hils et al.

US011072634B2

(10) Patent No.: US 11,072,634 B2
(45) Date of Patent: Jul. 27, 2021

(54) INHIBITORS OF TRANSGLUTAMINASES

(71) Applicant: Zedira GmbH, Darmstadt (DE)

(72) Inventors: Martin Hils, Darmstadt (DE); Ralf Pasternack, Griesheim (DE); Christian Büchold, Karben (DE)

(73) Assignee: Zedira GmbH, Darmstadt (DE)

( * ) Notice: Subject to any disclaimer, the term of this patent is extended or adjusted under 35 U.S.C. 154(b) by 0 days.

(21) Appl. No.: 16/473,265

(22) PCT Filed: Jan. 2, 2018

(86) PCT No.: PCT/EP2018/050085
§ 371 (c)(1),
(2) Date: Jun. 25, 2019

(87) PCT Pub. No.: WO2018/122419
PCT Pub. Date: Jul. 5, 2018

(65) Prior Publication Data
US 2019/0322700 A1    Oct. 24, 2019

Related U.S. Application Data

(60) Provisional application No. 62/499,528, filed on Jan. 30, 2017.

(30) Foreign Application Priority Data

Dec. 27, 2016  (EP) .................................. 16 207 029

(51) Int. Cl.
*C07K 5/117*    (2006.01)
*C07K 5/097*    (2006.01)
*A61K 38/00*   (2006.01)

(52) U.S. Cl.
CPC .......... *C07K 5/1024* (2013.01); *C07K 5/0821* (2013.01); *A61K 38/00* (2013.01)

(58) Field of Classification Search
None
See application file for complete search history.

(56) References Cited

U.S. PATENT DOCUMENTS

2011/0229568 A1   9/2011   Erfinder

FOREIGN PATENT DOCUMENTS

WO   2008055488   5/2008

OTHER PUBLICATIONS

Ettmayer P. et al. J. Med. Chem. (2004) 47(10), pp. 2393-2404 (Year: 2004).*
Singh, Yashveer et al, "Recent Trends in Targeted Anticancer Prodrug and Conjugate," DesignCurr Med Chem. 2008 ; 15(18): 1802-1826 (Year: 2008).*
Muller, Christa E. "Prodrug Approaches for Enhancing the Bioavailability of Drugs with Low Solubility," Chemistry & Biodiversity, vol. 6 (2009), pp. 2071-2083 (Year: 2009).*
Beaumont, et, al "Design of Ester Prodrugs to Enhance Oral Absorption of Poorly Permeable Compounds: Challenges to the Discovery Scientist," Current Drug Metabolism, 2003, 4, 461-485 (Year: 2003).*
Han, H.-K.. AAPS Pharmsci. (2000) 2(1), Article 6, pp. 1-11 (Year: 2000).*
Testa Prodrug research: futile or fertile? Biochemical Pharmacology (2004) 2097-2106 (Year: 2004).*
International Search Report and Written Opinion for International Patent Application No. PCT/EP2018/050085 dated Apr. 3, 2018, 12 pages.
Pohner, et al. "Chemoselective coupling of sugar oximes and [alpha]-ketoacids to glycosyl amides and N-glycopeptides", Tetrahedron Letters, vol. 55, No. 14, Feb. 26, 2014, pp. 2197-2200.
Obkircher, et al. "Photochemical Synthesis of N-Substituted 3-Hydroxy-2pyrrolidinones", Synlett, No. 7, Jan. 1, 2005, pp. 1182-1184.
Seufert, et al. "Cyclizations of [alpha]-Keto Ester Modified Aspartic Acids in Peptides", Synlett, vol. 2006, No. 11, Jul. 1, 2006, pp. 1774-1776.
Cox, et al. "Synthesis and in vitro enzyme activity of peptide derivatives of bacterial cell wall biosynthesis inhibitors", Royal Chemical Society, vol. 1, No. 13, Jan. 1, 2000, pp. 2023-2036.
Otvos, et al. The flexible termini of conantokin G define its interactions with NMDA receptors, vol. 4, No. 2, Apr. 1, 1997, pp. 85-93.
Doyle, et al. "Peptides incorporating electrophilic glutamine analogues as potential transglutaminase inhibitors", vol. 18, No. 6, Dec. 1, 1990, pp. 1318-1320.

* cited by examiner

*Primary Examiner* — Thomas S Heard
(74) *Attorney, Agent, or Firm* — Amin, Turocy & Watson, LLP

(57) ABSTRACT

The invention relates to the compound of general formula (I) as novel inhibitors of transglutaminases, to methods for producing the inventive compounds, to pharmaceutical compositions containing said inventive compounds and to their use for the prophylaxis and treatment of diseases associated with transglutaminases.

13 Claims, 8 Drawing Sheets

A)

B)

A)

B)

INHIBITORS OF TRANSGLUTAMINASES

The invention relates to novel inhibitors or novel reversible inhibitors of transglutaminases, methods for their synthesis and to their use for the prophylaxis and treatment of diseases associated with transglutaminases.

BACKGROUND OF THE INVENTION

Transglutaminases are part of the class of transferases and according to EC nomenclature they are correctly designated as "protein-glutamine: amine γ-glutamyl transferases" (EC 2.3.2.13). They link the ε-amino group of the amino acid lysine and the γ-glutamyl group of the amino acid glutamine forming an isopeptide bond while ammonia is released. In the absence of suitable amines and/or under certain conditions, deamidation of the glutamine may occur resulting in the corresponding glutamic acid.

Additionally, transglutaminases play an important role in many therapeutic areas such as the cardiovascular diseases (thrombosis and atherosclerosis), autoimmune diseases (coeliac disease, Duhring-Brocq-disease, gluten ataxia), neurodegenerative diseases (Alzheimer's disease, Parkinson's disease, Huntington's disease), dermatological diseases (ichthyosis, psoriasis, acne) as well as in wound healing and inflammatory diseases (e.g. tissue fibrosis) (J. M. Wodzinska, Mini-Reviews in medical chemistry, 2005, 5, 279-292).

Coeliac disease, a gluten intolerance, however, is one of the most important indications. Coeliac disease is characterized by a chronic inflammation of the mucosa of the small intestine. In susceptible patients, the intestinal epithelium is successively destroyed after ingestion of gluten-containing food resulting in reduced absorption of nutrients which again has massive impact on the patients affected and is for example associated with symptoms such as loss of weight, anemia, diarrhea, nausea, loss of appetite and fatigue. Due to these findings, there is a large demand for the development of a medicament for the treatment of coeliac disease as well as of other diseases associated with tissue transglutaminase (transglutaminase 2, TG2). The tissue transglutaminase is a central element during pathogenesis. The endogenous enzyme catalyses the deamidation of gluten/gliadin in the small intestinal mucosa and thus triggers the inflammatory response. Therefore inhibitors of tissue transglutaminase are suitable to be used as active agents for medication. Another very important group of indications for tissue transglutaminase inhibitors are fibrotic disorders. Fibrotic disorders are characterized by the accumulation of cross-linked extracellular matrix proteins. Diabetic nephropathy, cystic fibrosis, idiopathic pulmonary fibrosis, kidney fibrosis as well as liver fibrosis belong to the most important fibrotic disorders to be addressed with the compounds disclosed.

The human transglutaminase family consists of eight members catalyzing the unique formation of "cross-links" or isopeptide bonds between distinct substrate proteins. Since blood coagulation factor XIII (FXIII, F13) is the major factor influencing clot maturation and accretion the enzyme is considered a suitable target to potentially achieve a safer and more efficient thrombolysis at even lower dosage of clot dissolving agents and also even for thrombus prevention.

The blood coagulation factor XIII (EC 2.3.2.13), also called plasma transglutaminase or fibrin stabilizing factor (FSF), has a unique function stabilizing the fibrin clot. The enzymatic introduction of covalent cross-links between the γ-chains and subsequently the α-chains of fibrin provides mechanical stability and modulates the visco-elastic properties.

In addition, the plasma transglutaminase decorates the clot with anti-fibrinolytic factors, especially with $\alpha_2$-antiplasmin. For decades factor XIII is considered a suitable target for anti-coagulation in certain risk patients due to the unique mode-of-action. Targeting factor XIIIa with a direct acting blocker would not impair the thrombin level or the platelet activity avoiding critical bleeding episodes.

In addition, specific inhibitors may be of benefit for patients to prevent atherosclerosis. Very few inhibitors of factor XIIIa have been described so far. For example, a 66 amino acid peptide derived from the salivary gland of the giant Amazon leech *Haementeria ghilianii* is reported [Finney et al. *Biochem. J.* 1997, 324, pp. 797-805]. Further, the pharmaceutical company Merck Sharp and Dohme developed a set of small molecule thioimidazole blockers targeting Factor XIII [Freund et al., Biochemistry (1994), 33, 10109-10119].

However, also the other transglutaminases may be considered as targets for drug development. For example, TG6 is expressed in neuronal tissue. Therefore TG6 inhibitors may address neurodegenerative diseases characterized by intracellular or extracellular cross-linked and insoluble protein aggregates in the brain tissue.

Since TG1, TG3 and TG5 are expressed in the skin, inhibitors of said enzymes may be used to modulate dysregulated transglutaminase activity to therapy certain skin disorders. Inhibition of skin expressed transglutaminases can modulate the skin structure ("anti-aging") and improve skin conditions like acne or scarring.

The irreversible inhibitors of transglutaminase are developed by the applicants but the intrinsic reactivity of these warheads (e.g. Michael-acceptors like vinylesters) may lead to adverse drug reactions. It is known that electrophilic warheads can react with biological nucleophiles such as thiols. The unspecific reaction with off-targets can cause severe adverse effects and trigger certain immune responses. One example is idiosyncratic drug-related toxicity disfavoring such compounds from a more general perspective. Further, the direct damage of tissue has been described for irreversible acting compounds or metabolites. Also haptenization of proteins by reactive substances may elicit an immune response. Quite often, the liver is affected by such adverse effects.

Therefore, it is advantageous if the transglutaminase is inhibited reversibly.

The objective of the present invention is to provide novel, most probably reversible inhibitors of transglutaminases and methods for the synthesis of said inhibitors as well as several uses of these inhibitors.

Said objective is solved by the technical teachings of the independent claims. Further advantageous embodiments, aspects and details of the invention are evident from the dependent claims, the description and the examples.

Surprisingly, it has been found that reversible inhibitors having a chemical warhead as disclosed herein inhibit effectively transglutaminases including tissue transglutaminase called transglutaminase 2 or TG2 and plasma transglutaminase also called coagulation factor XIII. Herein these terms are used synonymous. However, depending on the respective backbone the warheads also address other human transglutaminases like TG1, TG3, TG4, TG5, TG6 and TG7 or transglutaminases derived from other species like animals or microorganisms.

Preferably, such chemical warhead moiety is particularly selected from aldehydes (including so called masked aldehydes), ketones, α-ketoaldehydes, α-ketoketones, α-ketoacids, α-ketoesters, and α-ketoamides as well as halogenmethylketones. The compounds of the present invention act most probably as reversible inhibitors of transglutaminases.

Thus, the present invention relates to compounds of the general formula (I):

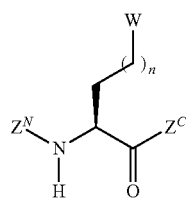

(I)

wherein
n is an integer selected from 1, 2 or 3;
W represents

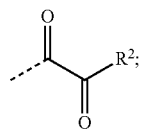

$R^2$ represents —H, —$R^1$, —$OR^1$, —$NH_2$, —$NH(R^1)$, —$NH(OR^1$, —$N(R^1)(R^3)$;
$R^1$ and $R^3$ represent independently of each other —$CH_3$, —$CH_2CH_3$, —$CH_2CH_2CH_3$, —$CH(CH_3)_2$, —$CH_2CH_2CH_2CH_3$, —$CH_2CH_2CH_2CH_2CH_3$, —$CH_2CH_2CH_2CH_2CH_2CH_3$, —$CH_2CH_2CH_2CH_2CH_2CH_2CH_3$, —$CH_2CH(CH_3)_2$, —$CH(CH_3)CH_2CH_3$, —$CH(C_2H_5)_2$, —$CH_2CH(C_2H_5)_2$, —$C(CH_3)_3$, —$CH_2$—$C(CH_3)_3$, -cyclo-$C_3H_5$, -cyclo-$C_4H_7$, -cyclo-$C_5H_9$, -cyclo-$C_6H_{11}$, —$CH_2$-cyclo-$C_3H_5$, —$CH_2$-cyclo-$C_4H_7$, —$CH_2$-cyclo-$C_5H_9$, —$CH_2$-cyclo-$C_6H_{11}$, -Ph, —$CH_2$-Ph, —$CH_2OCH_3$, —$CH_2OCH_2CH_3$, —$CH_2CH_2OCH_3$, —$CH_2CH_2OCH_2CH_3$, —$CH_2CO_2CH_3$, —$CH_2CO_2CH_2CH_3$, —$CH_2CH_2NHCH_3$, —$CH_2CH_2N(CH_3)_2$, —$CH_2S(O)_2$-(4-methyl-phenyl),

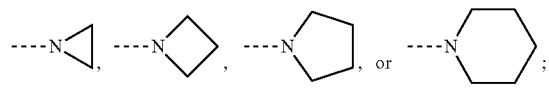

or
—$N(R^1)(R^3)$ forms

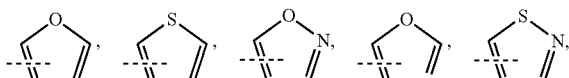

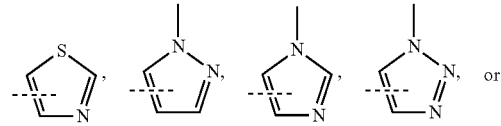

or

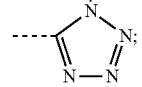

$Z^N$ represents $E^N$-, $E^N$-$AS^{N1}$-, $E^N$-$AS^{N2}$-$AS^{N1}$-, $E^N$-$AS^{N3}$-$AS^{N2}$-$AS^{N1}$- or $E^N$-$AS^{N4}$-$AS^{N3}$-$AS^{N2}$-$AS^{N1}$-;

$Z^C$ represents -$E^C$, -$AS^{C1}$-$E^C$, -$AS^{C1}$-$AS^{C2}$-$E^C$, -$AS^{C1}$-$AS^{C2}$-$AS^{C3}$-$E^C$, -$AS^{C1}$-$AS^{C2}$-$AS^{C3}$-$AS^{C4}$-$E^C$, -$AS^{C1}$-$AS^{C2}$-$AS^{C3}$-$AS^{C4}$-$AS^{C5}$-$E^C$, -$AS^{C1}$-$AS^{C2}$-$AS^{C3}$-$AS^{C4}$-$AS^{C5}$-$AS^{C6}$-$E^C$, -$AS^{C1}$-$AS^{C2}$-$AS^{C3}$-$AS^{C4}$-$AS^{C5}$-$AS^{C6}$-$AS^{C7}$-$E^C$, -$AS^{C1}$-$AS^{C2}$-$AS^{C3}$-$AS^{C4}$-$AS^{C5}$-$AS^{C6}$-$AS^{C7}$-$AS^{C8}$-$E^C$;

$AS^{C1}$-$AS^{C8}$ and $AS^{N1}$-$AS^{N4}$ are independently of each other selected from the group consisting of:

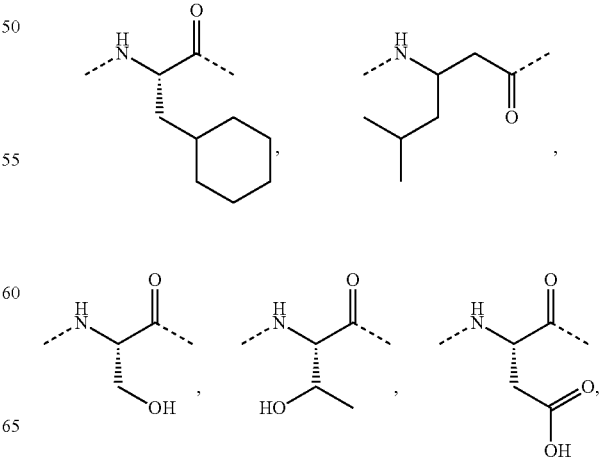

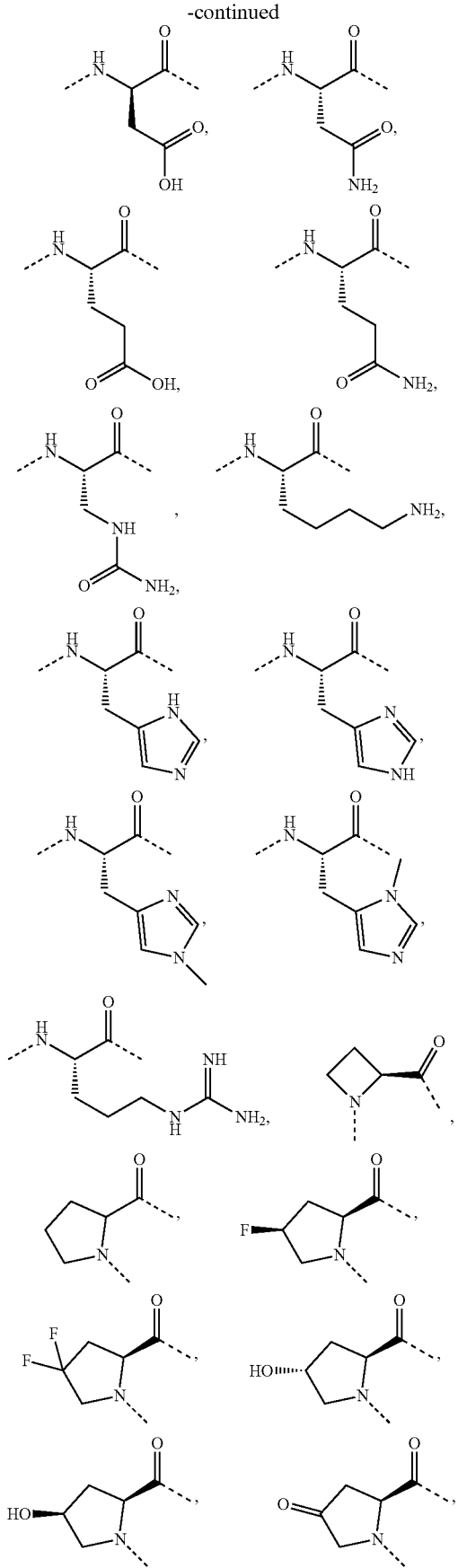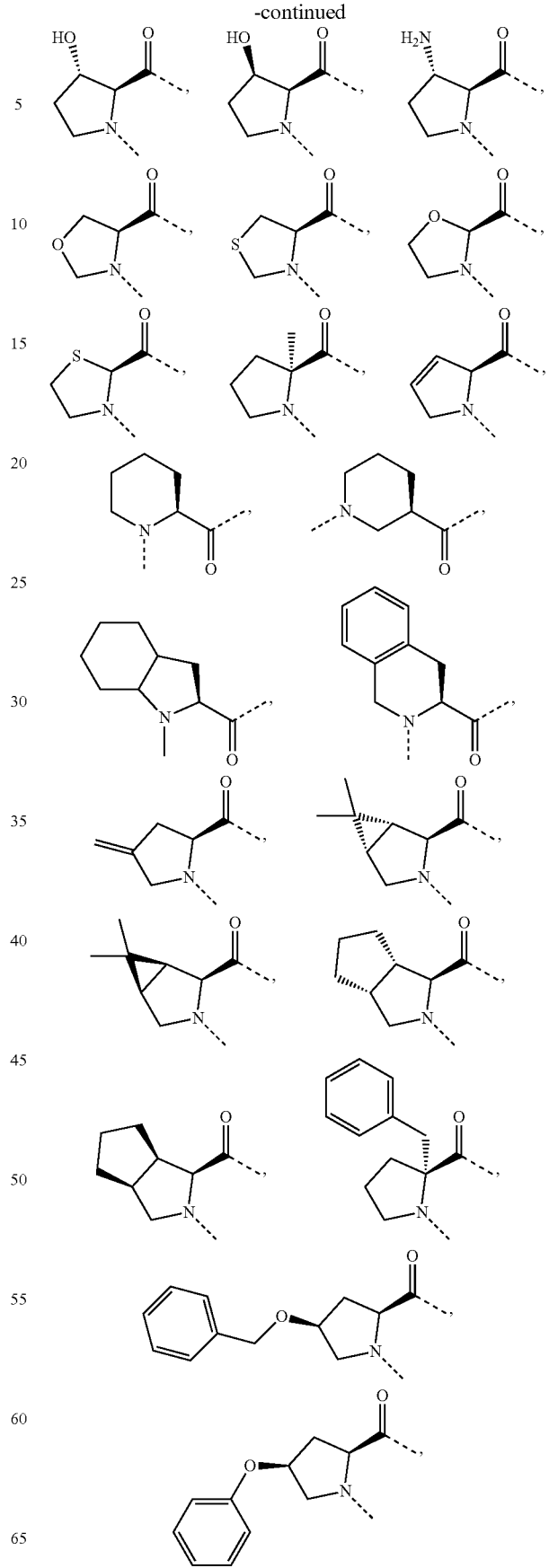

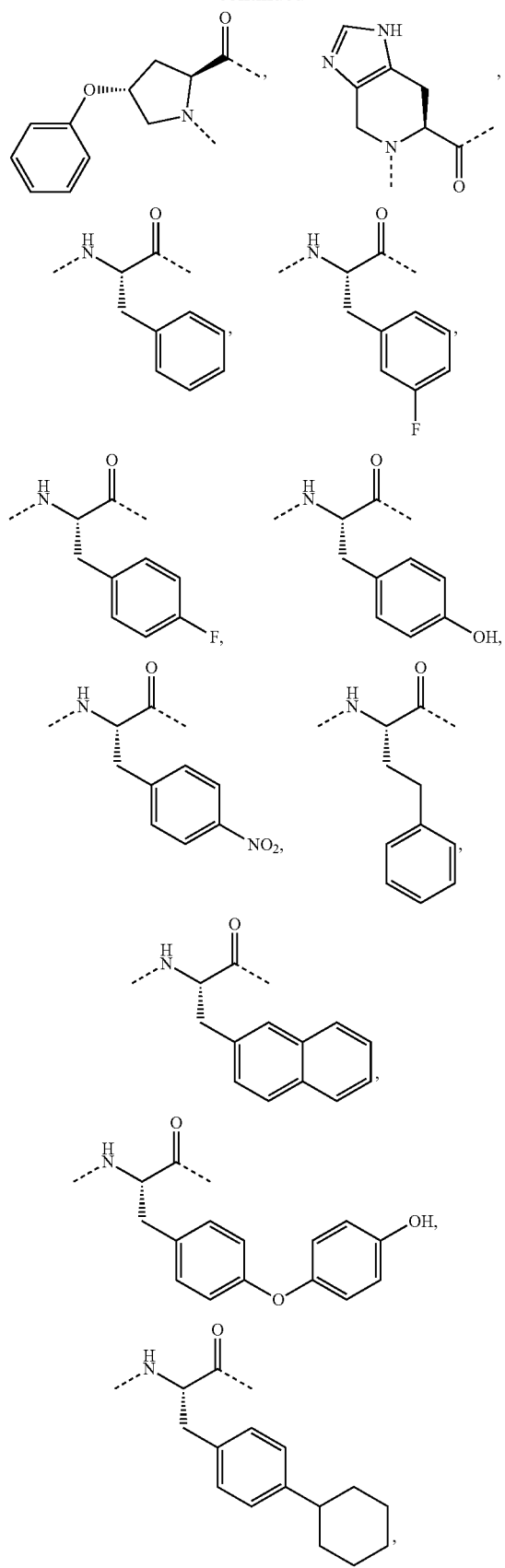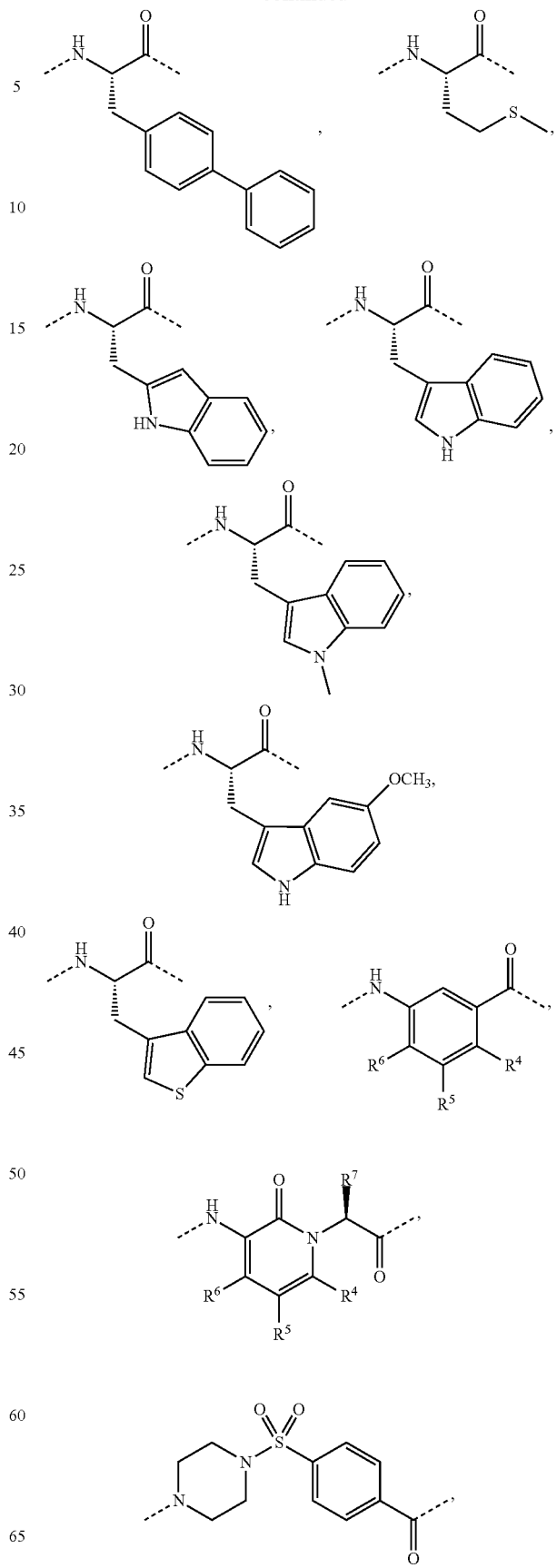

-continued

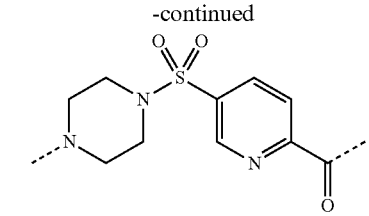

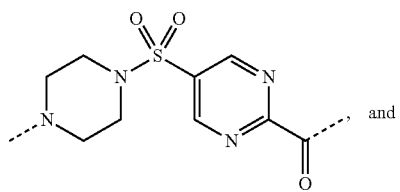
and

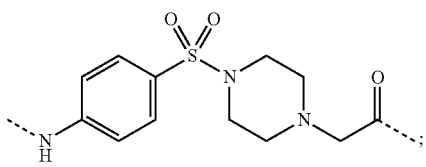

with proviso that AS$^{N1}$ is not

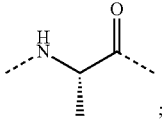

and AS$^{N2}$ is not

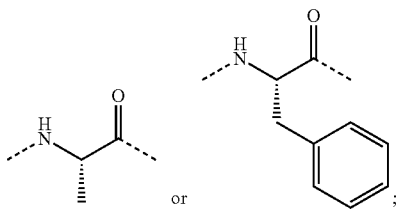

E$^C$ is selected from C terminal groups consisting of: —OR$^8$, —NR$^9$R$^{10}$, —NHSO$_2$R$^{11}$, —O-L$_1$-R$^8$, —O-L$_1$-O—R$^8$, —NH-L$_1$-O—R$^8$, —NH-L$_1$-NR$^9$R$^{10}$, —NHSO$_2$-L$_1$-R$^{11}$, -continued

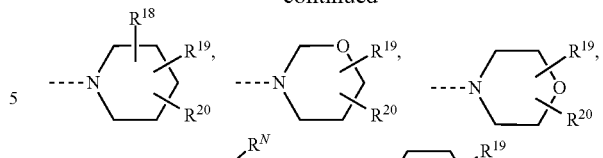

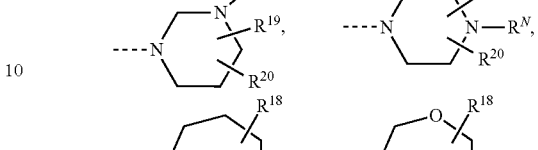

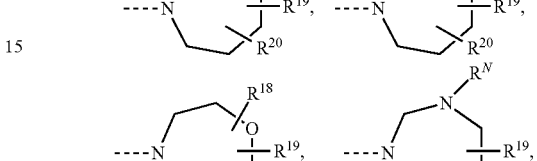

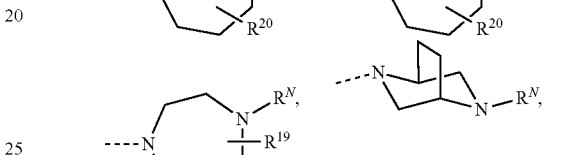

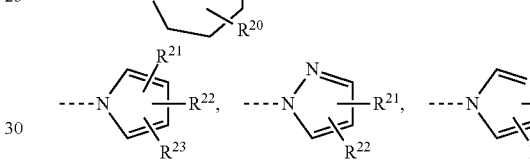

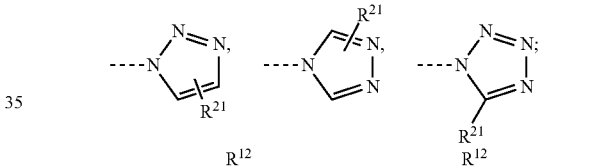

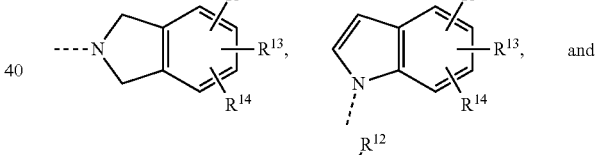

E$^N$ is selected from N terminal groups consisting of: —H, —COCF$_3$, —CH$_3$, —C$_2$H$_5$, —C$_3$H$_7$, —CH(CH$_3$)$_2$, —CH(C$_2$H$_5$)$_2$, —C$_4$H$_9$, —C$_5$H$_{11}$, —C$_6$H$_{13}$, —CH$_2$—CH(CH$_3$)$_2$, —CH$_2$—CH(C$_2$H$_5$)$_2$, —CH(CH$_3$)—C$_2$H$_5$, —C(CH$_3$)$_3$, —CH$_2$—C(CH$_3$)$_3$, -cyclo-C$_3$H$_5$, -cyclo-C$_4$H$_7$, -cyclo-C$_6$H$_{11}$, —CH$_2$-cyclo-C$_3$H$_5$, —CH$_2$-cyclo-C$_4$H$_7$, —CH$_2$-cyclo-C$_5$H$_9$, —CH$_2$-cyclo-C$_6$H$_{11}$, -Ph, —CH$_2$-Ph, —CH$_2$F, —CHF$_2$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$CH$_2$Br, —CH$_2$—CH$_2$I, —CH$_2$—CH=CH$_2$, —CH$_2$—C≡CH, —CHO, —COCH$_3$, —COC$_2$H$_5$, —COC$_3$H$_7$, —COCH(CH$_3$)$_2$, —COCH(C$_2$H$_5$)$_2$, —COC$_5$H$_{11}$, —COC$_6$H$_{13}$, —COCH$_2$—CH(CH$_3$)$_2$, —COCH$_2$—CH(C$_2$H$_5$)$_2$, —COCH(CH$_3$)—C$_2$H$_5$, —COC(CH$_3$)$_3$, —COCH$_2$—C(CH$_3$)$_3$, —CO-cyclo-C$_3$H$_5$, —CO-cyclo-C$_4$H$_7$, —CO-cyclo-C$_5$H$_9$, —CO-cyclo-C$_6$H$_{11}$, —COCH$_2$-cyclo-C$_3$H$_5$, —COCH$_2$-cyclo-C$_4$H$_7$, —COCH$_2$-cyclo-C$_5$H$_9$, —COCH$_2$-cyclo-C$_6$H$_{11}$, —COPh, —COCH$_2$-

Ph, —COOCH₃, —COOC₂H₅, —COOC₃H₇, —COOCH(CH₃)₂, —COOCH(C₂H₅)₂, —COOC₄H₉, —COOC₅H₁₁, —COOC₆H₁₃, —COOCH₂—CH(CH₃)₂, —COOCH₂—CH(C₂H₅)₂, —COOCH(CH₃)—C₂H₅, —COOC(CH₃)₃, —COOCH₂—C(CH₃)₃, —COO-cyclo-C₃H₅, —COO-cyclo-C₄H₇, —COO-cyclo-C₅H₉, —COO-cyclo-C₆H₁₁, —COOCH₂-cyclo-C₃H₅, —COOCH₂-cyclo-C₄H₇, —COOCH₂-cyclo-C₅H₉, —COOCH₂-cyclo-C₆H₁₁, —COOPh, —COOCH₂-Ph,

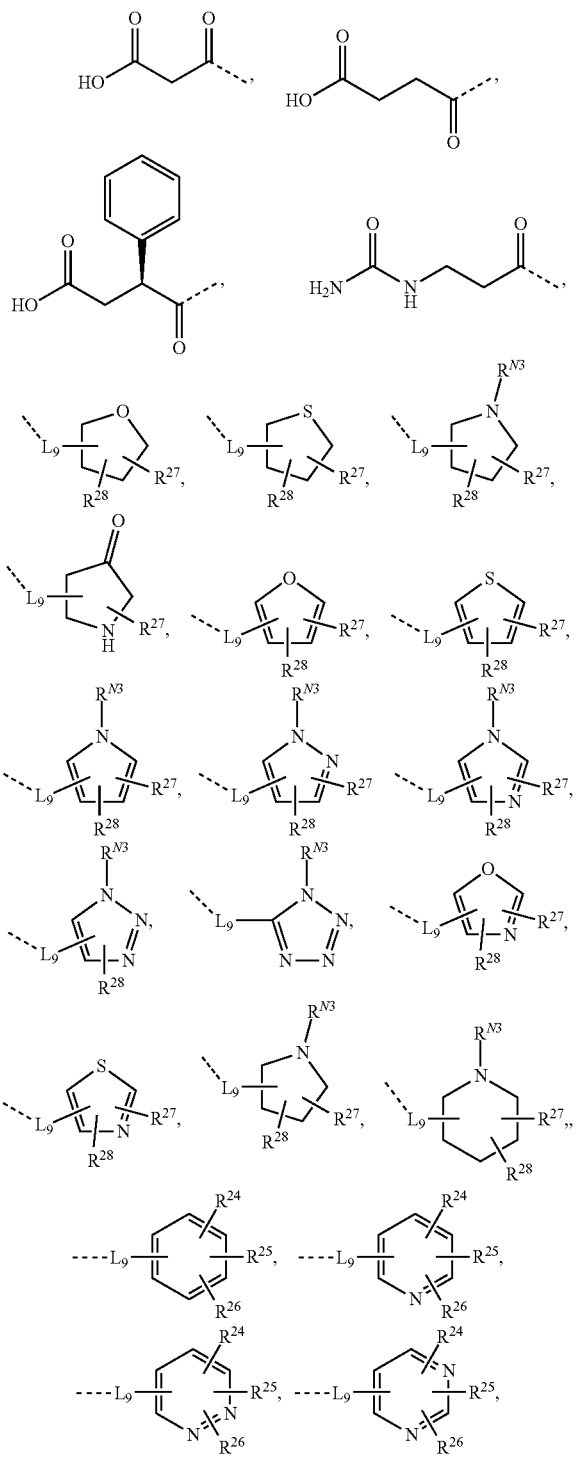
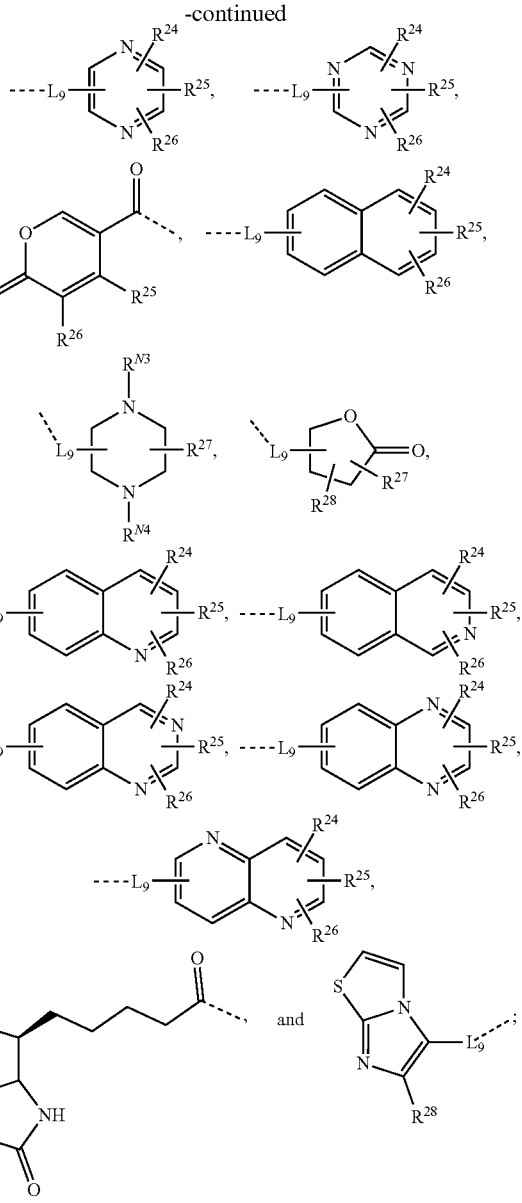

with proviso that when $Z^N$ is $E^N$ and $Z^C$ is $E^C$, then $E^C$ is not —OR⁸ and/or $E^N$ is not —H, R⁴, R⁵ and R⁶ represent independently of each other: —H, —F, —Cl, —Br, —CH₃, —CH₂CH₃, —CH(CH₃)₂, -cyclo-C₃H₅, —OCH₃, —OCH₂CH₃, —OCH(CH₃)₂, —O-cyclo-C₃H₅, —CF₃, —CF₂CF₃, —OCHF₂, —OCF₃, —OCF₂CF₃, —OH, —CN, —CHO, —COCH₃, —COCH₂CH₃, —COCH(CH₃)₂, —COCH₂F, —COCH₂Cl, —COCF₃, —COCCl₃, —CO₂H, —CO₂Me, —CO₂CH₂CH₃, —CO₂CH(CH₃)₂, —OCOCH₃, —OCOCH₂CH₃, —OCOCH(CH₃)₂, —OCOCF₃, —OCOCCl₃, —NH₂, —NHCH₃, —N(CH₃)₂, —NHCH₂CH₃, —NHCH(CH₃)₂, —N(CH₂CH₃)₂, —NH-cyclo-C₃H₅, —NHCOCH₃, —NHCOCF₃, —NHSO₂CH₃, —NHSO₂CF₃, —SCH₃, —SCH₂CH₃, —SCH(CH₃)₂, —S-cyclo-C₃H₅, —SOCH₃, —SOCF₃, —SO₂CH₃, —SO₂CF₃, —SO₂NH₂, —SO₂NHCH₃, —SO₂N(CH₃)₂, —SO₂NHCH₂CH₃, —SO₂NHCH(CH₃)₂, —SO₂NH-cyclo-C₃H₅, —SO₂N(CH₂CH₃)₂, or R⁴ and R⁵ or R⁵ and R⁶ form together the following five or six rings:

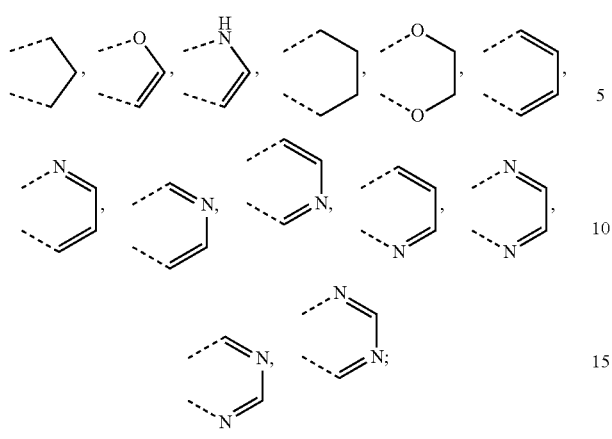
$R^7$ represents —H, —CH$_2$CO$_2$H, —CH$_2$CH$_2$CO$_2$H, —CH$_2$CH$_2$CH$_2$CO$_2$H, —CH$_2$CONH$_2$, —CH$_2$CH$_2$CONH$_2$, or —CH$_2$NHCONH$_2$;
$R^8$, $R^9$, $R^{10}$ and $R^{11}$ represent independently of each other: —H, —CH$_3$, —CH$_2$CH$_3$, —CH$_2$CH$_2$CH$_3$, —CH(CH$_3$)$_2$, —CH(C$_2$H$_5$)$_2$, —CH$_2$CH(CH$_3$)$_2$, —CH$_2$—CH(C$_2$H$_5$)$_2$, —C$_4$H$_9$, —C$_6$H$_{13}$, —CH(CH$_3$)—C$_2$H$_5$, —C(CH$_3$)$_3$, —CH$_2$—C(CH$_3$)$_3$,
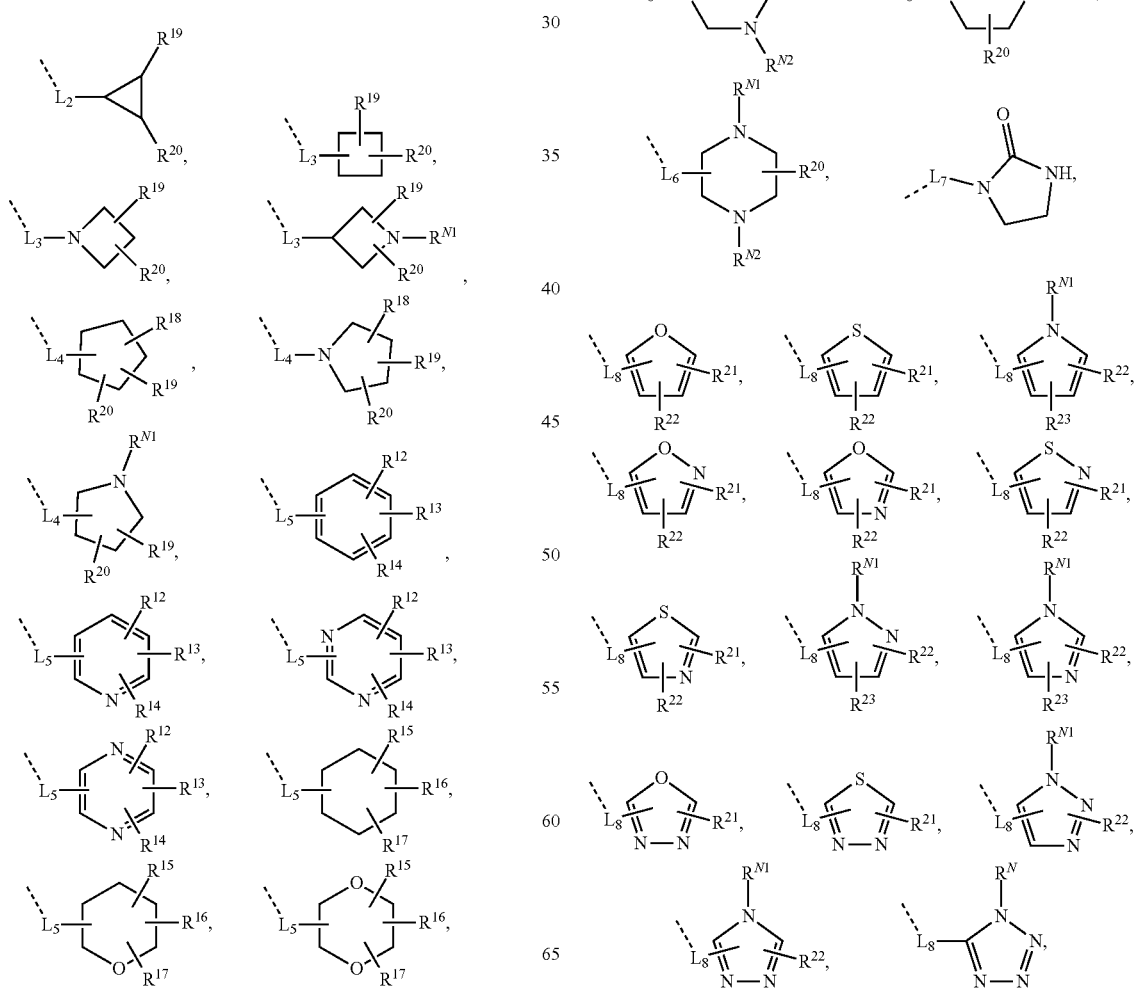

-continued

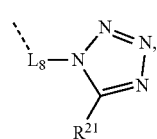 or 

$R^{12}$-$R^{29}$ represents independently of each other —H, —F, —Cl, —Br, —I, —OH, —CN, —NO$_2$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, -cyclo-C$_3$H$_5$, —CH$_2$-cyclo-C$_3$H$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$O, —CH$_2$—CH$_2$Br, —CH$_2$—CH$_2$I, —OCH$_3$, —OC$_2$H$_5$, —OC$_3$H$_7$, —OCH(CH$_3$)$_2$, —OC(CH$_3$)$_3$, —OC$_4$H$_9$, —OCHF$_2$, —OCF$_3$, —OCH$_2$CF$_3$, —OC$_2$F$_5$, —OCH$_2$OCH$_3$, —O-cyclo-C$_3$H$_5$, —OCH$_2$-cyclo-C$_3$H$_5$, —O—C$_2$H$_4$-cyclo-C$_3$H$_5$, —CHO, —COCH$_3$, —COCF$_3$, —COC$_2$H$_5$, —COC$_3$H$_7$, —COCH(CH$_3$)$_2$, —COC(CH$_3$)$_3$, —COOH, —COOCH$_3$, —COOC$_2$H$_5$, —COOC$_3$H$_7$, —COOCH(CH$_3$)$_2$, —COOC(CH$_3$)$_3$, —OOC—CH$_3$, —OOC—CF$_3$, —OOC—C$_2$H$_5$, —OOC—C$_3$H$_7$, —OOC—CH(CH$_3$)$_2$, —OOC—C(CH$_3$)$_3$, —NH$_2$, —NHCH$_3$, —NHC$_2$H$_5$, —NHC$_3$H$_7$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N[CH(CH$_3$)$_2$]$_2$, —N[C(CH$_3$)$_3$]$_2$, —NHCOCH$_3$, —NHCOCF$_3$, —NHCOC$_2$H$_5$, —NHCOC$_3$H$_7$, —NHCOCH(CH$_3$)$_2$, —NHCOC(CH$_3$)$_3$, —CONH$_2$, —CONHCH$_3$, —CONHC$_2$H$_5$, —CONHC$_3$H$_7$, —CONHCH(CH$_3$)$_2$, —CONH-cyclo-C$_3$H$_5$, —CONHC(CH$_3$)$_3$, —CON(CH$_3$)$_2$, —CON(C$_2$H$_5$)$_2$, —CON(C$_3$H$_7$)$_2$, —CON[CH(CH$_3$)$_2$]$_2$, —CON[C(CH$_3$)$_3$]$_2$, —SO$_2$NH$_2$, —SO$_2$NHCH$_3$, —SO$_2$NHC$_2$H$_5$, —SO$_2$NHC$_3$H$_7$, —SO$_2$NHCH(CH$_3$)$_2$, —SO$_2$NH-cyclo-C$_3$H$_5$, —SO$_2$NHC(CH$_3$)$_3$, —SO$_2$N(CH$_3$)$_2$, —SO$_2$N(C$_2$H$_5$)$_2$, —SO$_2$N(C$_3$H$_7$)$_2$, —SO$_2$N[CH(CH$_3$)$_2$]$_2$, —SO$_2$N[C(CH$_3$)$_3$]$_2$, —NHSO$_2$CH$_3$, —NHSO$_2$CF$_3$, —NHSO$_2$C$_2$H$_5$, —NHSO$_2$C$_3$H$_7$, —NHSO$_2$CH(CH$_3$)$_2$, —NHSO$_2$C(CH$_3$)$_3$, —CH=CH$_2$, —CH$_2$—CH=CH$_2$, —C(CH$_3$)=CH$_2$, —CH=CH—CH$_3$, —C≡CH, —C≡C—CH$_3$, —CH$_3$, —CH$_2$—C≡CH, -Ph, —O-Ph, —O—CH$_2$-Ph,

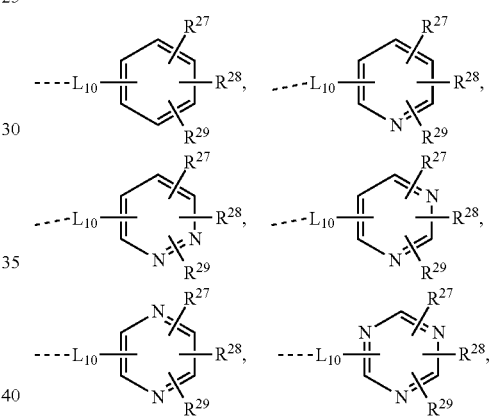

or $R^{12}$ and $R^{13}$, $R^{13}$ and $R^{14}$, $R^{24}$ and $R^{25}$, $R^{25}$ and $R^{26}$, $R^{27}$ and $R^{28}$, $R^{28}$ and $R^{29}$ can form together the following five or six rings, when $R^{12}$-$R^{14}$, $R^{24}$-$R^{29}$ are substituted at six-membered ring;

$R^N$, represents independently of each other —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, -cyclo-C$_3$H$_5$, —CH$_2$-cyclo-C$_3$H$_5$, —CH$_2$F, —CHF$_2$, —CF$_3$, —CH$_2$Cl, —CH$_2$Br, —CH$_2$I. —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —CH$_2$—CH=CH$_2$, —CH$_2$—C≡CH, —CHO, —COCH$_3$, —OOC$_2$H$_5$, —OOC$_3$H$_7$, —COCH(CH$_3$)$_2$, —COC(CH$_3$)$_3$, —COOCH$_3$, —COOC$_2$H$_5$, —COOC$_3$H$_7$, —COOCH(CH$_3$)$_2$, —COOC(CH$_3$)$_3$,

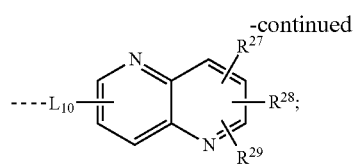

$R^{N1}$-$R^{N4}$ represent independently of each other —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$) C$_2$H$_5$, —C(CH$_3$)$_3$, cyclo-C$_3$H$_5$, —CH$_2$-cyclo-C$_3$H$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —CH$_2$—CH=CH$_2$, —CH$_2$—C≡CH, —CH$_2$Ph, —CHO, —COCH$_3$, —OOC$_2$H$_5$, —OOC$_3$H$_7$, COCH(CH$_3$)$_2$, —COC(CH$_3$)$_3$, —COOCH$_3$, —COOC$_2$H$_5$, —COOC$_3$H$_7$, —COOCH(CH$_3$)$_2$, —COOC(CH$_3$)$_3$, or —COOCH$_2$Ph;

$L^1$-$L^8$ represent independently of each other a covalent bond, —CH$_2$—, —CH(CH$_3$)—, —CH(CH$_3$)$_2$—, —CO—, —SO—, —SO$_2$—,

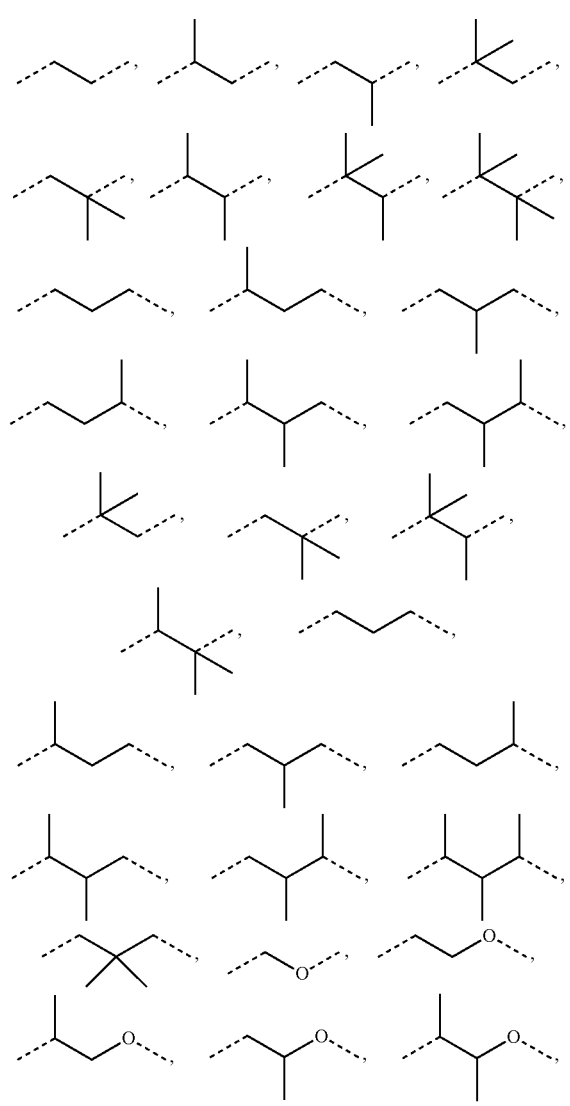

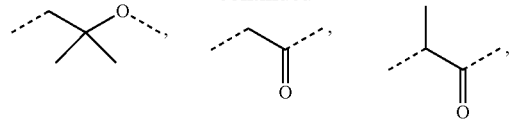
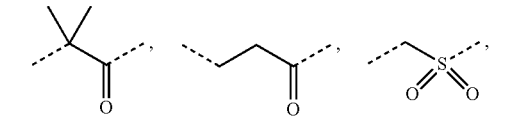
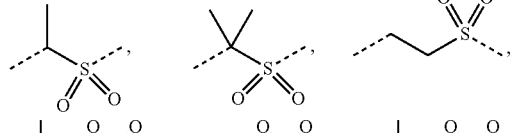
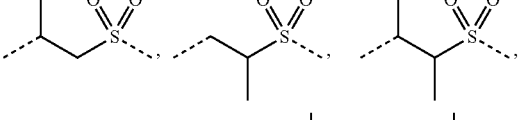
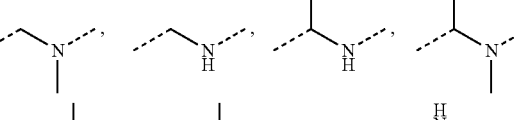
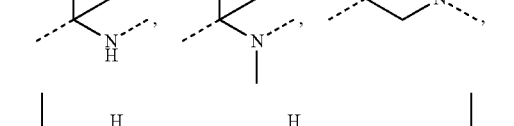
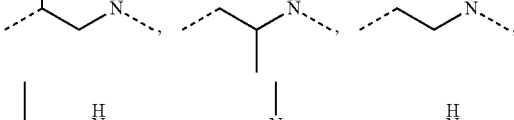
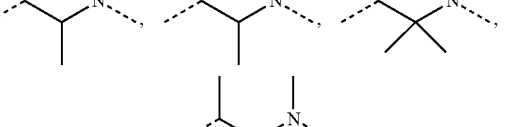
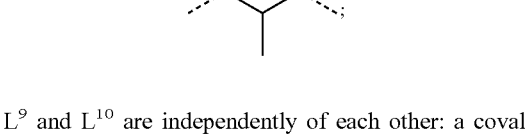, or $L^9$ and $L^{10}$ are independently of each other: a covalent bond, —CH$_2$—, —CH$_2$CH$_2$—, —CO—, —CH$_2$CO—, —COCH$_2$—, —CO—CH=CH—, —COO—, —O—CO—, —CH$_2$CO$_2$—, —CO$_2$CH$_2$—, —CONH—, —NHCO—, —CH$_2$CONH—, —CONHCH$_2$—, —CSNH—, —NHCS—, —SO$_2$—, —SO$_2$CH$_2$—, —SO$_2$NH—, or —SO$_2$NHCH$_2$—;

and diastereomer, enantiomer, mixture of diastereomers, mixture of enantiomer, racemates, prodrugs, solvates, hydrates, or pharmaceutically acceptable salts thereof.

Preferred are compounds of the general formula (I):

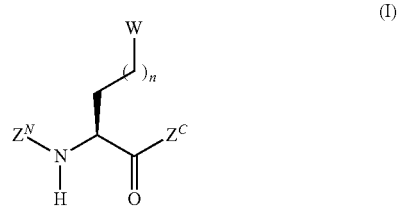

(I)

wherein
n is an integer selected from 1, 2 or 3;
W represents

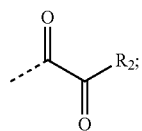

R² represents —H, —R¹, —OR¹, —NH₂, —NH(R¹), —NH(OR¹)—N(R¹)(R³);
R¹ and R³ represent independently of each other —CH₃, —CH₂CH₃, —CH₂CH₂CH₃, —CH(CH₃)₂, —CH₂CH₂CH₂CH₃, —CH₂CH₂CH₂CH₂CH₃, —CH₂CH₂CH₂CH₂CH₂CH₃, —CH₂CH₂CH₂CH₂CH₂CH₂CH₃, —CH₂CH(CH₃)₂, —CH(CH₃)CH₂CH₃, —CH(C₂H₅)₂, —CH₂CH(C₂H₅)₂, —C(CH₃)₃, —CH₂—C(CH₃)₃, -cyclo-C₃H₅, -cyclo-C₄H₇, -cyclo-C₅H₉, -cyclo-C₆H₁₁, —CH₂-cyclo-C₃H₅, —CH₂-cyclo-C₄H₇, —CH₂-cyclo-C₅H₉, —CH₂-cyclo-C₆H₁₁, -Ph, —CH₂-Ph, —CH₂OCH₃, —CH₂OCH₂CH₃, —CH₂CH₂OCH₃, —CH₂CH₂OCH₂CH₃, —CH₂CO₂CH₃, —CH₂CO₂CH₂CH₃, —CH₂CH₂NHCH₃, —CH₂CH₂N(CH₃)₂, —CH₂S(O)₂-(4-methyl-phenyl),

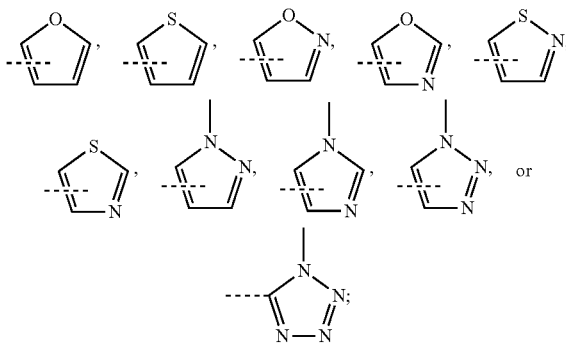

$Z^N$ represents $E^N$-, $E^N$-$AS^{N1}$-, $E^N$-$AS^{N2}$-$AS^{N1}$-, $E^N$-$AS^{N3}$-$AS^{N2}$-$AS^{N1}$- or $E^N$-$AS^{N4}$-$AS^{N3}$-$AS^{N2}$-$AS^{N1}$-;

$Z^C$ represents -$E^C$, -$AS^{C1}$-$E^C$, -$AS^{C1}$-$AS^{C2}$-$E^C$, -$AS^{C1}$-$AS^{C2}$-$AS^{C3}$-$E^C$, -$AS^{C1}$-$AS^{C2}$-$AS^{C3}$-$AS^{C4}$-$E^C$, -$AS^{C1}$-$AS^{C2}$-$AS^{C3}$-$AS^{C4}$-$AS^{C5}$-$E^C$, or -$AS^{C1}$-$AS^{C2}$-$AS^{C3}$-$AS^{C4}$-$AS^{C5}$-$AS^{C6}$-$E^C$;

$AS^{C1}$-$AS^{C8}$ and $AS^{N1}$-$AS^{N4}$ are independently of each other selected from the group consisting of:

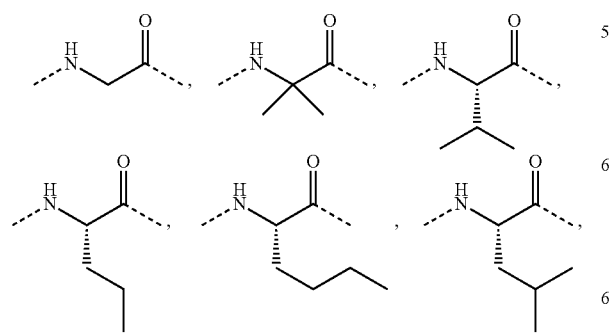

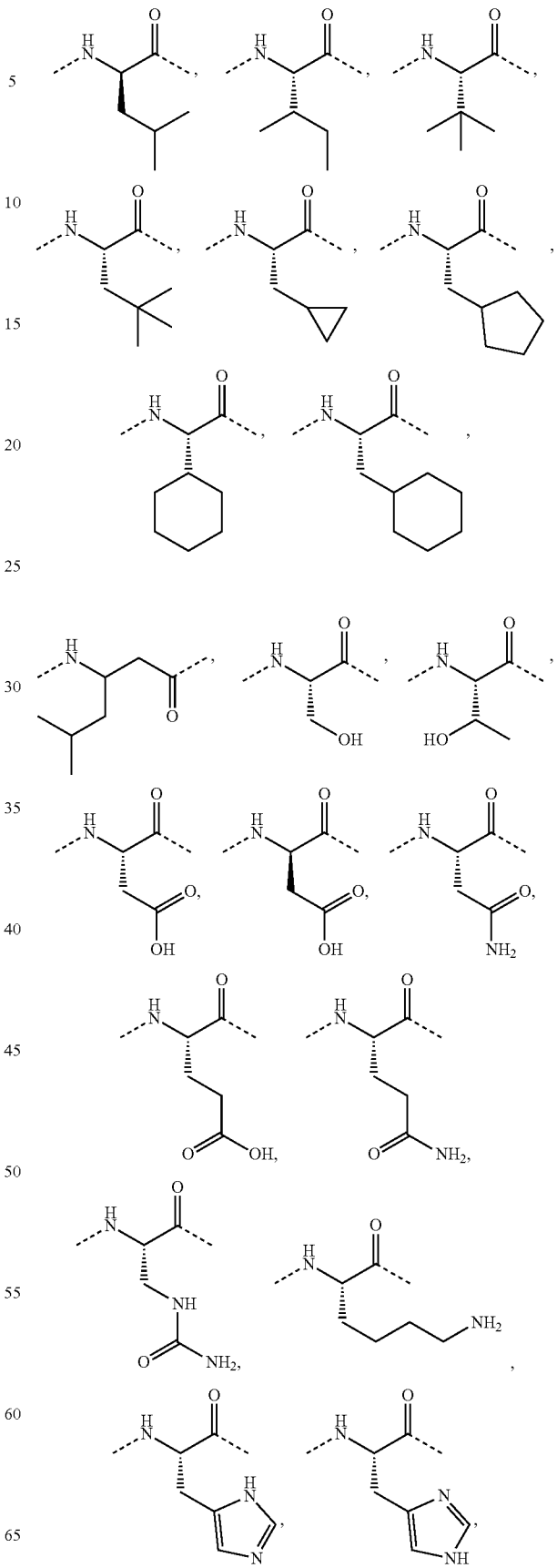

-continued
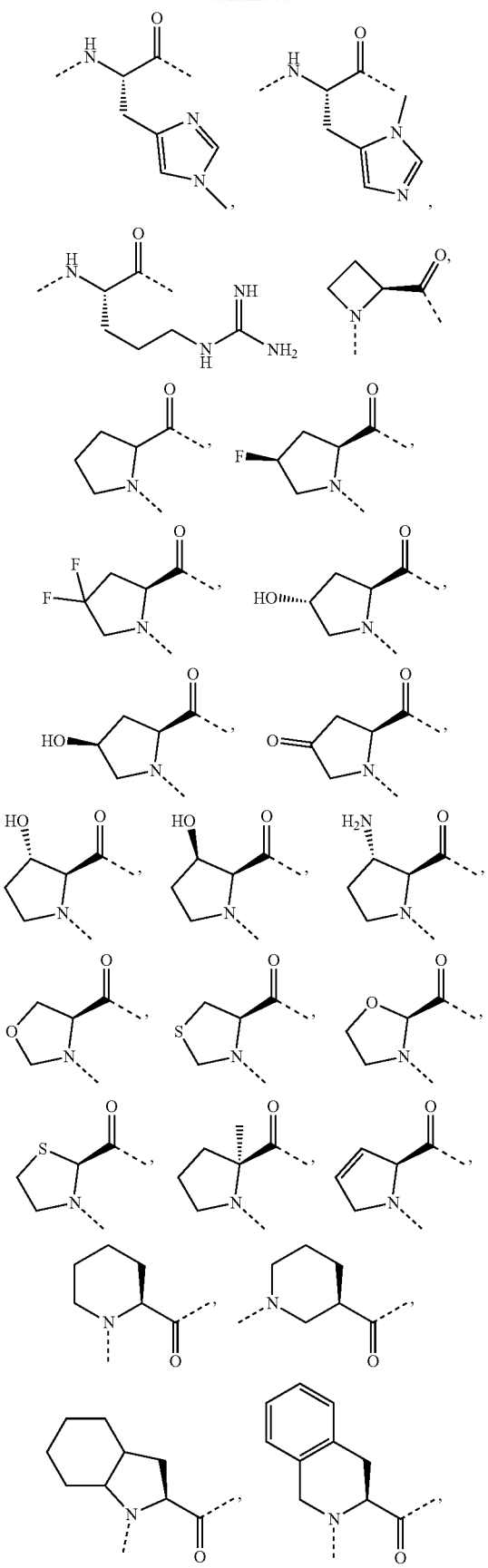
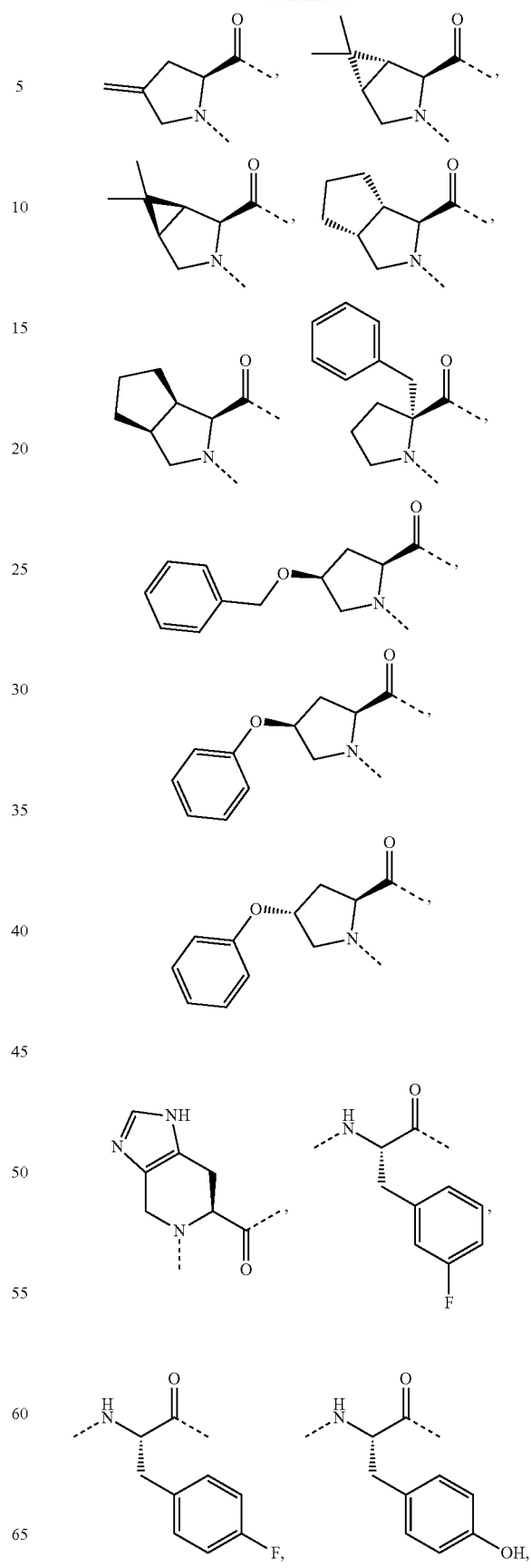

23
-continued
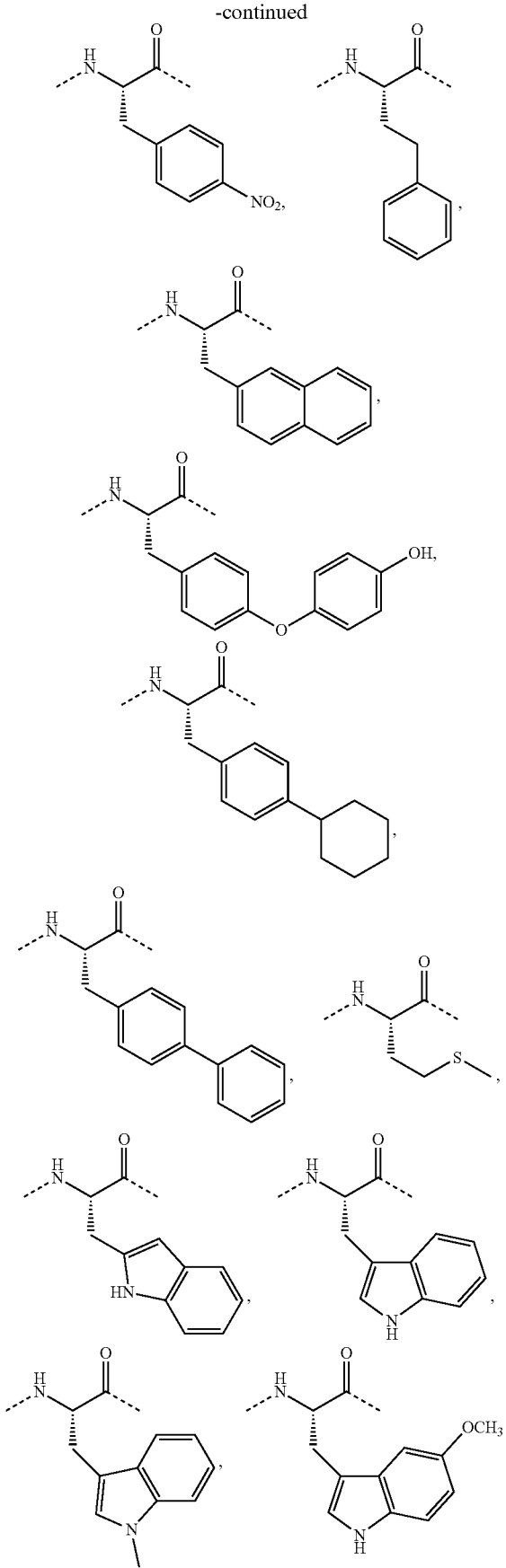
24
-continued
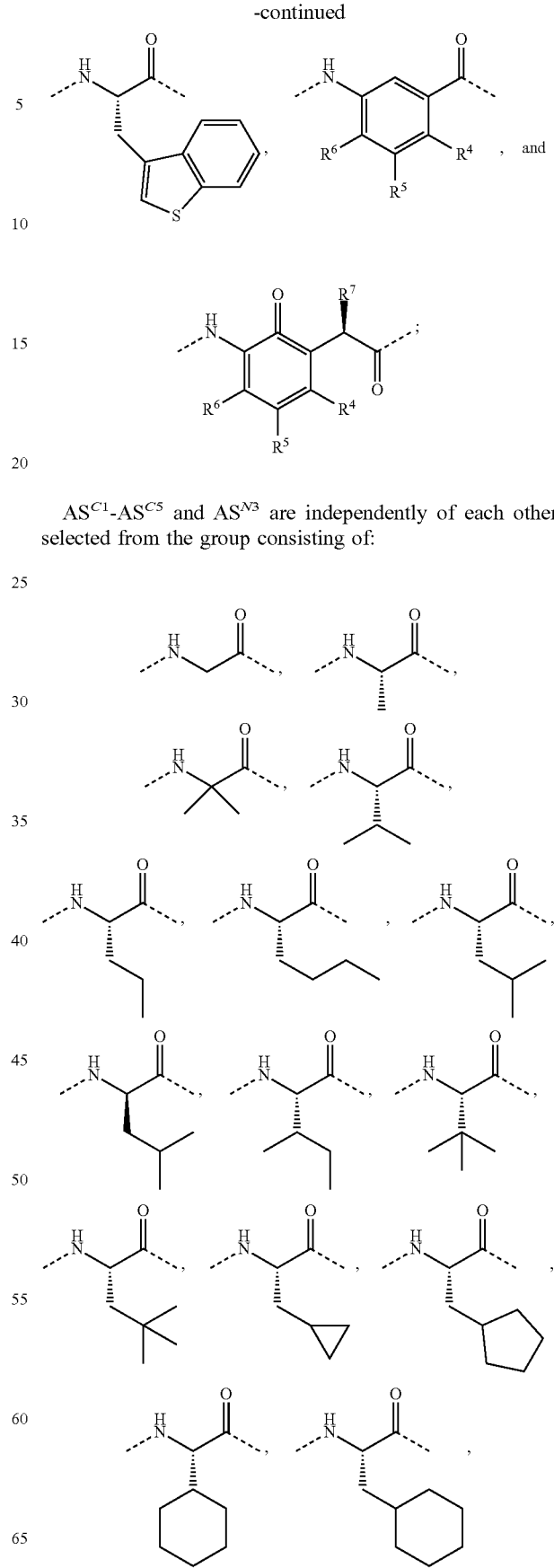
$AS^{C1}$-$AS^{C5}$ and $AS^{N3}$ are independently of each other selected from the group consisting of:

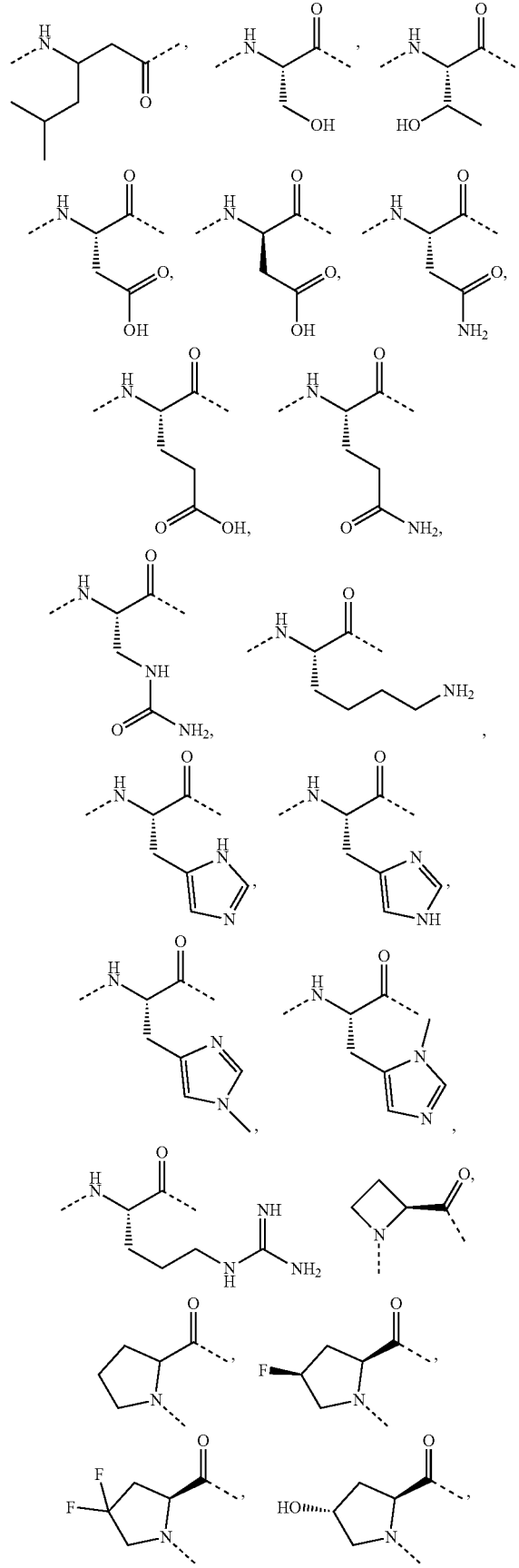
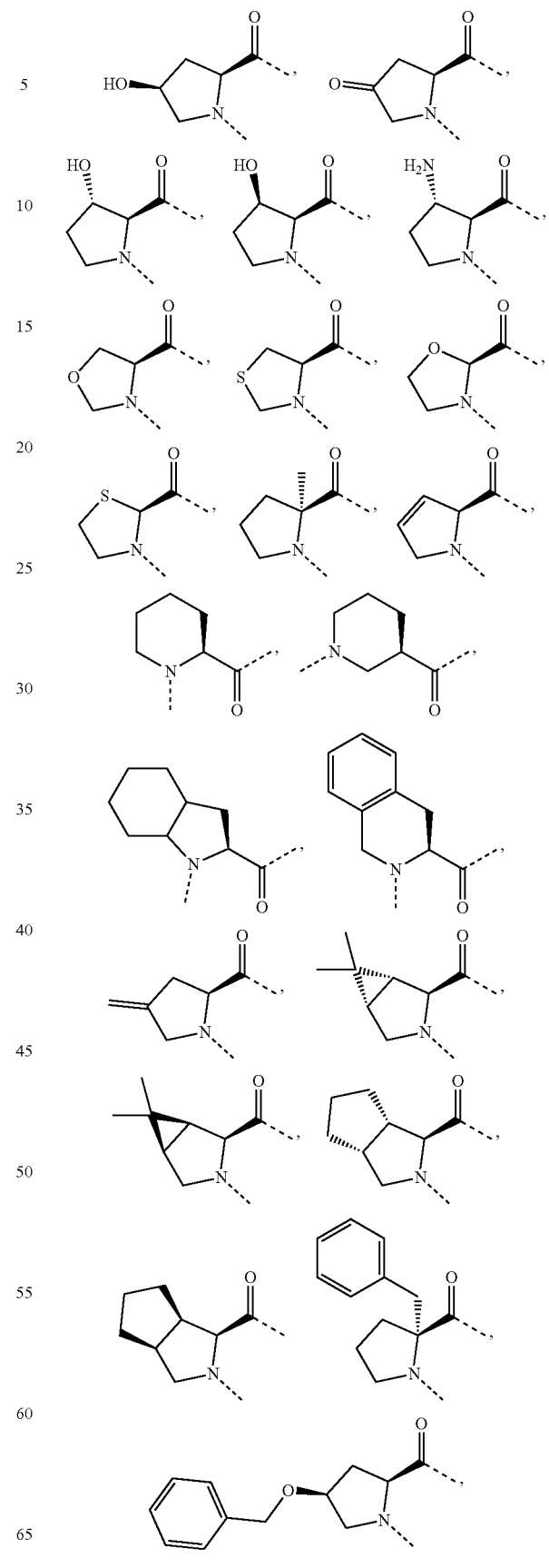

-continued
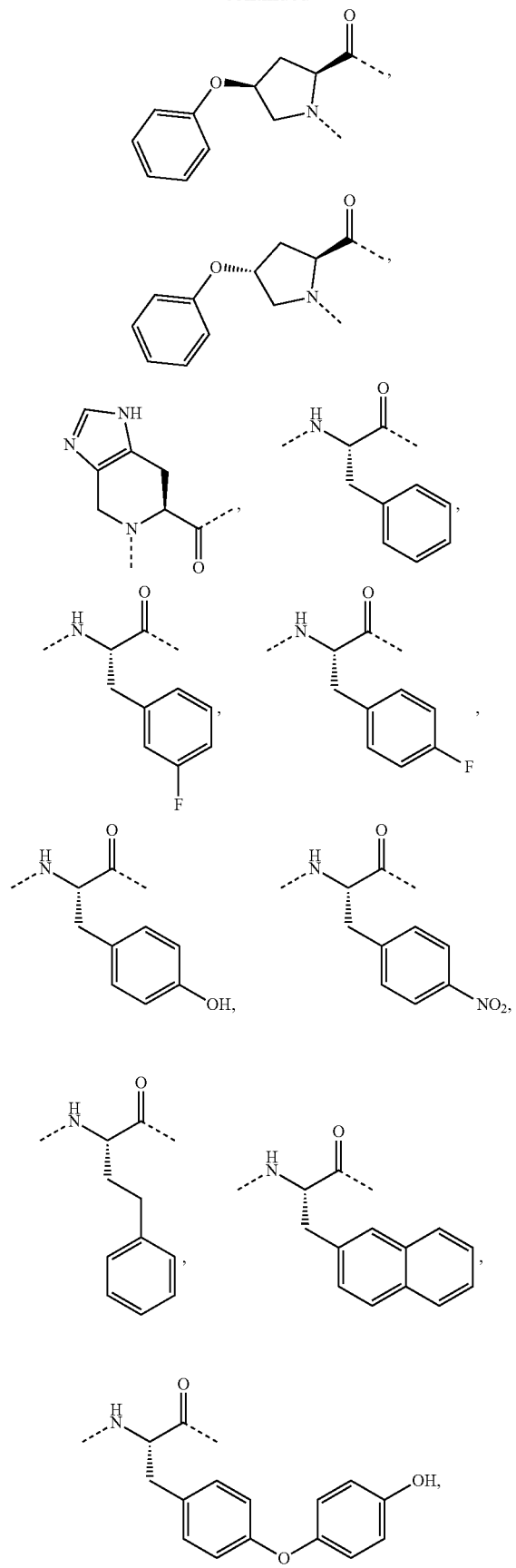
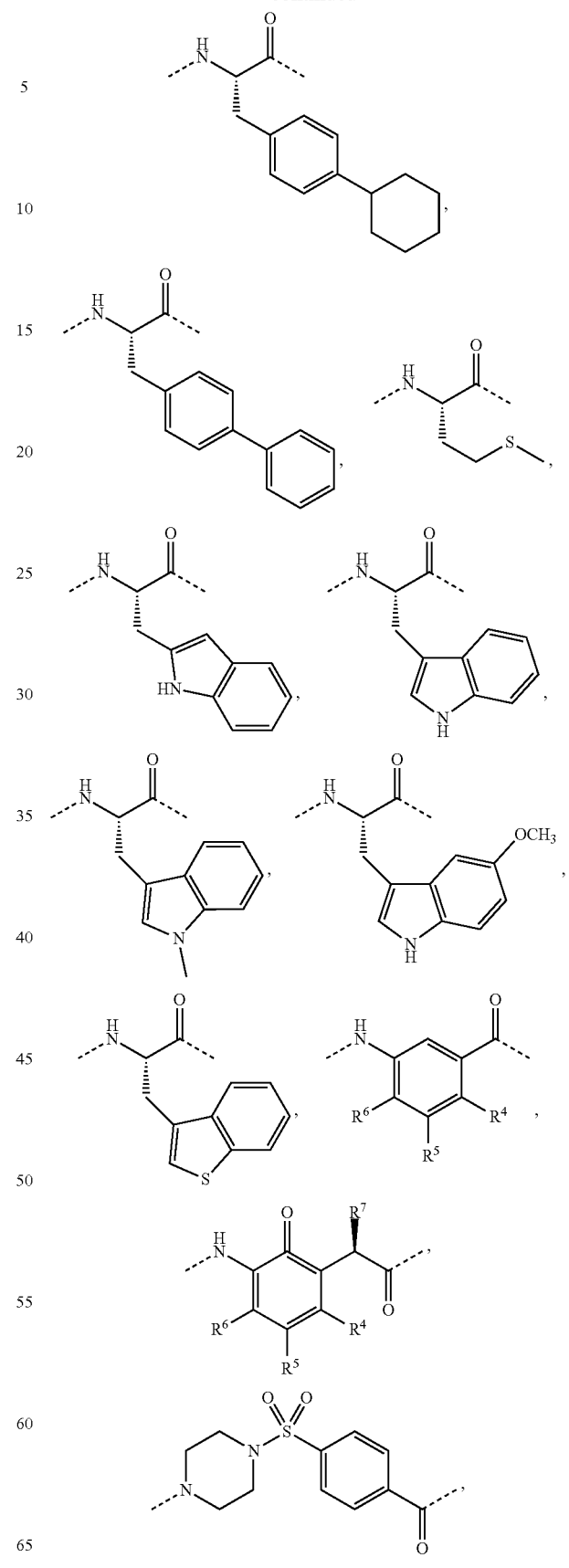

29
-continued

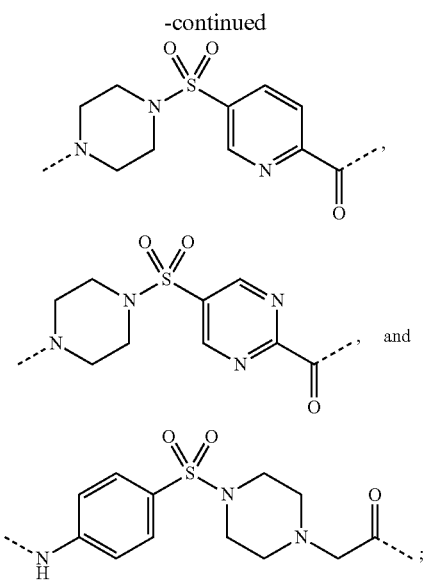

and

30
-continued

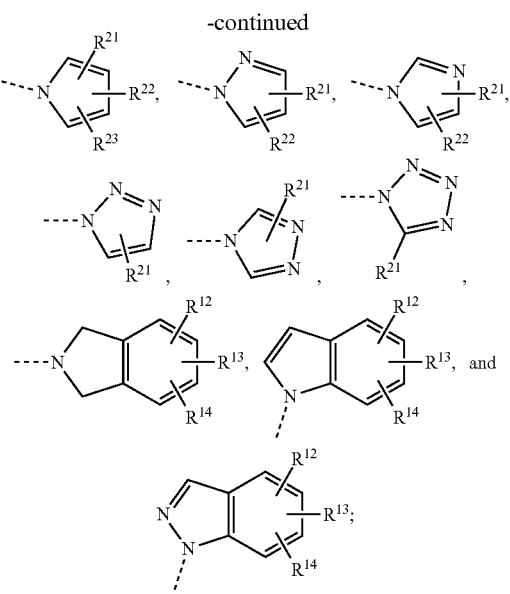

$E^C$ is selected from C terminal groups consisting of: —$OR^8$, —$NR^9R^{10}$, —$NHSO_2R^{11}$, —O-$L_1R^8$, —O-$L_1$-O—$R^8$, —NH-$L_1$-O—$R^8$, —NR-$L_1$-$NR^9R^{10}$, —$NHSO_2$-$L_1$-$R^{11}$,

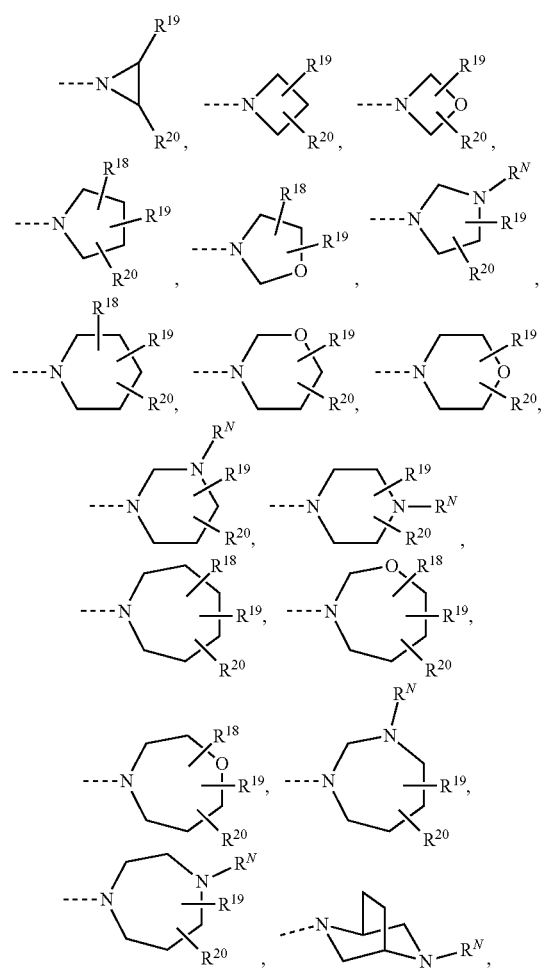

$E^N$ is selected from N terminal groups consisting of: —H, —$COCF_3$, —$CH_3$, —$C_2H_5$, —$C_3H_7$, —$CH(CH_3)_2$, —$CH(C_2H_5)_2$, —$C_4H_9$, —$C_5H_{11}$, —$C_6H_{13}$, —$CH_2$—$CH(CH_3)_2$, —$CH_2$—$CH(C_2H_5)_2$, —$CH(CH_3)$—$C_2H_5$, —$C(CH_3)_3$, —$CH_2$—$C(CH_3)_3$, cyclo-$C_3H_5$, -cyclo-$C_4H_7$, -cyclo-$C_5H_9$, -cyclo-$C_6H_{11}$, —$CH_2$-cyclo-$C_3H_5$, —$CH_2$-cyclo-$C_4H_7$, —$CH_2$-cyclo-$C_5H_9$, —$CH_2$-cyclo-$C_6H_{11}$, -Ph, —$CH_2$-Ph, —$CH_2F$, —$CHF_2$, —$CF_3$, —$CH_2Cl$, —$CH_2Br$, —$CH_2I$, —$CH_2$—$CH_2F$, —$CH_2$—$CHF_2$, —$CH_2$—$CF_3$, —$CH_2$—$CH_2Cl$, —$CH_2$—$CH_2Br$, —$CH_2$—$CH_2I$, —$CH_2$—$CH=CH_2$, —$CH_2$—C≡CH, —CHO, —$COCH_3$, —$COC_2H_5$, —$COC_3H_7$, —$COCH(CH_3)_2$, —$COCH(C_2H_5)_2$, —$COC_4H_9$, —$COC_5H_{11}$, —$COC_6H_{13}$, —$COCH_2$—$CH(CH_3)_2$, —$COCH_2$—$CH(C_2H_5)_2$, —$COCH(CH_3)$— $C_2H_5$, —$COC(CH_3)_3$, —$COCH_2$—$C(CH_3)_3$, —CO-cyclo-$C_3H_5$, —CO-cyclo-$C_4H_7$, —CO-cyclo-$C_5H_9$, —CO-cyclo-$C_6H_{11}$, —$COCH_2$-cyclo-$C_3H_5$, —$COCH_2$-cyclo-$C_4H_7$, —$COCH_2$-cyclo-$C_5H_9$, —$COCH_2$-cyclo-$C_6H_{11}$, —COPh, —$COCH_2$-Ph, —$COOCH_3$, —$COOC_2H_5$, —$COOC_3H_7$, —$COOCH(CH_3)_2$, —$COOCH(C_2H_5)_2$, —$COOC_4H_9$, —$COOC_5H_{11}$, —$COOC_6H_{13}$, —$COOCH_2$—$CH(CH_3)_2$, —$COOCH_2$—$CH(C_2H_5)_2$, —$COOCH(CH_3)$— $C_2H_5$, —$COOC(CH_3)_3$, —$COOCH_2$—$C(CH_3)_3$, —COO-cyclo-$C_3H_5$, —COO-cyclo-$C_4H_7$, —COO-cyclo-$C_5H_9$, —COO-cyclo-$C_6H_1$—$COOCH_2$-cyclo-$C_3H_5$, —$COOCH_2$-cyclo-$C_4H_7$, —$COOCH_2$-cyclo-$C_5H_9$, —$COOCH_2$-cyclo-$C_6H_1$, —COOPh, —$COOCH_2$-Ph,

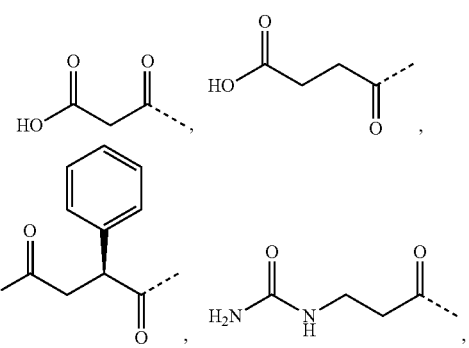

-continued

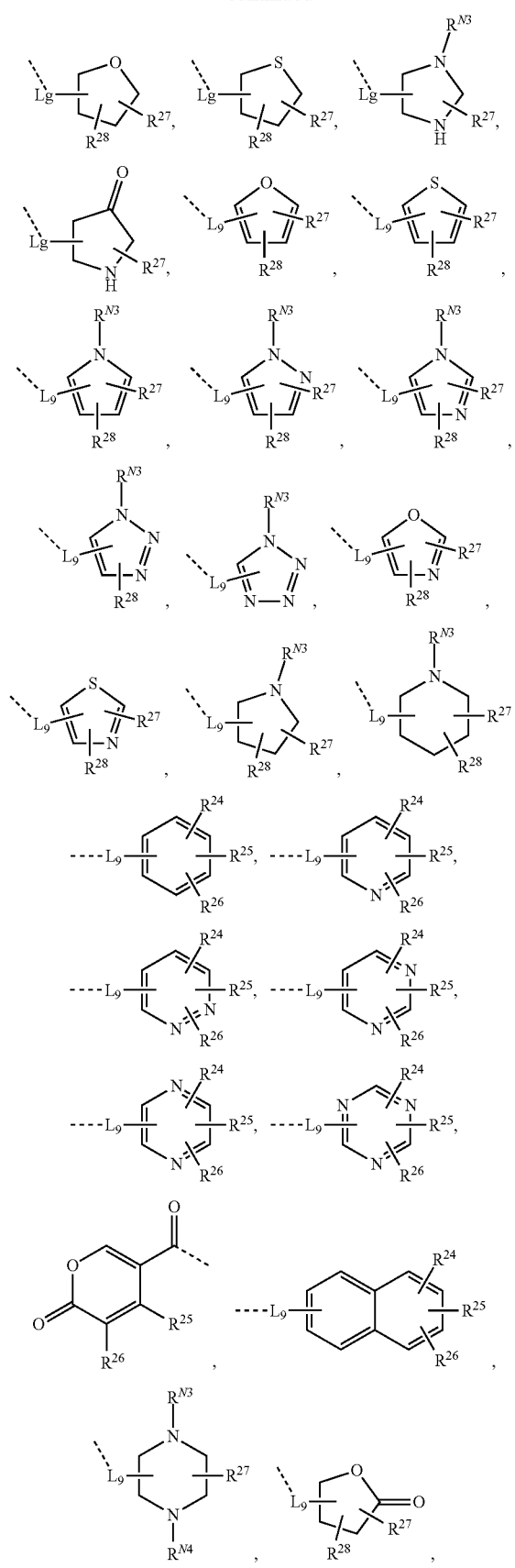

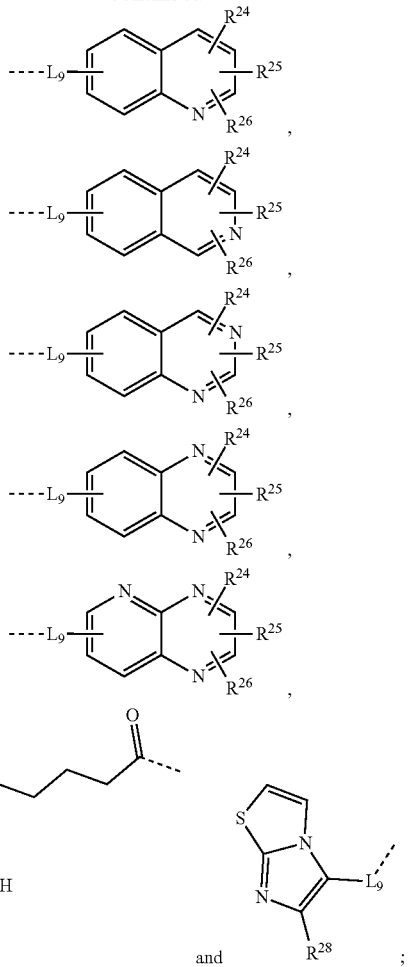

with proviso that when $Z^N$ is $E^N$ and $Z^C$ is $E^C$, then $E^C$ is not —$OR^8$ and/or $E^N$ is not —H, $R^4$, $R^5$ and $R^6$ represent independently of each other: —H, —Cl, —Br, —I, —$CH_3$, —$CH_2CH_3$, —$CH(CH_3)_2$, -cyclo-$C_3H_5$, —$OCH_3$, —$OCH_2CH_3$, —$CCH(CH_3)_2$, —O-cyclo-$C_3H_5$, —$CF_3$, —$CF_2CF_3$, —$OCHF_2$, —$OCF_3$, —$OCF_2CF_3$, —OH, —CN, —CHO, —$COCH_3$, —$COCH_2CH_3$, —$COCH(CH_3)_2$, —$COCH_2F$, —$OOCH_2Cl$, —$COCF_3$, —$COCCl_3$, —$CO_2H$, —$CO_2Me$, —$CO_2CH_2CH_3$, —$CO_2CH(CH_3)_2$, —$OCOCH_3$, —$OCOCH_2CH_3$, —$OCOCH(CH_3)_2$, —$OCOCF_3$, —$OCOCCl_3$, —$NH_2$, —$NHCH_3$, —$N(CH_3)_2$, —$NHCH_2CH_3$, —$NHCH(CH_3)_2$, —$N(CH_2CH_3)_2$, —NH-cyclo-$C_3H_5$, —$NHCOCH_3$, —$NHCOCF_3$, —$NHSO_2CH_3$, —$NHSO_2CF_3$, —$SCH_3$, —$SCH_2CH_3$, —$SCH(CH_3)_2$, —S-cyclo-$C_3H_5$, —$SOCH_3$, —$SOCF_3$, —$SO_2CH_3$, —$SO_2CF_3$, —$SO_2NH_2$, —$SO_2NHCH_3$, —$SO_2N(CH_3)_2$, —$SO_2NHCH_2CH_3$, —$SO_2NHCH(CH_3)_2$, —$SO_2NH$-cyclo-$C_3H_5$, —$SO_2N(CH_2CH_3)_2$, or $R^7$ represents —H, —$CH_2CO_2H$, —$CH_2CH_2CO_2H$, —$CH_2CH_2CH_2CO_2H$, —$CH_2CONH_2$, —$CH_2CH_2CONH_2$, or —$CH_2NHCONH_2$;

$R^8$, $R^9$, $R^{10}$ and $R^{11}$ represent independently of each other: —H, $H_3$, —$CH_2CH_3$, —$CH_2CH_2CH_3$, —$CH(CH_3)_2$, —$CH(C_2H_5)_2$, —$CH_2CH(CH_3)_2$, —$CH_2$—$CH(C_2H_5)_2$, —$C_4H_9$, —$C_5H_{11}$, —$C_6H_{13}$, —$CH(CH_3)$—$C_2H_5$, —$C(CH_3)_3$, —$CH_2$—$C(CH_3)_3$,

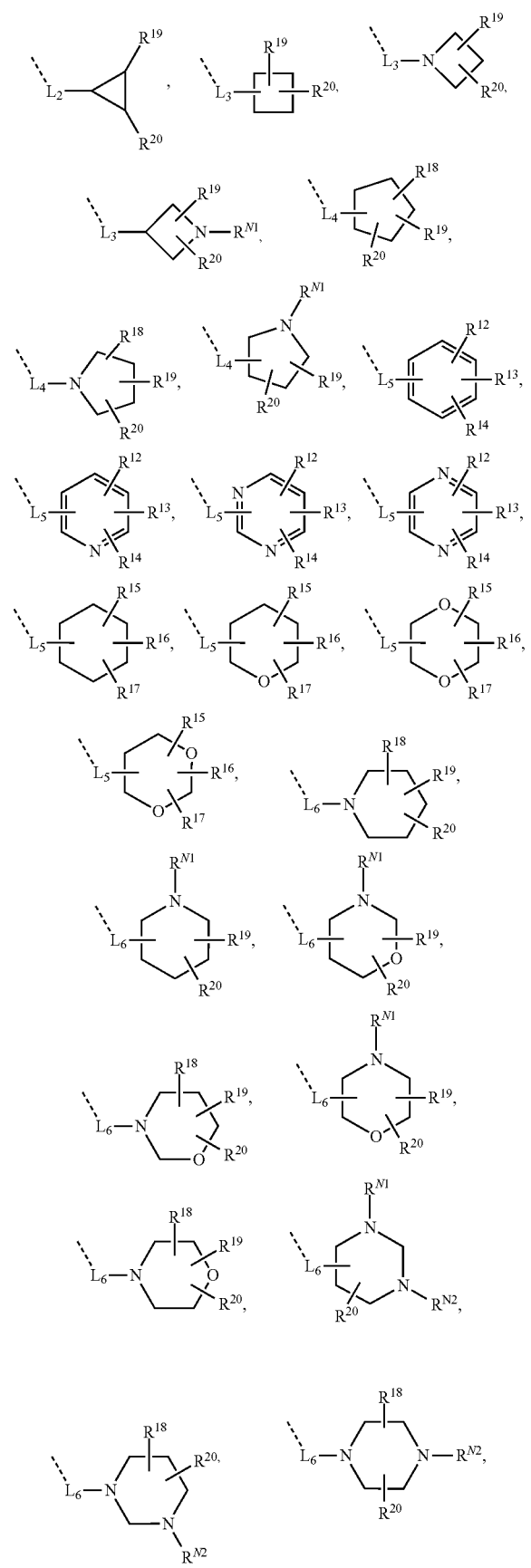
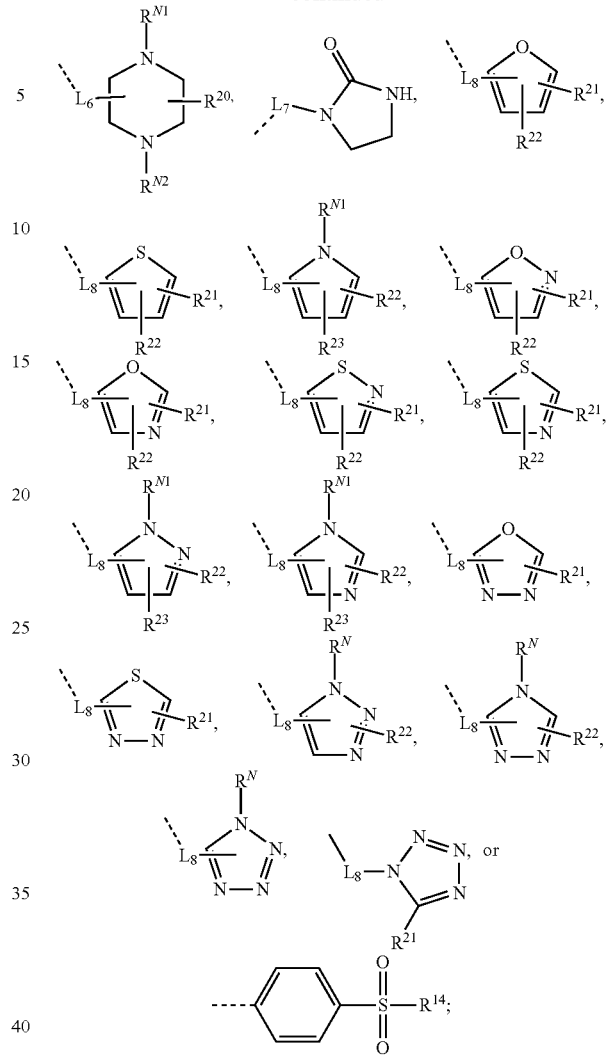

$R^{12}$-$R^{29}$ represents independently of each other —H, —F, —Cl, —Br, —I, —OH, —CN, —NO$_2$, —CH$_3$, —C$_2$H$_5$, —C$_3$H$_7$, —CH(CH$_3$)$_2$, —C$_4$H$_9$, —CH$_2$CH(CH$_3$)$_2$, —CH(CH$_3$)—C$_2$H$_5$, —C(CH$_3$)$_3$, -cyclo-C$_3$H$_5$, —CH$_2$ cyclo-C$_3$H$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —OCH$_3$, —OC$_2$H$_5$, —OC$_3$H$_7$, —OCH(CH$_3$)$_2$, —OC(CH$_3$)$_3$, —OCHF$_2$, —OCF$_3$, —OCH$_2$CF$_3$, —OC$_2$F$_5$, —OCH$_2$OCH$_3$, —O-cyclo-C$_3$H$_5$, —OCH$_2$-cyclo-C$_3$H$_5$, —O—C$_2$H$_4$-cyclo-C$_3$H$_5$, —CHO, —COCH$_3$, —COCF$_3$, —COC$_2$H$_5$, —COC$_3$H$_7$, —COCH(CH$_3$)$_2$, —COC(CH$_3$)$_3$, —COOH, —COOCH$_3$, —COOC$_2$H$_5$, —COOC$_3$H$_7$, —COOCH(CH$_3$)$_2$, —COOC(CH$_3$)$_3$, —OOC—CH$_3$; —OOC—CF$_3$, —OOC—C$_2$H$_5$, —OOC—C$_3$H$_7$, —OOC—CH(CH$_3$)$_2$, —OOC—C(CH$_3$)$_3$, —NH$_2$. —NHCH$_3$, —NHC$_2$H$_5$, —NHC$_3$H$_7$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N[CH(CH$_3$)$_2$]$_2$, —N[C(CH$_3$)$_3$]$_2$, —NHCOCH$_3$, —NHCOCF$_3$, —NHCOC$_2$H$_5$, —NHCOC$_3$H$_7$, —NHCOCH(CH$_3$)$_2$, —NHCOC(CH$_3$)$_3$, —CONH$_2$, —CONHCH$_3$, —CONHC$_2$H$_5$, —CONHC$_3$H$_7$, —CONHCH(CH$_3$)$_2$, —CONH-cyclo-C$_3$H$_5$, —CONHC(CH$_3$)$_3$, —CON(CH$_3$)$_2$, —CON(C$_2$H$_5$)$_2$, —CON(C$_3$H$_7$)$_2$, —CON[CH(CH$_3$)$_2$]$_2$, —CON[(CH$_3$)$_3$]$_2$, —SO$_2$NH$_2$, —SO$_2$NHCH$_3$, —SO$_2$NHC$_2$H$_5$, —SO$_2$NHC$_3$H$_7$, —SO$_2$NHCH(CH$_3$)$_2$, —SO$_2$NH-cyclo-C$_3$H$_5$, —SO$_2$NHC(CH$_3$)$_3$, —SO$_2$N(CH$_3$)$_2$, —SO$_2$N(C$_2$H$_5$)$_2$, —SO$_2$N(C$_3$H$_7$)$_2$, —SO$_2$N[CH(CH$_3$)$_2$]$_2$, —SO$_2$N[C(CH$_3$)$_3$]$_2$, —NHSO$_2$CH$_3$, —NHSO$_2$CF$_3$, —NHSO$_2$C$_2$H$_5$, —NHSO$_2$C$_3$H$_7$, —NHSO$_2$CH(CH$_3$)$_2$, —NHSO$_2$C(CH$_3$)$_3$, —CH=CH$_2$, —CH$_2$—CH=CH$_2$, —C(CH$_3$)=CH$_2$, —CH=CH—CH$_3$, —C≡CH, —C≡C—CH$_3$, —CH$_2$—C≡CH, -Ph, —O-Ph, and —O—CH$_2$-Ph, R$^N$, represents independently of each other —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$) C$_2$H$_5$, —C(CH$_3$)$_3$, cyclo-C$_3$H$_5$, —CH$_2$ cyclo C$_3$H$_5$, —CH$_2$F, —CHF$_2$, —CF$_3$, —CH$_2$Cl; CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —CH$_2$—CH=CH$_2$, —CH$_2$—C≡CH, —CHO, —COCH$_3$, —OOC$_2$H$_5$, —OOC$_3$H$_7$, —COCH(CH$_3$)$_2$, —COC(CH$_3$)$_3$, —COOCH$_3$, —COOC$_2$H$_5$, —COOC$_3$H$_7$, —COOCH(CH$_3$)$_2$, —COOC(CH$_3$)$_3$,

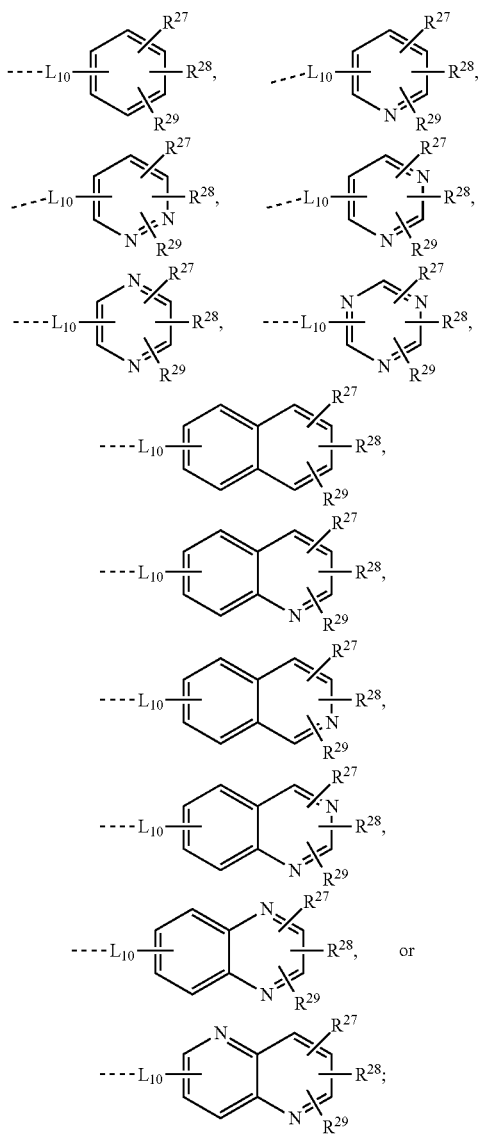

R$^{N1}$-R$^{N4}$ represent independently of each other —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$) C$_2$H$_5$, —C(CH$_3$)$_3$, cyclo-C$_3$H$_5$, —CH$_2$-cyclo-C$_3$H$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —CH$_2$—CH=CH$_2$, —CH$_2$Ph, —CHO, —COCH$_3$, —OOC$_2$H$_5$, —OOC$_3$H$_7$, —COCH(CH$_3$)$_2$, —COC(CH$_3$)$_3$, —COOCH$_3$, —COOC$_2$H$_5$, —COOC$_3$H$_7$, —COOCH(CH$_3$)$_2$, —COOC(CH$_3$)$_3$, or —COOCH$_2$Ph;

L$^1$-L$^8$ represent independently of each other a covalent bond, —CH$_2$—, —CH(CH$_3$)—, —CH(CH$_3$)$_2$—, —CO—, —SO—, —SO$_2$—,

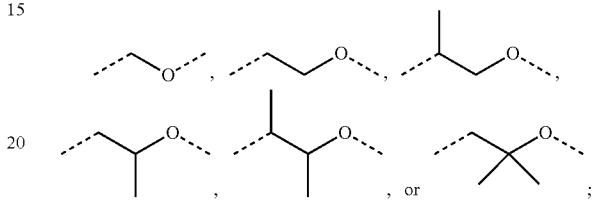

L$^9$ and L$^{10}$ are independently of each other: a covalent bond, —CH$_2$—, —CH$_2$CH$_2$—, —CO—, —CH$_2$CO—, —COCH$_2$—, —CO—CH=CH—, —COO—, —O—CO—, —CH$_2$CO$_2$—, —CO$_2$CH$_2$—, —CONH—, —NHCO—, —CH$_2$CONH—, —CONHCH$_2$—, —CSNH—, —NHCS—, —SO$_2$—, —SO$_2$CH$_2$—, —SO$_2$NH—, or —SO$_2$NHCH$_2$—:

and diastereomer, enantiomer, mixture of diastereomers, mixture of enantiomer, racemates, prodrugs, solvates, hydrates, or pharmaceutically acceptable salts thereof.

Preferred are compounds of the general formula (IV)

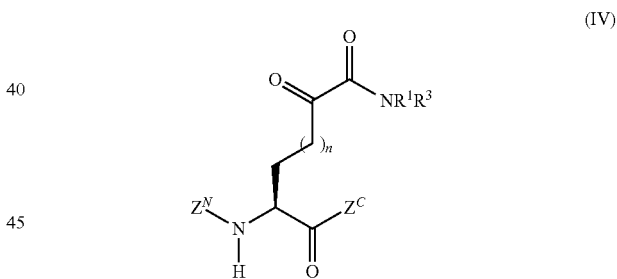

(IV)

wherein
n, R$^1$, R$^3$, Z$^C$ and Z$^N$ have the meanings as defined herein.
In formula (IV) R$^3$ is most preferably hydrogen.
In analogy to compound E18 the compounds E18a to E18k were prepared and all compounds show IC$_{50}$ values for the inhibition of TG2 similar to E18 in the range of 100 to 500 nM.

| Compound No. | R$^1$ | R$^2$ |
|---|---|---|
| E18  | —CH$_2$CH$_2$CH$_2$CH$_2$CH$_3$ | —NH(R$^1$) |
| E18a | —CH$_2$CH$_2$CH$_3$ | —NH(R$^1$) |
| E18b | —CH$_2$CH$_2$CH$_2$CH$_2$CH$_2$CH$_2$CH$_3$ | —NH(R$^1$) |
| E18c | —CH$_2$CH(C$_2$H$_5$)$_2$ | —NH(R$^1$) |
| E18d | -cyclo-C$_5$H$_9$ | —NH(R$^1$) |
| E18e | -cyclo-C$_6$H$_{11}$ | —NH(R$^1$) |
| E18f | —CH$_2$cyclo-C$_3$H$_5$ | —NH(R$^1$) |
| E18g | —CH$_2$cyclo-C$_6$H$_{11}$ | —NH(R$^1$) |
| E18h | —CH$_2$—C(CH$_3$)$_3$ | —NH(R$^1$) |

| Compound No. | R¹ | R² |
| --- | --- | --- |
| E18i | —CH(C₂H₅)₂ | —NH(R¹) |
| E18j | —CH₂CH₂CH₂CH₃ | —NH(R¹) |
| E18k | —CH(CH₃)₂ | —NH(R¹) |

In analogy to compound E78 the compounds E78a to E78c were prepared and all compounds show $IC_{50}$ values for the inhibition of TG2 similar to E78 in the range of 250 to 550 nM.

| Compound No. | R¹ | R² |
| --- | --- | --- |
| E78  | —CH₂CH₂OCH₃ | —OR¹ |
| E78a | —CH₂OCH₂CH₃ | —OR¹ |
| E78b | —CH₂CH₂OCH₂CH₃ | —OR¹ |
| E78c | —CH₂OCH₃ | —OR¹ |

In analogy to compound E40 the compounds E40a to E40l were prepared and all compounds show $IC_{50}$ values for the inhibition of TG2 similar to E40 in the range of 300 to 700 nM.

| Compound No. | R¹ | R² |
| --- | --- | --- |
| E40  | 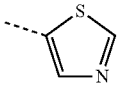 | —NH(R¹) |
| E40a | 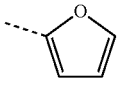 | —NH(R¹) |
| E40b | 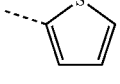 | —NH(R¹) |
| E40c | 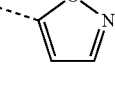 | —NH(R¹) |
| E40d | 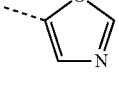 | —NH(R¹) |
| E40e | 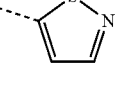 | —NH(R¹) |
| E40f | 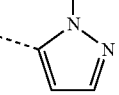 | —NH(R¹) |
| E40g | 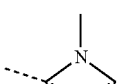 | —NH(R¹) |
| E40h | 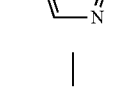 | —NH(R¹) |
| E40i | 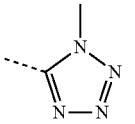 | —NH(R¹) |

Preferred are compounds of the general formula (V)

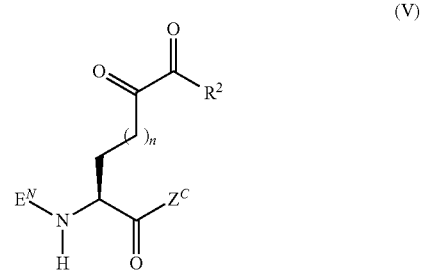

(V)

wherein $E^N$ is selected from N terminal groups consisting of: —COCF₃, —CH₃, —C₂H₅, —C₃H₇, —CH(CH₃)₂, —CH(C₂H₅)₂, —C₄H₉, —C₅H₁₁, —C₆H₁₃, —CH₂—CH(CH₃)₂, —CH₂—CH(C₂H₅)₂, —CH(CH₃)—C₂H₅, —C(CH₃)₃, —CH₂—C(CH₃)₃, cyclo-C₃H₅, -cyclo-C₄H₇, -cyclo-C₅H₉, -cyclo-C₆H₁₁, —CH₂-cyclo-C₃H₅, —CH₂-cyclo-C₄H₇, —CH₂-cyclo-C₅H₉, —CH₂-cyclo-C₆H₁₁, -Ph, —CH₂-Ph, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, —CH₂—CH═CH₂, —CH₂—C≡CH, —CHO, —COCH₃, —OOC₂H₅, —OOC₃H₇, —COCH(CH₃)₂, —COCH(C₂H₅)₂, —COC₄H₉, —COC₅H₁₁, —COC₆H₁₃, —COCH₂—CH(CH₃)₂, —COCH₂—CH(C₂H₅)₂, —COCH(CH₃)—C₂H₅, —OOC(CH₃)₃, —COCH₂—C(CH₃)₃, —CO-cyclo-C₃H₅, —CO-cyclo-C₄H₇, —CO-cyclo-C₅H₉, —CO-cyclo-C₆H₁₁, —COCH₂-cyclo-C₃H₅, —COCH₂-cyclo-C₄H₇, —COCH₂-cyclo-C₅H₉, —COCH₂-cyclo-C₆H₁₁, —COPh, —COCH₂-Ph, —COOCH₃, —COOC₂H₅, —COOC₃H₇, —COOCH(CH₃)₂, —COOCH(C₂H₅)₂, —COOC₄H₉, —COOC₅H₁₁, —COOC₆H₁₃, —COOCH₂—CH(CH₃)₂, —COOCH₂—CH(C₂H₅)₂, —COOCH(CH₃)—C₂H₅, —COOC(CH₃)₃, —COOCH₂—C(CH₃)₃, —COO-cyclo-C₃H₅, —COO-cyclo-C₄H₇, —COO-cyclo-C₅H₉, —COOCH₂-cyclo-C₃H₅, —COOCH₂-cyclo-C₄H₇, —COOCH₂-cyclo-C₅H₃, —COOCH₂-cyclo-C₆H₁₁, —COOPh, —COOCH₂-Ph,

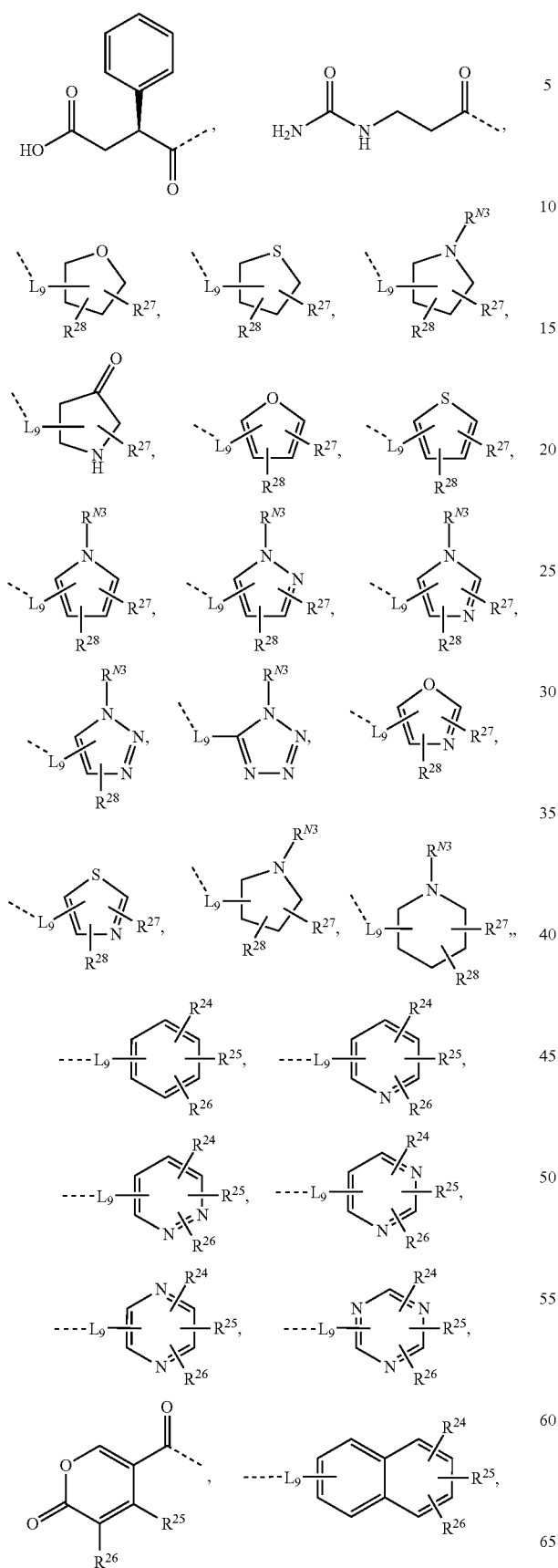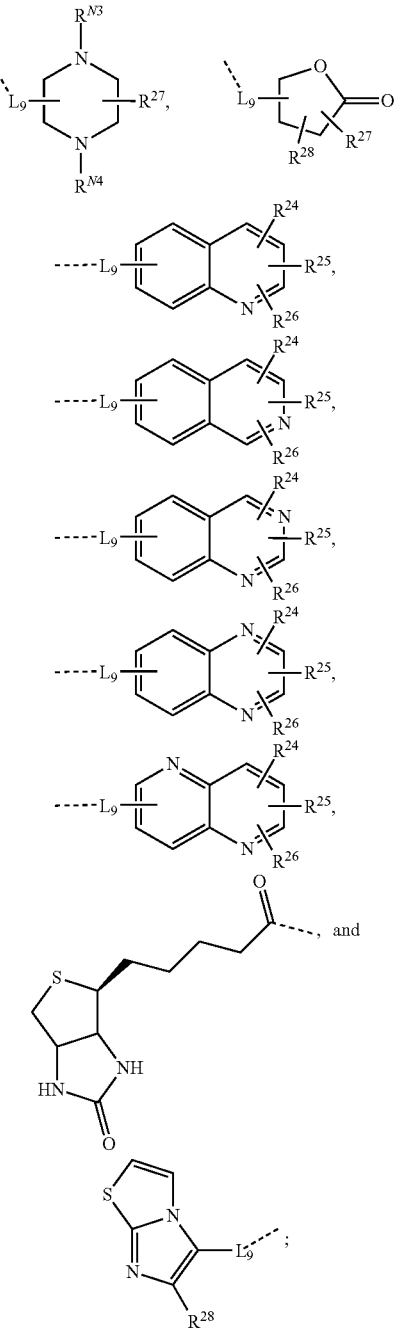
and n, $L_9$, $R^2$, $R^{24}$-$R^{28}$, $R^{N3}$, $R^{N4}$ and $Z^C$ have the meanings as defined herein.
Preferably, $E^C$ is selected from C terminal groups consisting of: —OH, —OCH$_3$, —NH$_2$, —NHCH$_3$, —N(CH$_3$)$_2$, —NHCH$_2$CH$_3$, —N(CH$_2$CH$_3$)$_2$, —NHCH$_2$CH$_2$CH$_3$, —N(CH$_2$CH$_2$CH$_3$)$_2$,
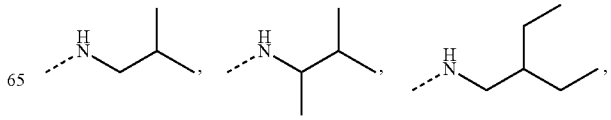

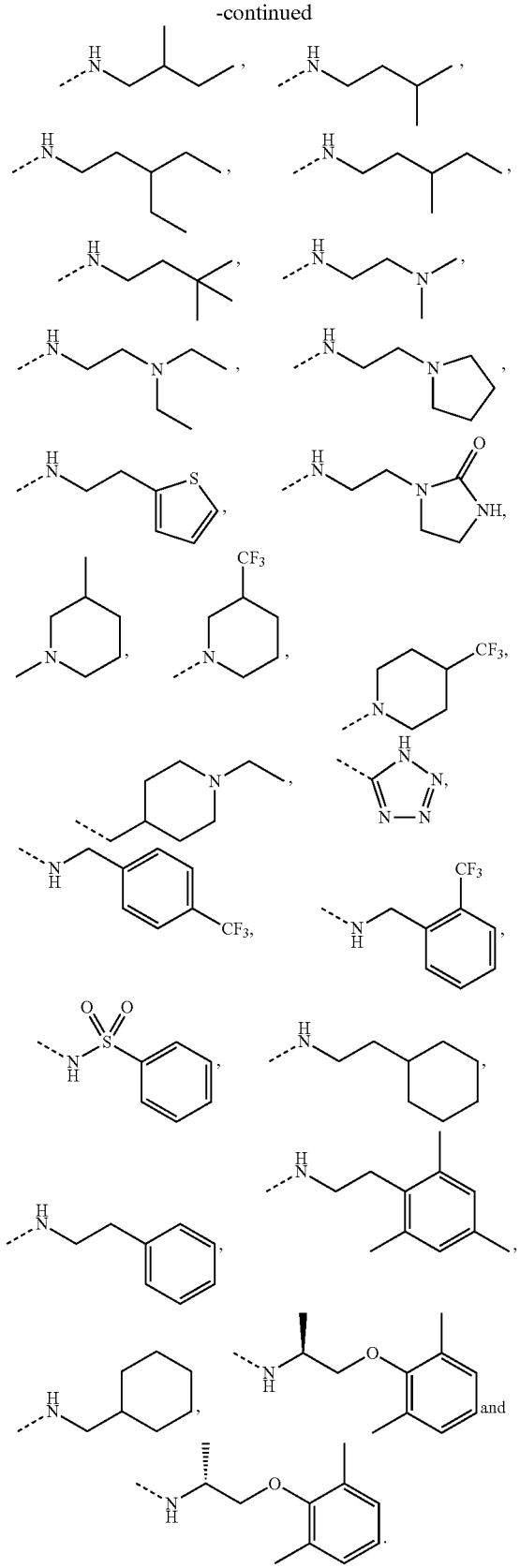

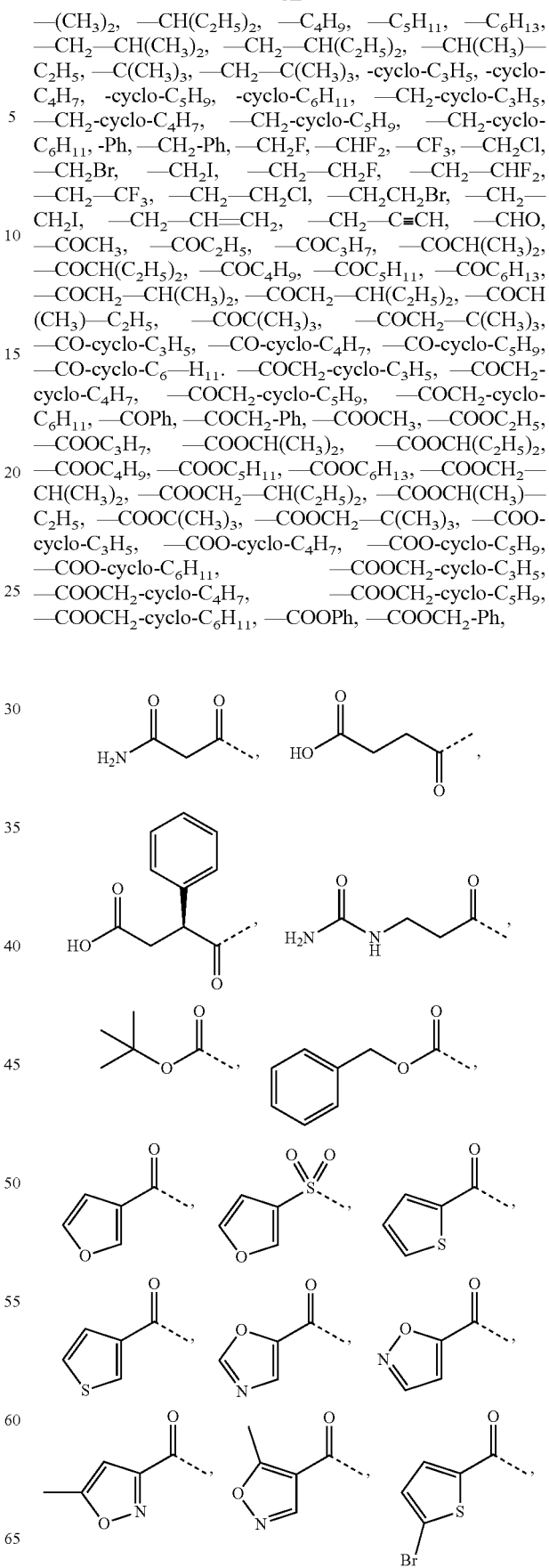

Preferably, $E^N$ is selected from N terminal groups consisting of: —H, —COCF$_3$, —CH$_3$, —C$_2$H$_5$, —C$_3$H$_7$, —(CH$_3$)$_2$, —CH(C$_2$H$_5$)$_2$, —C$_4$H$_9$, —C$_5$H$_{11}$, —C$_6$H$_{13}$, —CH$_2$—CH(CH$_3$)$_2$, —CH$_2$—CH(C$_2$H$_5$)$_2$, —CH(CH$_3$)—C$_2$H$_5$, —C(CH$_3$)$_3$, —CH$_2$—C(CH$_3$)$_3$, -cyclo-C$_3$H$_5$, -cyclo-C$_4$H$_7$, -cyclo-C$_5$H$_9$, -cyclo-C$_6$H$_{11}$, —CH$_2$-cyclo-C$_3$H$_5$, —CH$_2$-cyclo-C$_4$H$_7$, —CH$_2$-cyclo-C$_5$H$_9$, —CH$_2$-cyclo-C$_6$H$_{11}$, -Ph, —CH$_2$-Ph, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$CH$_2$Br, —CH$_2$—CH$_2$I, —CH$_2$—CH═CH$_2$, —CH$_2$—C≡CH, —CHO, —COCH$_3$, —COC$_2$H$_5$, —COC$_3$H$_7$, —COCH(CH$_3$)$_2$, —COCH(C$_2$H$_5$)$_2$, —COC$_4$H$_9$, —COC$_5$H$_{11}$, —COC$_6$H$_{13}$, —COCH$_2$—CH(CH$_3$)$_2$, —COCH$_2$—CH(C$_2$H$_5$)$_2$, —COCH(CH$_3$)—C$_2$H$_5$, —COC(CH$_3$)$_3$, —COCH$_2$—C(CH$_3$)$_3$, —CO-cyclo-C$_3$H$_5$, —CO-cyclo-C$_4$H$_7$, —CO-cyclo-C$_5$H$_9$, —CO-cyclo-C$_6$—H$_{11}$. —COCH$_2$-cyclo-C$_3$H$_5$, —COCH$_2$-cyclo-C$_4$H$_7$, —COCH$_2$-cyclo-C$_5$H$_9$, —COCH$_2$-cyclo-C$_6$H$_{11}$, —COPh, —COCH$_2$-Ph, —COOCH$_3$, —COOC$_2$H$_5$, —COOC$_3$H$_7$, —COOCH(CH$_3$)$_2$, —COOCH(C$_2$H$_5$)$_2$, —COOC$_4$H$_9$, —COOC$_5$H$_{11}$, —COOC$_6$H$_{13}$, —COOCH$_2$—CH(CH$_3$)$_2$, —COOCH$_2$—CH(C$_2$H$_5$)$_2$, —COOCH(CH$_3$)—C$_2$H$_5$, —COOC(CH$_3$)$_3$, —COOCH$_2$—C(CH$_3$)$_3$, —COO-cyclo-C$_3$H$_5$, —COO-cyclo-C$_4$H$_7$, —COO-cyclo-C$_5$H$_9$, —COO-cyclo-C$_6$H$_{11}$, —COOCH$_2$-cyclo-C$_3$H$_5$, —COOCH$_2$-cyclo-C$_4$H$_7$, —COOCH$_2$-cyclo-C$_5$H$_9$, —COOCH$_2$-cyclo-C$_6$H$_{11}$, —COOPh, —COOCH$_2$-Ph,

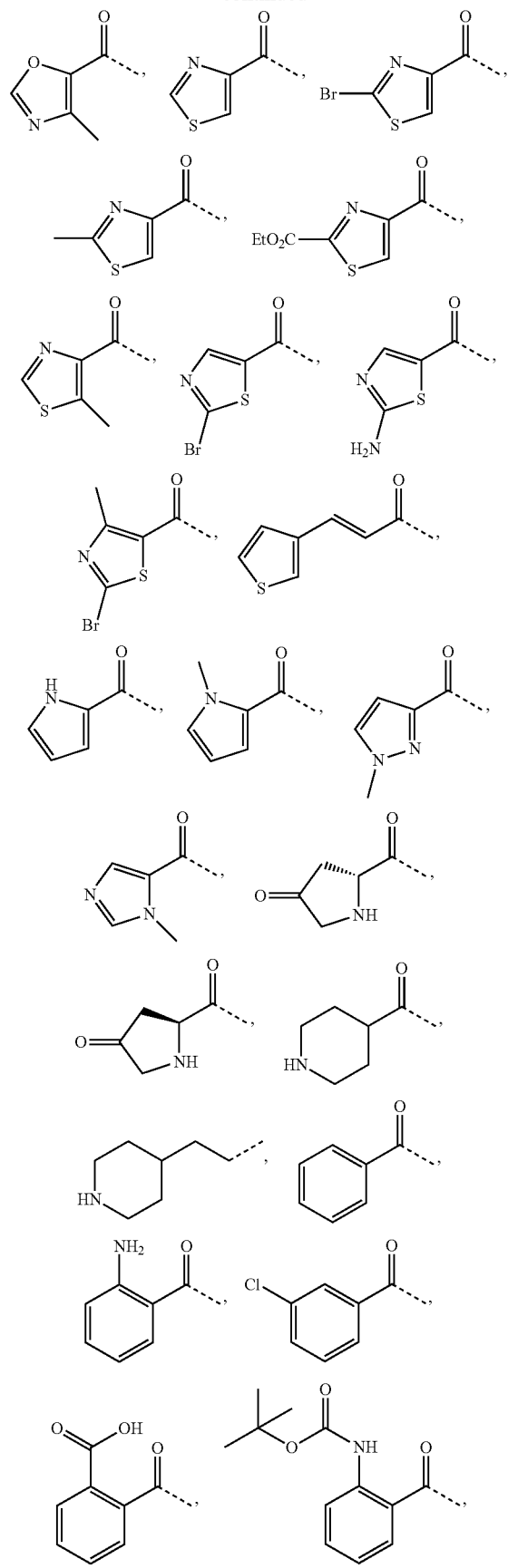
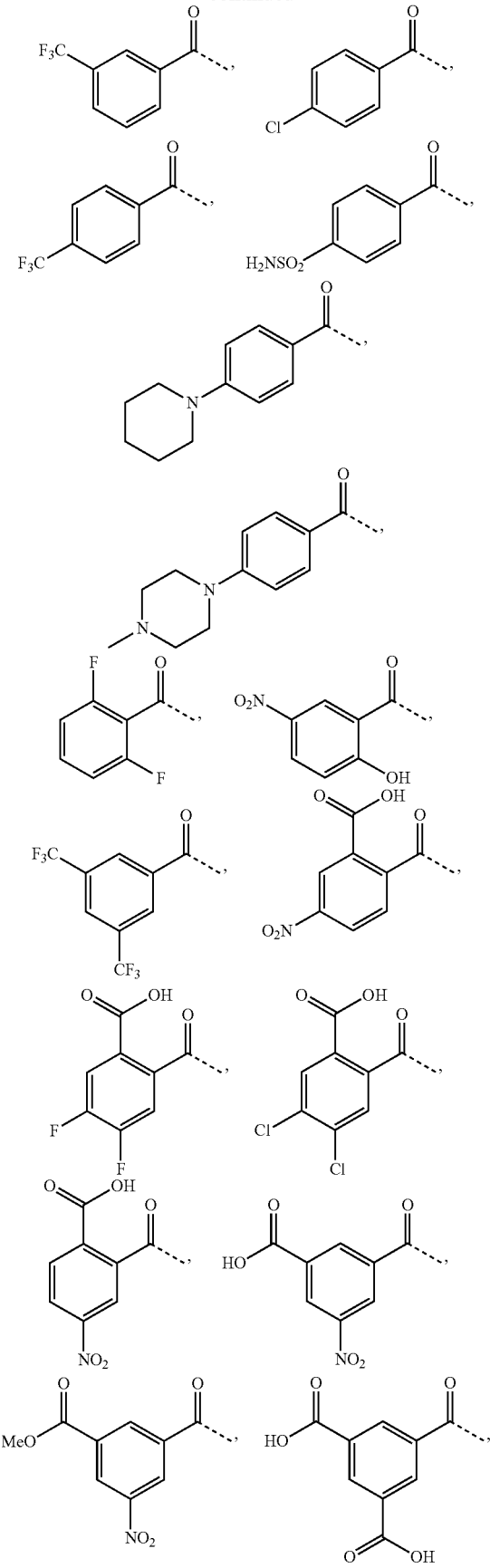

-continued

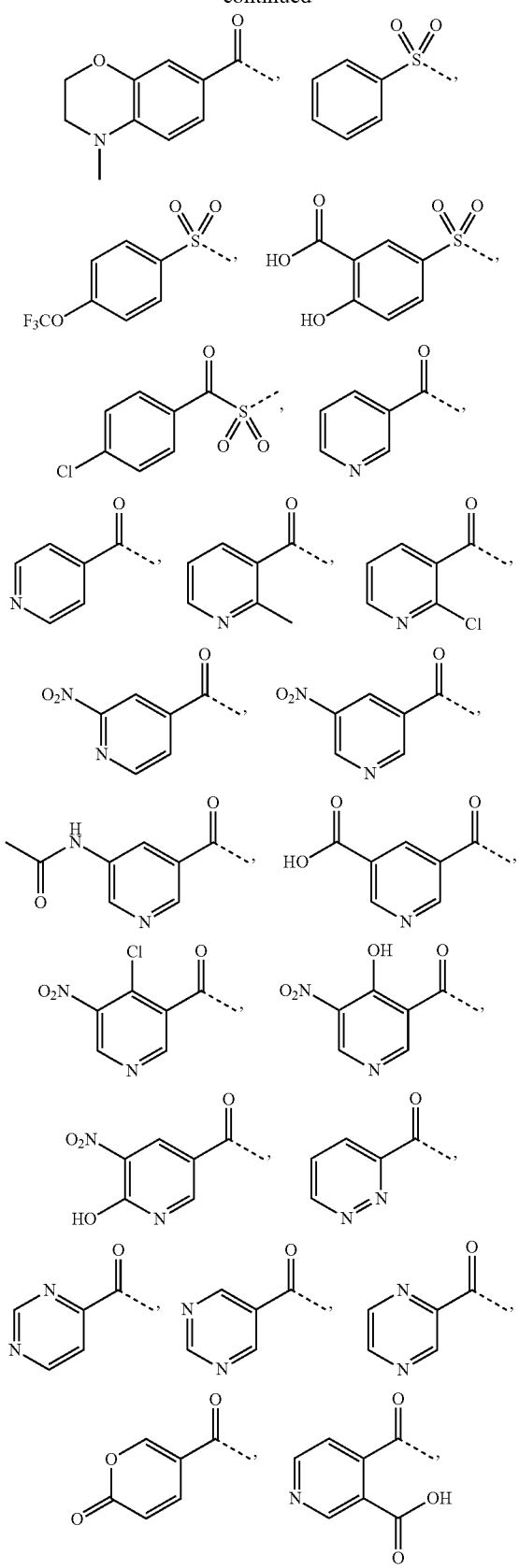

-continued

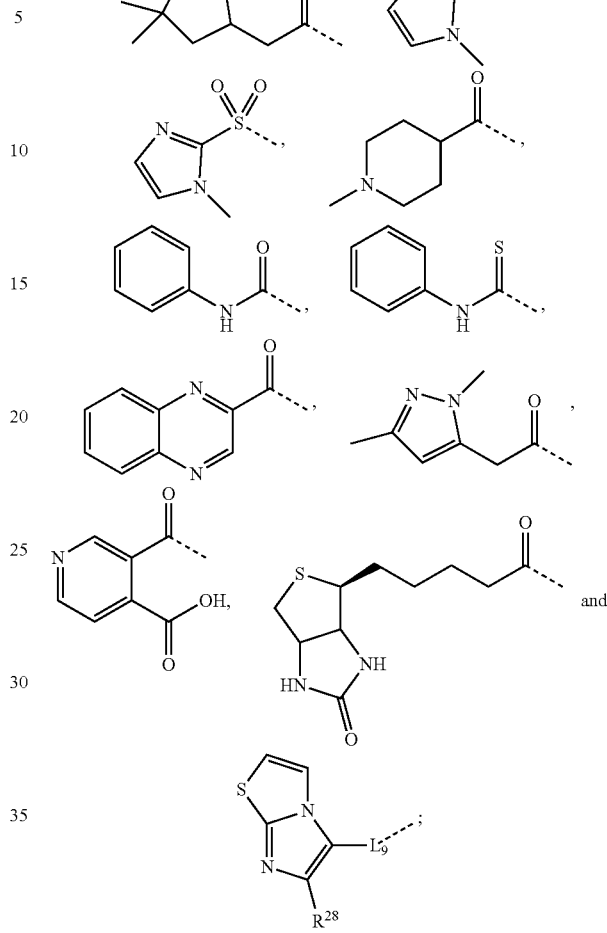

Preferably, $R^4$, $R^5$ and $R^6$ represent independently of each other: —H, —F, —Cl, —Br, H, —$CH_3$, —$CH_2CH_3$, —$CH(CH_3)_2$, -cyclo-$C_3H_5$, —$OCH_3$, —$OCH_2CH_3$, —$OCH(CH_3)_2$, —$CF_3$, —$OCHF_2$, —$OCF_3$, —OH, —CN, —CHO, —$COCH_3$, —$COCH_2CH_3$, —$COCH(CH_3)_2$, —$COCH_2F$, —$COCH_2Cl$, —$COCF_3$. —$CO_2Me$, —$CO_2CH_2CH_3$, —$CO_2CH(CH_3)_2$, —$COOCH_3$, —$COOCF_3$, —$COOCCl_3$, —$NHCH_3$, —$N(CH_3)_2$, —$NHCH_2CH_3$, —$NHCH(CH_3)_2$, —NH-cyclo-$C_3H_5$, —$NHCOCH_3$, —$NHCOCF_3$, —$NHSO_2CH_3$, —$NHSO_2CF_3$, —$SCH_3$, —$SO_2CH_3$, —$SO_2CF_3$, —$SO_2NH_2$, —$SO_2NHCH_3$, —$SO_2N(CH_3)_2$, —$SO_2NHCH_2CH_3$, —$SO_2NHCH(CH_3)_2$, or —$SO_2NH$-cyclo-$C_3H_5$.

Preferably, $R^7$ represents —H or —$CH_2CH_2CO_2H$.

The term "prodrug" describes compounds according to one of the general formulae (I) to (XIV-2), wherein the compounds comprises at least one carboxylate group which is modified with a rest that is generally known by a person skilled in the art in that way that the carboxylate group of the compound is released under physiological conditions and/or at least one modified hydroxyl group which is modified with a rest that is generally known by a person skilled in the art in that way that the hydroxyl group of the inventive compound is released under physiological conditions.

Due to the specially selected substituents $E^C$ on the C-terminal side and substituents $E^N$ on the N-terminal side of the inventive compound according to the invention the steric dimension can be adjusted very precisely, so that a binding pocket of a desired target molecule may be addressed with highly matching measurements.

Surprisingly, it was found that the inventive compounds bound to the transglutaminases reversibly and inhibit the transglutaminase effectively. The electrophilic warheads can react with highly nucleophilic thiols in the active site of the transglutaminase. Therefore, it was found that potential unspecific reactions with off-targets are reduced. It would be expected that the inventive compounds as reversible transglutaminase inhibitor may be less toxic than the irreversible transglutaminase inhibitors.

Preferred, $AS^{N1}$ is an amino acid selected from the group consisting of:

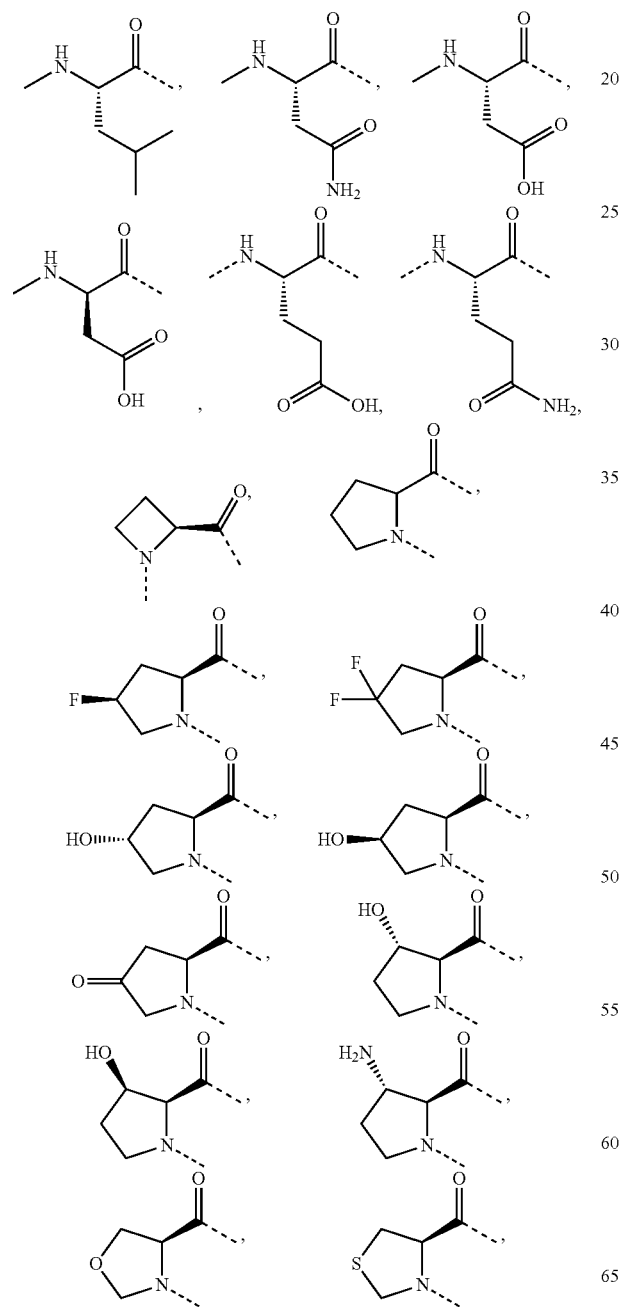

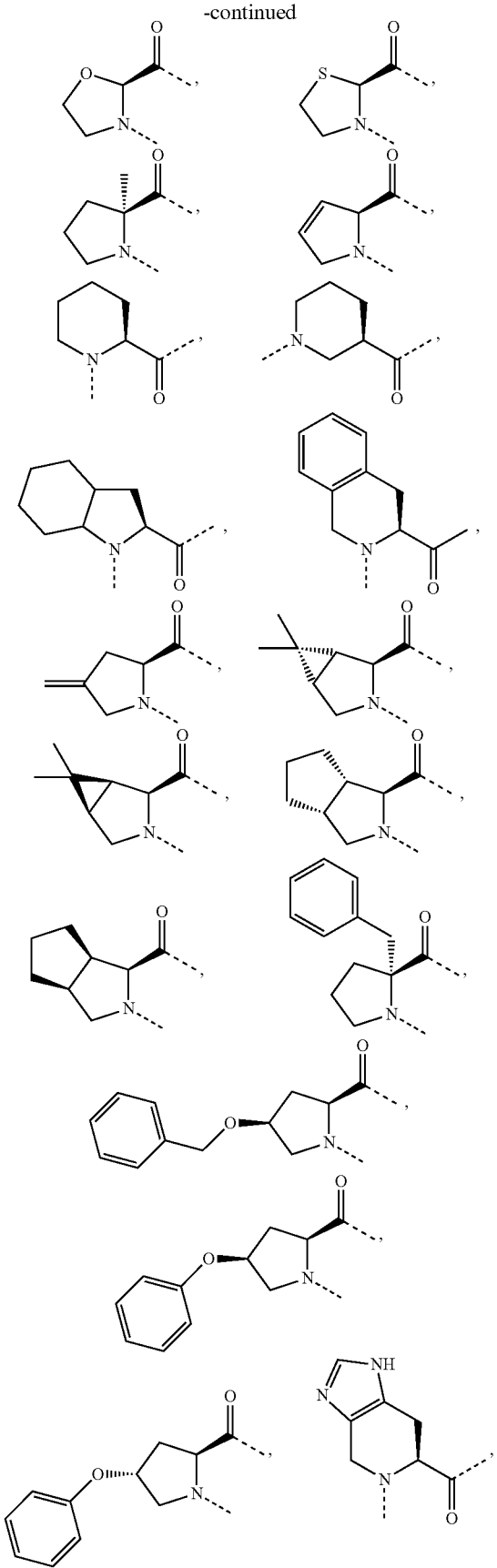

Preferred, $AS^{N2}$ is an amino acid selected from the group consisting of:
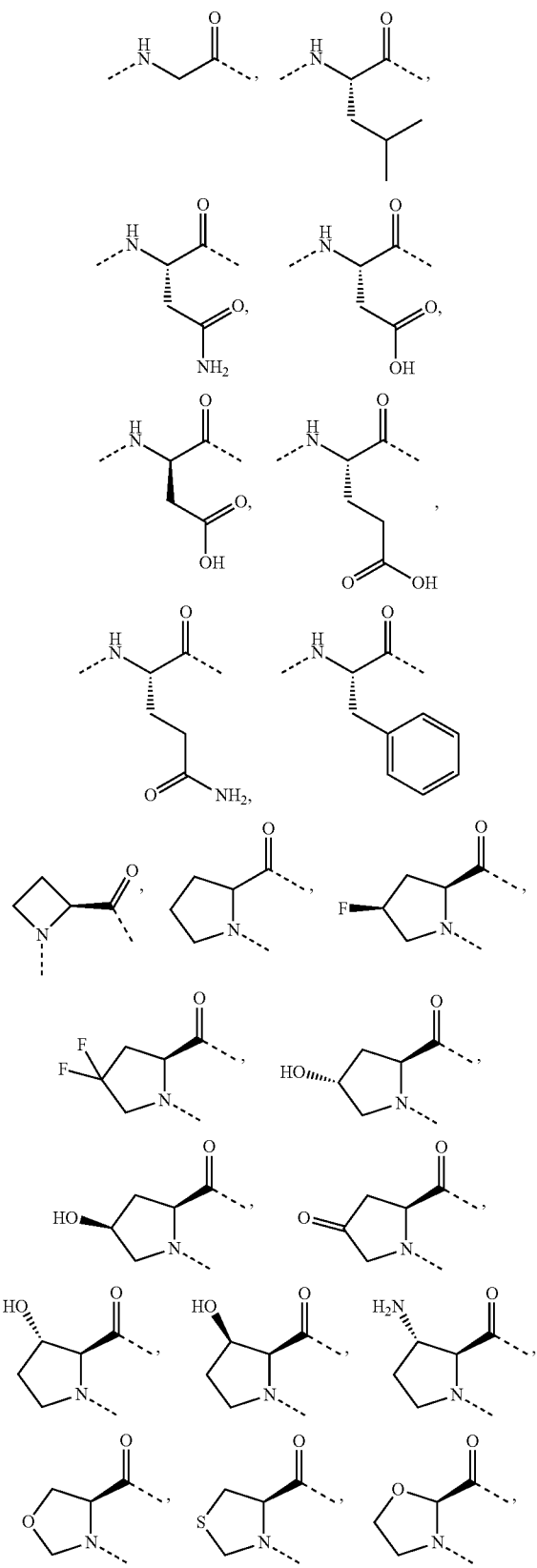
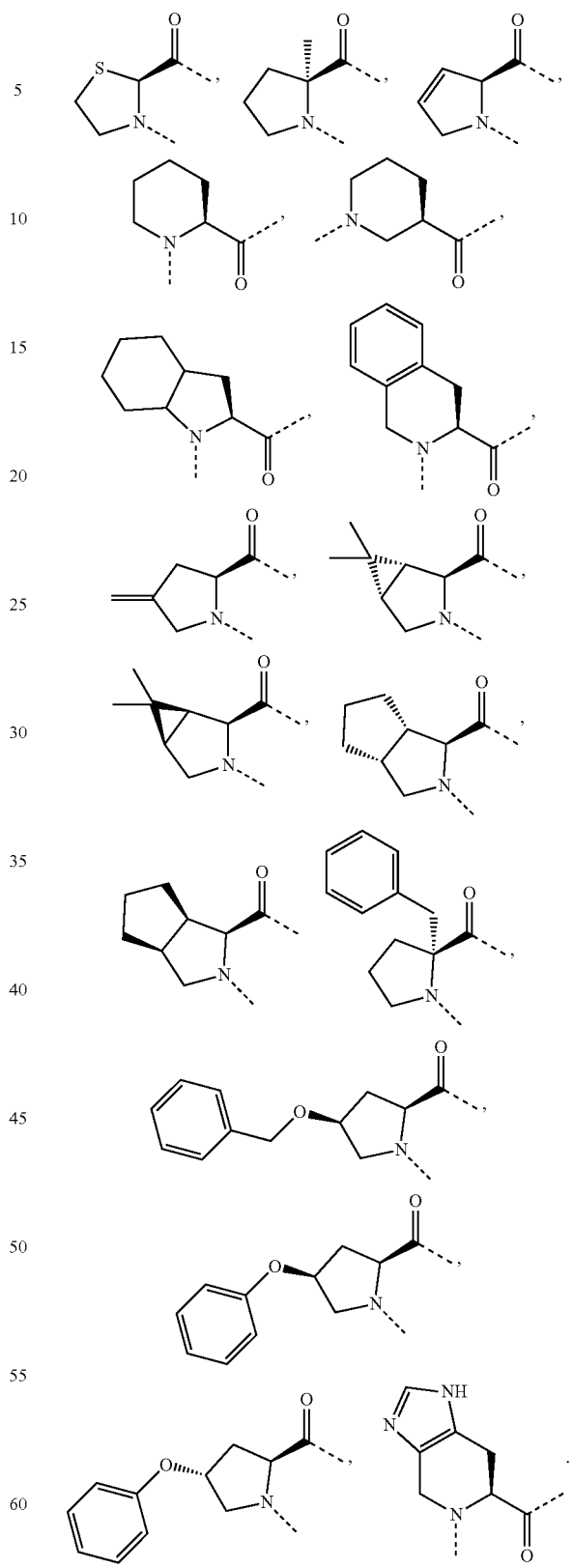
Preferred, $AS^{C1}$-$AS^{C4}$ are independently of each other selected from the group consisting of:

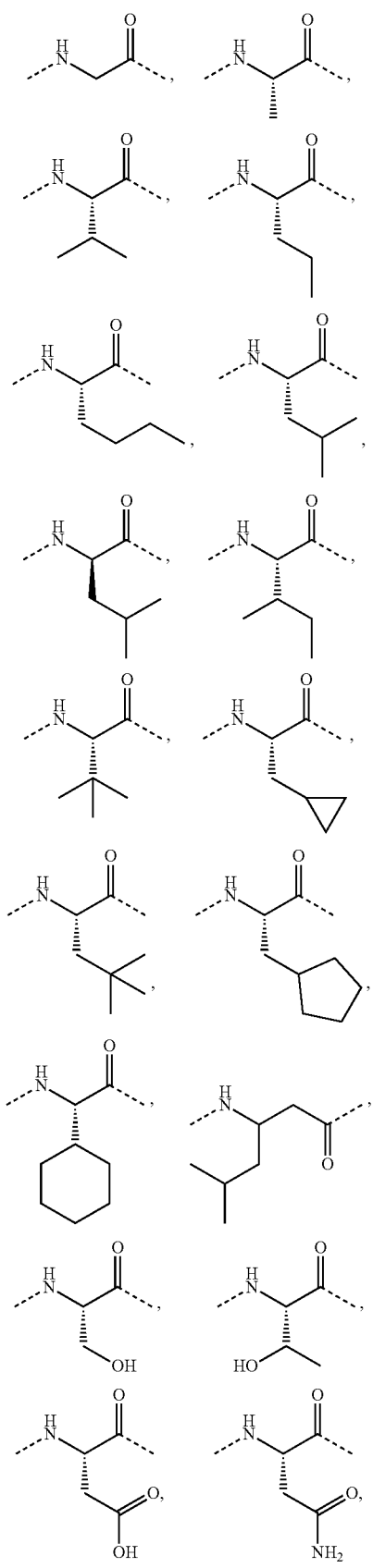
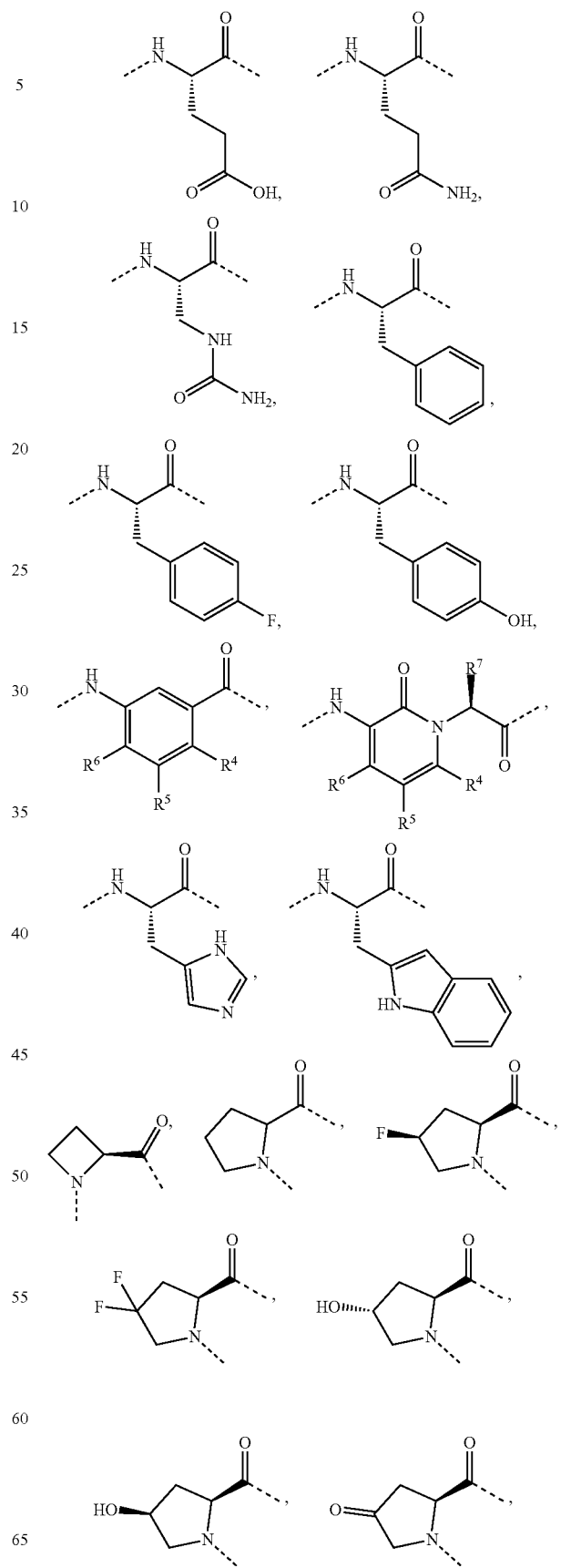

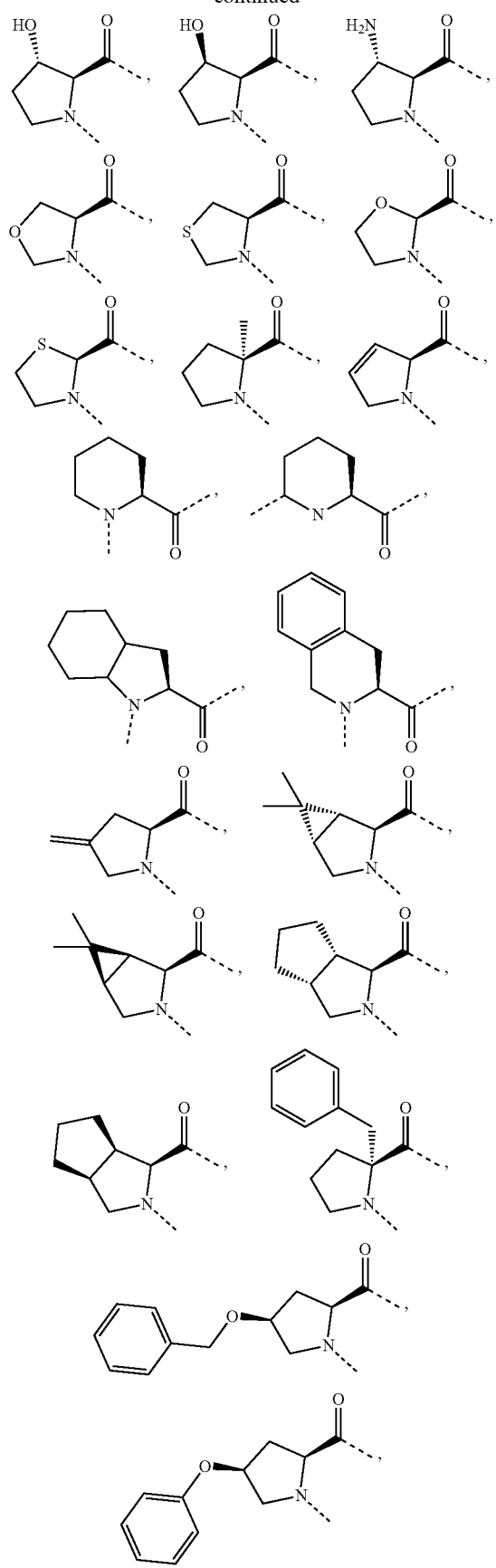
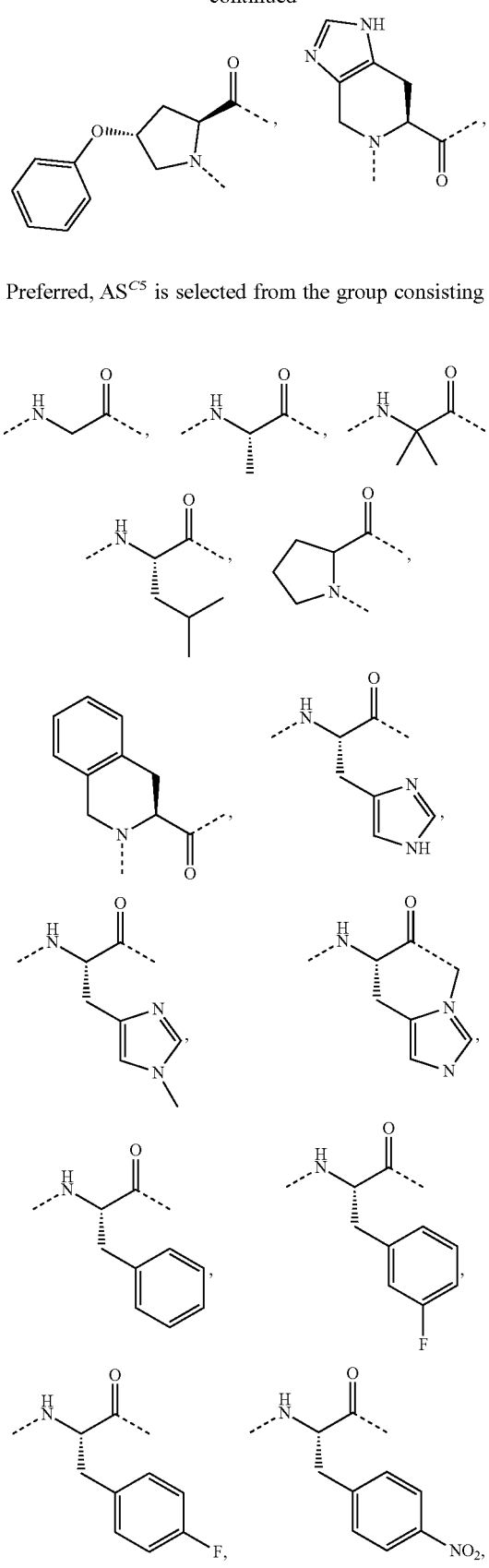
Preferred, AS^(C5) is selected from the group consisting of:

-continued
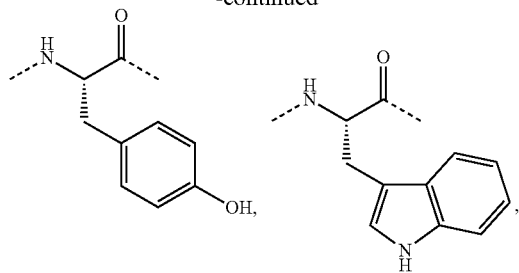
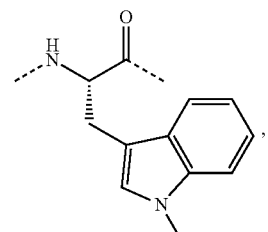
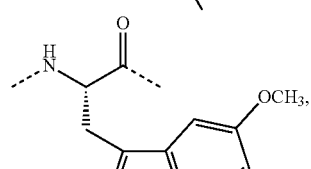
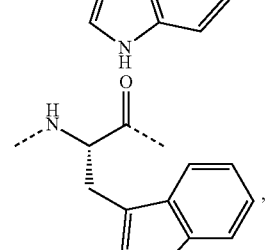
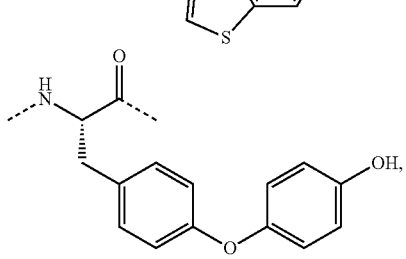
-continued
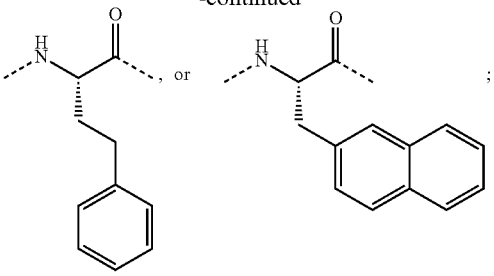
Preferred, $AS^{C6}$-$AS^{C6}$ are independently of each other selected from the group consisting of:
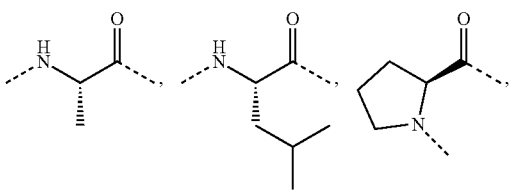
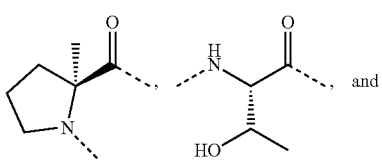
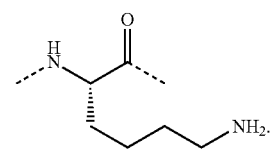
In analogy to compound E34 the compounds E34a to E34h were prepared and all compounds show $IC_{50}$ values for the inhibition of TG2 similar to E34 in the range of 150 to 580 nM.
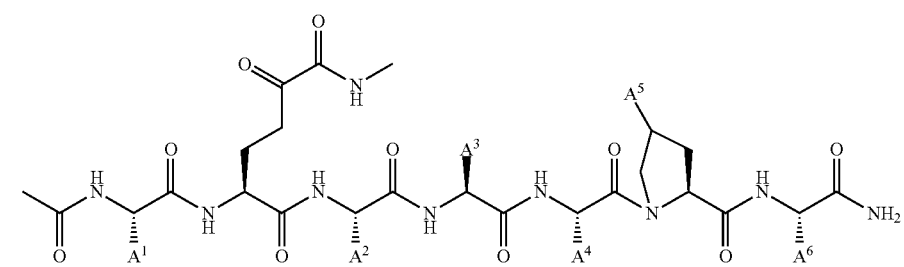
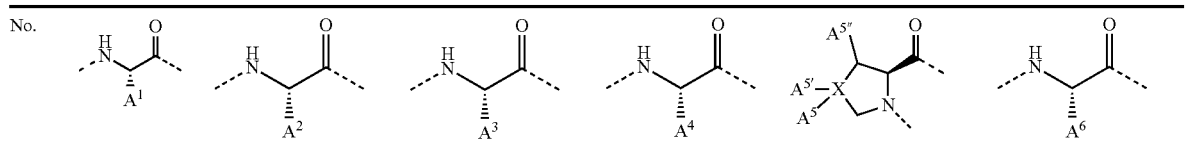
| No. | $A^1$ | $A^2$ | $A^3$ | $A^4$ | $A^{5'}$-X $A^5$ $A^{5''}$ | $A^6$ |
|---|---|---|---|---|---|---|

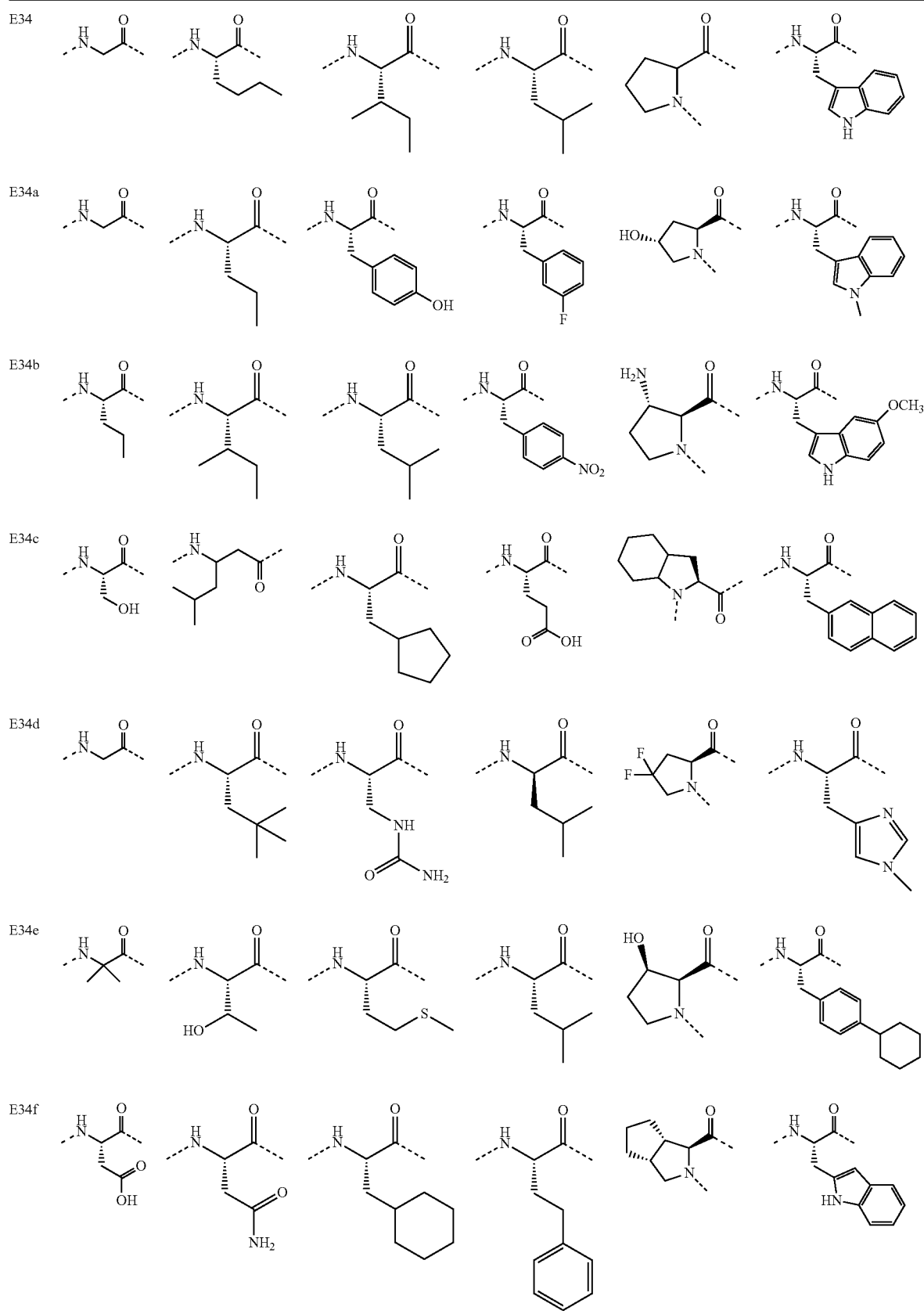

E34g
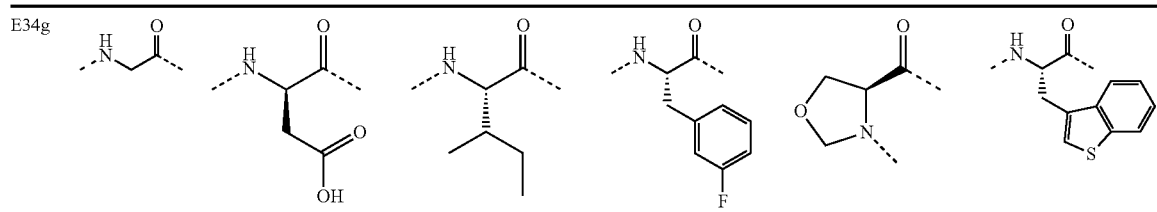

In the definitions of the following formulae (II-1) (XIV-2), the terms $Z^{C1}$-$Z^{C5}$ and $Z^{N1}$-$Z^{N3}$ are used and they are defined as follows:

$Z_{C1}$ represents -$E^C$, -$AS_{C2}$-$E^C$, -$AS^{C2}$-$AS^{C3}$-$E^C$, -$AS^{C2}$-$AS^{C3}$-$AS^{C4}$-$E^C$, -$AS^{C2}$-$AS^{C3}$-$AS^{C4}$-$AS^{C5}$-$E^C$, -$AS^{C2}$-$AS^{C3}$-$AS^{C4}$-$AS^{C5}$-$AS^{C6}$-$E^C$, -$AS^{C2}$-$AS^{C3}$-$AS^{C4}$-$AS^{C5}$-$AS^{C6}$-$AS^{C7}$-$E^C$, or -$AS^{C2}$-$AS^{C3}$-$AS^{C4}$-$AS^{C5}$-$AS^{C6}$-$AS^{C7}$-$AS^{C8}$-$E^C$;

$Z^{C2}$ represents -$E^C$, -$AS_{C3}$-$E^C$, -$AS^{C3}$-$AS^{C4}$-$E^C$, -$AS^{C3}$-$AS^{C4}$-$AS^{C5}$-$E^C$, -$AS^{C3}$-$AS^{C4}$-$AS^{C5}$-$AS^{C6}$-$E^C$, -$AS^{C3}$-$AS^{C4}$-$AS^{C5}$-$AS^{C6}$-$AS^{C7}$-$E^C$, or -$AS^{C3}$-$AS^{C4}$-$AS^{C5}$-$AS^{C6}$-$AS^{C7}$-$AS^{C8}$-$E^C$, $Z^{C3}$ represents -$E^C$, -$AS_{C4}$-$E^C$, -$AS^{C4}$-$AS^{C5}$-$E^C$, -$AS^{C4}$-$AS^{C5}$-$AS^{C6}$-$E^C$, -$AS^{C4}$-$AS^{C5}$-$AS^{C6}$-$AS^{C7}$-$E^C$, -$AS^{C4}$-$AS^{C5}$-$AS^{C6}$-$AS^{C7}$-$AS^{C8}$-$E^C$;

$Z^{C4}$ represents -$E^C$, -$AS_{C5}$-$E^C$, -$AS^{C5}$-$AS^{C6}$-$E^C$, -$AS^{C5}$-$AS^{C6}$-$AS^{C7}$-$E^C$, or -$AS^{C5}$-$AS^{C6}$-$AS^{C7}$-$AS^{C8}$-$E^C$;

$Z^{C5}$ represents -$E^C$, -$AS_{C6}$-$E^C$, -$AS^{C6}$-$AS^{C7}$-$E^C$, -$AS^{C6}$-$AS^{C7}$-$AS^{C8}$-$E^C$;

$Z^{N1}$ represents $E^N$-, $E^N$-$AS^{N2}$-, $E^N$-$AS^{N3}$-$AS^{N2}$, or $E^N$-$AS^{N4}$-$AS^{N3}$-$AS^{N2}$-;

$Z^{N2}$ represents $E^N$-, $E^N$-$AS^{N3}$, or $E^N$-$AS^{N4}$-$AS^{N3}$; and $Z^{N3}$ represents $E^N$ or -$E^N$-$AS^{N4}$-.

Preferably, the compound has any one of the formulae (II-1)-(II-5):

(II-1)
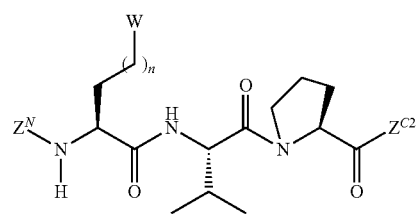

(II-2)
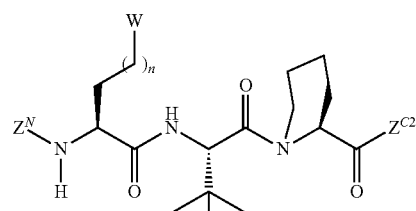

(II-3)
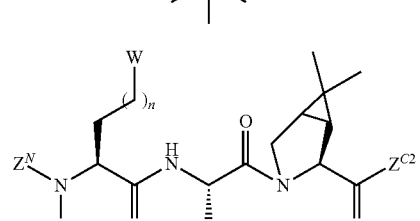

(II-4)
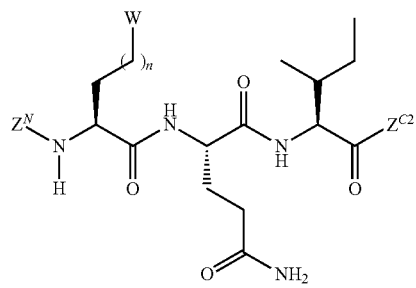

(II-5)
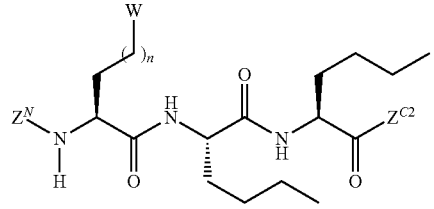

wherein $Z^{C2}$ represents -$E^C$, -$AS_{C3}$-$E^C$, -$AS^{C3}$-$AS^{C4}$-$E^C$, -$AS^{C3}$-$AS^{C4}$-$AS^{C5}$-$E^C$, -$AS^{C3}$-$AS^{C4}$-$AS^{C5}$-$AS^{C6}$-$E^C$, -$AS^{C3}$-$AS^{C4}$-$AS^{C5}$-$AS^{C6}$-$AS^{C7}$-$E^C$, or -$AS^{C3}$-$AS^{C4}$-$AS^{C5}$-$AS^{C6}$-$AS^{C7}$-$AS^{C8}$-$E^C$;

preferably, $Z^{C2}$ is -$E^C$, -$AS^{C3}$-$E^C$, or -$AS^{C3}$-$AS^{C4}$-$E^C$; and $Z^N$ represents $E^N$-, $E^N$-$AS^{N1}$-, $E^N$-$AS^{N2}$-$AS^{N1}$-, $E^N$-$AS^{N3}$-$AS^{N2}$-$AS^{N1}$-; or $E^N$-$AS^{N4}$-$AS^{N3}$-$AS^{N2}$-$AS^{N1}$-;

preferably, $Z^N$ is $E^N$-, or $E^N$-$AS^{N1}$-; and $E^C$, $E^N$, n, $AS^{C3}$-$AS^{C8}$, $AS^{N1}$-$AS^{N4}$, and W have the same meanings as defined in the formula (I).

More preferred is the compound having any one of (III-1)-(III-5):

(III-1)
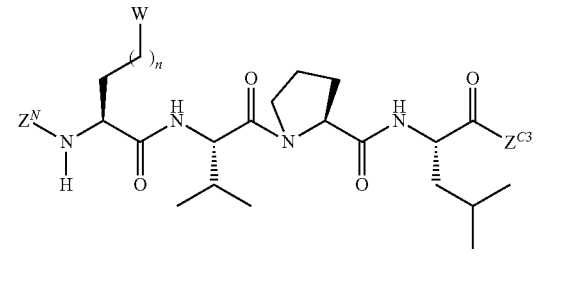

-continued (III-2)

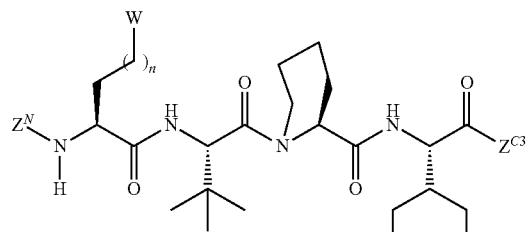

(III-3)

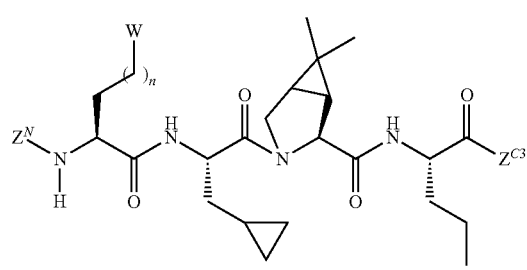

(III-4)

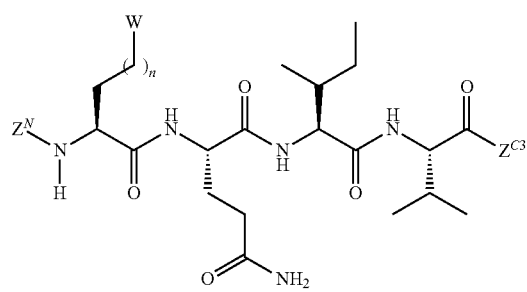

(III-5)

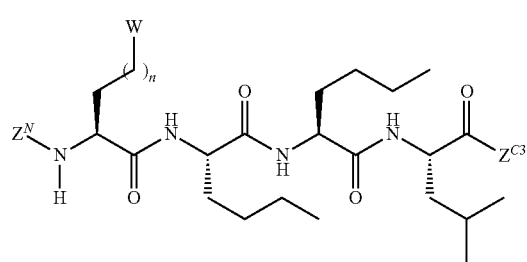

wherein $Z^{C3}$ represents $-E^C$, $-AS_{C4}-E^C$, $-AS^{C4}-AS^{C5}-E^C$, $-AS^{C4}-AS^{C5}-AS^{C6}-E^C$, $-AS^{C4}-AS^{C5}-AS^{C6}-AS^{C7}-E^C$, or $-AS^{C4}-AS^{C5}-AS^{C6}-AS^{C7}-AS^{C8}-E^C$;

preferably, $Z^{C3}$ is $-E^C$, or $-AS^{C4}-E^C$; and $Z^N$ represents $E^N-$, $E^N-AS^{N1}-$, $E^N-AS^{N2}-AS^{N1}-$, $E^N-AS^{N3}-AS^{N2}-AS^{N1}-$; or $E^N-AS^{N4}-AS^{N3}-AS^{N2}-AS^{N1}-$;

preferably, $Z^N$ is $E^N-$, or $E^N-AS^{N1}-$; and $E^C$, $E^N$, n, $AS^{C4}-AS^{C8}$, $AS^{N1}-AS^{N4}$, and W have the same meanings as defined in the formula (I);

preferably, $Z^{C3}$ is $OCH_3$ or $NH_2$.

Still preferred is the compound having the formula (III-6):

(III-6)

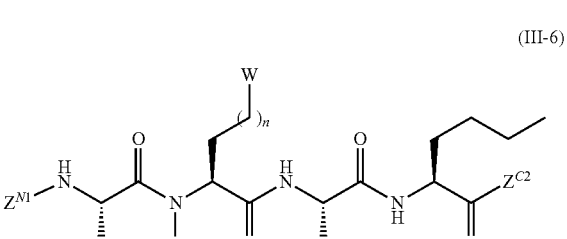

wherein $Z^{N1}$ represents $E^N-$, or $E^N-AS^{N2}-$;

$Z^{C2}$ represents $-E^C$, $-AS_{C3}-E^C$, $-AS^{C3}-AS^{C4}-E^C$, $-AS^{C3}-AS^{C4}-AS^{C5}-E^C$, $-AS^{C3}-AS^{C4}-AS^{C5}-AS^{C6}-E^C$, $-AS^{C3}-AS^{C4}-AS^{C5}-AS^{C6}-AS^{C7}-E^C$, or $-AS^{C3}-AS^{C4}-AS^{C5}-AS^{C6}-AS^{C7}-AS^{C8}-E^C$; and $AS^{C3}-AS^{C8}$, $AS^{N2}$, $E^C$, $E^N$, n, and W have the same meanings as defined in the formula (I).

Still more preferred is the compound having any one of the formulae (VI-1)-(VI-5):

(VI-1)

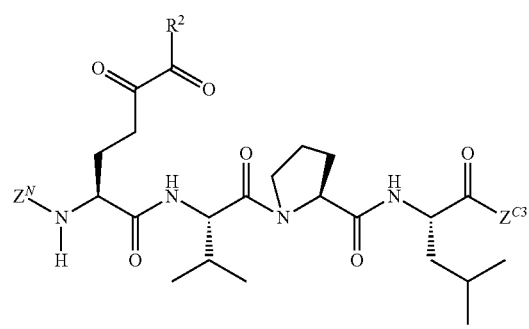

(VI-2)

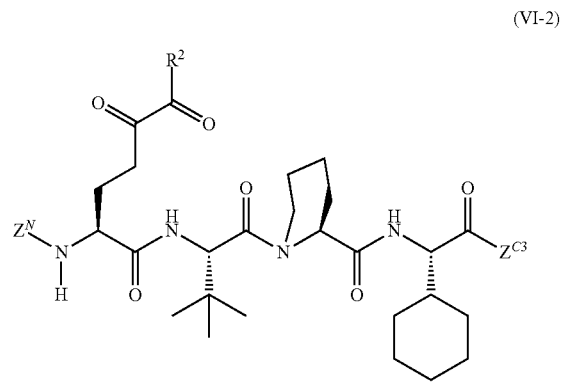

(VI-3)

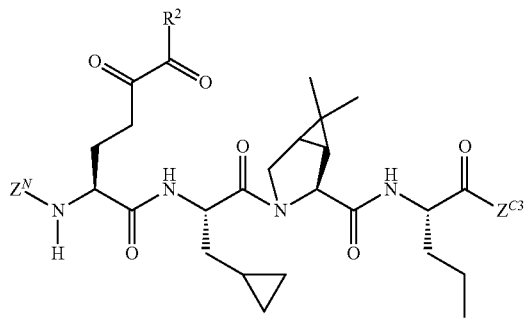

(VI-4)

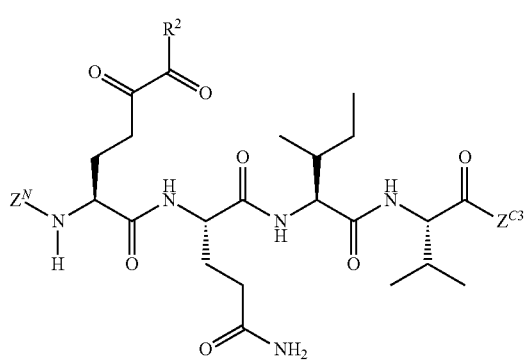

(VI-5)

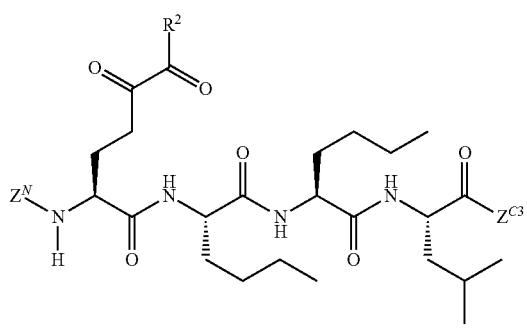

wherein $Z^N$ represents $E^N$-, $E^N$-$AS^{N1}$-, $Z^{C3}$ represents -$E^C$, -$AS_{C4}$-$E^C$, -$AS^{C4}$-$AS^{C5}$-$E^C$, -$AS^{C4}$-$AS^{C5}$-$AS^{C6}$-$E^C$;

$R^2$ represents —H, —OH, —OCH$_3$, —NH$_2$, —NHCH$_3$, or —N(CH$_3$)$_2$; and $AS^{C4}$-$AS^{C6}$, $AS^{N1}$, $E^C$, and $E^N$ have the same meanings as defined in the formula (I), preferably, $Z^N$ is acetyl or benzyloxycarbonyl, and/or $Z^{C3}$ is OCH$_3$ or —NH$_2$.

Still more preferred is the compound having any one of the formulae (VII-3) (VII-4

(VII-3)

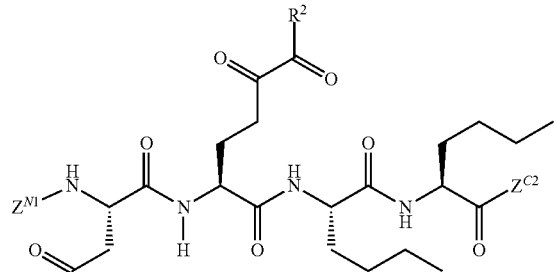

(VII-4)

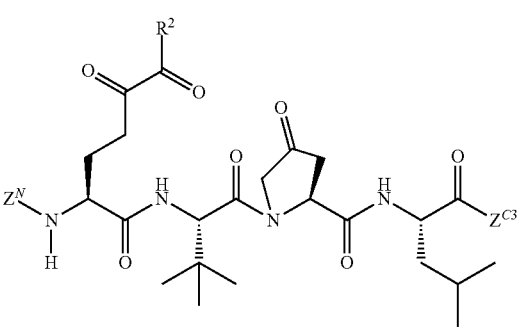

wherein $Z^{N1}$ represents $E^N$-, $E^N$-$AS^{N2}$-, $Z^{C2}$ represents -$E^C$, -$AS^{C3}$-$E^C$, -$AS^{C3}$-$AS^{C4}$-$E^C$, -$AS^{C3}$-$AS^{C4}$-$AS^{C5}$-$E^C$, or -$AS^{C3}$-$AS^{C4}$-$AS^{C5}$-$AS^{C6}$-$E^C$;

$AS^{C3}$-$AS^{C6}$, $AS^{N2}$, $E^C$, and $E^N$ have the same meanings as defined in the formula (I), preferably, $Z^{N1}$ is acetyl, and/or $Z^{C2}$ is -$AS^{C3}$-$AS^{C4}$-$AS^{C5}$-$E^C$.

In the above-defined formulae (I), (IV), (V), and especially in the formulae (II-1), (III-1), and (VI-1), the proline backbone can be replaced by a proline analog backbone. It is apparent that a corresponding compounds having the proline analog backbone have a same or similar biological activity compared to the compound having the proline backbone. The proline backbone can be replaced by any one of the following proline analog backbones:

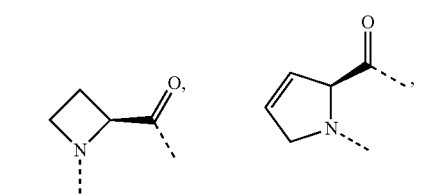

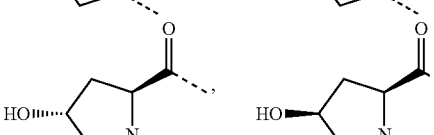

-continued

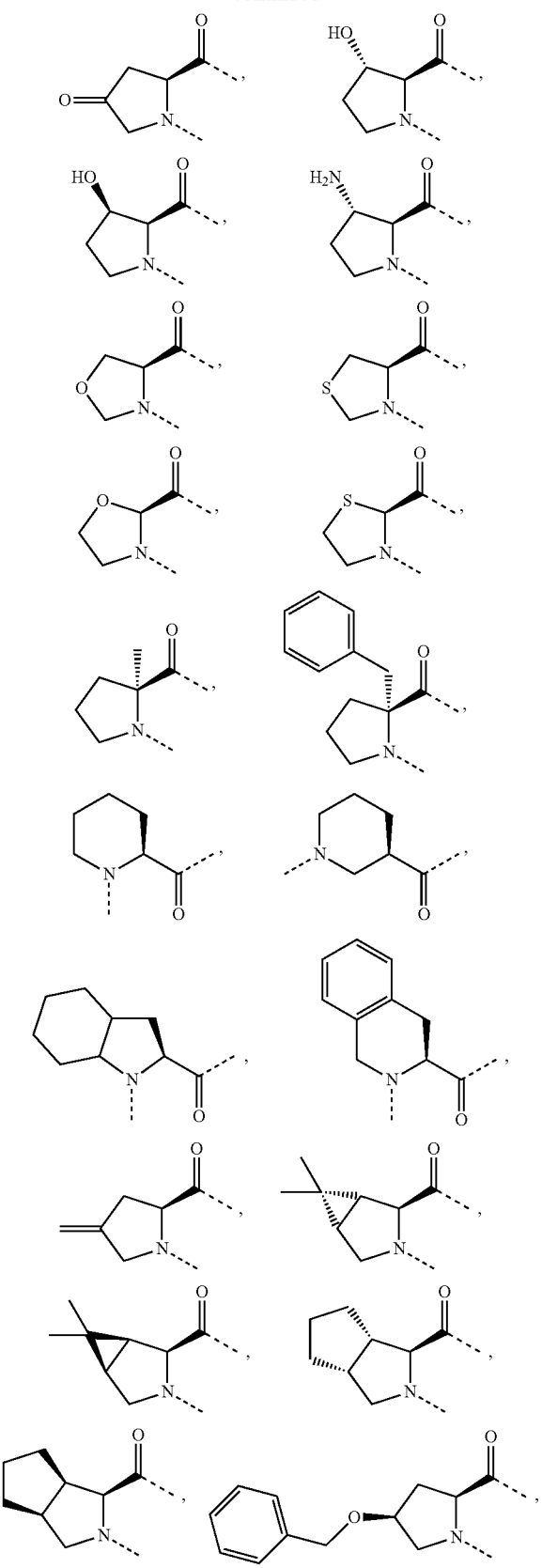

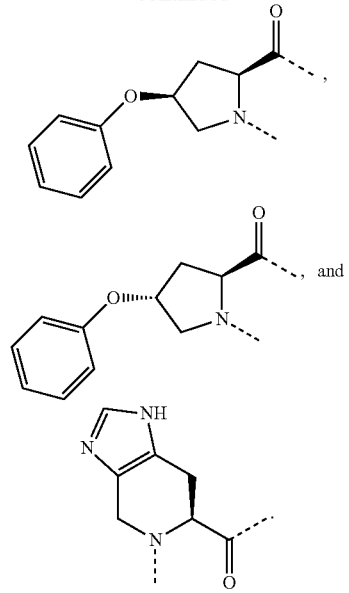

In one embodiment, the present invention refers to the compound of the formula (VIII):

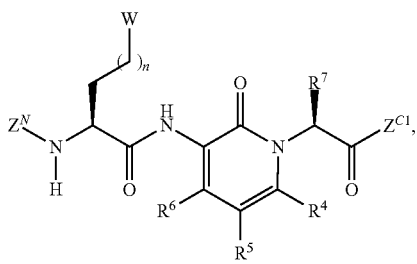

wherein
$Z^{C1}$ represents $-E^C$, $-AS_{C2}-E^C$, $-AS^{C2}-AS^{C3}-E^C$, $-AS^{C2}-AS^{C3}-AS^{C4}-E^C$, $-AS^{C2}-AS^{C3}-AS^{C4}-AS^{C5}-E^C$, $-AS^{C2}-AS^{C3}-AS^{C4}-AS^{C5}-AS^{C6}-E^C$, $-AS^{C2}-AS^{C3}-AS^{C4}-AS^{C5}-AS^{C6}-AS^{C7}-E^C$, or $-AS^{C2}-AS^{C3}-AS^{C4}-AS^{C5}-AS^{C6}-AS^{C7}-AS^{C8}-E^C$; and
$AS^{C2}-AS^{C8}$, $E^C$, n, $R^4$-$R^7$, W, and $Z^N$ have the same meanings as defined in the formula (I).

Most preferred are the compounds of formula (IX)

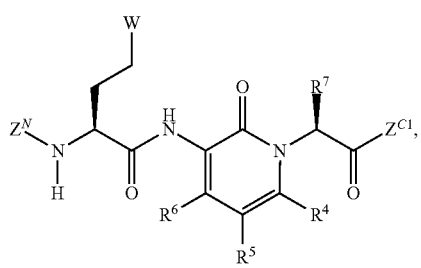

(IX)

wherein
$Z^{C1}$ represents $-E^C$; and
$R^4$-$R^7$, W, and $Z^N$ have the same meanings as defined in the formula (I).

Preferably, $Z^N$ represents $E^N$-, $E^N$-$AS^{N1}$-; and $E^N$ is selected from N terminal groups consisting of: —H, —COCF$_3$, —CH$_3$, —C$_2$H$_5$, —C$_3$H$_7$, —CH(CH$_3$)$_2$, —CH(C$_2$H$_5$)$_2$, —C$_4$H$_9$, —C$_6$H$_{13}$, —CH$_2$—CH(CH$_3$)$_2$, —CH$_2$—CH(C$_2$H$_5$)$_2$, —CH(CH$_3$)—C$_2$H$_5$, —C(CH$_3$)$_3$, —CH$_2$—C(CH$_3$)$_3$, -cyclo-C$_3$H$_5$, -cyclo-C$_4$H$_7$, -cyclo-C$_5$H$_9$, —CH$_2$-cyclo-C$_3$H$_5$, —CH$_2$-cyclo-C$_4$H$_7$, —CH$_2$-cyclo-C$_5$H$_9$, —CH$_2$-cyclo-C$_6$H$_{11}$, -Ph, —CH$_2$-Ph, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —CH$_2$—CH=CH$_2$, —CH$_2$—C≡CH, —CHO, —COCH$_3$, —COC$_2$H$_5$, —COC$_3$H$_7$, —COCH(CH$_3$)$_2$, —COCH(C$_2$H$_5$)$_2$, —COC$_4$H$_9$, —COC$_5$H$_{11}$, —COC$_6$H$_{13}$, —COCH$_2$—CH(CH$_3$)$_2$, —COCH$_2$—CH(C$_2$H$_5$)$_2$, —COCH(CH$_3$)—C$_2$H$_5$, —COC(CH$_3$)$_3$, —COCH$_2$—C(CH$_3$)$_3$, —CO-cyclo-C$_3$H$_5$, —CO-cyclo-C$_4$H$_7$, —CO-cyclo-C$_5$H$_9$, —CO-cyclo-C$_6$H$_{11}$, —COCH$_2$-cyclo-C$_3$H$_5$, —COCH$_2$-cyclo-C$_4$H$_7$, —COCH$_2$-cyclo-C$_5$H$_9$, —COCH$_2$-cyclo-C$_6$H$_{11}$, —COPh, —COCH$_2$-Ph, —COOCH$_3$, —COOC$_2$H$_5$, —COOC$_3$H$_7$, —COOCH(CH$_3$)$_2$, —COOCH(C$_2$H$_5$)$_2$, —COOC$_4$H$_9$, —COOC$_5$H$_{11}$, —COOC$_6$H$_{13}$, —COOCH$_2$—CH(CH$_3$)$_2$, —COOCH$_2$—CH(C$_2$H$_5$)$_2$, —COOCH(CH$_3$)—C$_2$H$_5$, —COOC(CH$_3$)$_3$, —COOCH$_2$—C(CH$_3$)$_3$, —COO-cyclo-C$_3$H$_5$, —COO-cyclo-C$_4$H$_7$, —COO-cyclo-C$_5$H$_9$, —COO-cyclo-C$_6$H$_{11}$, —COOCH$_2$-cyclo-C$_3$H$_5$, —COOCH$_2$-cyclo-C$_4$H$_7$, —COOCH$_2$-cyclo-C$_5$H$_9$, —COOCH$_2$-cyclo-C$_6$H$_{11}$, —COOPh, —COOCH$_2$-Ph,

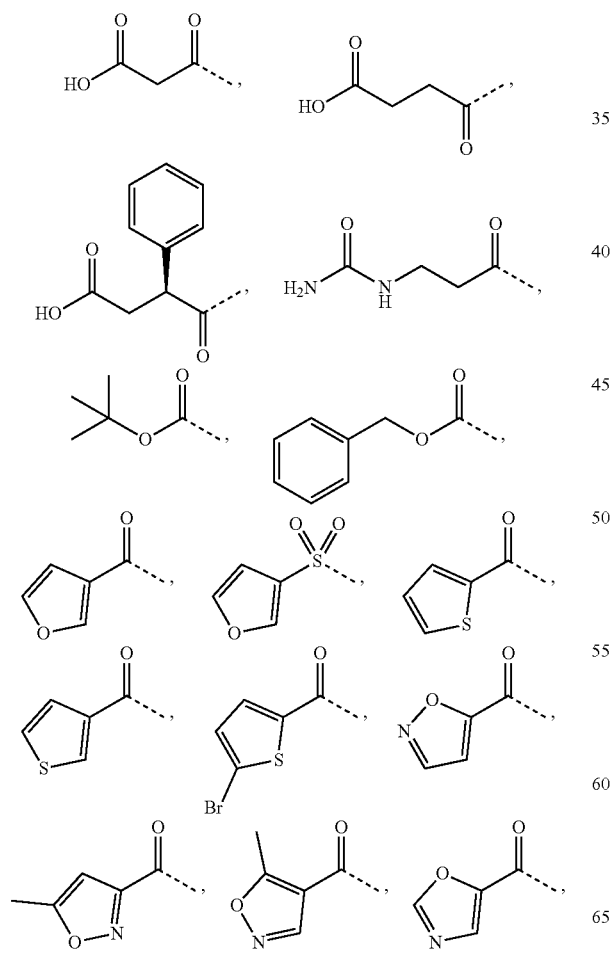

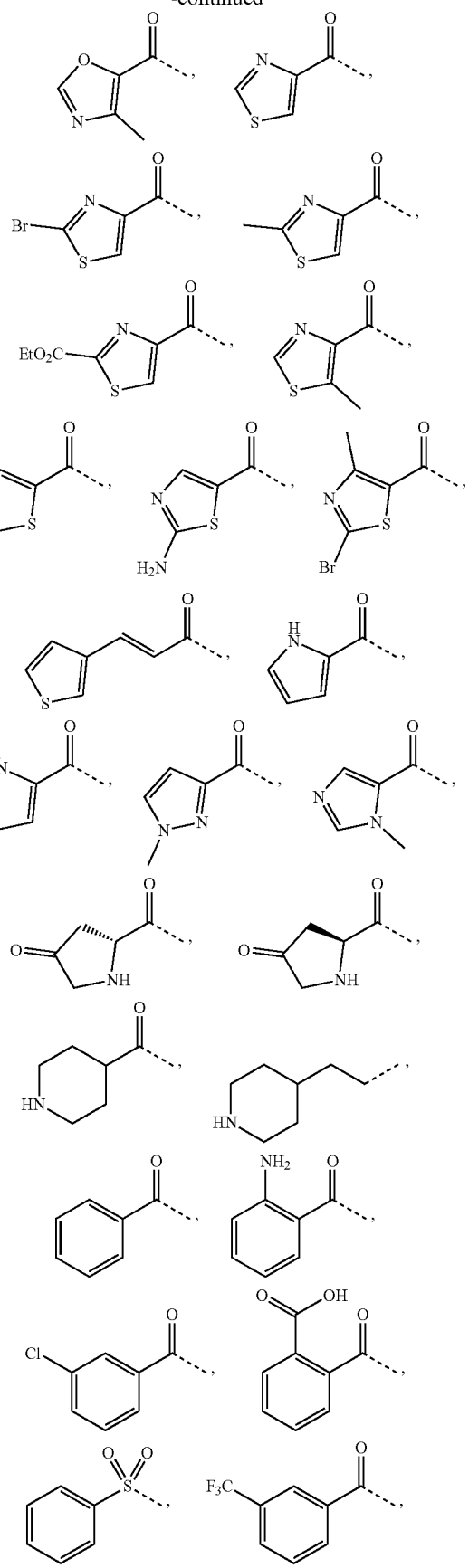

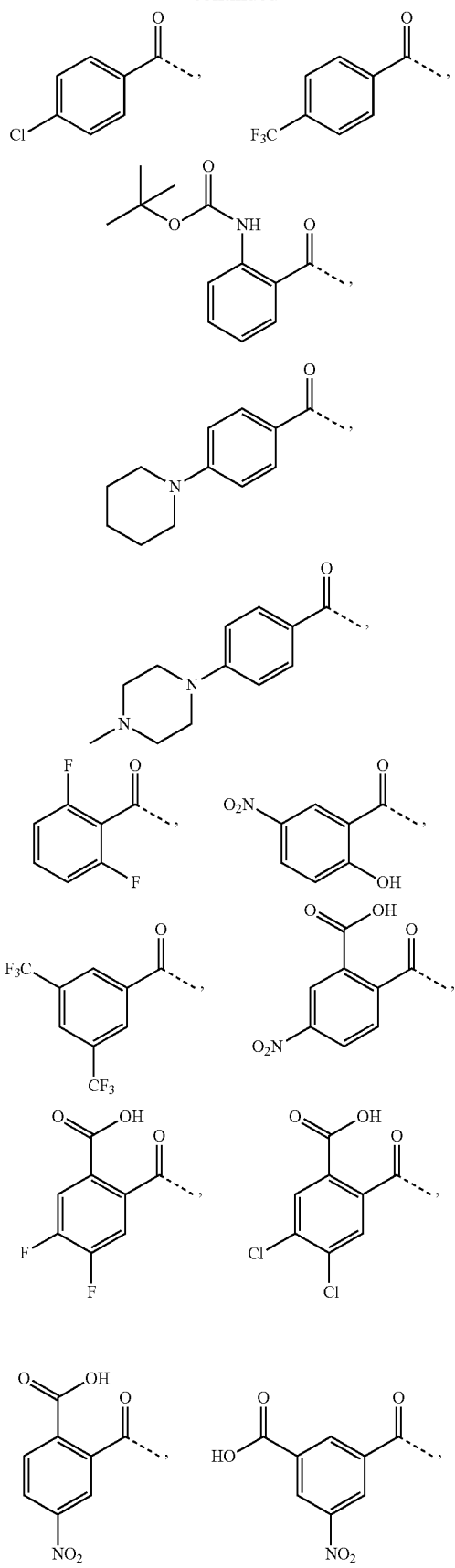
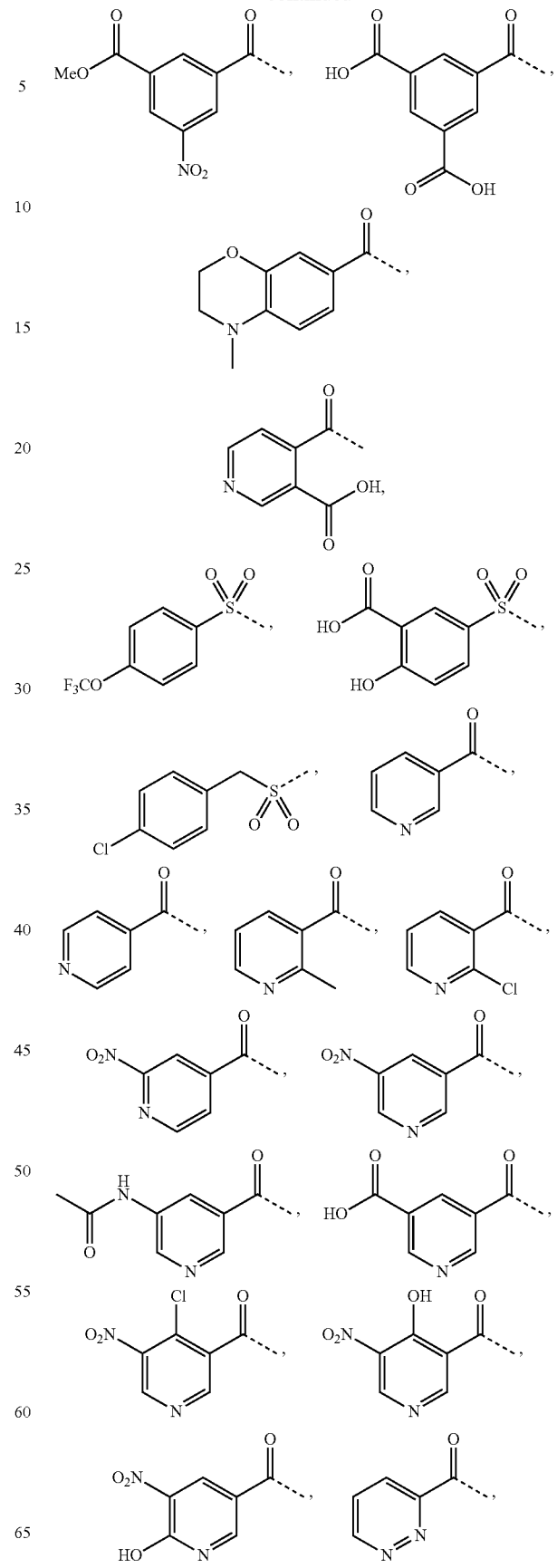

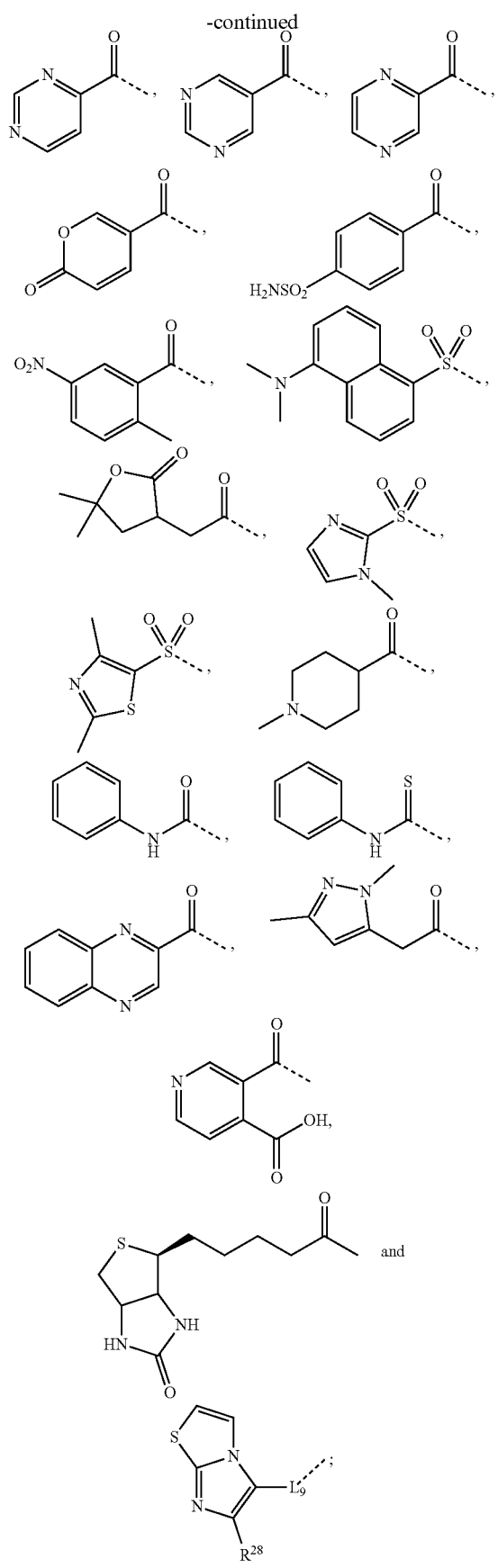

Preferably, $R^4$, $R^5$ and $R^6$ represent independently of each other: —H, —F, —Cl, —Br, —I, —CH$_3$, —CH$_2$CH$_3$, —CH(CH$_3$)$_2$, -cyclo-C$_3$H$_5$, —OCH$_3$, —CF$_3$, —OCF$_3$, —OH, —ON, —COCH$_3$, —CO$_2$H, —CO$_2$Me, —OCOCH$_3$, —NH$_2$, —NHCH$_3$, —N(CH$_3$)$_2$, —NHCOCH$_3$, —NHCOCF$_3$, —NHSO$_2$CH$_3$, —NHSO$_2$CF$_3$, —SCH$_3$, —SO$_2$CH$_3$, —SO$_2$CF$_3$, —SO$_2$NH$_2$, —SO$_2$NHCH$_3$, or —SO$_2$N(CH$_3$)$_2$;

Preferably, $R^7$ represents —H, or —CH$_2$CH$_2$CO$_2$H,

Preferably, $Z^{C1}$ represents $E^C$, and $E^C$ is selected from C terminal groups consisting of: —OH, —OCH$_3$, —OC$_2$H$_5$, —OC$_2$H$_4$—OCH$_3$, —NH$_2$, —NHCH$_3$, —N(CH$_3$)$_2$, —N(C$_2$H$_5$)$_2$, —NHCH$_2$—OCH$_3$, —NHCH$_2$N(CH$_3$)$_2$, —NHSO$_2$CH$_3$, —NHSO$_2$C$_2$H$_5$,

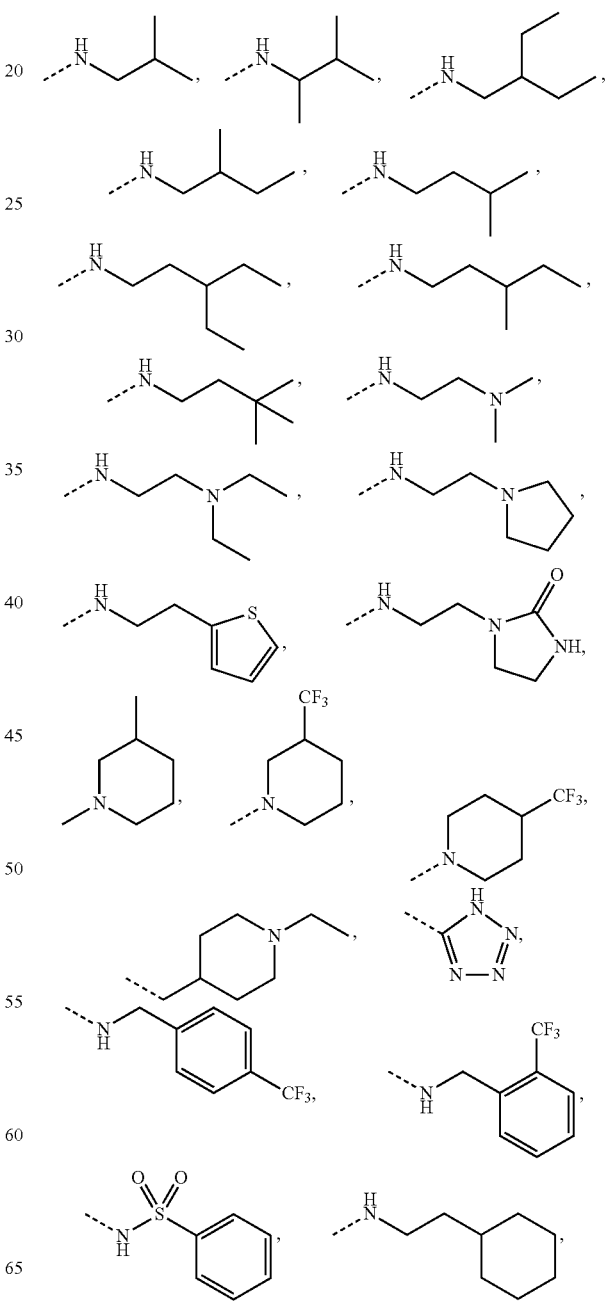

Therefore, one embodiment of the present invention is directed to the compound of the formula (IX), wherein W represents $Z^{C1}$ represents -$E^C$ or -$AS^{C2}$-$E^C$;

$Z^N$ represents $E^N$- or $E^N$-$AS^{N1}$-; and $R^4$, $R^5$ and $R^6$ represent independently of each other: —H, —F, —Cl, —Br, H, —CH$_3$, —CH$_2$CH$_3$, —CH(CH$_3$)$_2$, -cyclo-C$_3$H$_5$, —OCH$_3$, —CF$_3$, —OCF$_3$, —OH, —CN, —COCH$_3$, —CO$_2$H, —CO$_2$Me, —OCOCH$_3$, —NH$_2$, —NHCH$_3$, —N(CH$_3$)$_2$, —NHCOCH$_3$, —NHCOCF$_3$, —NHSO$_2$CH$_3$, —NHSO$_2$CF$_3$, —SCH$_3$, —SO$_2$CH$_3$, —SO$_2$CF$_3$, —SO$_2$NH$_2$, —SO$_2$NHCH$_3$, or —SO$_2$N(CH$_3$)$_2$.

Preferably, $R^7$ represents —H, or —CH$_2$CH$_2$CO$_2$H,

One embodiment of the present invention refers to the compound of the following formulae (X-1)-(X-3);

wherein
$Z^{C2}$ represents -$E^C$ or -$AS^{C3}$-$E^C$; and
$AS^{C3}$, $E^C$, n, $R^4$-$R^7$, $Z^N$, and W have the same meaning as defined in the formula (I).

More preferred is the compound of the formula (XI-3):

wherein
$Z^{C1}$ represents -$E^C$;
$Z^N$ represents $E^N$- or $E^N$-$AS^{N1}$-;
$R^2$ represents —CH$_3$, —CH$_2$CH$_3$, —CH(CH$_3$)$_2$, -cyclo-C$_3$H$_5$, -Ph, —OCH$_3$, —OCH$_2$CH$_3$, —NH$_2$, —NHCH$_3$, —N(CH$_3$)$_2$, —NH-cyclo-C$_3$H$_5$, —NH—CH$_2$Ph, —NC(CH$_3$)$_3$, —NHCH$_2$OCH$_3$, —NHCH$_2$CH$_2$OCH$_3$, —NHCH$_2$COOCH$_3$, —NH—OCH$_2$-cyclo-C$_5$H$_9$; and
$R^4$, $R^5$ and $R^6$ represent independently of each other: —H, —F, —Cl, —Br, —CH$_3$, —CH$_2$CH$_3$, —CH(CH$_3$)$_2$, -cyclo-C$_3$H$_5$, —OCH$_3$, —CF$_3$, —OCF$_3$, —OH, —CN, —COCH$_3$, —CO$_2$H, —CO$_2$Me, —OCOCH$_3$, —NH$_2$, —NHCH$_3$, —N(CH$_3$)$_2$, —NHCOCH$_3$, —NHCOCF$_3$, —NHSO$_2$CH$_3$, —NHSO$_2$CF$_3$, —SCH$_3$, —SO$_2$CH$_3$, —SO$_2$CF$_3$, —SO$_2$NH$_2$, —SO$_2$NHCH$_3$, or —SO$_2$N(CH$_3$)$_2$.
$R^7$ represents —H or —CH$_2$CH$_2$CO$_2$H; and
$AS^{N1}$, $E^C$, and $E^N$ have the same meanings as defined in the formula (I)

Still more preferred is the compound of the formulae (XI-6)

(XI-6)
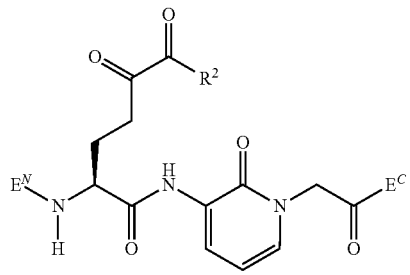
wherein
R² represents —CH₃, —CH₂CH₃, —CH(CH₃)₂, -cyclo-C₃H₅, -Ph, —OCH₃, —OCH₂CH₃, —NH₂, —NHCH₃, —N(CH₃)₂, —NH-cyclo-C₃H₅, —NH—CH₂Ph, —NC(CH₃)₃, —NH—C₅H₁₁, —NHCH₂OCH₃, —NHCH₂CH₂OCH₃, —NHCH₂COOCH₃, —NH—OCH₂-cyclo-C₅H₉; and
E^C represents
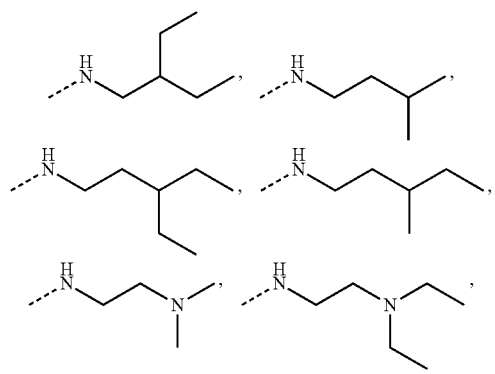
E^N is selected from N terminal groups consisting of: —H, —COCH₃, —COCF₃,
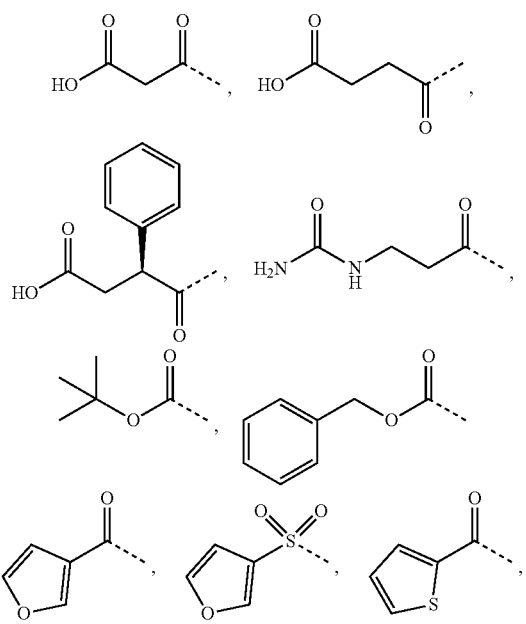
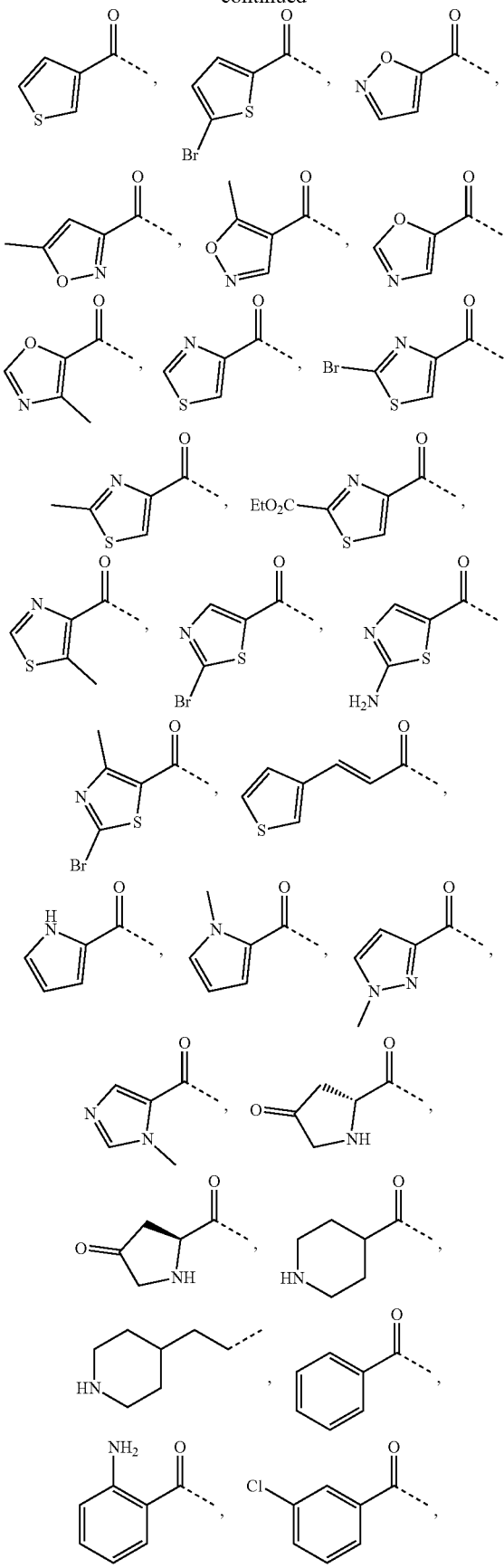

-continued
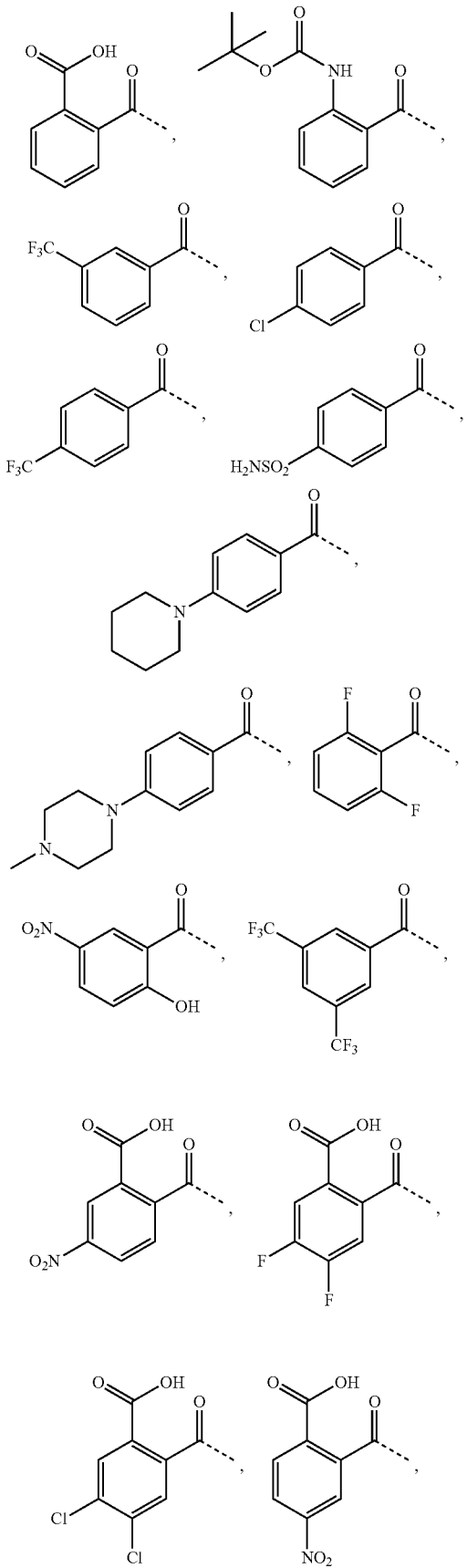
-continued
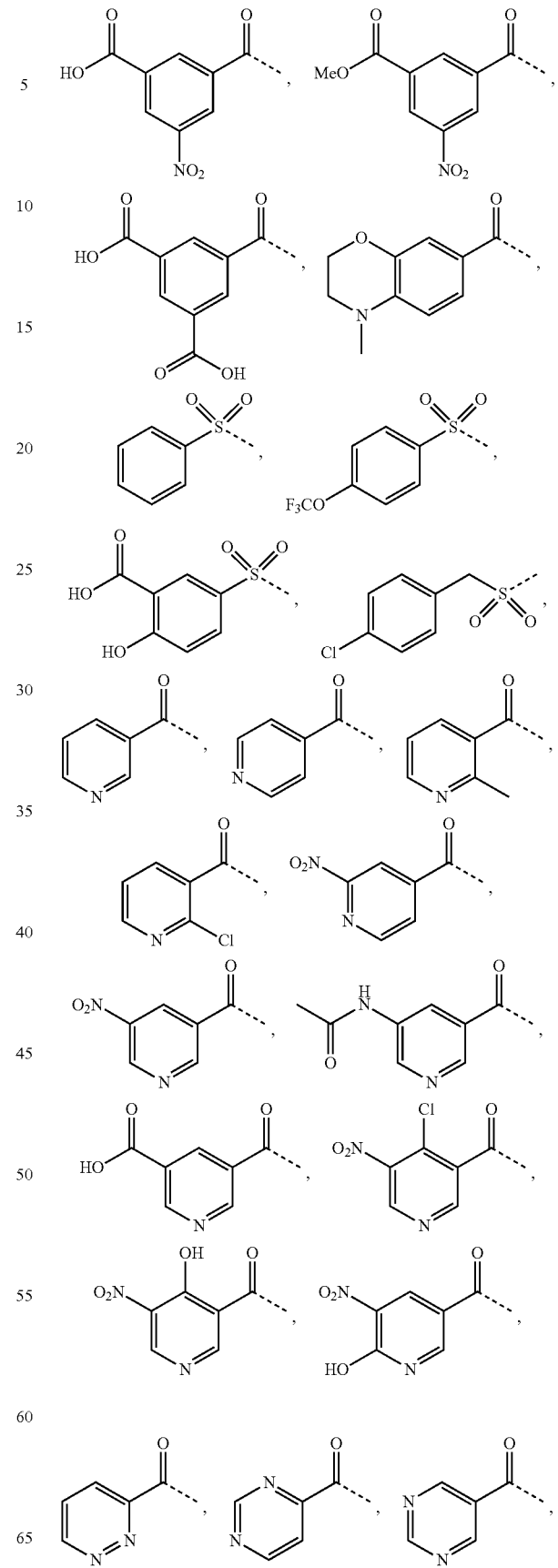

-continued

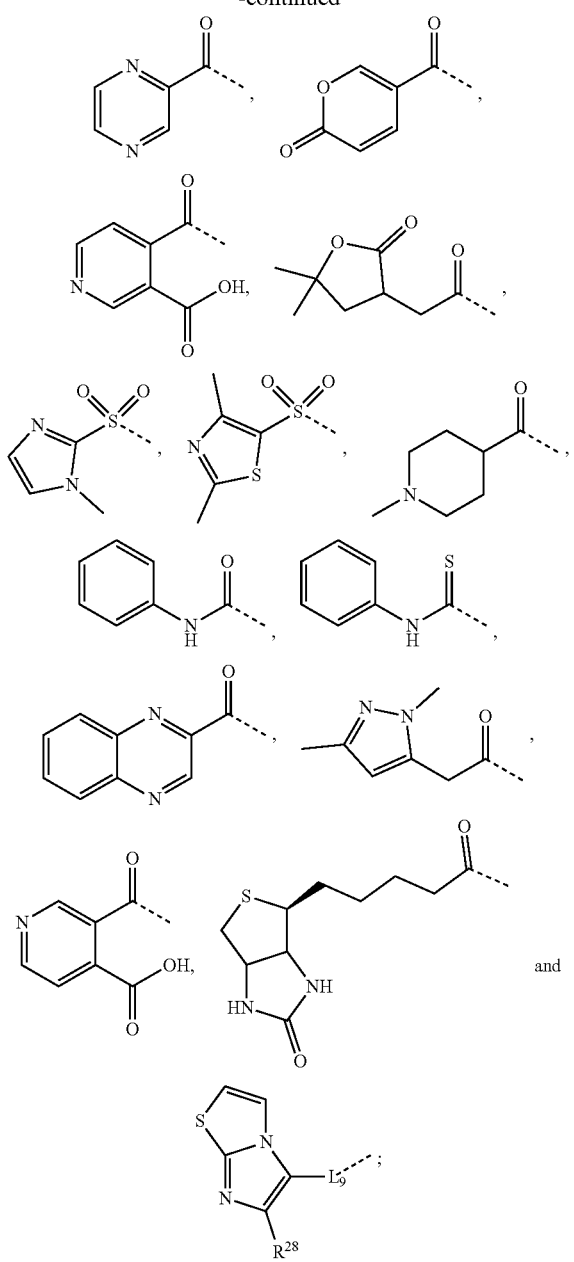

Preferred are compounds of the general formula (XII):

(XII)

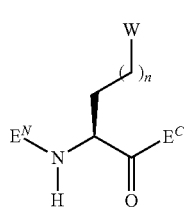

wherein
n is an integer selected from 1, 2 or 3;

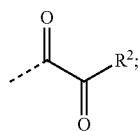

W represents
$R^2$ represents H, —$R^1$, —$OR^1$, —$NH_2$, —$NH(R^1)$, —NH($OR^1$), —$N(R^1)(R^3)$;
$R^1$ and $R^3$ represent independently of each other $CH_3$, —$CH_2CH_3$, —$CH_2CH_2CH_3$, —$CH(CH_3)_2$, —$CH_2CH_2CH_2CH_3$, —$CH_2CH_2CH_2CH_2CH_3$, —$CH_2CH_2CH_2CH_2CH_2CH_3$, —$CH_2CH_2CH_2CH_2CH_2CH_2CH_3$, —$CH_2CH(CH_3)_2$, —$CH(CH_3)CH_2CH_3$, —$CH(C_2H_5)_2$, —$CH_2CH(C_2H_5)_2$, —$C(CH_3)_3$, —$CH_2C(CH_3)_3$, -cyclo-$C_3H_5$, cyclo-$C_4H_7$, cyclo-$C_5H_9$, cyclo-$C_6H_{11}$, —$CH_2$-cyclo-$C_3H_5$, —$CH_2$-cyclo-$C_4H_7$, —$CH_2$-cyclo-$C_5H_9$, —$CH_2$-cyclo-$C_6H_{11}$, —$CH_2Ph$, —$CH_2OCH_3$, —$CH_2OCH_2CH_3$, —$CH_2CH_2OCH_3$, —$CH_2CH_2OCH_2CH_3$, —$CH_2CH_2NHCH_3$, —$CH_2CH_2N(CH_3)_2$, —$CH_2S(O)_2$-(4-methyl-phenyl),

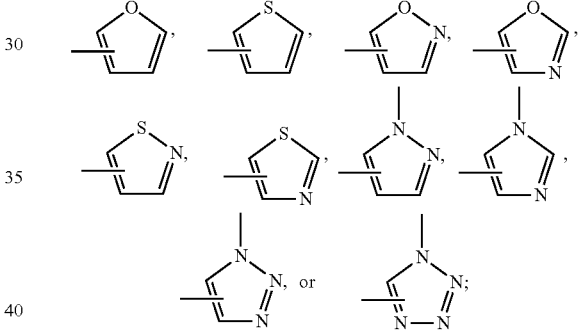

or
$N(R^1)(R^3)$ forms

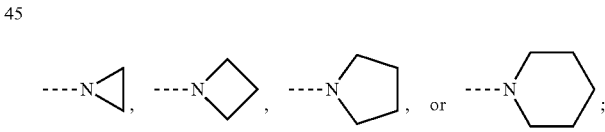

$E^C$ is a C terminal group selected from: —$NR^9R^{10}$, —$NHSO_2R^{11}$, —O-$L_1R^8$, —O-$L_1$-O—$^8$, —NH-$L_1$-O—$R^8$, —NH-$L_1$-$NR^9R^{10}$, —$NHSO_2$-$L_1$-$R^{11}$,

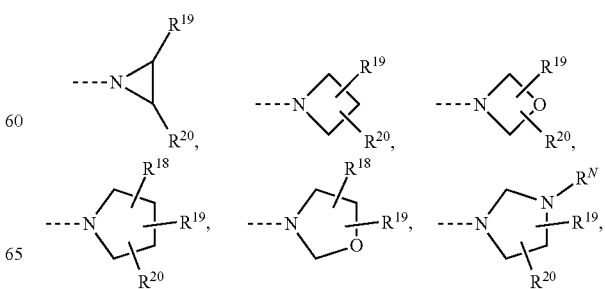

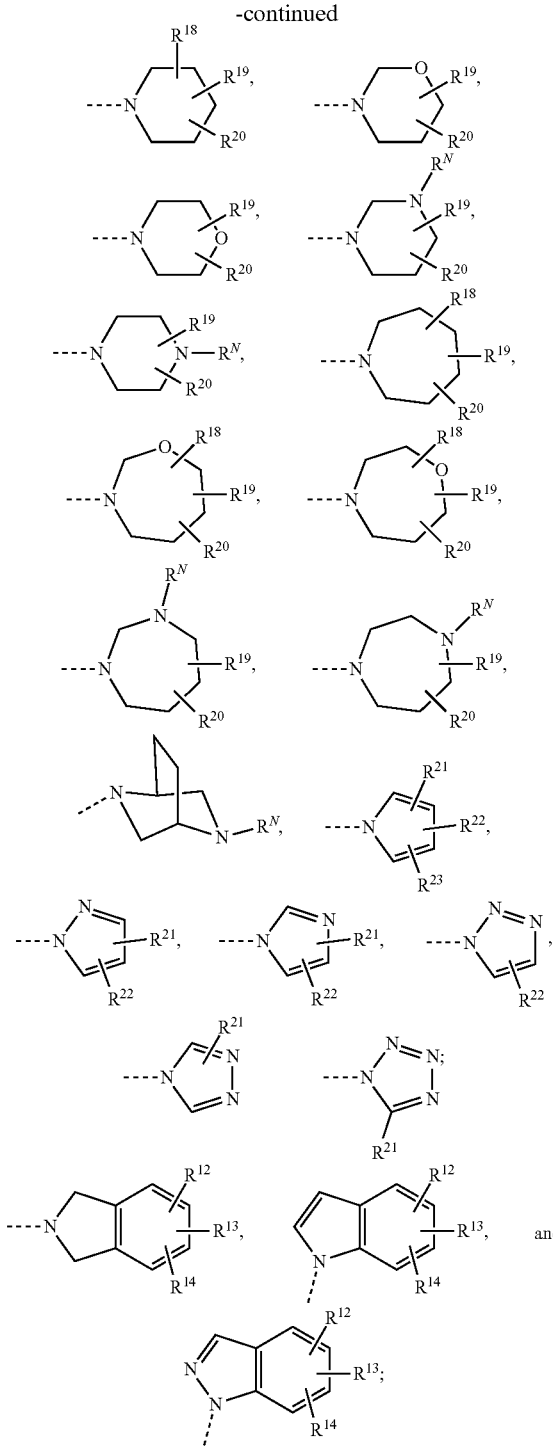

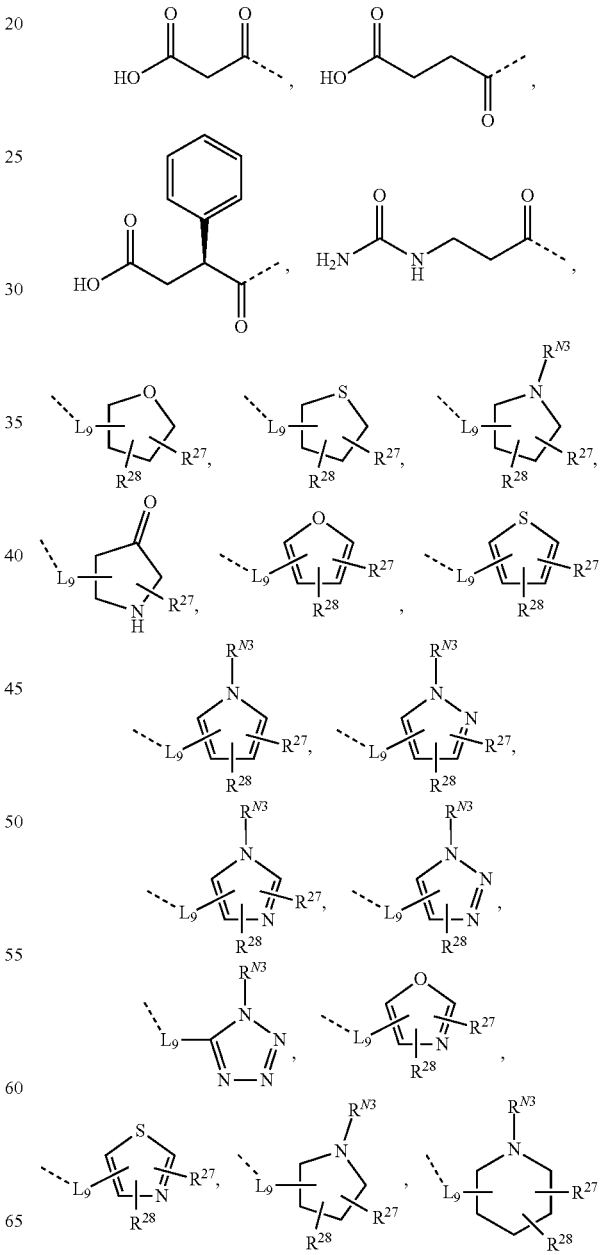

$E^N$ is selected from N terminal groups consisting of: —H, —COCF₃, —CH₃, —C₂H₅, —C₃H₇, —CH(CH₃)₂, —CH(C₂H₅)₂, —C₄H₉, —C₅H₁₁, —C₆H₁₃, —CH₂—CH(CH₃)₂, —CH₂—CH(C₂H₅)₂, —CH(CH₃)—C₂H₅, —C(CH₃)₃, —CH₂—C(CH₃)₃, -cyclo-C₃H₅, -cyclo-C₄H₇, -cyclo-C₅H₉, -cyclo-C₆H₁₁, —CH₂-cyclo-C₃H₅, —CH₂-cyclo-C₄H₇, —CH₂-cyclo-C₅H₉, —CH₂-cyclo-C₆H₁₁, -Ph, —CH₂-Ph, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, —CH₂—CH=CH₂, —CH₂—C≡CH, —CHO, —COCH₃, —COC₂H₅, —COC₃H₇, —COCH(CH₃)₂, —COCH(C₂H₅)₂, —COC₄H₉, —COC₅H₁₁, —COC₆H₁₃, —COCH₂—CH(CH₃)₂, —COCH₂—CH(C₂H₅)₂, —COCH(CH₃)—C₂H₅, —COC(CH₃)₃, —COCH₂—C(CH₃)₃, —CO-cyclo-C₃H₅, —CO-cyclo-C₄H₇, —CO-cyclo-C₅H₉, —CO-cyclo-C₆H₁₁, —COCH₂-cyclo-C₃H₅, —COCH₂-cyclo-C₄H₇, —COCH₂-cyclo-C₅H₉, —COCH₂-cyclo-C₆H₁₁, —COPh, —COCH₂-Ph, —COOCH₃, —COOC₂H₅, —COOC₃H₇, —COOCH(CH₃)₂, —COOCH(C₂H₅)₂, —COOC₄H₉, —COOC₅H₁, —COOC₆H₁₃, —COOCH₂—CH(CH₃)₂, —COOCH₂—CH(C₂H₅)₂, —COOCH(CH₃)—C₂H₅, —COOC(CH₃)₃, —COOCH₂—C(CH₃)₃, —COO-cyclo-C₃H₅, —COO-cyclo-C₄H₇, —COO-cyclo-C₅H₉, —COO-cyclo-C₆H₁₁, —COOCH₂-cyclo-C₃H₅, —COOCH₂-cyclo-C₄H₇, —COOCH₂-cyclo-C₅H₉, —COOCH₂-cyclo-C₆H₁, —COOPh, —COOCH₂-Ph,

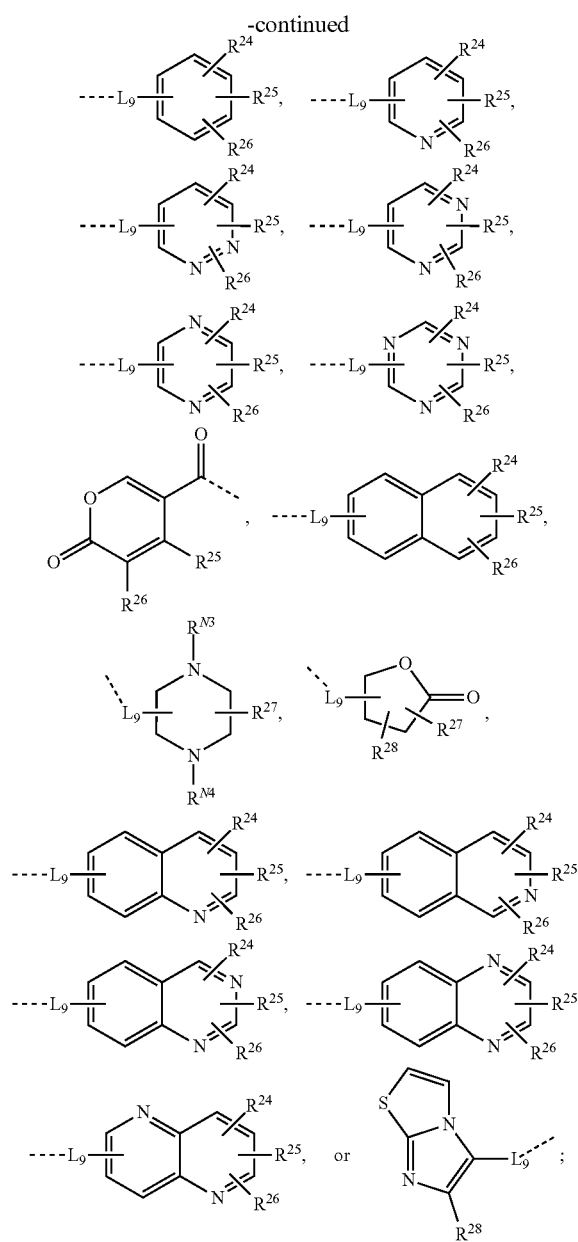
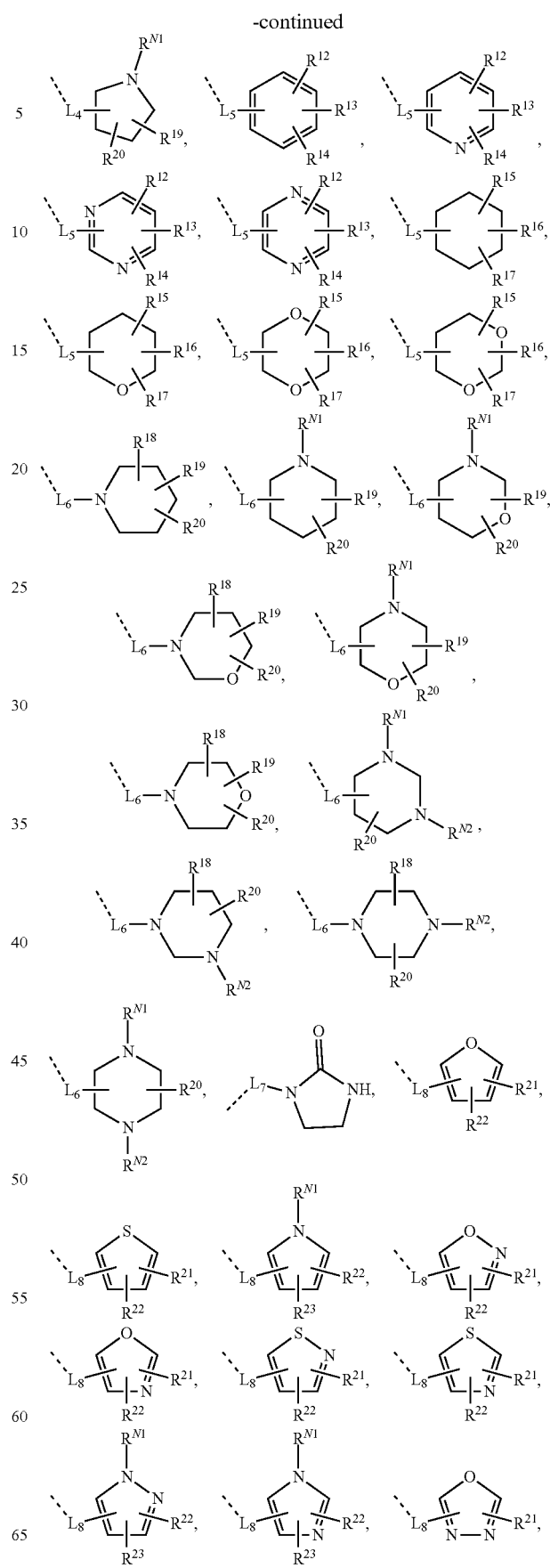
$R^8$, $R^9$, $R^{10}$ and $R^{11}$ represent independently of each other:
—H, —$CH_3$, —$CH_2CH_3$, —$CH_2CH_2CH_3$, —$CH(CH_3)_2$, —$CH(C_2H_5)_2$, —$CH_2CH(CH_3)_2$, —$CH_2$—$CH(C_2H_5)_2$, —$C_4H_9$, —$C_5H_{11}$, —$C_6H_{13}$, —$CH(CH_3)$—$C_2H_5$, —$C(CH_3)_3$, —$CH_2$—$C(CH_3)_3$,
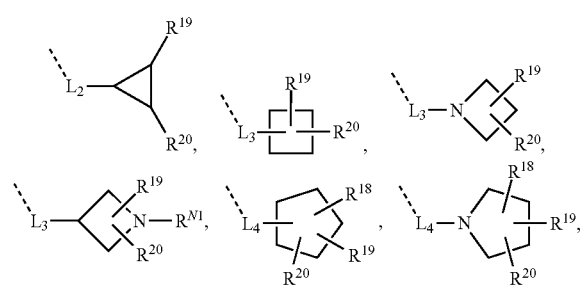

-continued

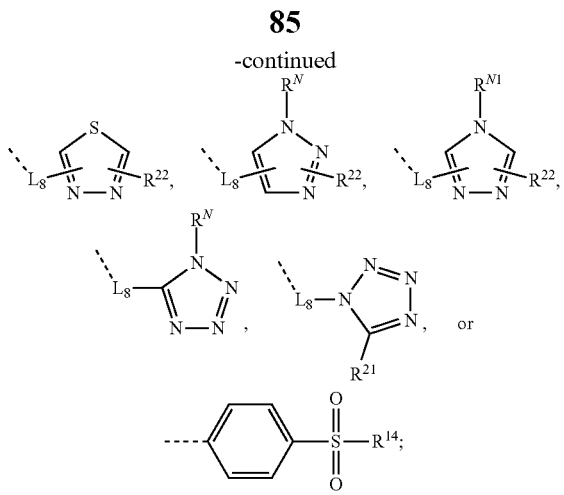

$R^{12}$-$R^{29}$ represents independently of each other —H, —F, —Cl, —Br, —I, —OH, —CN, —NO$_2$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$) C$_2$H$_5$, —C(CH$_3$)$_3$, cyclo-C$_3$H$_5$, —CH$_2$ cyclo C$_3$H$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —OCH$_3$, —OC$_2$H$_5$, —OC$_3$H$_7$, —OCH(CH$_3$)$_2$, —OC(CH$_3$)$_3$, —OC$_4$H$_9$, —OCHF$_2$, —OCF$_3$, —OCH$_2$CF$_3$, —OC$_2$F$_5$, —OCH$_2$OCH$_3$, —O-cyclo-C$_3$H$_5$, —OCH$_2$-cyclo-C$_3$H$_5$, —O—C$_2$H$_4$-cyclo-C$_3$H$_5$, —CHO, —COCH$_3$, —COCF$_3$, —COC$_2$H$_5$, —COC$_3$H$_7$, —COCH(CH$_3$)$_2$, —COC(CH$_3$)$_3$, —COOH, —COOCH$_3$, —COOC$_2$H$_5$, —COOC$_3$H$_7$, —COOCH(CH$_3$)$_2$, —COOC(CH$_3$)$_3$, —OOC—CH$_3$, —OOC—CF$_3$, —OOC—C$_2$H$_5$, —OOC—C$_3$H$_7$, —OOC—CH(CH$_3$)$_2$, —OOC—C(CH$_3$)$_3$, —NH$_2$, —NHCH$_3$, —NHC$_2$H$_5$, —NHC$_3$H$_7$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N[CH(CH$_3$)$_2$]$_2$, —N[C(CH$_3$)$_3$]$_2$, —NHCOCH$_3$, —NHCOCF$_3$, —NHCOC$_2$H$_5$, —NHCOC$_3$H$_7$, —NHCOCH(CH$_3$)$_2$, —NHCOC(CH$_3$)$_3$, —CONH$_2$, —CONHCH$_3$, —CONHC$_2$H$_5$, —CONHC$_3$H$_7$, —CONHCH(CH$_3$)$_2$, —CONH-cyclo-C$_3$H$_5$, —CONHC(CH$_3$)$_3$, —CON(CH$_3$)$_2$, —CON(C$_2$H$_5$)$_2$, —CON(C$_3$H$_7$)$_2$, —CON[CH(CH$_3$)$_2$]$_2$, —CON[C(CH$_3$)$_3$]$_2$, —SO$_2$NH$_2$, —SO$_2$NHCH$_3$, —SO$_2$NHC$_2$H$_5$, —SO$_2$NHC$_3$H$_7$, —SO$_2$NHCH(CH$_3$)$_2$, —SO$_2$NH-cyclo-C$_3$H$_5$, —SO$_2$NHC(CH$_3$)$_3$, —SO$_2$N(CH$_3$)$_2$, —SO$_2$N(C$_2$H$_5$)$_2$, —SO$_2$N(C$_3$H$_7$)$_2$, —SO$_2$N[CH(CH$_3$)$_2$]$_2$, —SO$_2$N[C(CH$_3$)$_3$]$_2$, —NHSO$_2$CH$_3$, —NHSO$_2$CF$_3$, —NHSO$_2$C$_2$H$_5$, —NHSO$_2$C$_3$H$_7$, —NHSO$_2$CH(CH$_3$)$_2$, —NHSO$_2$C(CH$_3$)$_3$, —CH=CH$_2$, —CH$_2$—CH=CH$_2$, —C(CH$_3$)=CH$_2$, —CH=CH—CH$_3$, —C≡CH, —C≡C—CH$_3$, —CH$_2$—C≡CH, -Ph, —O-Ph, or —O—CH$_2$-Ph,

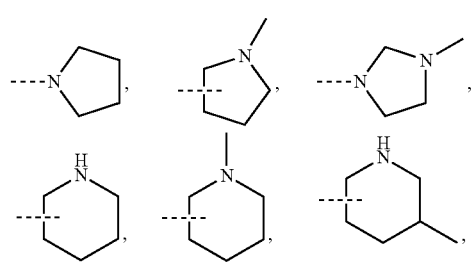

-continued

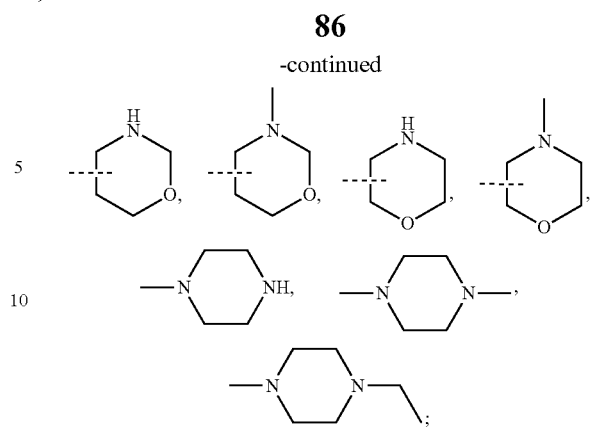

or $R^{12}$ and $R^{13}$, $R^{13}$ and $R^{14}$, $R^{24}$ and $R^{25}$, $R^{28}$ and $R^{28}$, $R^{27}$ and $R^{28}$, $R^{28}$ and $R^{29}$ can form together the following five or six rings, when $R^{29}$ are substituted at six-membered ring;

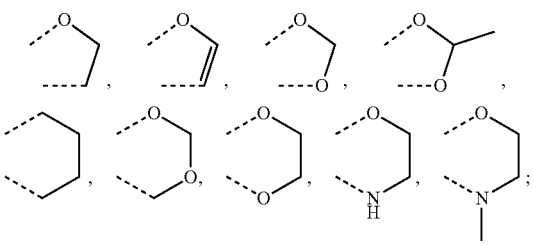

$R^N$, represents independently of each other —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, -cyclo-C$_3$H$_5$, —CH$_2$-cyclo-C$_3$H$_5$, —CHF$_2$, —CF$_3$, —CH$_2$Cl, —CH$_2$Br, —CH$_2$I, —CH$_2$—CHF$_2$, —CH$_2$—CF$_3$, —CH$_2$—CH$_2$Cl, —CH$_2$—CH$_2$Br, —CH$_2$—CH$_2$I, —CH$_2$—CH=CH$_2$, —CH$_2$—C≡CH, —CHO, —COCH$_3$, —COC$_2$H$_5$, —COC$_3$H$_7$, —COCH(CH$_3$)$_2$, —COC(CH$_3$)$_3$, —COOCH$_3$, —COOC$_2$H$_5$, —COOC$_3$H$_7$, —COOCH(CH$_3$)$_2$, —COOC(CH$_3$)$_3$,

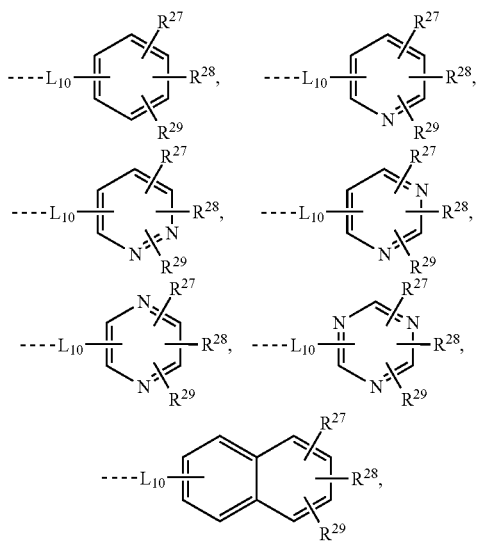

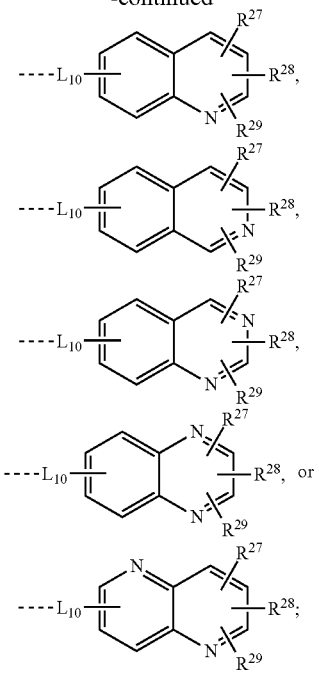

$R^{N1}$-$R^{N4}$ represent independently of each other —H, —CH$_3$, —C$_2$H$_5$, —C$_3$H$_7$, —CH(CH$_3$)$_2$, —CH$_2$—CH(CH$_3$)$_2$, —CH(CH$_3$)—C$_2$H$_5$, —C(CH$_3$)$_3$, -cyclo-C$_3$H$_5$, —CH$_2$-cyclo-C$_3$H$_5$, —CH$_2$F, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —CH$_2$CH=CH$_2$, —CH$_2$—C≡CH, —CH$_2$Ph, —CHO, —COCH$_3$, —COC$_2$H$_5$, —COC$_3$H$_7$, —COCH(CH$_3$)$_2$, —COC(CH$_3$)$_3$, —COOCH$_3$, —COOC$_2$H$_5$, —COOC$_3$H$_7$, —COOCH(CH$_3$)$_2$, —COOC(CH$_3$)$_3$, or —COOCH$_2$Ph;

$L^1$-$L^8$ represent independently of each other a covalent bond, —CH$_2$—, —CH(CH$_3$), —CH(CH$_3$)$_2$—, —CO—, —SO—, —SO$_2$—,

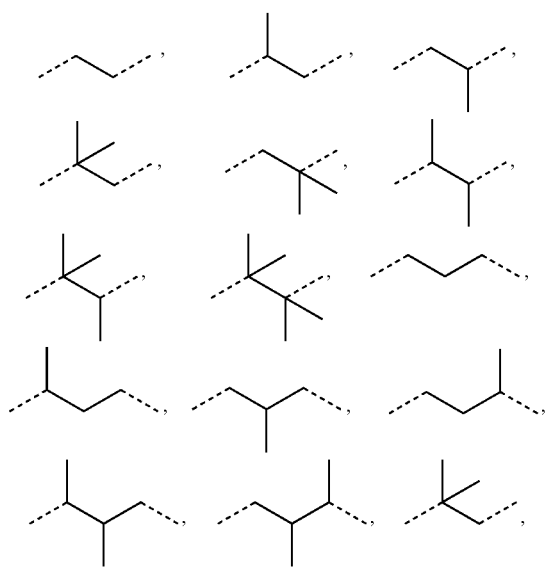

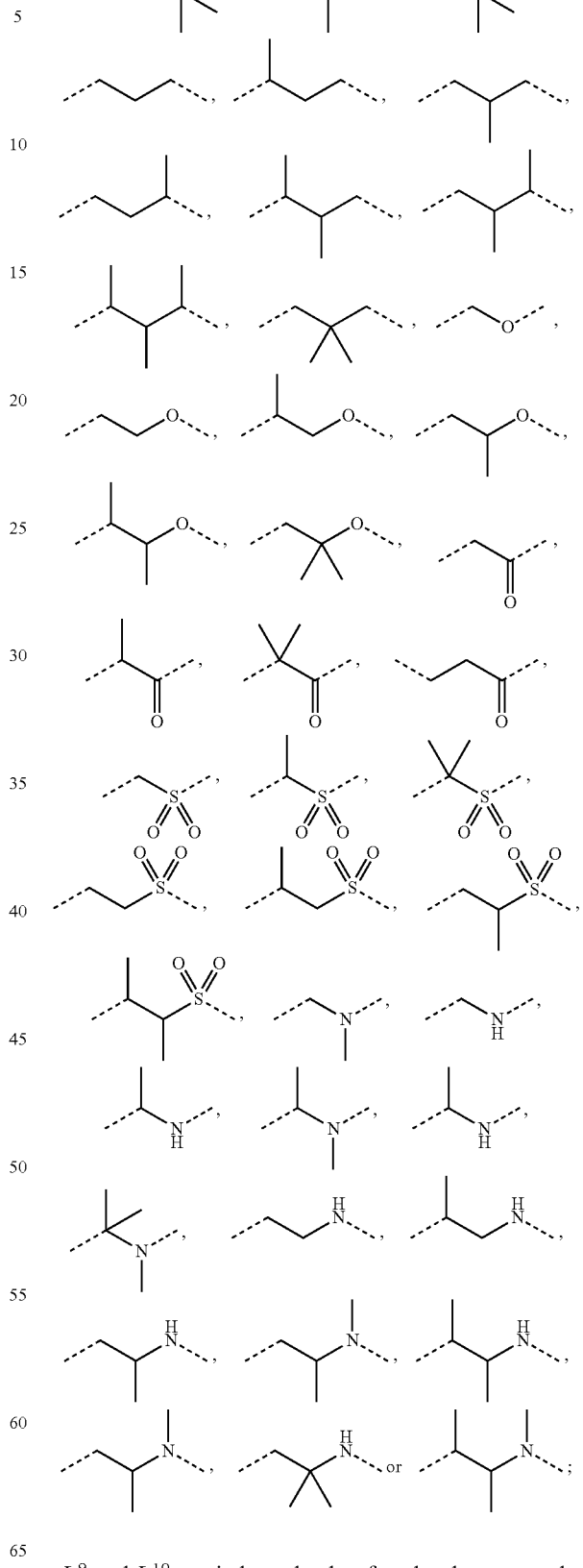

$L^9$ and $L^{10}$ are independently of each other: a covalent bond, —CH$_2$—, —CH$_2$CH$_2$—, —CO—, —CH$_2$CO—, —COCH$_2$—, —CO—CH=CH—, —COO—, —O—CO—, —CH$_2$CO$_2$—, —CO$_2$CH$_2$—, —CONH—, —NHCO—, —CH$_2$CONH—, —CONHCH$_2$—, —CSNH—, —NHCS—, —SO$_2$—, —SO$_2$CH$_2$—, —SO$_2$NH—, or —SO$_2$NHCH$_2$—;

and diastereomer, enantiomer, mixture of diastereomers, mixture of enantiomer, racemates, prodrugs, solvates, hydrates, or pharmaceutically acceptable salts thereof.

Preferred, the compound of the formula (XIII):

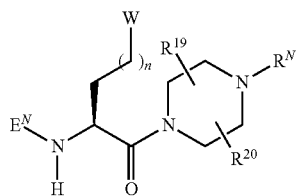

(XIII)

wherein n is an integer selected from 1, 2 or 3;

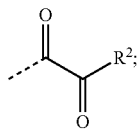

W represents

R$^2$ represents —H, —R$^1$, —OR$^1$, —NH$_2$, —NH(R$^1$), —N(R$^1$)(R$^3$);

R$^1$ and R$^3$ represent independently of each other —CH$_3$, —CH$_2$CH$_3$, —CH$_2$CH$_2$CH$_3$, —CH(CH$_3$)$_2$, —CH$_2$CH$_2$CH$_2$CH$_3$, —CH$_2$CH$_2$CH$_2$CH$_2$CH$_3$, —CH$_2$CH$_2$CH$_2$CH$_2$CH$_2$CH$_3$, —CH$_2$CH$_2$CH$_2$CH$_2$CH$_2$CH$_2$CH$_3$, —CH$_2$CH(CH$_3$)$_2$, —CH(CH$_3$)CH$_2$CH$_3$, —CH(C$_2$H$_5$)$_2$, —CH$_2$CH(C$_2$H$_5$)$_2$, —C(CH$_3$)$_3$, —CH$_2$—C(CH$_3$)$_3$, -cyclo-C$_3$H$_5$, -cyclo-C$_4$H$_7$, -cyclo-C$_5$H$_9$, -cyclo-C$_6$H$_{11}$, —CH$_2$-cyclo-C$_3$H$_5$, —CH$_2$-cyclo-C$_4$H$_7$, —CH$_2$-cyclo-C$_5$H$_9$, —CH$_2$-cyclo-C$_6$H$_{11}$, -Ph, —CH$_2$-Ph, —CH$_2$OCH$_3$, —CH$_2$OCH$_2$CH$_3$, —CH$_2$CH$_2$OCH$_3$, —CH$_2$CH$_2$OCH$_2$CH$_3$, —CH$_2$CO$_2$CH$_3$,—CH$_2$CO$_2$CH$_2$CH$_3$,—CH$_2$CH$_2$NHCH$_3$, —CH$_2$CH$_2$N(CH$_3$)$_2$, —CH$_2$S(O)$_2$-(4-methyl-phenyl),

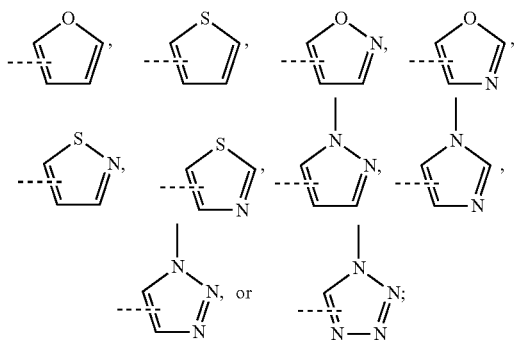

or

—N(R$^1$)(R$^3$) forms

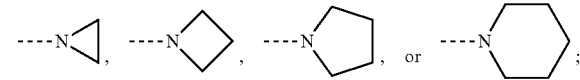

R$^{19}$-R$^{20}$ represents independently of each other —H, —F, —Cl, —Br, —I, —OH, —CN, —NO$_2$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, -cyclo-C$_3$H$_5$, —CH$_2$-cyclo-C$_3$H$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —OCH$_3$, —OC$_2$H$_5$, —OC$_3$H$_7$, —OCH(CH$_3$)$_2$, —OC(CH$_3$)$_3$, —OC$_4$H$_9$, —OCHF$_2$, —OCF$_3$, —OCH$_2$CF$_3$, —OC$_2$F$_5$, —OCH$_2$OCH$_3$, —O-cyclo-C$_3$H$_5$, —OCH$_2$-cyclo-C$_3$H$_5$, —O—C$_2$H$_4$-cyclo-C$_3$H$_5$, —CHC, —COCH$_3$, —COCF$_3$, —COC$_2$H$_5$, —COC$_3$H$_7$, —COCH(CH$_3$)$_2$, —COC(CH$_3$)$_3$, —COOH, —COOCH$_3$, —COOC$_2$H$_5$, —COOC$_3$H$_7$, —COOCH(CH$_3$)$_2$, —COOC(CH$_3$)$_3$, —OOC—CH$_3$, —OOC—CF$_3$, —OOC—C$_2$H$_5$, —OOC—C$_3$H$_7$, —CCC—CH(CH$_3$)$_2$, —OOC—C(CH$_3$)$_3$, —NH$_2$, —NHCH$_3$, —NHC$_2$H$_5$, —NHC$_3$H$_7$, —NHCH(CH$_3$)$_2$, —NHC(CH$_3$)$_3$. —N(C$_2$H$_5$)$_2$, —N(C$_3$H$_7$)$_2$, —N[CH(CH$_3$)$_2$]$_2$, —N[C(CH$_3$)$_3$]$_2$, —NHCOCH$_3$, —NHCOCF$_3$, —NHCOC$_2$H$_5$, —NHCOC$_3$H$_7$, —NHCOCH(CH$_3$)$_2$, —NHCOC(CH$_3$)$_3$, —CONH$_{29}$—CONHCH$_{39}$—CONHC$_2$H$_5$, —CONHC$_3$H$_7$, —CONHCH(CH$_3$)$_2$, —CONH-cyclo-C$_3$H$_5$, —CONHC(CH$_3$)$_3$, —CON(CH$_3$)$_2$, —CON(C$_2$H$_5$)$_2$, —CON(C$_3$H$_7$)$_2$, —CON[CH(CH$_3$)$_2$]$_2$, —CON[C(CH$_3$)$_3$]$_2$, —SO$_2$NH$_2$, —SO$_2$NHCH$_3$, —SO$_2$NHC$_2$H$_5$, —SO$_2$NHC$_3$H$_7$, —SO$_2$NHCH(CH$_3$)$_2$, —SO$_2$NH-cyclo-C$_3$H$_5$, —SO$_2$NHC(CH$_3$)$_3$, —SO$_2$N(CH$_3$)$_2$, —SO$_2$N(C$_2$H$_5$)$_2$, —SO$_2$N(C$_3$H$_7$)$_2$, —SO$_2$N[CH(CH$_3$)$_2$]$_2$, —SO$_2$N[C(CH$_3$)$_3$]$_2$, —NHSO$_2$CH$_3$, —NHSO$_2$CF$_3$, —NHSO$_2$C$_2$H$_5$, —NHSO$_2$C$_3$H$_7$, —NHSO$_2$CH(CH$_3$)$_2$, —NHSO$_2$C(CH$_3$)$_3$, —CH=CH$_2$, —CH$_2$—CH=CH$_2$, —C(CH$_3$)=CH$_2$, —CH=CH—CH$_3$, —C≡CH, —C≡C—CH$_3$, and —CH$_2$—C≡CH;

E$^N$ is selected from N terminal groups consisting of:
—H, —COCH$_3$, —COCF$_3$, —CH$_3$, —C$_2$H$_5$, —C$_3$H$_7$, —CH(CH$_3$)$_2$, —CH$_2$—CH(CH$_3$)$_2$, —CH(CH$_3$)—C$_2$H$_5$, —C(CH$_3$)$_3$, -cyclo-C$_3$H$_5$, —CH$_2$-cyclo-C$_3$H$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —CH$_2$—CH=CH$_2$, —CH$_2$—C≡CH, —CHO, —COCH$_3$, —COC$_2$H$_5$, —COC$_3$H$_7$, —COCH(CH$_3$)$_2$, —COC(CH$_3$)$_3$, —COOCH$_3$, —COOC$_2$H$_5$, —COOC$_3$H$_7$, —COOCH(CH$_3$)$_2$, —COOC(CH$_3$)$_3$,

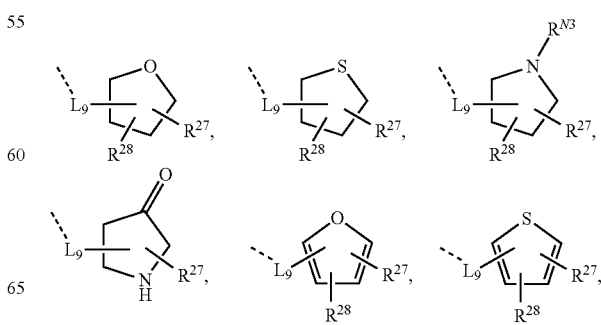

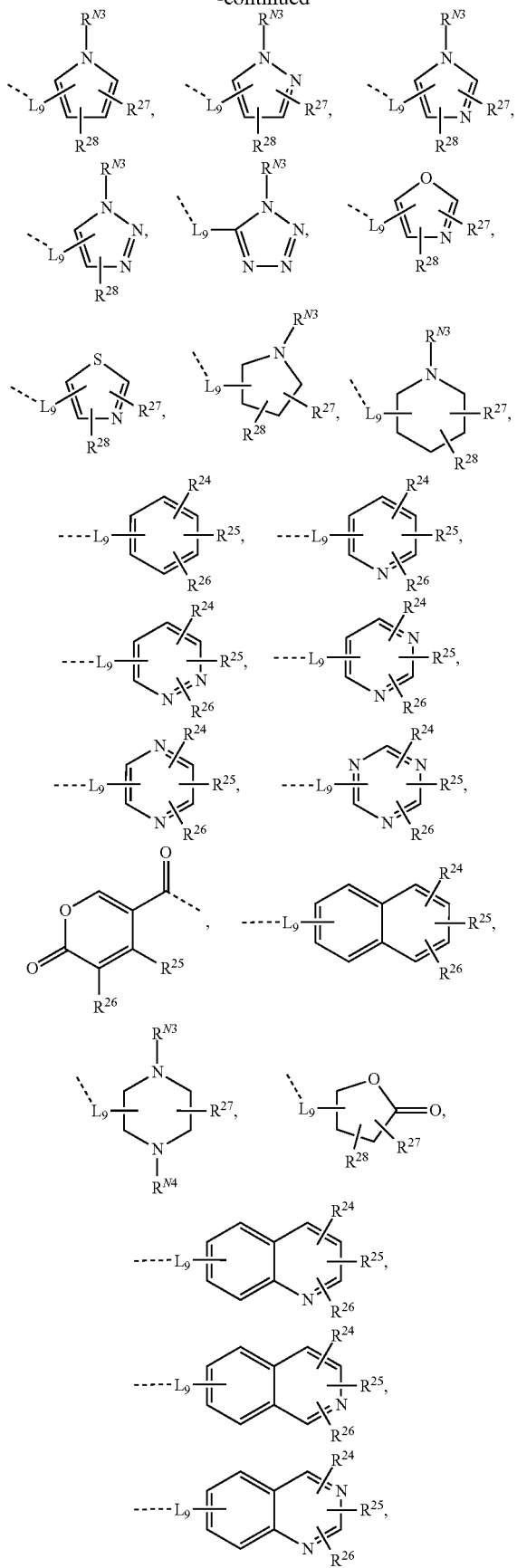
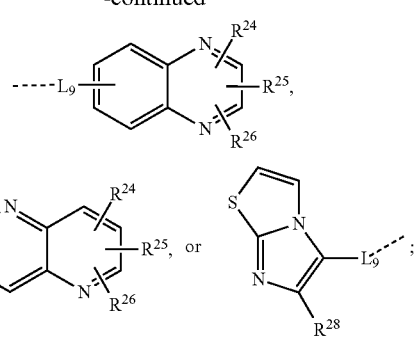
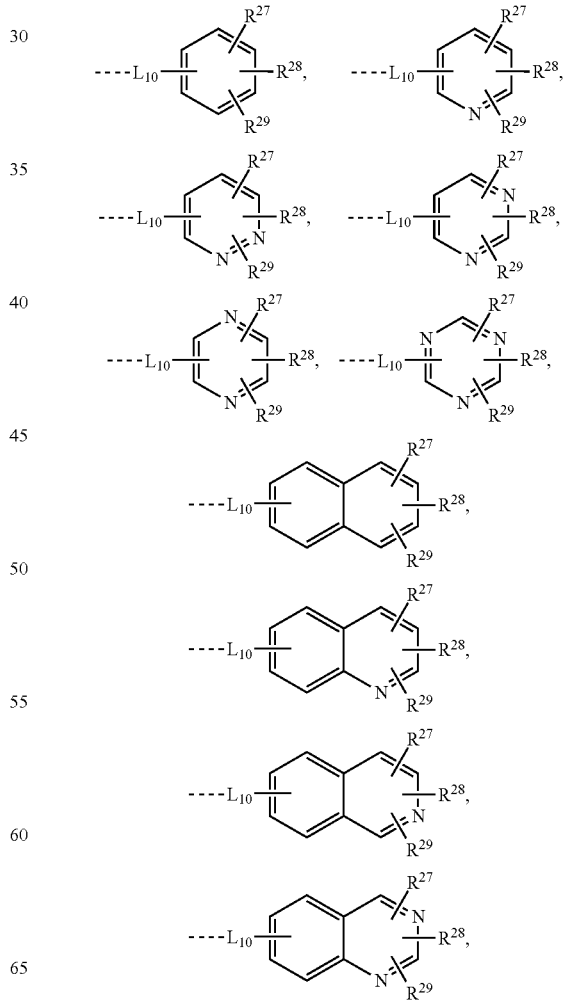

$R^N$, represents independently of each other —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, -cyclo-C$_3$H$_5$, —CH$_2$-cyclo-C$_3$H$_5$, —CH$_2$F, —CF$_3$, —CH$_2$Cl, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —CH$_2$—CH=CH$_2$, —CH$_2$—C≡CH, —CHO, —COCH$_3$, —COC$_2$H$_5$, —COC$_3$H$_7$, —COCH(CH$_3$)$_2$, —COC(CH$_3$)$_3$, —COOCH$_3$, —COOC$_2$H$_5$, —COOC$_3$H$_7$, —COOCH(CH$_3$)$_2$, —COOC(CH$_3$)$_3$, -continued

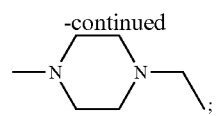

$R^{24}$-$R^{29}$ represents independently of each other
—H, —F, —Cl, —Br, —I, —OH, —CN, —NO$_2$, —CH$_3$, —C$_2$H$_5$, —C$_3$H$_7$, —CH(CH$_3$)$_2$, —C$_4$H$_9$, —CH$_2$—CH (CH$_3$)$_2$, —CH(CH$_3$)—C$_2$H$_5$, —C(CH$_3$)$_3$, —CH$_2$-cyclo-C$_3$H$_5$, —CH$_2$F, —CHF$_2$, —CF$_3$, —CH$_2$Br, —CH$_2$I, —CH$_2$—CH$_2$F, —CH$_2$—CHF$_2$, —CH$_2$CF$_3$, —CH$_2$—CH$_2$Cl, —CH$_2$—CH$_2$Br, —CH$_2$—CH$_2$I, —OCH$_3$, —OC$_2$H$_5$, —OC$_3$H$_7$, —OCH(CH$_3$)$_2$, —OC(CH$_3$)$_3$, —OC$_4$H$_9$, —OCHF$_2$, —OCF$_3$, —OCH$_2$CF$_3$, —OC$_2$F$_5$, —OCH$_2$OCH$_3$, —O-cyclo-C$_3$H$_5$, —OCH$_2$-cyclo-C$_3$H$_5$, —O—C$_2$H$_4$-cyclo-C$_3$H$_5$, —CHO, —COCH$_3$, —COCF$_3$, —COC$_2$H$_5$, —COC$_3$H$_7$, —COCH(CH$_3$)$_2$, —OOC(CH$_3$)$_3$, —COOH, —COOCH$_3$, —COOC$_2$H$_5$, —COOC$_3$H$_7$, —COOCH(CH$_3$)$_2$, —COOC(CH$_3$)$_3$, —OOC—CH$_3$, —OOC—CF$_3$, —OOC—C$_2$H$_5$, —OOC—C$_3$H$_7$, —OOC—CH(CH$_3$)$_2$, —OOC—C(CH$_3$)$_3$, —NH$_2$, —NHCH$_3$, —NHC$_2$H$_5$, —NHC$_3$H$_7$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N[CH(CH$_3$)$_2$]$_2$, —N[C(CH$_3$)$_3$]$_2$, —NHCOCH$_3$, —NHCOCF$_3$, —NHCOC$_2$H$_5$, —NHCOC$_3$H$_7$, —NHCOCH(CH$_3$)$_2$, —NHCOC(CH$_3$)$_3$, —CONH$_2$, —CONHCH$_3$, —CONHC$_2$H$_5$, —CONHC$_3$H$_7$, —CONHCH(CH$_3$)$_2$, —CONH-cyclo-C$_3$H$_5$, —CONHC(CH$_3$)$_3$, —CON(CH$_3$)$_2$, —CON(C$_2$H$_5$)$_2$, —CON(C$_3$H$_7$)$_2$, —CON[CH(CH$_3$)$_2$]$_2$, —CON[C(CH$_3$)$_3$]$_2$, —SO$_2$NH$_2$, —SO$_2$NHCH$_3$, —SO$_2$NHC$_2$H$_5$, —SO$_2$NHC$_3$H$_7$, —SO$_2$NHCH(CH$_3$)$_2$, —SO$_2$NH-cyclo-C$_3$H$_5$, —SO$_2$NHC(CH$_3$)$_3$, —SO$_2$N(CH$_3$)$_2$, —SO$_2$N(C$_2$H$_5$)$_2$, —SO$_2$N(C$_3$H$_7$)$_2$, —SO$_2$N[CH(CH$_3$)$_2$]$_2$, —SO$_2$N[C(CH$_3$)$_3$]$_2$, —NHSO$_2$CH$_3$, —NHSO$_2$CF$_3$, —NHSO$_2$C$_2$H$_5$, —NHSO$_2$C$_3$H$_7$, —NHSO$_2$CH(CH$_3$)$_2$, —NHSO$_2$C(CH$_3$)$_3$, —CH═CH$_2$, —CH$_2$—CH═CH$_2$, —C(CH$_3$)═CH$_2$, —CH═CH—CH$_3$, —C≡CH, —C≡C—CH$_3$, —CH$_2$—C≡CH, -Ph, —O-Ph, or —O—CH$_2$-Ph,

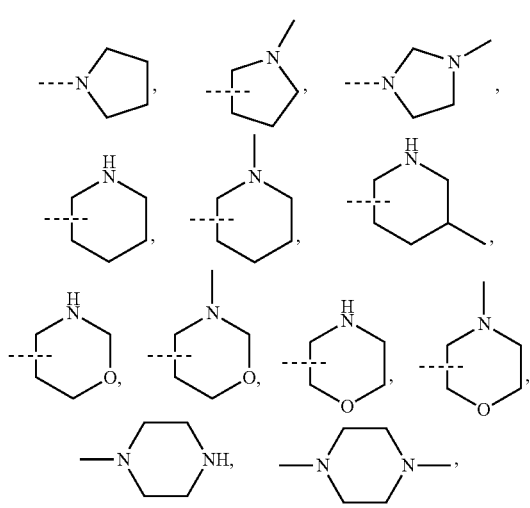

$R^{N3}$ and $R^{N4}$ represent independently of each other —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, -cyclo-C$_3$H$_5$, —CH$_2$-cyclo-C$_3$H$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH═CH$_2$, —CH$_2$Ph, —CHO, —COCH$_3$, —COC$_2$H$_5$, —COC$_3$H$_7$, —COCH(CH$_3$)$_2$, —COC(CH$_3$)$_3$, —COOCH$_3$, —COOC$_2$H$_5$, —COOC$_3$H$_7$, —COOCH(CH$_3$)$_2$, —COOC(CH$_3$)$_3$, or —COOCH$_2$Ph;

$L^9$ and $L^{10}$ are independently of each other: a covalent bond, —CH$_2$—, —CH$_2$CH$_2$—. —CO—, —CH$_2$CO—, —COCH$_2$—, —CO—CH═CH—, —COO—, —O—CO—, —CH$_2$CO$_2$—, —CO$_2$CH$_2$—, —CONH—, —NHCO—, —CH$_2$CONH—, —CONHCH$_2$—, —CSNH—, —NHCS—, —SO$_2$—, —SO$_2$CH$_2$—, —SO$_2$NH—, or —SO$_2$NHCH$_2$—;

and diastereomer, enantiomer, mixture of diastereomers, mixture of enantiomer, racemates, prodrugs, solvates, hydrates, or pharmaceutically acceptable salts thereof.

More preferred, the compound of the following formulae (XIV-1) and (XIV-2):

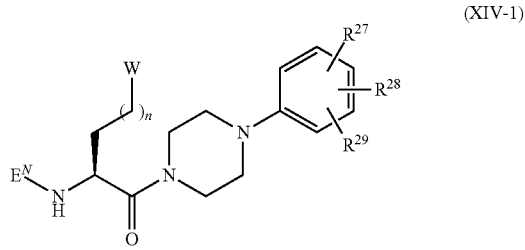

(XIV-1)

wherein n, W, $E^N$ and $R^{27}$-$R^{29}$ have the same meanings as defined above.

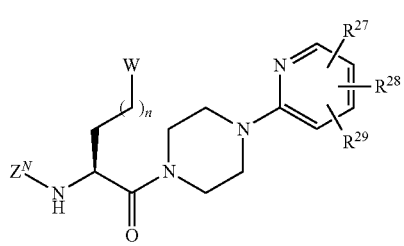

(XIV-2)

wherein $Z^N$ represents $E^N$-, or $E^N$-$AS^{N1}$-; preferred, $AS^{N1}$ is proline backbone;

n, W, and $R^{27}$-$R^{29}$ have the same meanings as defined above.

In the present invention, the following amino acids containing a chemical warhead are especially useful for producing the inventive compounds:

AS^{W4}
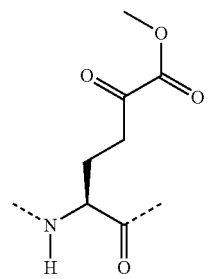
AS^{W20}
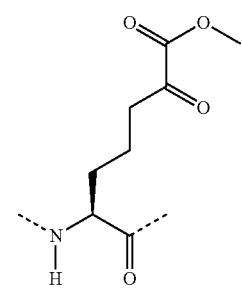
AS^{W5}
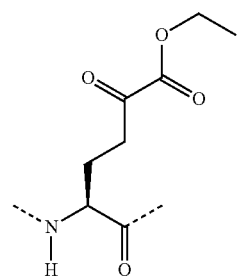
AS^{W21}
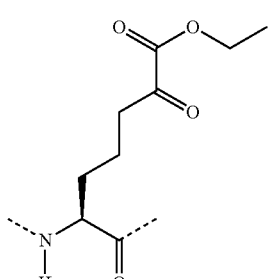
AS^{W6}
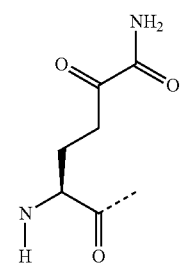
AS^{W22}
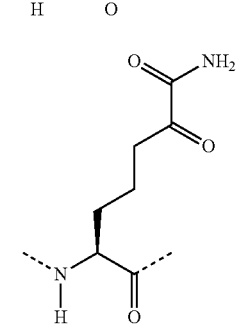
AS^{W7}
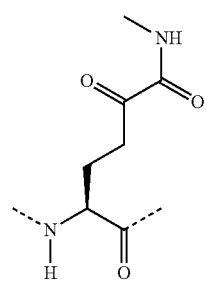
AS^{W23}
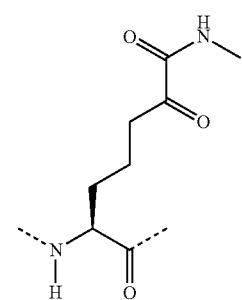
AS^{W8}
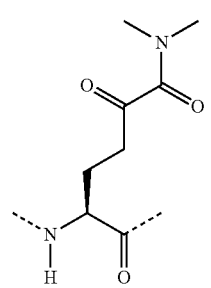
AS^{W24}
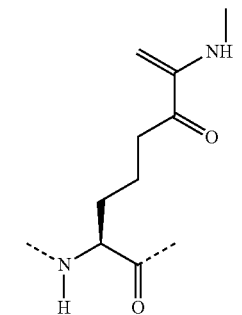

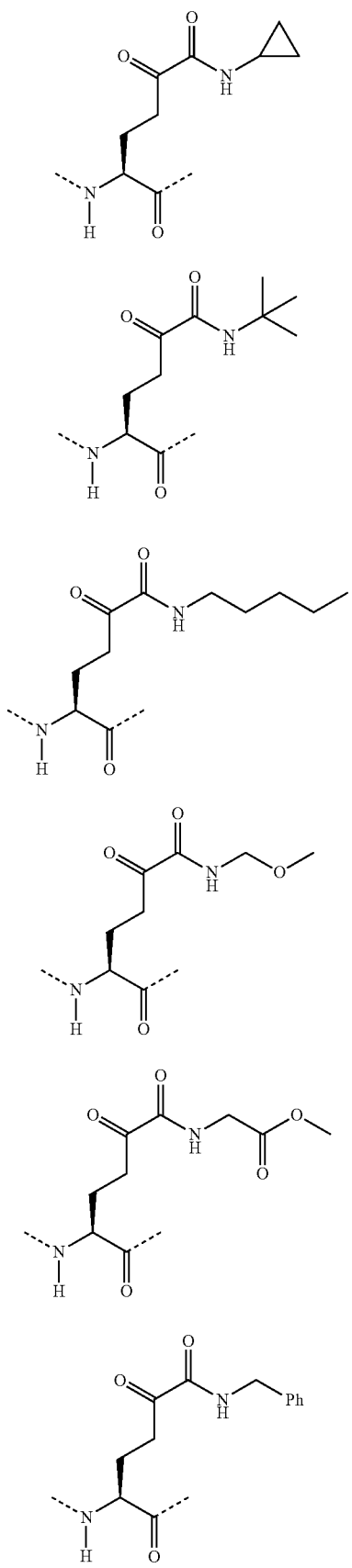
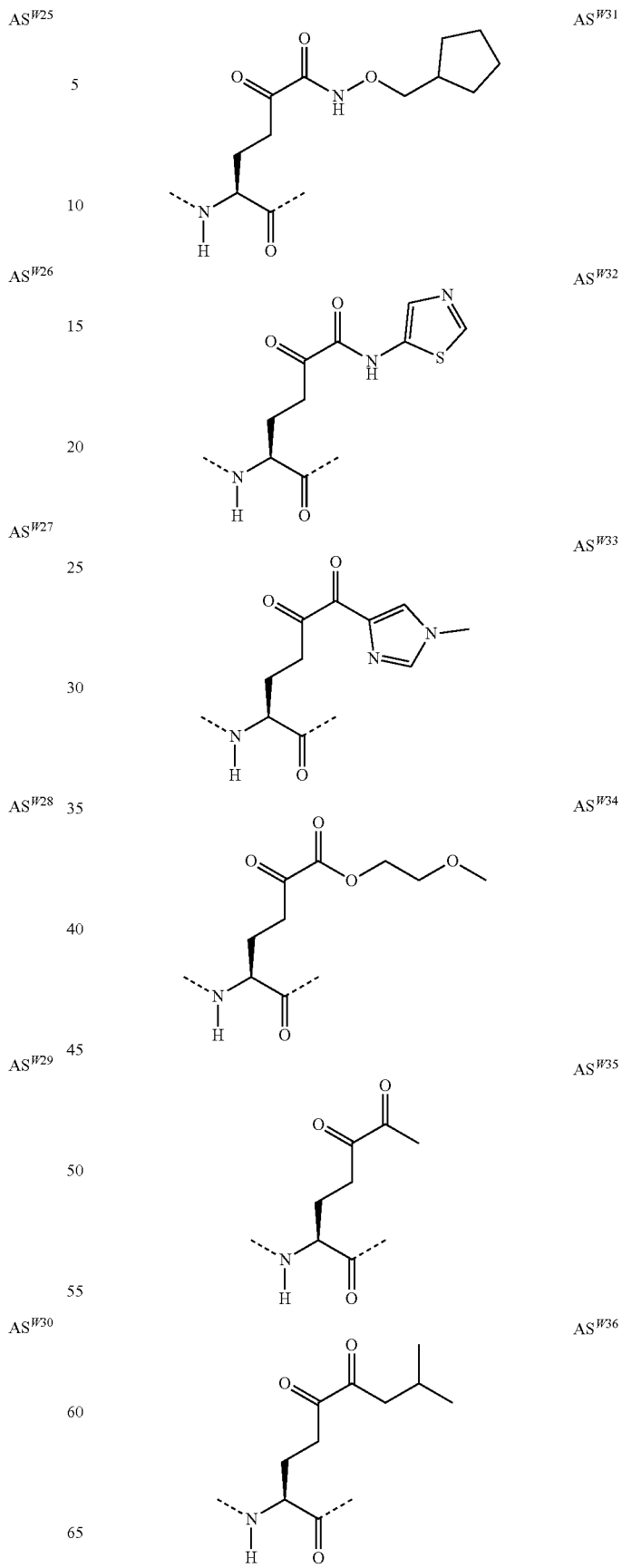

-continued

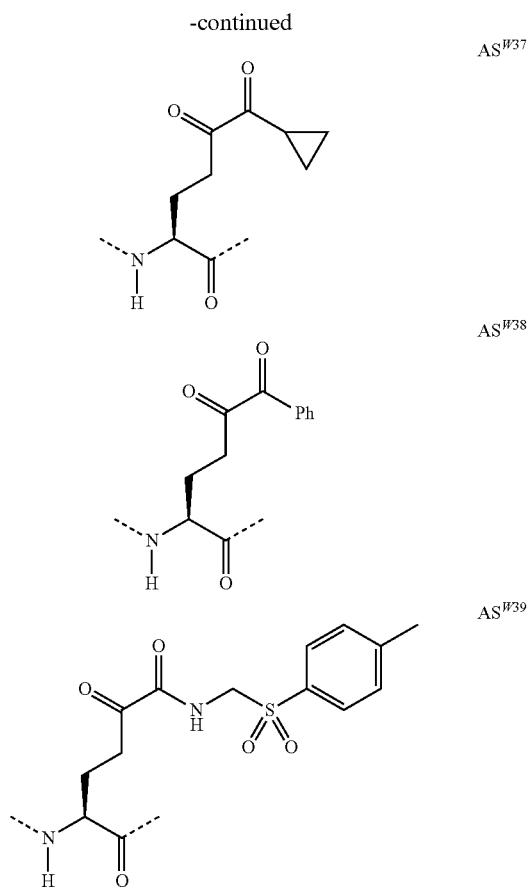

According to the present invention, compounds selected from the group consisting of:
- (S)-methyl 2-((S)-1-((S)-2-((S)-2-acetamido-6-amino-5,6-dioxohexanamido)-3-methylbutanoyl)pyrrolidine-2-carboxamido)-4-methylpentanoate (E01),
- (S)-methyl 2-((S)-1-((S)-2-((S)-6-amino-2-(benzyloxycarbonylamino)-5,6-dioxo-hexanamido)-3-methylbutanoyl)pyrrolidine-2-carboxamido)-4-methylpentanoate (E02),
- (S)-2-acetamido-N1-((S)-5-amino-1-((2S,3R)-1-((S)-1-amino-3-methyl-1-oxobutan-2-ylamino)-3-methyl-1-oxopentan-2-ylamino)-1,5-dioxopentan-2-yl)-5-oxo-hexanediamide (E03),
- (S)—N1-(1-(2-(2-ethylbutylamino)-2-oxoethyl)-2-oxo-1,2-dihydropyridin-3-yl)-2-(1-methyl-1H-imidazole-5-carboxamido)-5-oxohexanediamide (E04),
- (S)-2-(2-bromo-4-methylthiazole-5-carboxamido)-N1-(1-(2-(isopentylamino)-2-oxoethyl)-2-oxo-1,2-dihydropyridin-3-yl)-5-oxohexanediamide (E05),
- (S)-5-acetamido-6-(4-(2-chlorophenyl)piperazin-1-yl)-2,6-dioxohexanamide (E06),
- (S)-1-acetyl-N—((S)-6-amino-1-(4-(3-methylpyridin-2-yl)piperazin-1-yl)-1,5,6-trioxohexan-2-yl)pyrrolidine-2-carboxamide (E07),
- (S)-1-((S)-2-((S)-1-((4R,7S,10S,13S,16S)-7-(4-amino-3,4-dioxobutyl)-10, -dibutyl-4-(carboxymethyl)-18-methyl-2,5,8,11,14-pentaoxo-3,6,9,12,15-pentaazanonadecanecarbonyl)pyrrolidine-2-carboxamido)-3-(1H-indol-3-yl)propanoyl)pyrrolidine-2-carboxylic acid (E08),
- (S)—N1-((S)-1-((R)-2-((S)-2-((S)-2-amino-1-cyclohexyl-2-oxoethylamino)-1-cyclohexyl-2-oxoethylcarbamoyl)piperidin-1-yl)-3,3-dimethyl-1-oxobutan-2-yl)-2-(6-hydroxy-5-nitronicotinamido)-5-oxohexanediamide (E09),
- 3-((2S)-6-amino-1-((2S)-3-cyclopropyl-1-((1R,2S)-2-((2S)-1-((2S)-2-(1-(2,6-dimethylphenoxy)propan-2-ylcarbamoyl)-2-methylpyrrolidin-1-yl)-1-oxopentan-2-ylcarbamoyl)-6,6-dimethyl-3-azabicyclo[3.1.0]hexan-3-yl)-1-oxopropan-2-ylamino)-1,5,6-trioxonexan-2-ylcarbamoyl)-5-nitrobenzoic acid (E10),
- (S)—N1-(1-(2-(2-ethylbutylamino)-2-oxoethyl)-2-oxo-1,2-dihydropyridin-3-yl)-5-oxo-2-(pyrazine-2-carboxamido)hexanediamide (E11),
- (S)-2-benzamido-N1-(1-(2-(2-ethylbutylamino)-2-oxoethyl)-2-oxo-1,2-dihydropyridin-3-yl)-5-oxonexanediamide (E12),
- (S)—N1-(1-(2-(2-ethylbutylamino)-2-oxoethyl)-2-oxo-1,2-dihydropyridin-3-yl)-2-(2-ethyl-5-nitrobenzamido)-5-oxohexanediamide (E13),
- (S)—N1-(1-(2-(2-ethylbutylamino)-2-oxoethyl)-2-oxo-1,2-dihydropyridin-3-yl)-2-(4-methylthiazole-5-carboxamido)-5-oxohexanediamide (E14),
- (S)-2-(5-(dimethylamino)naphthalene-1-sulfonamido)-N1-(1-(2-(2-ethylbutylamino)-2-oxoethyl)-2-oxo-1,2-dihydropyridin-3-yl)-5-oxonexanediamide (E15),
- (S)—N1-(1-(2-(2-ethylbutylamino)-2-oxoethyl)-2-oxo-1,2-dihydropyridin-3-yl)-N6-methyl-2-(1-methyl-1H-imidazole-5-carboxamido)-5-oxonexanediamide (E16),
- (S)—N1-ethyl-N6-(1-(2-(2-ethylbutylamino)-2-oxoethyl)-2-oxo-1,2-dihydropyridin-3-yl)-5-(1-methyl-1H-imidazole-5-carboxamido)-2-oxonexanediamide (E17),
- (S)—N1-(1-(2-(2-ethylbutylamino)-2-oxoethyl)-2-oxo-1,2-dihydropyridin-3-yl)-2-(1-methyl-1H-imidazole-5-carboxamido)-5-oxo-N6-pentylnexanediamide (E18),
- (S)—N1-cyclopropyl-N6-(1-(2-(2-ethylbutylamino)-2-oxoethyl)-2-oxo-1,2-dihydropyridin-3-yl)-5-(1-methyl-1H-imidazole-5-carboxamido)-2-oxonexanediamide (E19),
- (S)—N1-benzyl-N6-(1-(2-(2-ethylbutylamino)-2-oxoethyl)-2-oxo-1,2-dihydropyridin-3-yl)-5-(1-methyl-1H-imidazole-5-carboxamido)-2-oxonexanediamide (E20),
- (S)—N1-tert-butyl-N6-(1-(2-(2-ethylbutylamino)-2-oxoethyl)-2-oxo-1,2-dihydropyridin-3-yl)-5-(1-methyl-1H-imidazole-5-carboxamido)-2-oxonexanediamide (E21),
- (S)-2-((S)-1-acetylpyrrolidine-2-carboxamido)-N1-(1-(2-(2-ethylbutylamino)-2-oxoethyl)-2-oxo-1,2-dihydropyridin-3-yl)-5-oxo-N6-pentylhexanediamide (E22),
- (S)-2-benzamido-N6-cyclopropyl-N1-(1-(2-(2-ethylbutylamino)-2-oxoethyl)-2-oxo-1,2-dihydropyridin-3-yl)-5-oxonexanediamide (E23),
- (S)-methyl 2-((S)-1-((S)-2-((S)-2-benzamido-6-(cyclopropylamino)-5,6-dioxonexan-amido)-3-methylbutanoyl)pyrrolidine-2-carboxamido)-4-methylpentanoate (E24),
- 4-((S)-1-((S)-1-((S)-2-((S)-2-amino-1-cyclonexyl-2-oxoethylamino)-1-cyclonexyl-2-oxoethylcarbamoyl)-4-oxopyrrolidin-1-yl)-3,3-dimethyl-1-oxobutan-2-ylamino)-6-(methylamino)-1,5,6-trioxohexan-2-ylcarbamoyl)nicotinic acid (E25),
- 4-((S)-1-((S)-1-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-6-(ethylamino)-1,5,6-trioxohexan-2-ylcarbamoyl)nicotinic acid (E26),
- 4-((S)-1-((S)-1-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-6-1,5,6-trioxo-6-(pentylamino)hexan-2-ylcarbamoyl)nicotinic acid (E27),
- 4-((S)-1-((S)-1-((S)-2-((S)-2-amino-1-cyclohexyl-2-oxoethylamino)-1-cyclo-hexyl-2-oxoethylcarbamoyl)-4-oxopyrrolidin-1-yl)-3,3-dimethyl-1-oxobutan-2-ylamino)-6-(cyclopropylamino)-1,5,6-trioxohexan-2-ylcarbamoyl)nicotinic acid (E28),
4-((S)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-6-(benzylamino)-1,5,6-trioxohexan-2-ylcarbamoyl)nicotinic acid (E29),
4-((S)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-6-(tert-butylamino)-1,5,6-trioxohexan-2-ylcarbamoyl)nicotinic acid (E30),
4-((S)-6-amino-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-1,5,6-trioxohexan-2-ylcarbamoyl)nicotinic acid (E31),
(S)—N1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-yl)-N6-cyclopropyl-2-(2-methylthiazole-4-carboxamido)-5-oxohexanediamide (E32),
(S)—N1-((S)-1-((2R,3S)-1-((S)-1-((S)-2-((S)-1-((S)-2-carbamoylpyrrolidin-1-yl)-3-(1H-indol-3-yl)-1-oxopropan-2-ylcarbamoyl)pyrrolidin-1-yl)-4-methyl-1-oxopentan-2-ylamino)-3-methyl-1-oxopentan-2-ylamino)-4-methyl-1-oxopentan-2-yl)-N6-cyclopropyl-2-(2-methylthiazole-4-carboxamido)-5-oxohexanediamide (E33),
(S)-2-(2-acetamidoacetamido)-N1-((S)-1-((2S,3S)-1-((S)-1-((S)-2-((S)-1-amino-3-(1H-indol-3-yl)-1-oxopropan-2-ylcarbamoyl)pyrrolidin-1-yl)-4-methyl-1-oxopentan-2-ylamino)-3-methyl-1-oxopentan-2-ylamino)-1-oxohexan-2-yl)-N6-methyl-5-oxohexanediamide (E34),
(S)-2-(2-((S)-1-acetylpyrrolidine-2-carboxamido)acetamido)-N1-((S)-1-((2S,3S)-1-((S)-1-((S)-2-((S)-1-amino-3-(1H-indol-3-yl)-1-oxopropan-2-ylcarbamoyl)pyrrolidin-1-yl)-4-methyl-1-oxopentan-2-ylamino)-3-methyl-1-oxopentan-2-ylamino)-1-oxohexan-2-yl)-N6-methyl-5-oxohexanediamide (E35),
(S)-2-(2-((S)-1-(2-acetamidoacetyl)pyrrolidine-2-carboxamido)acetamido)-N1-((S)-1-((2S,3S)-1-((S)-1-((S)-2-((S)-1-amino-3-(1H-indol-3-yl)-1-oxopropan-2-ylcarbamoyl)pyrrolidin-1-yl)-4-methyl-1-oxopentan-2-ylamino)-3-methyl-1-oxopentan-2-ylamino)-1-oxohexan-2-yl)-N6-methyl-5-oxohexanediamide (E36),
(S)-2-(2-((S)-1-(2-((S)-2-acetamido-4-methylpentanamido)acetyl)pyrrolidine-2-carboxamido)acetamido)-N1-((S)-1-((2S,3S)-1-((S)-1-((S)-2-((S)-1-amino-3-(1H-indol-3-yl)-1-oxopropan-2-ylcarbamoyl)pyrrolidin-1-yl)-4-methyl-1-oxopentan-2-ylamino)-3-methyl-1-oxopentan-2-ylamino)-1-oxohexan-2-yl)-N6-methyl-5-oxohexanediamide (E37),
(S)-methyl 2-(6-(1-(2-(2-ethylbutylamino)-2-oxoethyl)-2-oxo-1,2-dihydropyridin-3-ylamino)-5-(1-methyl-1H-imidazole-5-carboxamido)-2,6-dioxohexanamido)acetat (E38),
(S)—N1-(1-(2-(2-ethylbutylamino)-2-oxoethyl)-2-oxo-1,2-dihydropyridin-3-yl)-N6-(methoxymethyl)-2-(1-methyl-1H-imidazole-5-carboxamido)-5-oxohexanediamide (E39),
(S)—N1-(1-(2-(2-ethylbutylamino)-2-oxoethyl)-2-oxo-1,2-dihydropyridin-3-yl)-2-(1-methyl-1H-imidazole-5-carboxamido)-5-oxo-N6-(thiazol-5-yl)hexanediamide (E40),
(S)—N1-(1-(2-(2-ethylbutylamino)-2-oxoethyl)-2-oxo-1,2-dihydropyridin-3-yl)-2-(1-methyl-1H-imidazole-5-carboxamido)-5-oxo-N6-(tosylmethyl)hexanediamide (E41),
(S)—N1-(1-(2-(2-ethylbutylamino)-2-oxoethyl)-4-methyl-2-oxo-1,2-dihydropyridin-3-yl)-N6-methyl-2-(1-methyl-1H-imidazole-5-carboxamido)-5-oxohexanediamide (E42),
(S)—N1-(1-(2-(2-ethylbutylamino)-2-oxoethyl)-5-methyl-2-oxo-1,2-dihydropyridin-yl)-N6-methyl-2-(1-methyl-1H-imidazole-5-carboxamido)-5-oxohexanediamide (E43),
(S)—N1-(1-(2-(2-ethylbutylamino)-2-oxoethyl)-6-methyl-2-oxo-1,2-dihydropyridin-3-yl)-N6-methyl-2-(1-methyl-1H-imidazole-5-carboxamido)-5-oxohexanediamide (E44),
(S)—N1-(5-chloro-1-(2-(2-ethylbutylamino)-2-oxoethyl)-2-oxo-1,2-dihydropyridin -yl)-N6-methyl-2-(1-methyl-1H-imidazole-5-carboxamido)-5-oxohexanediamide (E45),
(S)—N1-(5-bromo-1-(2-(2-ethylbutylamino)-2-oxoethyl)-2-oxo-1,2-dihydropyridin-3-yl)-N6-methyl-2-(1-methyl-1H-imidazole-5-carboxamido)-5-oxohexanediamide (E46),
(S)—N1-(1-(2-(2-ethylbutylamino)-2-oxoethyl)-2-oxo-5-(trifluoromethyl)-1,2-dihydropyridin-3-yl)-N6-methyl-2-(1-methyl-1H-imidazole-5-carboxamido)-5-oxohexanediamide (E47),
(S)-1-methyl-N-(6-(methylamino)-1,5,6-trioxo-1-(4-(phenylsulfonyl)piperazin-1-yl)hexan-2-yl)-1H-imidazole-5-carboxamide (E48),
(S)—N1-(1-benzylpiperidin-4-yl)-N6-methyl-2-(1-methyl-1H-imidazole-5-carboxamido)-5-oxohexanediamide (E49),
(S)—N1-(1-(2-(diethylamino)-2-oxoethyl)-2-oxo-1,2-dihydropyridin-3-yl)-N6-methyl-2-(1-methyl-1H-imidazole-5-carboxamido)-5-oxohexanediamide (E50),
(S)—N1-methyl-5-(1-methyl-1H-imidazole-5-carboxamido)-N6-(1-(2-(methylsulfonamido)-2-oxoethyl)-2-oxo-1,2-dihydropyridin-3-yl)-2-oxohexanediamide (E51),
(S)-ethyl 2-(3-(2-(1-methyl-1H-imidazole-5-carboxamido)-6-(methylamino)-5,6-dioxohexanamido)-2-oxopyridin-1(2H)-yl)acetate (E52),
(S)-2-methoxyethyl 2-(3-(2-(1-methyl-1H-imidazole-5-carboxamido)-6-(methylamino)-5,6-dioxohexanamido)-2-oxopyridin-1(2H)-yl)acetate (E53),
(S)—N1-(1-(2-((methoxymethylamino)-2-oxoethyl)-2-oxo-1,2-dihydropyridin-3-yl)-N6-methyl-2-(1-methyl-1H-imidazole-5-carboxamido)-5-oxohexanediamide (E54),
(S)-N1-(1-(2-((dimethylamino)methylamino)-2-oxoethyl)-2-oxo-1,2-dihydropyridin-3-yl)-N6-methyl-2-(1-methyl-1H-imidazole-5-carboxamido)-5-oxohexanediamide (E55),
(S)—N1-(1-(2-(ethylsulfonamido)-2-oxoethyl)-2-oxo-1,2-dihydropyridin-3-yl)-N6-methyl-2-(1-methyl-1H-imidazole-5-carboxamido)-5-oxohexanediamide (E56),
(S)-benzyl 1-(1-(2-(2-ethylbutylamino)-2-oxoethyl)-2-oxo-1,2-dihydropyridin-3-ylamino)-6-(methylamino)-1,5,6-trioxohexan-2-ylcarbamate (E57),
(S)-tert-butyl 1-(1-(2-(2-ethylbutylamino)-2-oxoethyl)-2-oxo-1,2-dihydropyridin-3-ylamino)-6-(methylamino)-1,5,6-trioxohexan-2-ylcarbamate (E58),
(S)-4-(1-(1-(2-(2-ethylbutylamino)-2-oxoethyl)-2-oxo-1,2-dihydropyridin-3-ylamino)-6-(methylamino)-1,5,6-trioxohexan-2-ylamino)-4-oxobutanoic acid (E59),
(S)—N1-(1-(2-(2-ethylbutylamino)-2-oxoethyl)-2-oxo-1,2-dihydropyridin-3-yl)-N6-methyl-5-oxo-2-((S)-4-oxopyrrolidine-2-carboxamido)hexanediamide (E60), (S)—N1-(1-(2-(2-ethylbutylamino)-2-oxoethyl)-2-oxo-1,2-dihydropyridin-3-yl)-2-(furan-3-carboxamido)-N6-methyl-5-oxohexanediamide (E61), (S)—N1-(1-(2-(2-ethylbutylamino)-2-oxoethyl)-2-oxo-1,2-dihydropyridin-3-yl)-N6-methyl-2-(oxazole-5-carboxamido)-5-oxohexanediamide (E62), (S)—N1-(1-(2-(2-ethylbutylamino)-2-oxoethyl)-2-oxo-1,2-dihydropyridin-3-yl)-N6-methyl-2-(1-methylpiperidine-4-carboxamido)-5-oxohexanediamide (E63), (S)—N1-(1-(2-(2-ethylbutylamino)-2-oxoethyl)-2-oxo-1,2-dihydropyridin-3-yl)-N6-methyl-5-oxo-2-(pyrimidine-5-carboxamido)hexanediamide (E64), (S)—N1-(1-(2-(2-ethylbutylamino)-2-oxoethyl)-2-oxo-1,2-dihydropyridin-3-yl)-N6-methyl-5-oxo-2-(quinoxaline-2-carboxamido)hexanediamide (E65), (S)-2-(2,4-dimethylthiazole-5-sulfonamido)-N1-(1-(2-(2-ethylbutylamino)-2-oxoethyl)-26 oxo-1,2-dihydropyridin-3-yl)-N6-methyl-5-oxohexanediamide (E66), (S)-2-(6-chloroimidazo[2,1-b]thiazole-5-sulfonamido)-N1-(1-(2-(2-ethylbutylamino)-2-oxoethyl)-2-oxo-1,2-dihydropyridin-3-yl)-N6-methyl-5-oxohexanediamide (E67), (S)—N1-(1-(2-(2-ethylbutylamino)-2-oxoethyl)-2-oxo-1,2-dihydropyridin-3-yl)-N6-methyl-2-(1-methyl-1H-imidazole-2-sulfonamido)-5-oxohexanediamide (E68), (S)—N1-(1-(2-(2-ethylbutylamino)-2-oxoethyl)-2-oxo-1,2-dihydropyridin-3-yl)-N6-methyl-5-oxo-2-(3-phenylureido)hexanediamide (E69), (S)—N1-(1-(2-(2-ethylbutylamino)-2-oxoethyl)-2-oxo-1,2-dihydropyridin-3-yl)-N6-methyl-5-oxo-2-(3-phenylthioureido)hexanediamide (E70), (S)—N1-(1-(2-(2-ethylbutylamino)-2-oxoethyl)-2-oxo-1,2-dihydropyridin-3-yl)-N7-methyl-2-(1-methyl-1H-imidazole-5-carboxamido)-6-oxoheptanediamide (E71), (S)—N1-methyl-6-(1-methyl-1H-imidazole-5-carboxamido)-N7-(4-(4-methylpiperazin-1-ylsulfonyl)phenyl)-2-oxoheptanediamide (E72), (S)—N1-(1-(2-(2-ethylbutylamino)-2-oxoethyl)-2-oxo-1,2-dihydropyridin-3-yl)-N8-methyl-2-(1-methyl-1H-imidazole-5-carboxamido)-7-oxooctanediamide (E73), (S)—N-(1-(1-(2-(2-ethylbutylamino)-2-oxoethyl)-2-oxo-1,2-dihydropyridin-3-ylamino)-1,5,6-trioxoheptan-2-yl)-1-methyl-1H-imidazole-5-carboxamide (E74), (S)—N-(6-cyclopropyl-1-(1-(2-(2-ethylbutylamino)-2-oxoethyl)-2-oxo-1,2-dihydropyridin-3-ylamino)-1,5,6-trioxohexan-2-yl)-1-methyl-1H-imidazole-5-carboxamide (E75), (S)—N-(1-(1-(2-(2-ethylbutylamino)-2-oxoethyl)-2-oxo-1,2-dihydropyridin-3-ylamino)-1,5,6-trioxo-6-phenylhexan-2-yl)-1-methyl-1H-imidazole-5-carboxamide (E76), (S)-methyl 6-(1-(2-(2-ethylbutylamino)-2-oxoethyl)-2-oxo-1,2-dihydropyridin-3-ylamino)-5-(1-methyl-1H-imidazole-5-carboxamido)-2,6-dioxohexanoate (E77), (S)-2-methoxyethyl 6-(1-(2-(2-ethylbutylamino)-2-oxoethyl)-2-oxo-1,2-dihydropyridin-3-ylamino)-5-(1-methyl-1H-imidazole-5-carboxamido)-2,6-dioxohexanoate (E78), (S)—N1-(cyclopentylmethoxy)-N6-(1-(2-(2-ethylbutylamino)-2-oxoethyl)-2-oxo-1,2-di-hydropyridin-3-yl)-5-(1-methyl-1H-imidazole-5-carboxamido)-2-oxohexanediamide (E79), (S)—N-(1-(1-(2-(2-ethylbutylamino)-2-oxoethyl)-2-oxo-1,2-dihydropyridin-3-ylamino)-8-methyl-1,5,6-trioxononan-2-yl)-1-methyl-1H-imidazole-5-carboxamide (E80), (S)—N-(1-(1-(2-(2-ethylbutylamino)-2-oxoethyl)-2-oxo-1,2-dihydropyridin-3-ylamino)-6-(1-methyl-1H-imidazol-4-yl)-1,5,6-trioxohexan-2-yl)-1-methyl-1H-imidazole-5-carboxamide (E81), (2S)-N1-((S)-1-((S)-3-carbamoyl-3,4-dihydroisoquinolin-2(1H)-yl)-3-(4-hydroxy-phenyl)-1-oxopropan-2-ylamino)-3-(1H-imidazol-4-yl)-1-oxopropan-2-yl)-2-(2-(5,5-dimethyl-2-oxotetrahydrofuran-3-yl)acetamido)-N6-methyl-5-oxohexanediamide (E82), (S)—N1-(3-((S)-3-(biphenyl-4-yl)-1-((2S,4R)-2-carbamoyl-4-phenoxypyrrolidin-1-yl)-1-oxopropan-2-ylcarbamoyl)phenyl)-2-(2-(1,3-dimethyl-1H-pyrazol-5-yl)acetamido)-N6-methyl-5-oxohexanediamide (E83), and isopropyl (S)-1-((S)-1-(1-((2S,4R)-2-carbamoyl-4-hydroxy-pyrrolidin-1-yl)-2-methyl-1-oxopropan-2-ylamino)-5-guanidino-1-oxopentan-2-ylamino)-6-(methylamino)-1,5,6-trioxohexan-2-ylcarbamate (E84) are especially preferred.

A further aspect of the present invention relates to the production of compounds of the general formula (I).

As shown in Scheme 1, a method for producing the compound of the present invention comprises:

Step (0): providing a protected amino acid having a chemical warhead;

Step 1A: deprotecting a carboxyl protecting group $PG^3$;

Step 2A: performing coupling reaction with a C-terminal building block $E^C$-$AG^1$;

Step 3A: deprotecting two amino protecting groups $PG^1$ and $PG^2$;

Step 4A: performing coupling reaction with a N-terminal building block $E^N$-$AG^2$; to produce the compound of the formula (I).

Optionally, Step 1A° is carried out between the step 1A and the step 2A:

The Step 1K:
(a) performing coupling reaction of a resulting compound of Step 1A with a corresponding C-terminal amino acid building block $H_2AS^{Ci}$-$OPG^4$;
(b) deprotecting the protecting group $PG^4$;
(c) repeating the steps (a) and (b) i times, wherein i is 1-8.

In other option, Step 3A' is carried out between the step 3A and the step 4A:

The Step 3A':
(d) performing coupling reaction of a resulting compound of Step 3A with a corresponding N-terminal amino acid building block $(PG^5)HAS^{Nj}$-OH;
(e) deprotecting the protecting group $PG^5$;
(f) repeating the steps (a) and (b) j times, wherein j is 1-4.

Therefore, the following methods are preferred:

1. Step (0) -Step 1A -Step 1A'-Step 2A -Step 3A -Step 4A:

Step (0): providing a protected amino acid having a chemical warhead;

Step 1A: deprotecting a carboxyl protecting group $PG^3$;

Step 1A':
(a) performing coupling reaction of a resulting compound of Step 1A with a corresponding C-terminal amino acid building block $H_2AS^{Ci}$-$OPG^4$;
(b) deprotecting the protecting group $PG^4$;
(c) repeating the steps (a) and (b) i times, wherein i is 1-8;

Step 2A: performing coupling reaction with a C-terminal building block $E^C$-$AG^1$;

Step 3A: deprotecting two amino protecting groups $PG^1$ and $PG^2$;

Step 4A: performing coupling reaction with a N-terminal building block $E^N$-$AG^2$; to produce the compound of the formula (I).

2. Step (0) -Step 1A -Step 2A -Step 3A -Step 3A'-Step 4A:
Step (0): providing a protected amino acid having a chemical warhead;
Step 1A: deprotecting a carboxyl protecting group $PG^3$;
Step 2A: performing coupling reaction with a C-terminal building block $E^C$-$AG^1$;
Step 3A: deprotecting two amino protecting groups $PG^1$ and $PG^2$;
Step 3A':
  (d) performing coupling reaction of a resulting compound of Step 3A with a corresponding N-terminal amino acid building block $(PG^5)HAS^{Nj}$-OH;
  (e) deprotecting the protecting group $PG^5$;
  (f) repeating the steps (a) and (b) j times, wherein j is 1-4;
Step 4A: performing coupling reaction with a N-terminal building block $E^N$-$AG^2$; to produce the compound of the formula (I).

3. Step (0) -Step 1A -Step 1A'-Step 2A -Step 3A -Step 3A'-Step 4A:
Step (0): providing a protected amino acid having a chemical warhead;
Step 1A: deprotecting a carboxyl protecting group $PG^3$;
Step 1A':
  (a) performing coupling reaction of a resulting compound of Step 1A with a corresponding C-terminal amino acid building block $H_2AS^{Ci}$-$OPG^4$;
  (b) deprotecting the protecting group $PG^4$;
  (c) repeating the steps (a) and (b) i times, wherein i is 1-8
Step 2A: performing coupling reaction with a C-terminal building block $E^C$-$AG^1$;
Step 3A: deprotecting two amino protecting groups $PG^1$ and $PG^2$;
Step 3A':
  (d) performing coupling reaction of a resulting compound of Step 3A with a corresponding N-terminal amino acid building block $(PG^5)HAS^{Nj}$-OH;
  (e) deprotecting the protecting group $PG^5$;
  (f) repeating the steps (a) and (b) j times, wherein j is 1-4.
Step 4A: performing coupling reaction with a N-terminal building block $E^N$-$AG^2$; to produce the compound of the formula (I).

Scheme 1

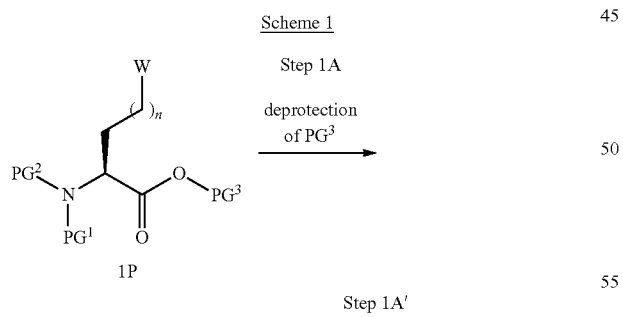

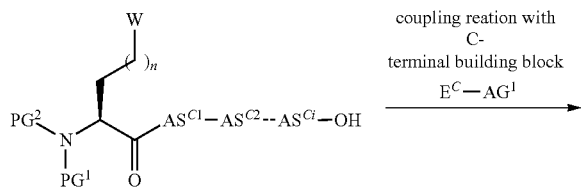

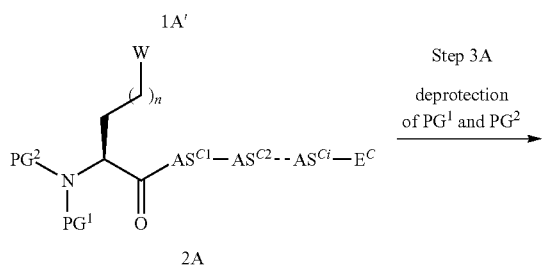

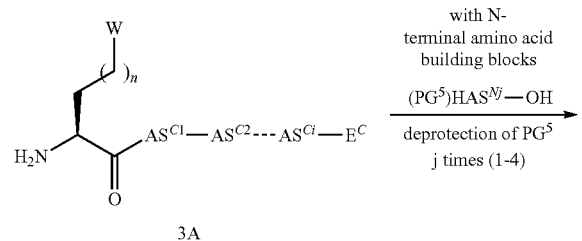

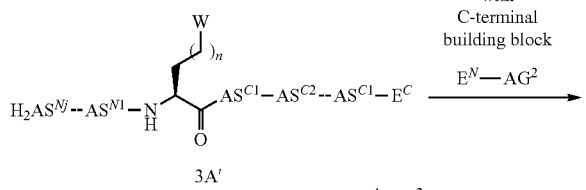

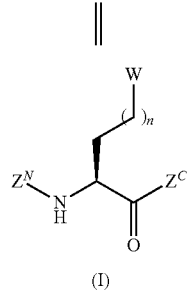

Scheme 2

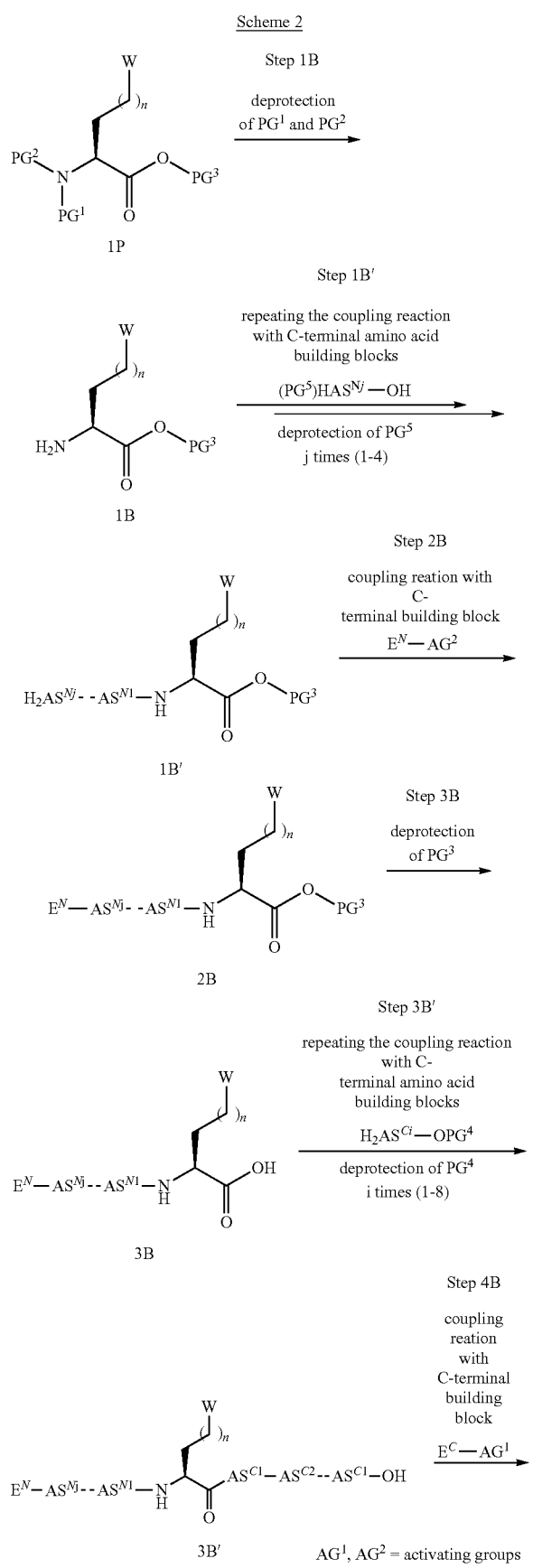

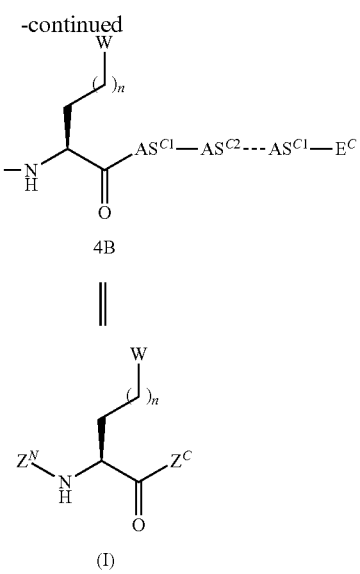

As shown in Scheme 2, an alternative method for producing the compound of the present invention comprises:

Step (0): providing a protected amino acid having a chemical warhead;

Step 1B: deprotecting two amino protecting groups $PG^1$ and $PG^2$;

Step 2B: performing coupling reaction with a N-terminal building block $E^N$-$AG^2$;

Step 3B: deprotecting a carboxyl protecting group $PG^3$;

Step 4B: performing coupling reaction with a C-terminal building block $E^C$-$AG^1$; to produce the compound of the formula (I).

Optionally, Step 1B' is carried out between the step 1B and the step 2B:

The Step 1B':
(a') performing coupling reaction of a resulting compound of Step 1A with a corresponding N-terminal amino acid building block $(PG^5)HAS^{Nj}$-OH;
(b') deprotecting the protecting group $PG^5$;
(c') repeating the steps (a) and (b) j times, wherein j is 1-4.

In other option, Step 3B' is carried out between the step 3B and the step 4B:

The Step 3B':
(d') performing coupling reaction of a resulting compound of Step 3B with a corresponding C-terminal amino acid building block $H_2AS^{Cj}$-$OPG^4$;
(e') deprotecting the protecting group $PG^4$;
(f') repeating the steps (a) and (b) i times, wherein i is 1-8.

Therefore, the following methods are available:

1. Step (0) -Step 1B -Step 1B'-Step 2B -Step 3B -Step 4B:

Step (0): providing a protected amino acid having a chemical warhead;

Step 1B: deprotecting two amino protecting groups $PG^1$ and $PG^2$;

Step 1B':
(a') performing coupling reaction of a resulting compound of Step 1A with a corresponding N-terminal amino acid building block $(PG^5)HAS^{Nj}$-OH:
(b') deprotecting the protecting group $PG^5$;
(c') repeating the steps (a) and (b) j times, wherein j is 1-4;

Step 2B: performing coupling reaction with a N-terminal building block $E^N$-$AG^2$;

Step 3B: deprotecting a carboxyl protecting group $PG^3$;

Step 4B: performing coupling reaction with a C-terminal building block $E^C$-$AG^1$; to produce the compound of the formula (I).

2. Step (0) -Step 1A -Step 2A -Step 3A -Step 3A' Step 4A:
Step (0): providing a protected amino acid having a chemical warhead;
Step 1B: deprotecting two amino protecting groups $PG^1$ and $PG^2$;
Step 2B: performing coupling reaction with a N-terminal building block $E^N$-$AG^2$;
Step 3B: deprotecting a carboxyl protecting group $PG^3$;
Step 3B':
 (d') performing coupling reaction of a resulting compound of Step 3B with a corresponding C-terminal amino acid building block $H_2AS^{Ci}$-$OPG^4$;
 (e') deprotecting the protecting group $PG^4$;
 (f') repeating the steps (a) and (b) i times, wherein i is 1-8; Step 4B: performing coupling reaction with a C-terminal building block $E^C$-$AG^1$; to produce the compound of the formula (I).

3. Step (0) -Step 1A -Step 1A'-Step 2A -Step 3A -Step 3A'-Step 4A:
Step (0): providing a protected amino acid having a chemical warhead;
Step 1B: deprotecting two amino protecting groups $PG^1$ and $PG^2$;
Step 1B':
 (a') performing coupling reaction of a resulting compound of Step 1A with a corresponding N-terminal amino acid building block $(PG^5)HAS^{Nj}$-OH;
 (b') deprotecting the protecting group $PG^5$;
 (c') repeating the steps (a) and (b) j times, wherein j is 1-4;
Step 2B: performing coupling reaction with a N-terminal building block $E^N$-$AG^2$;
Step 3B: deprotecting a carboxyl protecting group $PG^3$;
Step 3B':
 (d') performing coupling reaction of a resulting compound of Step 3B with a corresponding C-terminal amino acid building block $H_2AS^{Ci}$-$OPG^4$;
 (e') deprotecting the protecting group $PG^4$;
 (f') repeating the steps (a) and (b) i times, wherein i is 1-8;
Step 4B: performing coupling reaction with a C-terminal building block $E^C$-$AG^1$;
to produce the compound of the formula (I).

Herein, $AS^{Ci}$ represent one of $AS^{C1}$, $AS^{C2}$, $AS^{C3}$, $AS^{C4}$, $AS^{C5}$, $AS^{C6}$, $AS^{C7}$, and $AS^{C8}$. $AS^{Nj}$ represents one of $AS^{N1}$, $AS^{N2}$, $AS^{N3}$, and $AS^{N4}$. $H_2AS^{Ci}$-$OPG^4$ means amino acid having $AS^{Ci}$ (one of $AS^{C1}$-$AS^{C8}$) backbone and unprotected free amino ($H_2N$—) group and carboxyl moiety protected by $PG^4$ group. $(PG^5)HAS^{Nj}$-OH, means amino acid having $AS^{Nj}$ (one of $AS^{N1}$-$AS^{N4}$) backbone and amino group protected by a $PG^5$ group [$(PG^5)HN$—)] and unprotected free carboxylic acid (—$CO_2H$).

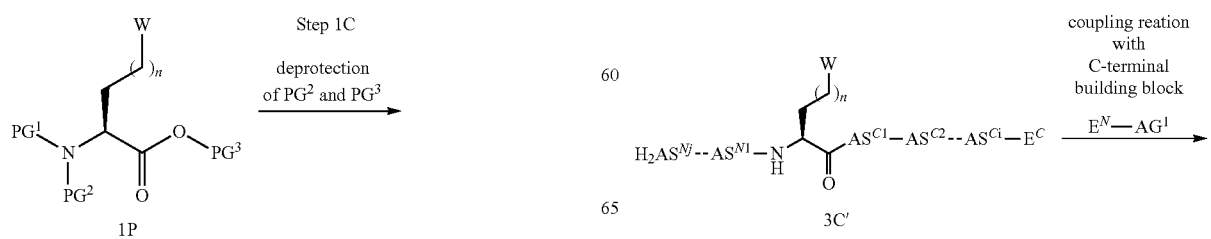

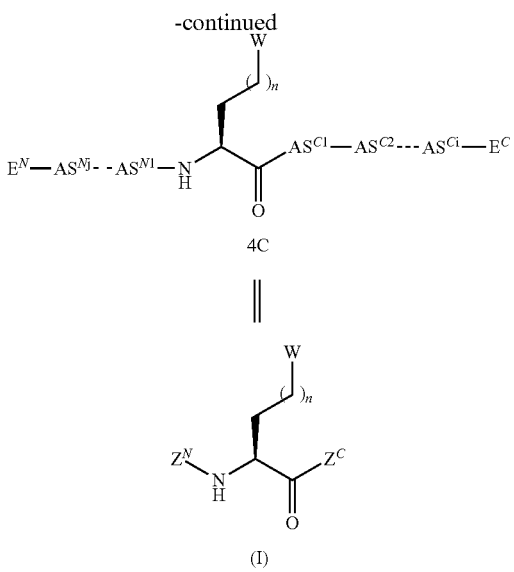

As shown in Scheme 3, an alternative method for producing the compound of the present invention comprises:

Step (0): providing a protected amino acid having a chemical warhead;

Step 1C: deprotecting an amino protecting group $PG^2$ and a carboxyl protecting group $PG^3$;

Step 2C: performing coupling reaction with a C-terminal building block $E^C$-H;

Step 3C: deprotecting an amino protecting group $PG^1$;

Step 4C: performing coupling reaction with a N-terminal building block $E^N$-$AG^1$; to produce the compound of the formula (I).

Optionally, Step 1C' is carried out between the step 1C and the step 2C:

The Step 1C':
- (d) performing coupling reaction of a resulting compound of Step 1C with a corresponding C-terminal amino acid building block $H_2AS^{Ci}$-$OPG^4$;
- (e) deprotecting the protecting group $PG^4$;
- (f) repeating the steps (a) and (b) i times, wherein i is 1-8.

In other option, Step 3C' is carried out between the step 3C and the step 4C:

The Step 3C':
- (d) performing coupling reaction of a resulting compound of Step 3C with a corresponding N-terminal amino acid building block $(PG^5)HAS^{Nj}$-OH;
- (e) deprotecting the protecting group $PG^5$;
- (f) repeating the steps (a) and (b) j times, wherein j is 1-4.

Therefore, the following methods are preferred:

1. Step (0) -Step 1C -Step 1C'-Step 2C-Step 3C-Step 4C:

Step (0): providing a protected amino acid having a chemical warhead;

Step 1C: deprotecting an amino protecting group $PG^2$ and a carboxyl protecting group $PG^3$;

Step 1C':
- (d) performing coupling reaction of a resulting compound of Step 1C with a corresponding C-terminal amino acid building block $H_2AS^{Ci}$-$OPG^4$;
- (e) deprotecting the protecting group $PG^4$;
- (f) repeating the steps (a) and (b) i times, wherein i is 1-8;

Step 2C: performing coupling reaction with a C-terminal building block $E^C$-H;

Step 3C: deprotecting an amino protecting group $PG^1$;

Step 4C: performing coupling reaction with a N-terminal building block $E^N$-$AG^1$;

to produce the compound of the formula (I).

2. Step (0) -Step 1C -Step 2C -Step 3C -Step 3C'-Step 4C:

Step (0): providing a protected amino acid having a chemical warhead;

Step 1C: deprotecting an amino protecting group $PG^2$ and a carboxyl protecting group $PG^3$;

Step 2C: performing coupling reaction with a C-terminal building block $E^C$-H;

Step 3C: deprotecting an amino protecting group $PG^1$;

Step 3O':
- (d) performing coupling reaction of a resulting compound of Step 3C with a corresponding N-terminal amino acid building block $(PG^5)HAS^{Nj}$-OH;
- (e) deprotecting the protecting group $PG^5$;
- (f) repeating the steps (a) and (b) j times, wherein j is 1-4;

Step 4C: performing coupling reaction with a N-terminal building block $E^N$-$AG^1$;

to produce the compound of the formula (I).

3. Step (0) -Step 1C -Step 1C'-Step 2C -Step 3C-Step 3C'-Step 4C:

Step (0): providing a protected amino acid having a chemical warhead;

Step 1C: deprotecting an amino protecting group $PG^2$ and a carboxyl protecting group $PG^3$;

Step 1C':
- (d) performing coupling reaction of a resulting compound of Step 1C with a corresponding C-terminal amino acid building block $H_2AS^{Nj}$-$OPG^4$;
- (e) deprotecting the protecting group $PG^4$;
- (f) repeating the steps (a) and (b) i times, wherein i is 1-8

Step 2C: performing coupling reaction with a C-terminal building block $E^C$-H;

Step 3C: deprotecting an amino protecting group $PG^1$;

Step 3C':
- (d) performing coupling reaction of a resulting compound of Step 3C with a corresponding N-terminal amino acid building block $(PG^5)HAS^{Nj}$-OH;
- (e) deprotecting the protecting group $PG^5$;
- (f) repeating the steps (a) and (b) j times, wherein j is 1-4.

Step 4C: performing coupling reaction with a N-terminal building block $E^N$-$AG^1$; to produce the compound of the formula (I).

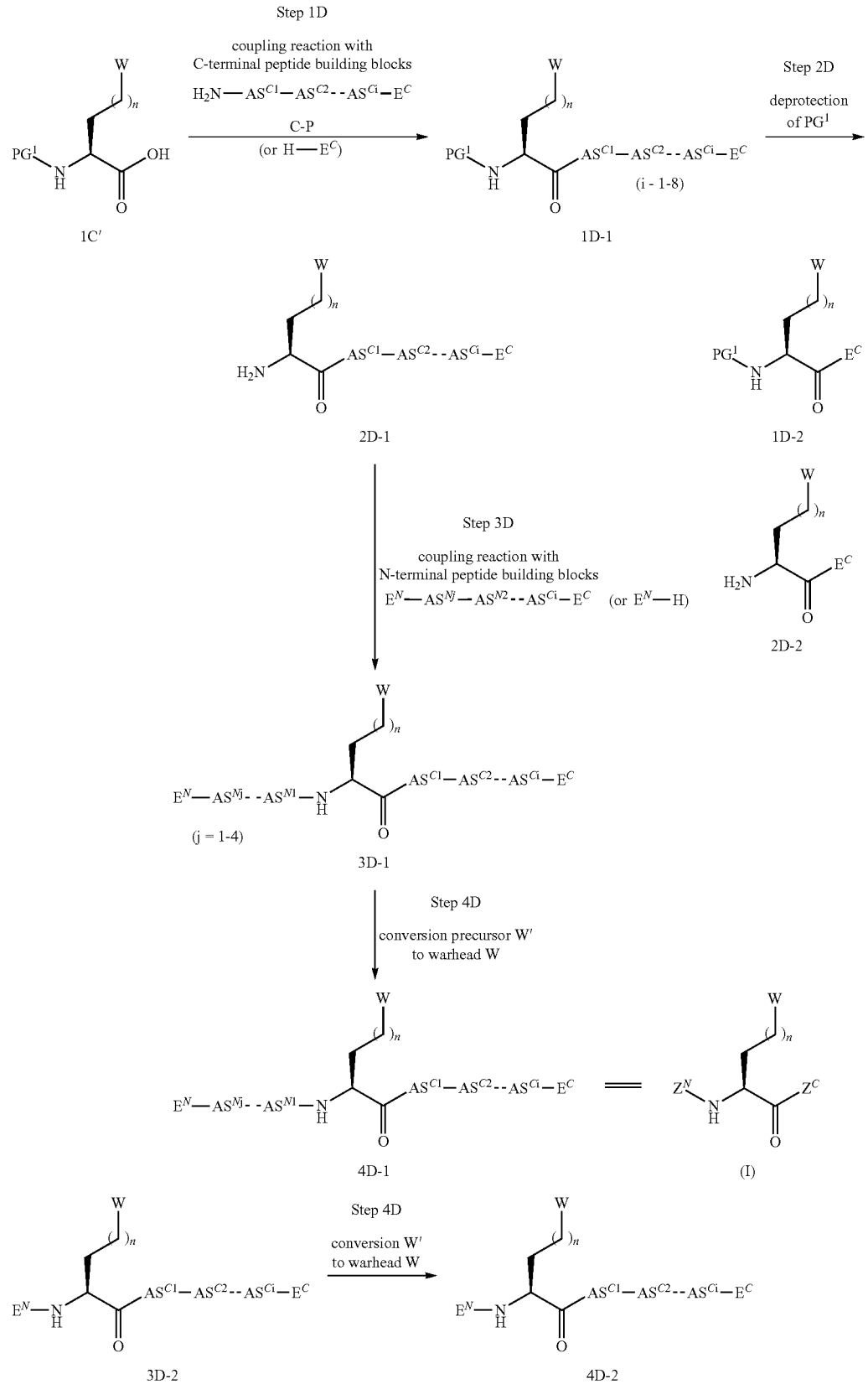

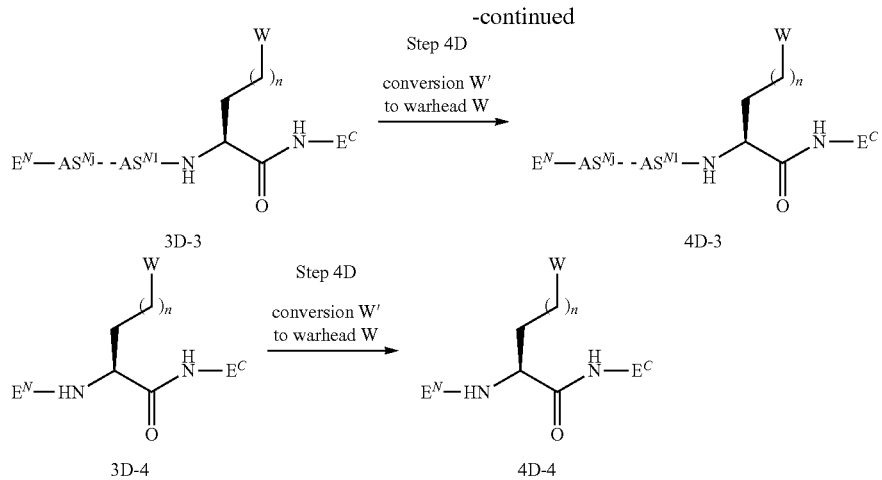

As shown in Scheme 4, an alternative method for producing the compound of the present invention comprises:
Step (0): providing a protected amino acid (1C') having a chemical warhead precursor (W');
Step 1D: performing coupling reaction of the protected amino acid (1C') with a C-terminal peptide building block (C-P) or a C-terminal building block ($E^C$-H) to obtain a compound 1D-1 or 1D-2;
Step 2D: deprotecting an amino protecting group $PG^1$; to obtain a compound 2D-1 or 2D-2;
Step 3D: performing coupling reaction of the compound 2D-1 or 2D-2 with a N-terminal peptide building block (N-P) or a N-terminal building block ($E^N$-H); to obtain a compound 3D-1, 3D-2, 3D-3, or 3D-4;
Step 4D: converting the chemical warhead precursor (W') of the compound 3D-1, 3D-2, 3D-3, or 3D-4 to a chemical precursor (W) to produce a compound 4D-1, 4D-2, 4D-3, or 4D-4 as compound of the formula (I).

Herein, $AS^{Ci}$ represenst one of $AS^{C1}$, $AS^{C2}$, $AS^{C3}$, $AS^{C4}$, $AS^{C5}$, $AS^{C5}$, and $AS^{C8}$. $AS^{Nj}$ represents one of $AS^{N1}$, $AS^{N2}$, $AS^{N3}$, and $AS^{N4}$. $H_2AS^{Ci}$-$OPG^4$ means amino acid having $AS^{Ci}$ (one of $AS^{C1}$-$AS^{C8}$) backbone and unprotected free amino ($H_2N$—) group and carboxyl moiety protected by $PG^4$ group. $(PG^5)HAS^{Nj}$-OH, means amino acid having $AS^{Ni}$ (one of $AS^{N1}$-$AS^{N4}$) backbone and amino group protected by a $PG^5$ group [$(PG^5)HN$—] and unprotected free carboxylic acid (—$CO_2H$).

In an alternative route first all protecting groups $PG^1$ and $PG^2$ and $PG^3$ are simultaneously removed and the protecting group $PG^1$ is selectively re-introduced.

The term "protecting groups" as used herein refers to commonly used protection groups in organic synthesis, preferably for amino and carboxyl groups. $PG^1$, $PG^2$, and $PG^5$ preferably are suitable protecting groups for amino groups. $PG^3$ and $PG^4$ preferably are suitable protecting groups for carboxyl groups. Preferably, $PG^1$, $PG^2$, and $PG^5$ may be selected from the group consisting of or comprising: acetyl, benzoyl, benzyloxycarbonyl (Cbz), tert-butylcarbonyl, tert-butyloxycarbonyl (Boc), and fluorenylmethylenoxy group (Fmoc). $PG^3$ and $PG^4$ may be selected from the group consisting of or comprising: methoxy, ethoxy, isobutoxy, tert-butoxy, benzyloxy; preferably, tert-butoxy group.

The term "activating group" as used herein refers to commonly used activating groups in peptide synthesis, preferably for activation of carboxyl acid and promote the coupling reaction with amino group of intermediate compound. $AG^1$ is an activating group of carboxylic acid of amino acid. This group may be introduced separate reaction or in situ reaction. Preferably, $AG^1$ may be selected from the group consisting of or comprising: halides such as —F, —Br, —Cl, —I, anhydride group such as —$OCOCH_3$. N-oxy-benzotriazol group and N-oxy-succinimide. Preferably, AG1 is introduced in situ and it is well-known in peptide chemistry. Any of the following coupling reagent can be used to introduce activating group AG1: BOP, PyBOP, AQP, PyAOP, TBTU, EEDQ, Polyphosphoric Acid (PPA), DPPA, HATU, HOBt, HOAt, DCC, EDCI, BOP-CI, TFFH, Brop, PyBrop, and CIP.

In Scheme 4, the chemical warhead precursor represent

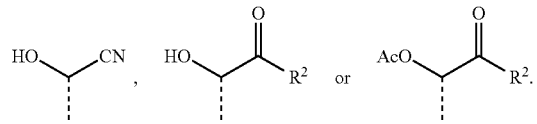

In the step 4D, said warhead precursor is converted to the corresponding chemical warhead,

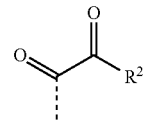

by oxidation method, preferred, by using Dess-Martin periodinane (DMP), iodoxybenzoic acid (IBX), or hydrogen peroxide($H_2O_2$) in a polar solvent, in particular in DMF as described in chemical examples.

Therefore another aspect of the present invention relates to compounds according to the general formula (I) as medicine as well as their use in medicine. Especially preferred is the use as inhibitors of transglutaminases.

The compounds according to general formula (I) described herein are especially suitable for the treatment and prophylaxis of diseases associated with and/or caused by transglutaminases.

TG1, TG3 and TG5 are expressed in the skin, inhibitors of said enzymes may be used to modulate transglutaminase activity to therapy certain skin disorders or to influence skin structure. TG6 inhibitors may address neurodegenerative diseases characterized by intracellular or extracellular cross-linked and insoluble protein aggregates.

Coeliac disease, a gluten intolerance is associated with tissue transglutaminase (TG 2). Another very important group of indications for tissue transglutaminase inhibitors are fibrotic disorders. Fibrotic disorders are characterized by the accumulation of cross-linked extracellular matrix proteins. Diabetic nephropathy, cystic fibrosis, idiopathic pulmonary fibrosis, kidney fibrosis as well as liver fibrosis belong to the most important fibrotic disorders to be addressed with the compounds disclosed.

Since blood coagulation factor XIII (FXIII, F13) is the major factor influencing clot maturation and accretion the enzyme is considered a suitable target to potentially achieve a safer and more efficient thrombolysis.

Therefore, another aspect of the present invention is the use of the inventive compounds of the general formula (I) for the treatment or prophylaxis of cardiovascular diseases, autoimmune diseases, neurodegenerative diseases, fibrotic disorders, dermatological diseases, wound healing, and inflammatory diseases.

In particular, the use of the inventive compounds of the general formula (I) for the treatment or prophylaxis of atherosclerosis, coeliac disease, Duhring-Brocq-disease, gluten ataxia, tissue fibrosis, cystic fibrosis, idiopathic pulmonary fibrosis, kidney fibrosis and diabetic nephropathy, liver fibrosis, thrombosis, Huntington's disease, Parkinson's disease, Alzheimer's disease, cataract, ichthyosis, acne, psoriasis, skin aging, candidosis, and other transglutaminase dependent diseases.

The term "transglutaminase dependent diseases" comprises all diseases, dysfunctions or other impairments of the health, which are caused by or in connection with a dysfunction, perturbance or hyperactivity of transglutaminases in the body. Alternatively, it might be of benefit for certain at risk patients to prophylactically block a transglutaminase like FXIII e.g. in thrombophilic patients.

The particular suitability of the inventive compounds of the general formula (I) is connected to the sterical and electronical properties which result from the molecule structure. The electrophilic warhead group appears to be an essential unit of the reversible transglutaminase inhibitors, and, especially in combination with the certain peptidomimetic backbone, the pyridinone-containing backbone, the conformationally constrained unnatural proline-based amino acids and the piperazine-containing backbone results in potent transglutaminase inhibitors, especially, transglutaminase 2 and blood coagulation factor XIII. Selectivity is obtained by implementing said components at selected positions within the backbone.

It is known from the literature on proteases that certain warheads form covalent but reversible complexes with the active site cysteine or serin. This is particularly relevant to provide affinity to the target while forming a thiohemiacetal or hemiacetal respectively. We surprisingly discovered that this principle is suitable for transglutaminase inhibitors. The discovered warheads need to be positioned in the correct orientation replacing the former substrate glutamine. The backbone positions the warhead so that the thiohemiacetal is formed.

In the biological example B-1, it is proven that the inventive compounds as reversible TG inhibitor effectively inhibit the activity of TGs, especially TG2 and FXIII.

Furthermore, it is also provent that the inventive compounds as reversible TG inhibitor have less toxicity compared with irreversible TG inhibitor. In the biological example B-2 that cytotoxicity of transglutaminase inhibitors is evaluated with two different assays. While irreversible TG inhibitor 2006 is cytotoxic at 125 µM, the inventive compound E02 shows no influence on cell proliferation or metabolic activity up to 1 mM (highest concentration measured). It is drawback of the irreversible TG inhibitor that the unspecific reaction with off-targets can cause severe adverse effects and trigger certain immune responses. Further, the direct damage of tissue has been described for irreversible acting compounds or metabolites. Also haptenization of proteins by reactive substances may elicit an immune response. Quite often, the liver is affected by such adverse effects.

Therefore, it is technical advantage that the inventive compound has not cytotoxicity in a high concentration, i.e. molar-range.

In addition, it is also demonstrated in the example B-3 that the tissue transglutaminase inhibition using the inventive compound reduces transglutaminase activity and reduces ECM accumulation. These results indicate that the inventive compound has an antifibrotic effect on renal cells in proximal tubular epithelial cells. Therefore, it is supported that the inventive compound is useful for treatment of fibrosis such as tissue fibrosis, cystic fibrosis, idiopathic pulmonary fibrosis, kidney fibrosis and liver fibrosis.

Figure 1:
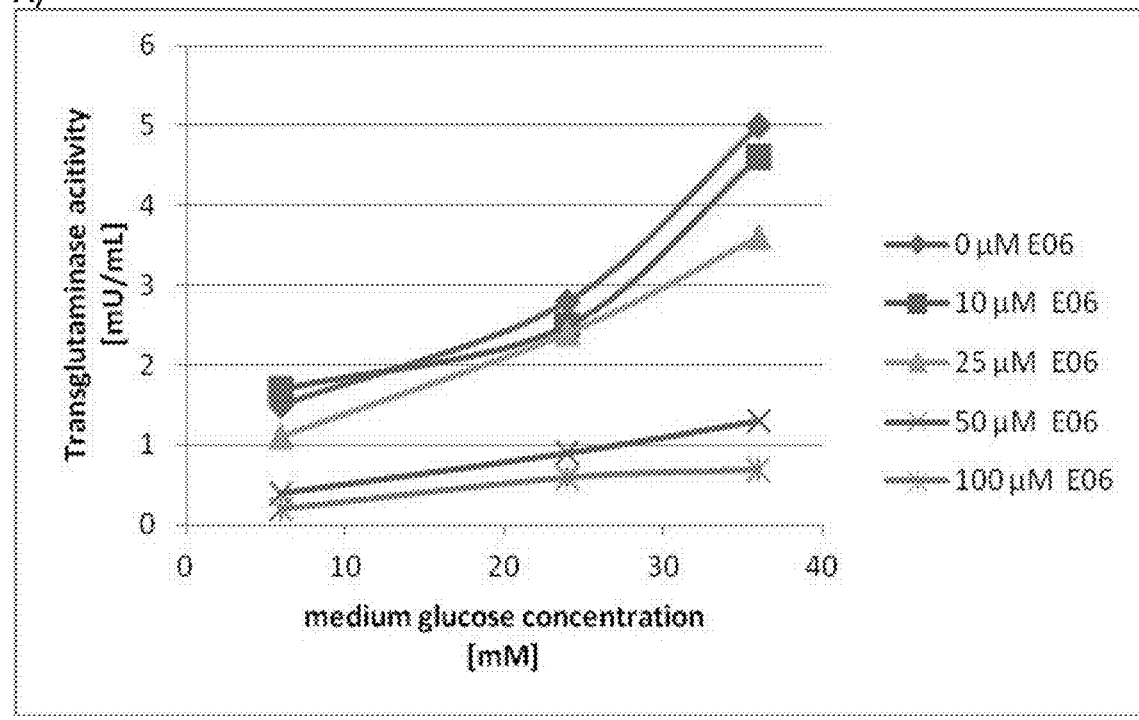
FIG. 1
A) Transglutaminase activity of homogenates from NRK52E-cell grown at physiological (6 mM) and hyperglycemic glucose concentrations (24 mM and 36 mM) in the presence of compound E06.
B) Extracellular matrix protein deposition from NRK52E-cell grown at physiological and hyperglycemic glucose concentrations in the presence of compound E06.
Figure 1:
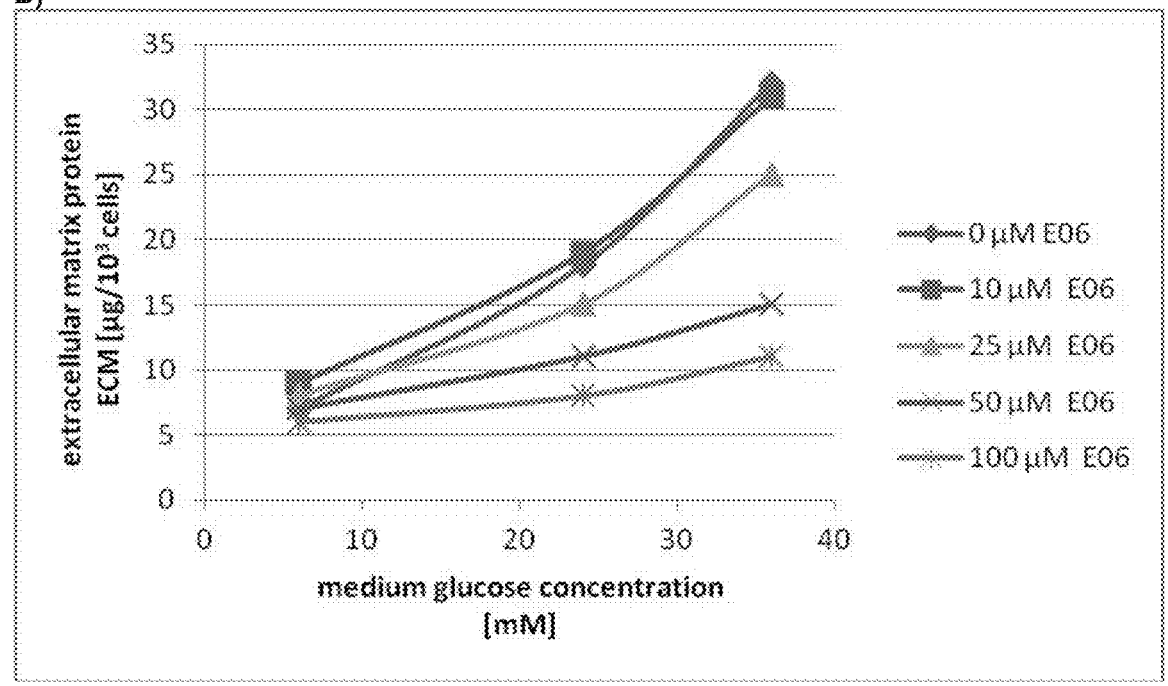

B) Detection of isopeptide bonds in an ELISA-Assay. Microtiter plate wells were coated with SDS-soluble and formic acid solubilized extracts of Htt-exon1-97Q transfected N2a-cells grown in the presence of 150 and 300 μM TG2-inhibitor E22. Antibody A023 (1:200, Zedira) recognizing $N^\varepsilon$-(γ-L-glutamyl)-L-lysine-isopeptide was used as detection antibody, followed by a conventional ELISA-protocol.

FIG. 7

A) Transglutaminase activity of homogenates from BEAS-2B-cell grown in the presence of 0-200 μM E22 and stimulated with LPS determined by TG2-selective Tissue Transglutaminase Pico-Assay Kit (#M003, Zedira, Darmstadt, Germany) according to the manufacturer's instructions.

B) Extracellular matrix protein deposition of homogenates from BEAS-2B-cell grown in the presence of 0-200 μM E22 and stimulated with LPS measured by the DC-protein-assay (BioRad, #5000111).

FIG. 8

A) Transglutaminase activity of homogenates from LX-2-cells grown in standard plastic 6-well plates in the presence of 0-200 μM E22 determined by TG2-selective Tissue Transglutaminase Pico-Assay Kit (#M003, Zedira, Darmstadt, Germany) according to the manufacturer's instructions.

B) Extracellular matrix protein deposition of homogenates from LX-2-cells grown in standard plastic 6-well plates in the presence of 0-200 μM E22 measured by the DC-protein-assay (BioRad, #5000111).

EXAMPLES

Following abbreviations used in the examples have the following meaning.
DMAP: 4-(Dimethylamino)-pyridine
TEA: Triethylamine
DMF: Dimethylformamide
DIPEA: N-Ethyldiisopropylamine
TFA: Trifluoroacetic acid
EtOAc Ethyl acetate
HATU 1-[Bis(dimethylamino)methylene]-1H-1,2,3-triazolo[4,5-b]pyridinium 3-oxid hexafluorophosphate
PyAOP (7-Azabenzotriazol-1-yloxy)tripyrrolidinophosphonium hexafluorophosphate

CHEMICAL EXAMPLES

The following examples are intended to illustrate the invention with selected compounds without limiting the protecting scope of the present intellectual property right on these concrete examples. It is clear for a person skilled in the art that analogous compounds and compounds produced according to analogous synthetic ways fall under the protecting scope of the present intellectual property right.

Example 1. Preparation of Compound E01

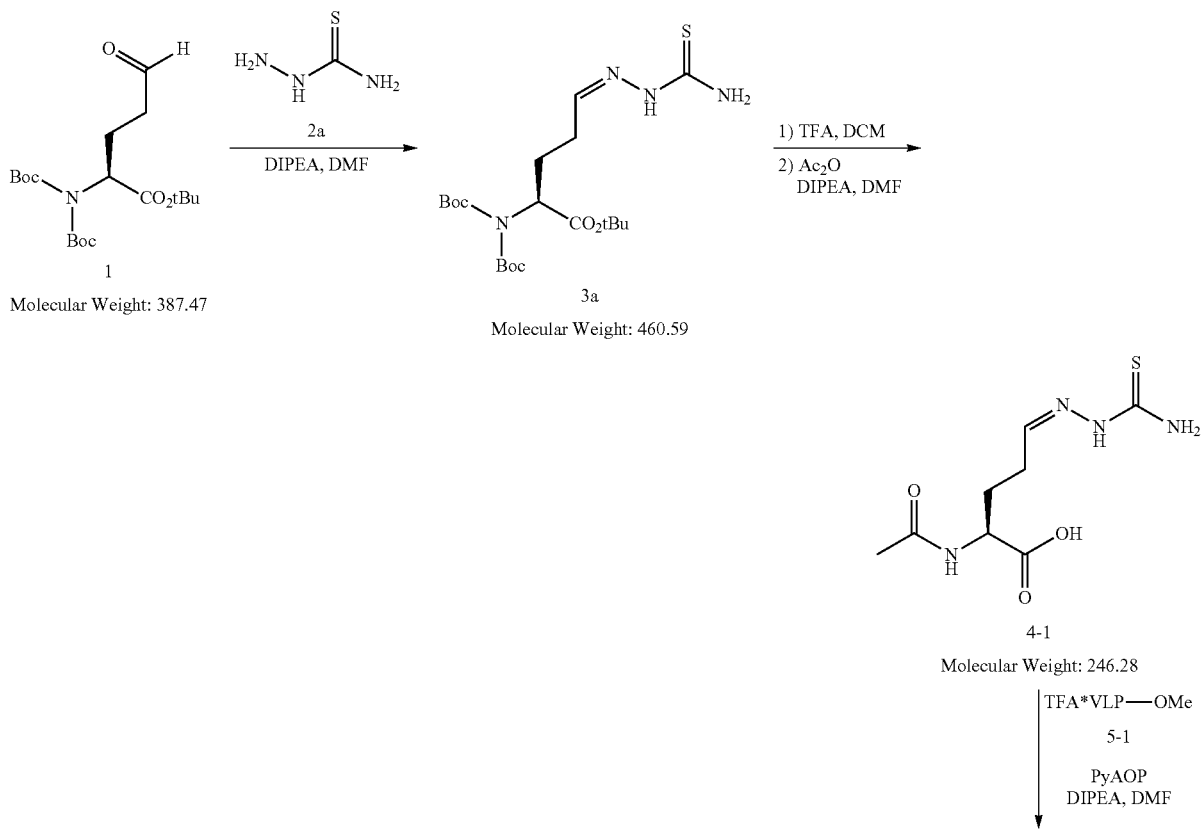

121
122
-continued
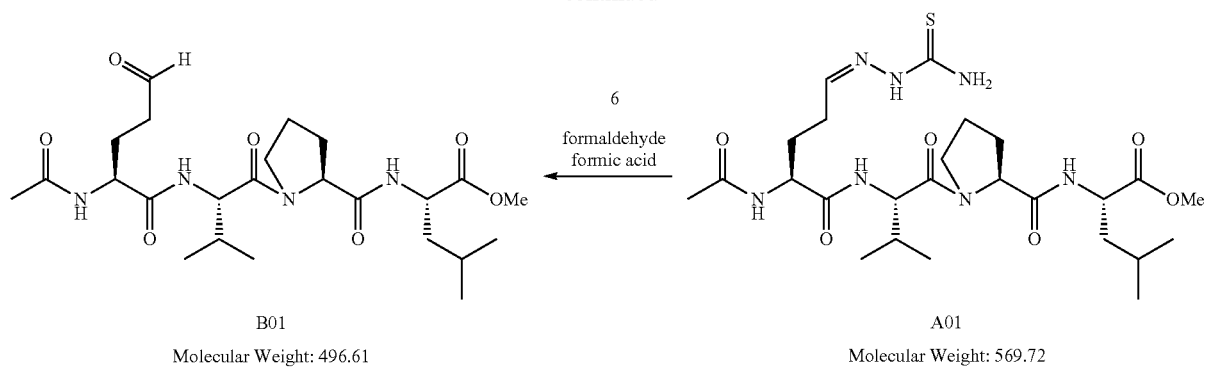
B01
Molecular Weight: 496.61
A01
Molecular Weight: 569.72
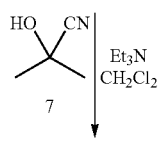
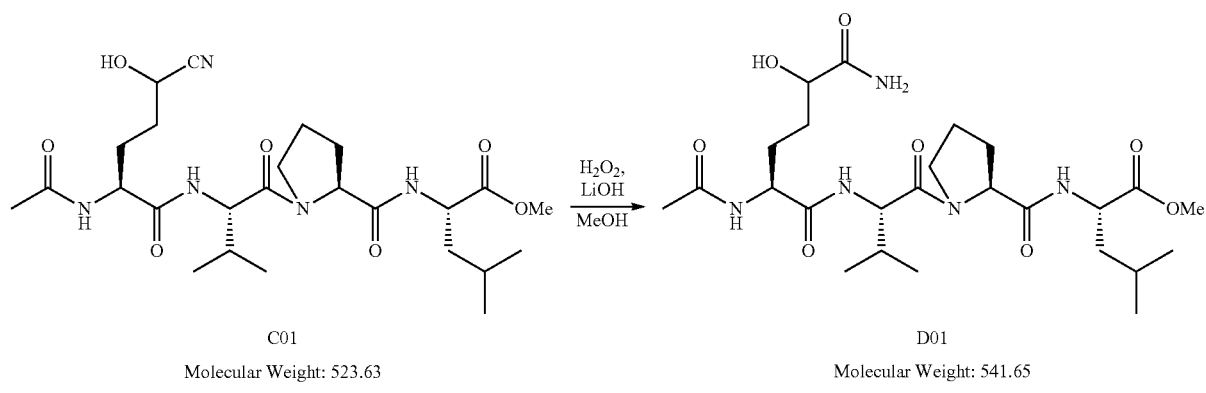
C01
Molecular Weight: 523.63
D01
Molecular Weight: 541.65
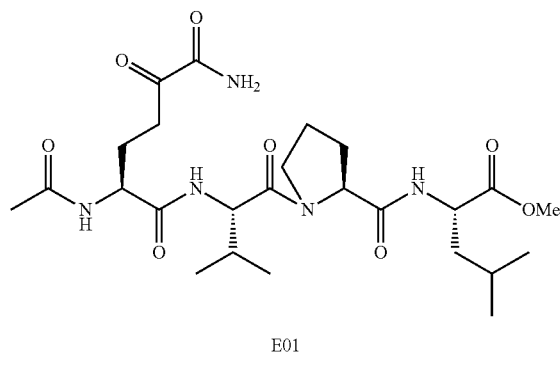
E01
Molecular Weight: 539.63

The synthesis was adapted from Venkatraman, S. et al. *J. Med. Chem.* 2006, 49, 6074-6086. The thiosemicabazone chemistry and the protection group chemistry was performed according to basic literature knowledge.

1.1 Preparation of Compound 3a

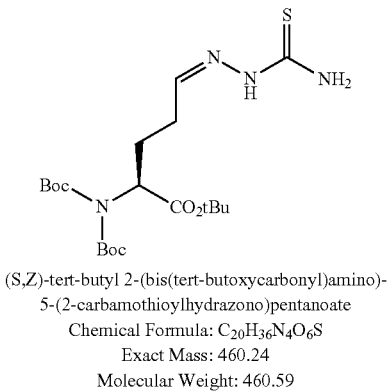 [SMILES: CC(C)(C)OC(=O)[C@H](CC/C=N\NC(N)=S)N(C(=O)OC(C)(C)C)C(=O)OC(C)(C)C]

(S,Z)-tert-butyl 2-(bis(tert-butoxycarbonyl)amino)-
5-(2-carbamothioylhydrazono)pentanoate
Chemical Formula: $C_{20}H_{36}N_4O_6S$
Exact Mass: 460.24
Molecular Weight: 460.59

3.14 g (8.10 mmol) of the aldehyde (S)-tert-butyl 2-(bis(tert-butoxycarbonyl)amino)-5-oxopentanoate 1 was dissolved in 10 ml DMF, 738 mg (1 eq) thiosemicarbazide 2a and 1.42 ml (1 eq) DIPEA were added and the reaction was stirred at room temperature overnight. The solvent was evaporated and the residue was dissolved in EtOAc. The solution was washed twice with $NaHCO_3$ solution (10%) and brine. The organic phase was dried over $Na_2SO_4$, filtered and the solvent was evaporated. The residue was used without further purification.

Yield: 4.18 g, >100%

ESI-MS: 461.2 $[M+H]^+$ 1.2 Preparation of Compound 4-1

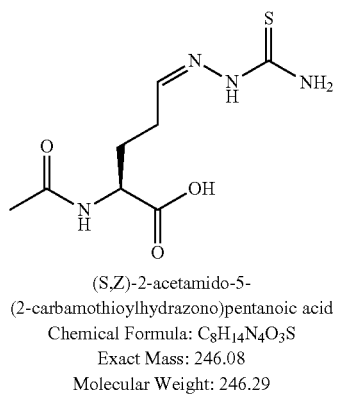 [SMILES: CC(=O)N[C@@H](CC/C=N\NC(N)=S)C(=O)O]

(S,Z)-2-acetamido-5-
(2-carbamothioylhydrazono)pentanoic acid
Chemical Formula: $C_8H_{14}N_4O_3S$
Exact Mass: 246.08
Molecular Weight: 246.29

4.18 g (~8.10 mmol) of the raw thiosemicarbazone 3a was dissolved in 20 ml DCM/TFA (1:1) and stirred at room temperature for 2 h. The solvent was evaporated and the residue was dissolved in 10 ml DMF, 1.26 ml (1 eq) DIPEA and 683 µl (1 eq) $Ac_2O$ were added and the reaction was stirred at room temperature overnight. The solvent was evaporated and the residue was purified by HPLC.

Yield: 1.01 g, 51%

ESI-MS: 247.3 $[M+H]^+$ 1.3 Preparation of Compound A01

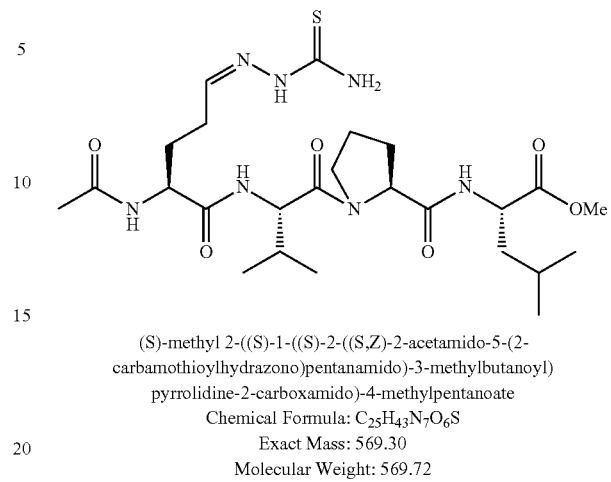

(S)-methyl 2-((S)-1-((S)-2-((S,Z)-2-acetamido-5-(2-
carbamothioylhydrazono)pentanamido)-3-methylbutanoyl)
pyrrolidine-2-carboxamido)-4-methylpentanoate
Chemical Formula: $C_{25}H_{43}N_7O_6S$
Exact Mass: 569.30
Molecular Weight: 569.72

400 mg (1.62 mmol) of the thiosemicarbazone 4-1 were dissolved in 5 ml DMF, 847 mg (1 eq) PyAOP, 555 mg (1 eq) of the tripeptide H-VPL-OMe 5-1 and 467 µl (3.25 mmol, 2 eq) DIPEA were added and the reaction was stirred at room temperature overnight. The solvent was evaporated and the residue was purified by HPLC.

Yield: 309 mg, 33%

ESI-MS: 570.5 $[M+H]^+$ 1.4 Preparation of Compound B01

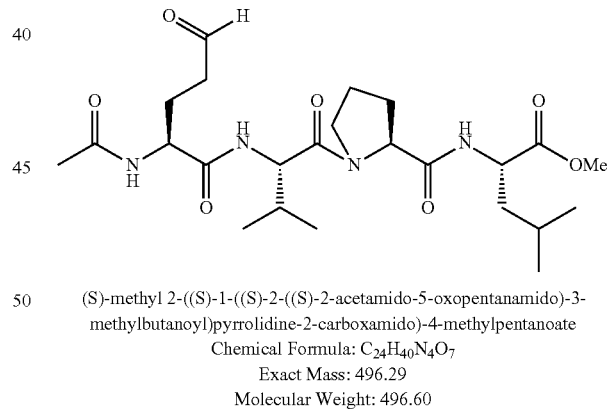

(S)-methyl 2-((S)-1-((S)-2-((S)-2-acetamido-5-oxopentanamido)-3-
methylbutanoyl)pyrrolidine-2-carboxamido)-4-methylpentanoate
Chemical Formula: $C_{24}H_{40}N_4O_7$
Exact Mass: 496.29
Molecular Weight: 496.60

413 mg (0.73 mmol) of the thiosemicarbazone A01 were dissolved in 1 ml formic acid (50%) and 4 ml formaldehyde (37%) (6). The solution was stirred at 40° C. for 1 h and purified by HPLC.

Yield: 205 mg, 57%

ESI-MS: 497.4 $[M+H]^+$

1.5 Preparation of Compound C01

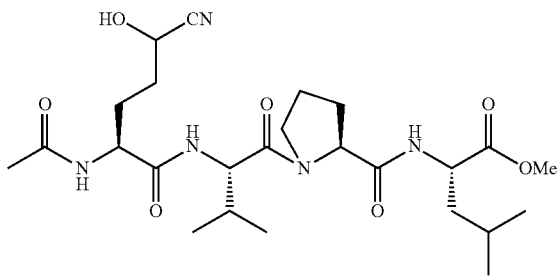

(2S)-methyl 2-((2S)-1-((2S)-2-((2S)-2-acetamido-5-cyano-
5-hydroxypentanamido)-3-methylbutanoyl)
pyrrolidine-2-carboxamido)-4-methylpentanoate
Chemical Formula: $C_{25}H_{41}N_5O_7$
Exact Mass: 523.30
Molecular Weight: 523.62

307 mg (0.62 mmol) of the aldehyde B01 were dissolved in 10 ml DCM under argon. 103 µl (0.74 mmol) $NEt_3$ and 117 µl (1.28 mmol, 2.1 eq) acetone cyanohydrin 7 were added and the reaction was stirred at room temperature overnight. The solvent was evaporated and the residue was purified by HPLC.

Yield: 172 mg, 53%

ESI-MS: 524.5 $[M+H]^+$

1.6 Preparation of Compound D01

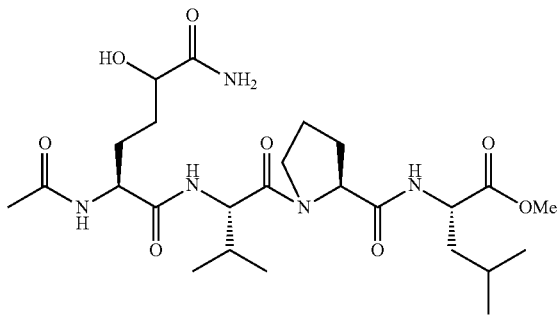

(2S)-methyl 2-((2S)-1-((2S)-2-((2S)-2-acetamido-6-amino-5-hydroxy-6-
oxohexanamido)-3-methylbutanoyl)pyrrolidine-2-carboxamido)-4-
methylpentanoate
Chemical Formula: $C_{25}H_{43}N_5O_8$
Exact Mass: 541.31
Molecular Weight: 541.64

172 mg (0.33 mmol) of the cyanohydrin C01 were dissolved in 3 ml MeOH. At 0° C., 16.5 mg (0.39 mmol, 1.2 eq) $LiOH*H_2O$ were added. After dropwise addition of 133 µl (3.29 mmol, 10 eq) $H_2O_2$ (35%), the reaction was stirred at room temperature for 2 h and purified by HPLC.

Yield: 40 mg, 23%

ESI-MS: 542.5 $[M+H]^+$

1.7 Preparation of Compound E01

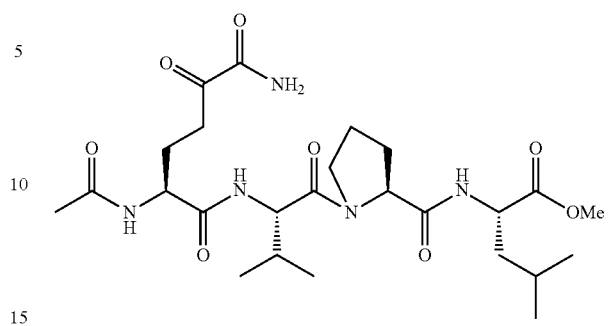

(S)-methyl 2-((S)-1-((S)-2-((S)-2-acetamido-6-amino-5,6-
dioxohexanamido)-3-methylbutanoyl)pyrrolidine-2-carboxamido)-
4-methylpentanoate
Chemical Formula: $C_{25}H_{41}N_5O_8$
Exact Mass: 539.30
Molecular Weight: 539.62

18.0 mg (33.2 µmol) of the hydroxy amide D01 were dissolved in 2 ml EtOAc, 22.6 mg (53.2 µmol, 1.6 eq) Dess-Martin periodinane (DMP) were added in three portions and stirred at room temperature over 2 h. The precipitate was filtered off and the filtrate was evaporated. The residue was purified by HPLC.

Yield: 11 mg, 61%

ESI-MS: 540.5 $[M+H]^+$

Example 2. Preparation of Compound E02

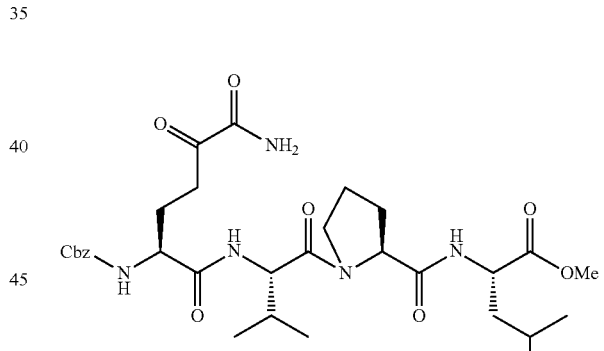

(S)-methyl 2-((S)-1-((S)-2-((S)-6-amino-2-(benzyloxycarbonylamino)-
5,6-dioxohexanamido)-3-methylbutanoyl)pyrrolidine-2-carboxamido)-
4-methylpentanoate
Chemical Formula: $C_{31}H_{45}N_5O_9$
Exact Mass: 631.32
Molecular Weight: 631.72

The synthesis of E02 was performed according to example 1, using benzyl chloroformate (Cbz-Cl) instead of $Ac_2O$ (see compound 4-1).

Yield: 16 mg, 57% (last step)

ESI-MS: 632.4 $[M+H]^+$

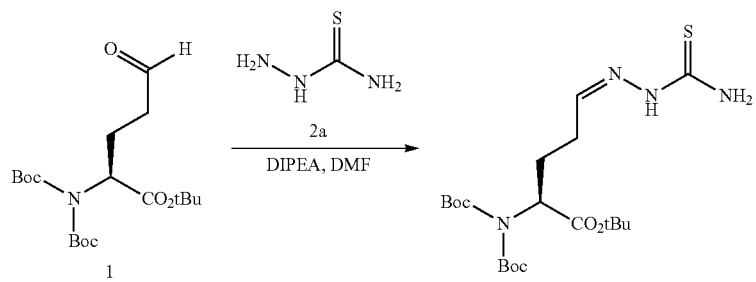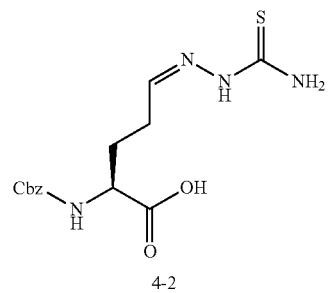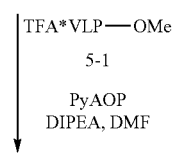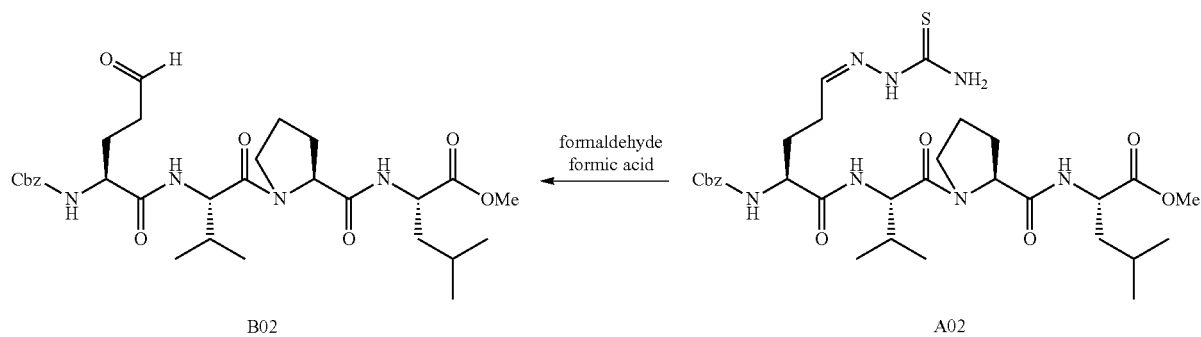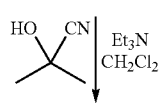

-continued
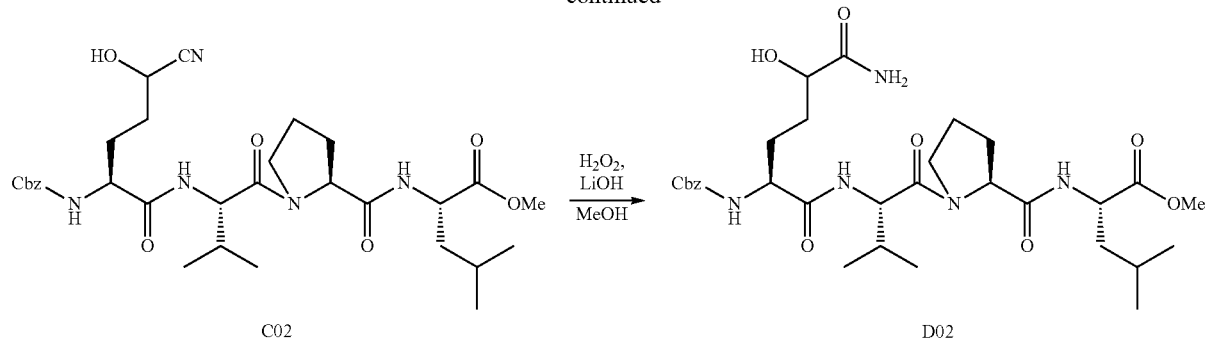
C02
Molecular Weight: 615.73
D02
Molecular Weight: 633.74
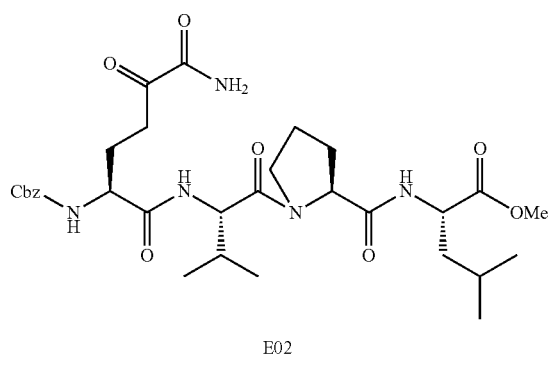
E02
Molecular Weight: 631.73
Example 3. Preparation of Compound E03
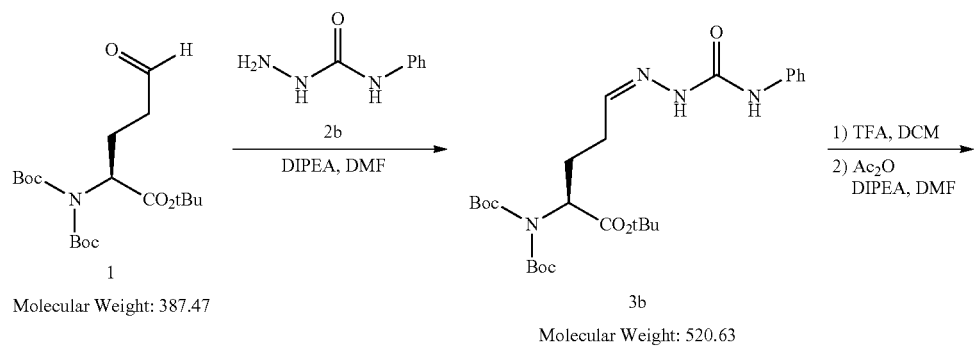
1
Molecular Weight: 387.47
3b
Molecular Weight: 520.63

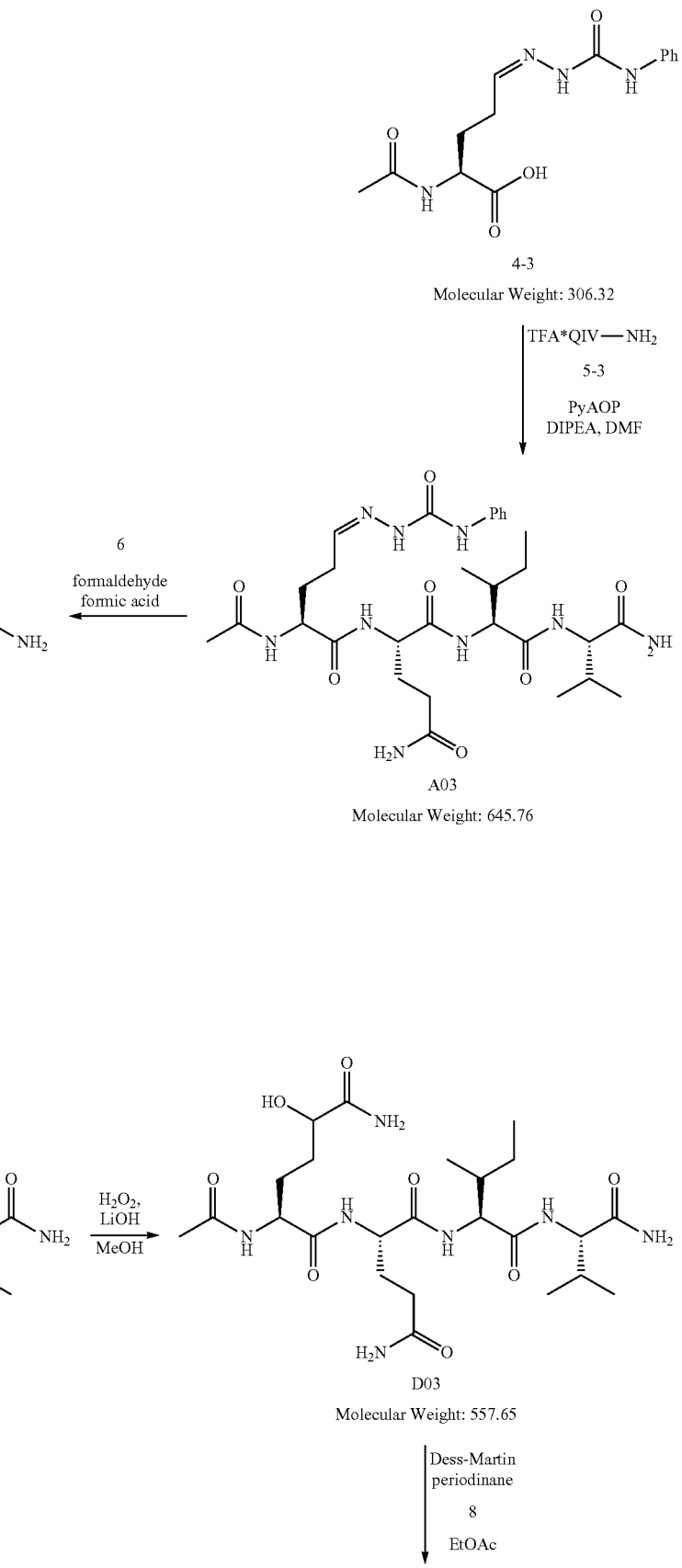

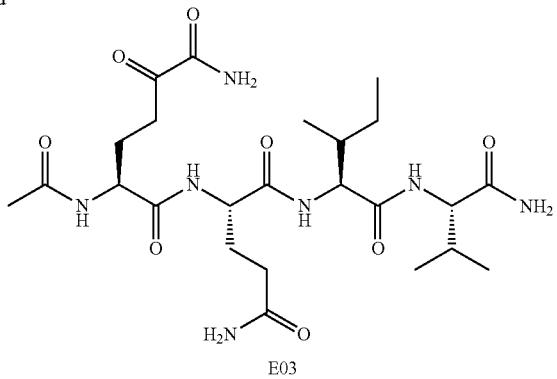

E03

Molecular Weight: 555.63

Example 4. Preparation of Compound E04

Compound E03

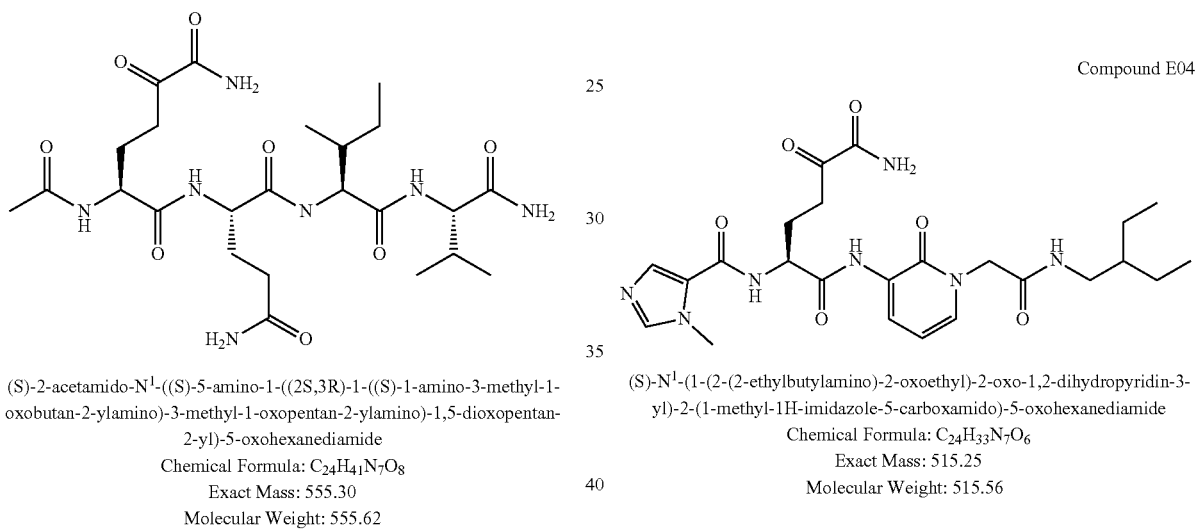

Compound E04

(S)-2-acetamido-N¹-((S)-5-amino-1-((2S,3R)-1-((S)-1-amino-3-methyl-1-oxobutan-2-ylamino)-3-methyl-1-oxopentan-2-ylamino)-1,5-dioxopentan-2-yl)-5-oxohexanediamide Chemical Formula: $C_{24}H_{41}N_7O_8$
Exact Mass: 555.30
Molecular Weight: 555.62

(S)-N¹-(1-(2-(2-ethylbutylamino)-2-oxoethyl)-2-oxo-1,2-dihydropyridin-3-yl)-2-(1-methyl-1H-imidazole-5-carboxamido)-5-oxohexanediamide Chemical Formula: $C_{24}H_{33}N_7O_6$
Exact Mass: 515.25
Molecular Weight: 515.56

The synthesis of Compound E03 was performed according to example 1, using 4-phenylsemicarbazide 2b instead of thiosemicarbazide (see comopund 3a) and the tripeptide H-QIV-NH₂ (compound 5-3) instead of H-VPL-OMe (compound 5-1) (see compound A01)
Yield: 14 mg, 49% (last step)
ESI-MS: 556.4 [M+H]⁺

The synthesis of Compound E04 was performed according to example 1, using 1-Methyl-1H-imidazole-5-carboxylic acid instead of Ac₂O (see Compound 4-1) and 2-(3-amino-2-oxopyridin-1(2H)-yl)-N-(2-ethylbutyl)acetamide (5-4) instead of H-VPL-OMe (5-1) (see Compound A01)
Yield: 10 mg, 43% (last step)
ESI-MS: 516.4 [M+H]⁺

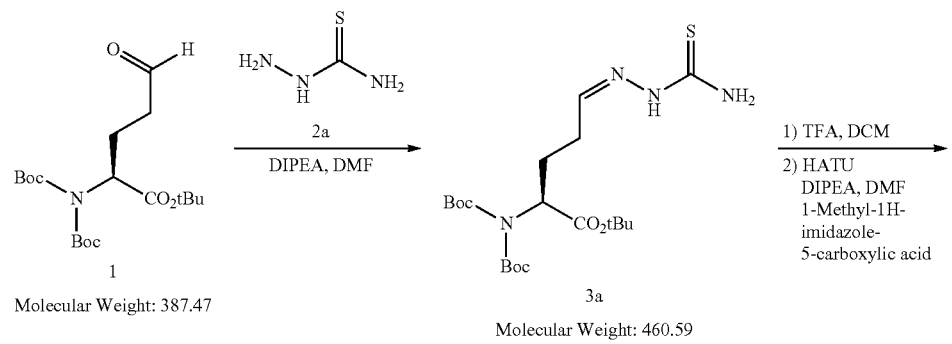

1
Molecular Weight: 387.47

3a
Molecular Weight: 460.59

-continued
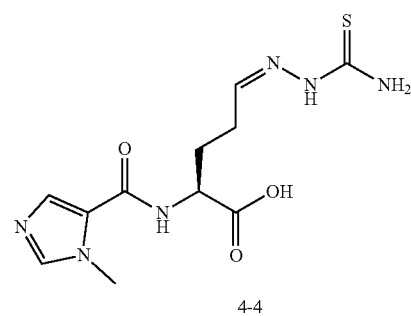
4-4
Molecular Weight: 312.35
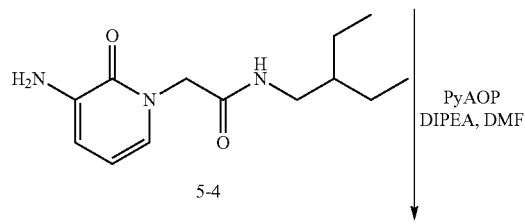
5-4
PyAOP
DIPEA, DMF
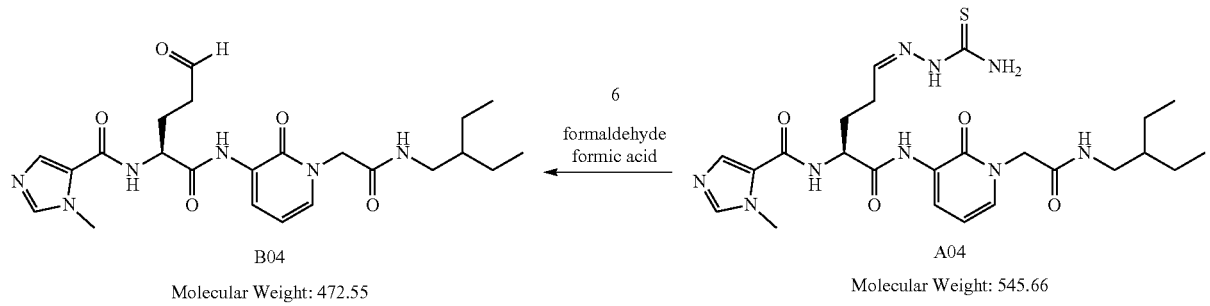
B04
Molecular Weight: 472.55
6
formaldehyde
formic acid
A04
Molecular Weight: 545.66
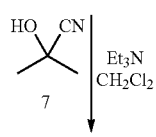
7
Et₃N
CH₂Cl₂
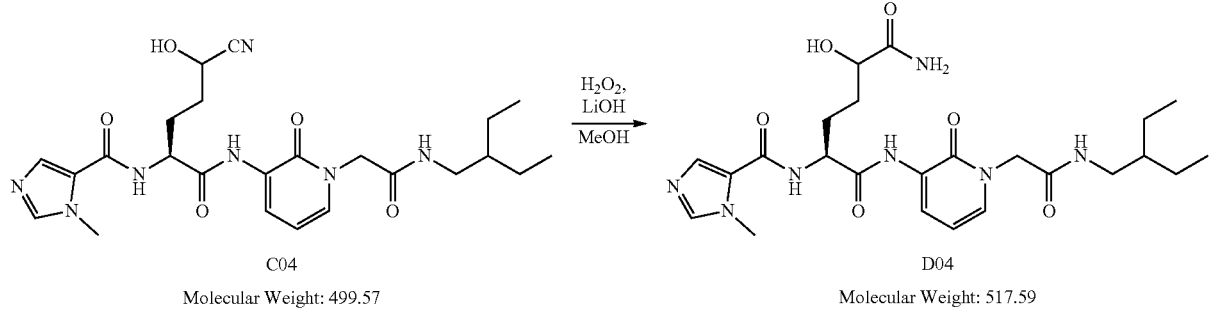
C04
Molecular Weight: 499.57
H₂O₂,
LiOH
MeOH
D04
Molecular Weight: 517.59
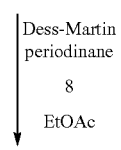
Dess-Martin
periodinane
8
EtOAc

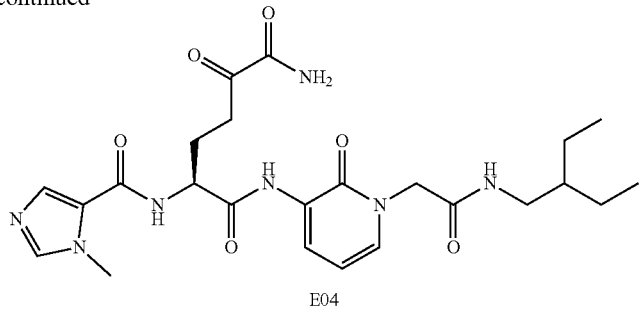

E04

Molecular Weight: 515.57

Example 5. Preparation of Compound E05

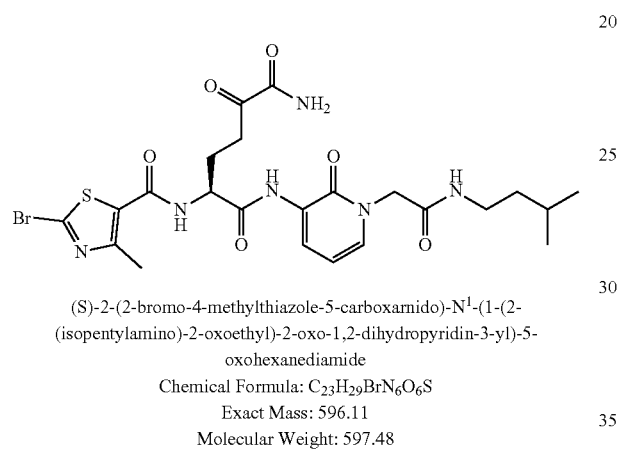

(S)-2-(2-bromo-4-methylthiazole-5-carboxamido)-$N^1$-(1-(2-(isopentylamino)-2-oxoethyl)-2-oxo-1,2-dihydropyridin-3-yl)-5-oxohexanediamide Chemical Formula: $C_{23}H_{29}BrN_6O_6S$ Exact Mass: 596.11

Molecular Weight: 597.48

The synthesis of Compound E05 was performed according to example 1, using di-tert-butyl Bicarbonate ($Boc_2O$) instead of $Ac_2O$ (see Compound 4-1) and 2-(3-amino-2-oxopyridin-1(2H)-yl)-N-isopentylacetamide (compound 5-5) instead of H-VPL-OMe (see compound 5-1). Furthermore, 2-Bromo-4-methylthiazole-5-carboxylic acid (compound 9-5) was introduced in the last step according to standard peptide coupling methods.

Yield: 15 mg, 72% (last step)

ESI-MS: 597.3 [M+H]$^+$

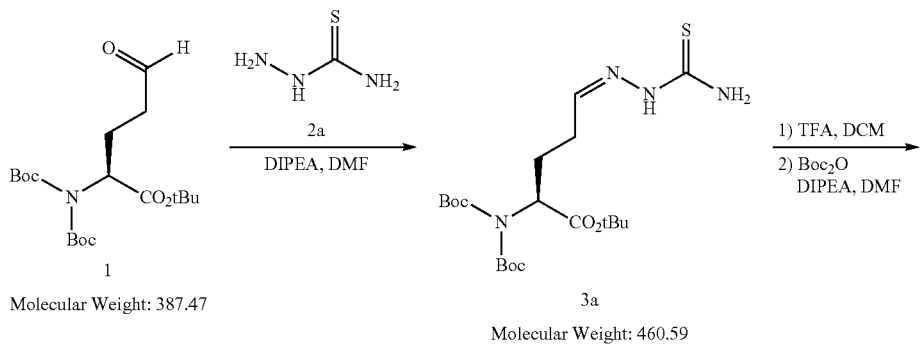

1

Molecular Weight: 387.47

3a

Molecular Weight: 460.59

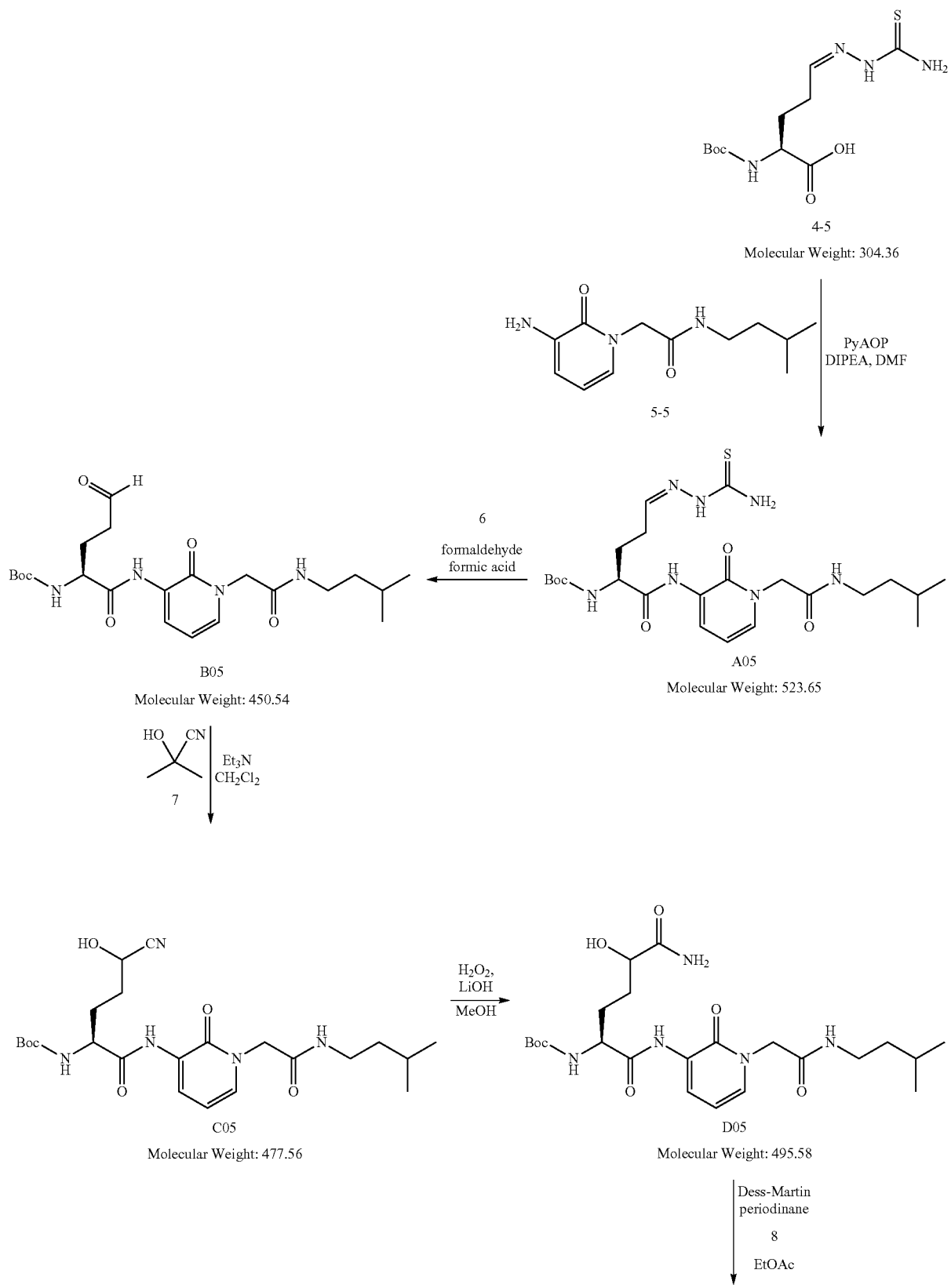

141                                                                                                          142

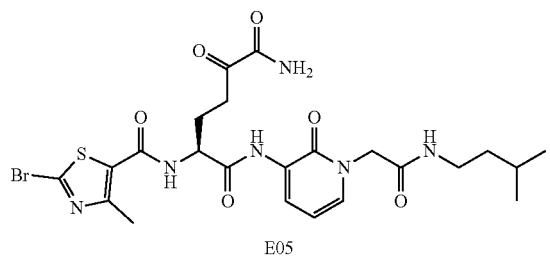
E05
Molecular Weight: 597.49

1) TFA, DCM
2) HATU
   DIPEA, DMF
   2-Bromo-4-
   methylthiazole-
   5-carboxylic acid
   9-5

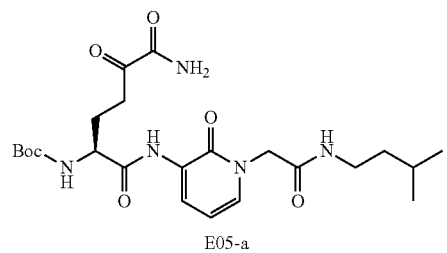
E05-a
Molecular Weight: 493.56

Example 6. Preparation of Compound E06

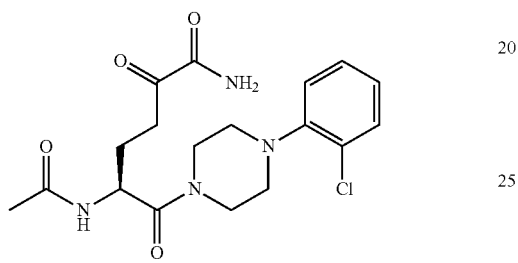

(S)-5-acetamido-6-(4-(2-chlorophenyl)piperazin-
1-yl)-2,6-dioxohexanamide
Chemical Formula: $C_{18}H_{23}ClN_4O_4$
Exact Mass: 394.14
Molecular Weight: 394.85

The synthesis of compound E06 was performed according to example 1, using 1-(2-chlorophenyl)piperazine (compound 5-6) instead of H-VPL-OMe (compound 5-1). Furthermore, the sequence was adjusted by first introducing the α-ketoamide moiety, followed by modifying the N-terminus and coupling of the backbone.
Yield: 19 mg, 64% (last step)
ESI-MS: 395.3 [M+H]$^+$

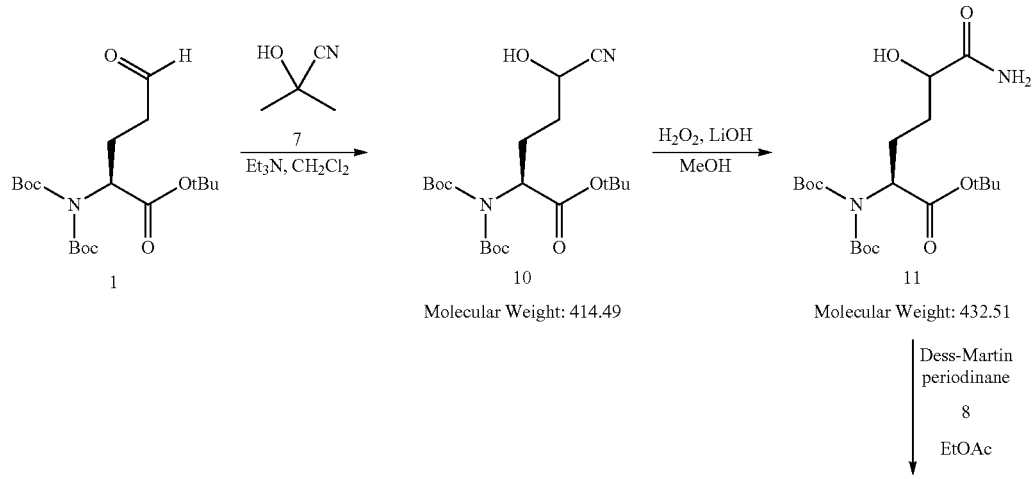

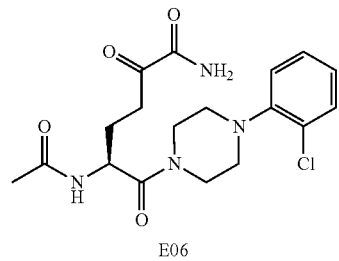 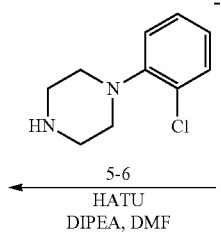 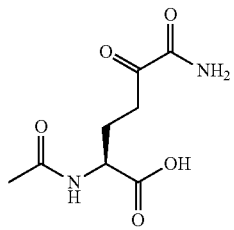 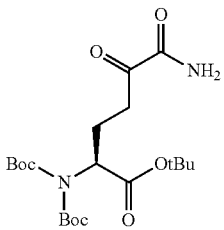

E06  
Molecular Weight: 394.86

13-1  
Molecular Weight: 216.19

12  
Molecular Weight: 430.50

Example 7. Preparation of Compound E07

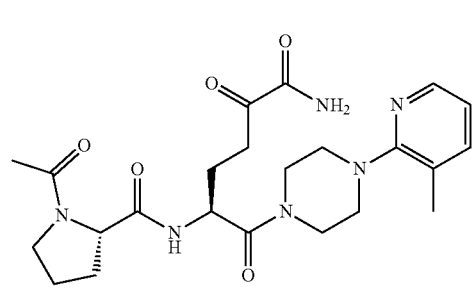

(S)-1-acetyl-N-((S)-6-amino-1-(4-(3-methylpyridin-2-yl)piperazin-1-yl)-1,5,6-trioxohexan-2-yl)pyrrolidine-2-carboxamide  
Chemical Formula: $C_{23}H_{32}N_6O_5$  
Exact Mass: 472.24  
Molecular Weight: 472.54

The synthesis of compound E07 was performed according to Example 6, using Ac-Pro-OSu instead of Ac$_2$O and 1-(3-methylpyridin-2-yl)piperazine (compound 5-7) instead of 1-(2-chlorophenyl)piperazine (compound 5-6).

Yield: 11 mg, 52% (last step)  
ESI-MS: 473.4 [M+H]$^+$

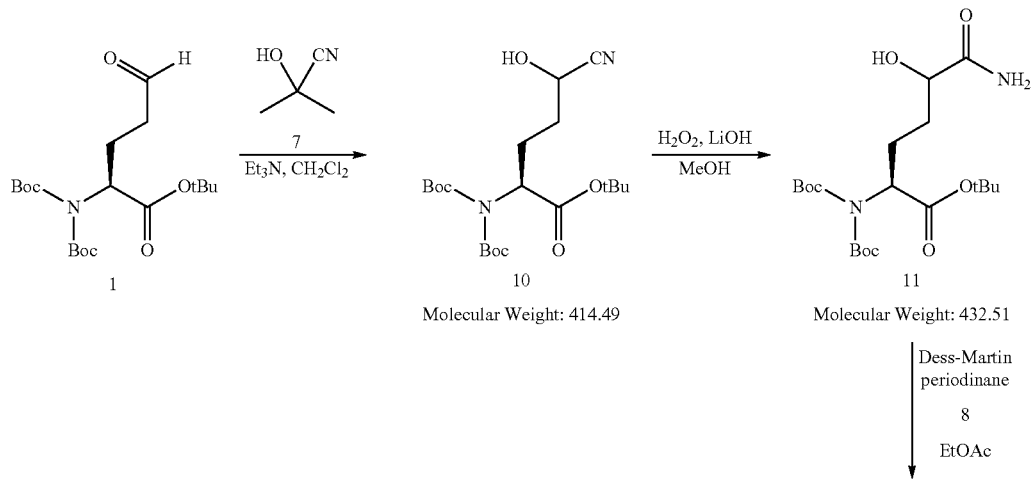

1

10  
Molecular Weight: 414.49

11  
Molecular Weight: 432.51

Dess-Martin periodinane

8

EtOAc

-continued

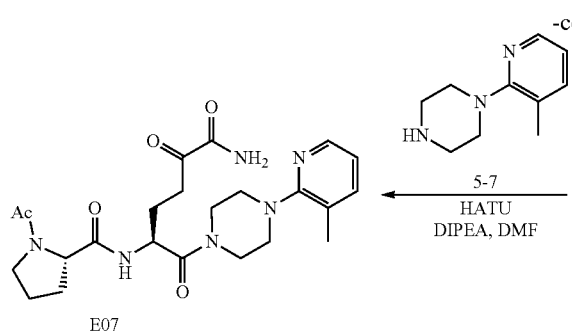

E07
Molecular Weight: 472.55

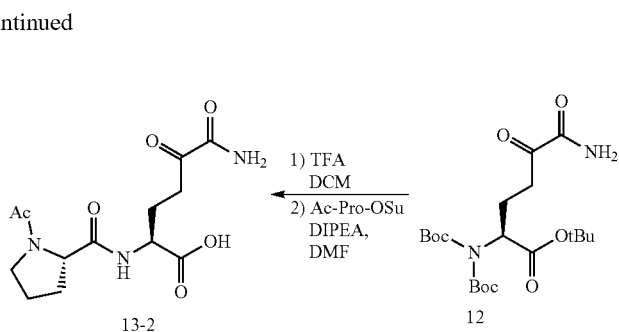

13-2
Molecular Weight: 313.31

12
Molecular Weight: 430.50

Example 8. Preparation of Compound E08

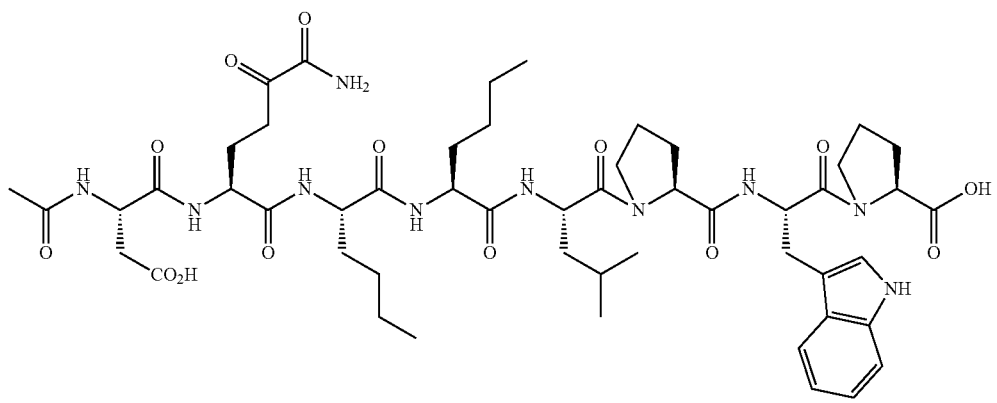

(S)-1-((S)-2-((S)-1-((4S,7S,10S,13S,16S)-7-(4-amino-3,4-dioxobutyl)-10,13-dibutyl-4-
(carboxymethyl-18-methyl-2,5,8,11,14-pentaoxo-3,6,9,12,15-
pentaazanonadecanecarbonyl)pyrrolidine-2-carboxamido)-3-(1H-indol-3-
yl)propanoyl)pyrrolidine-2-carboxylic acid
Chemical Formula: $C_{51}H_{74}N_{10}O_{14}$
Exact Mass: 1050.54
Molecular Weight: 1051.19

The synthesis of compound E08 was performed according to Example 6, using Ac-Asp-OSu (14-1) instead of $Ac_2O$ (via Boc intermediate) and H-Nle-Nle-LPWP-OH (compound 5-8) instead of 1-(2-chlorophenyl)piperazine (compound 5-6).

Yield: 8 mg, 29% (last step) ESI-MS: 1051.7 [M+H]$^+$

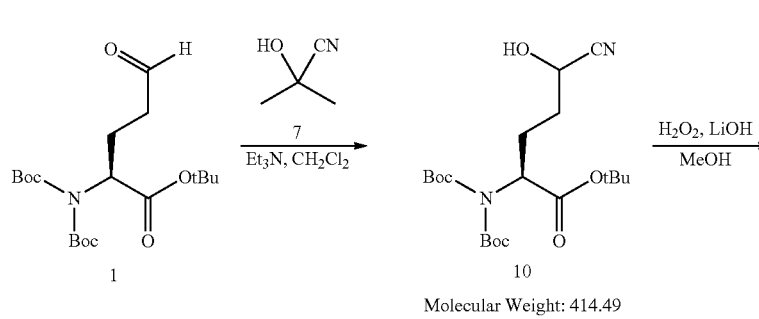
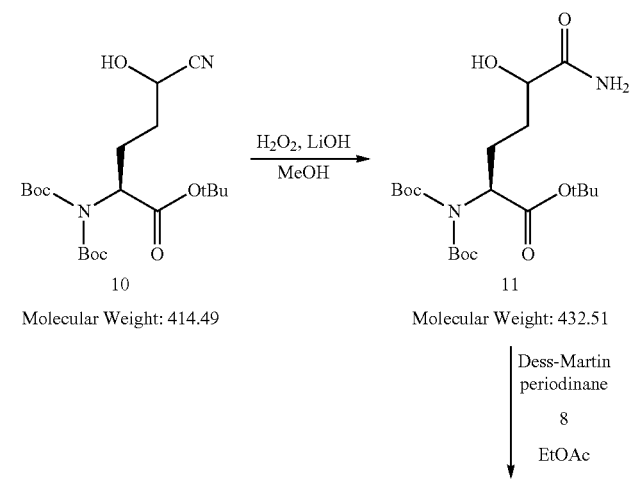
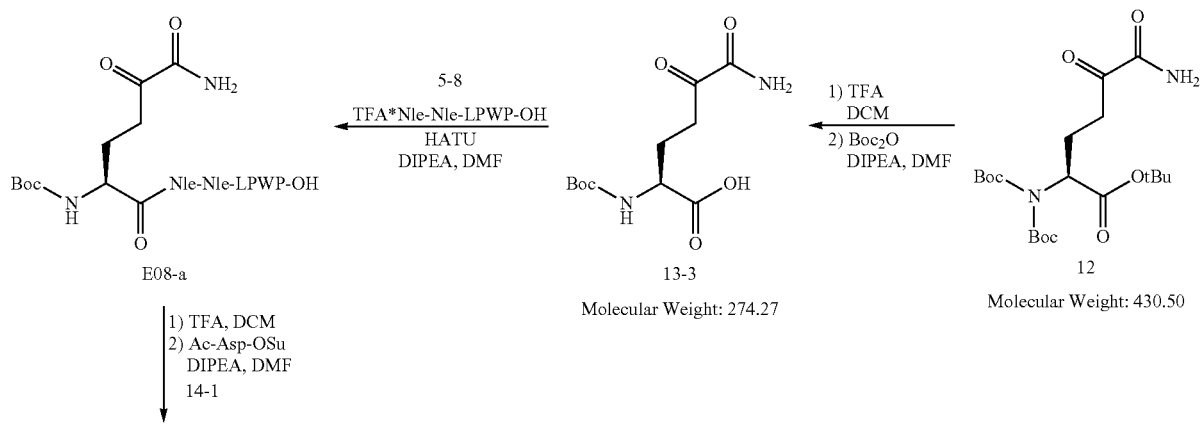
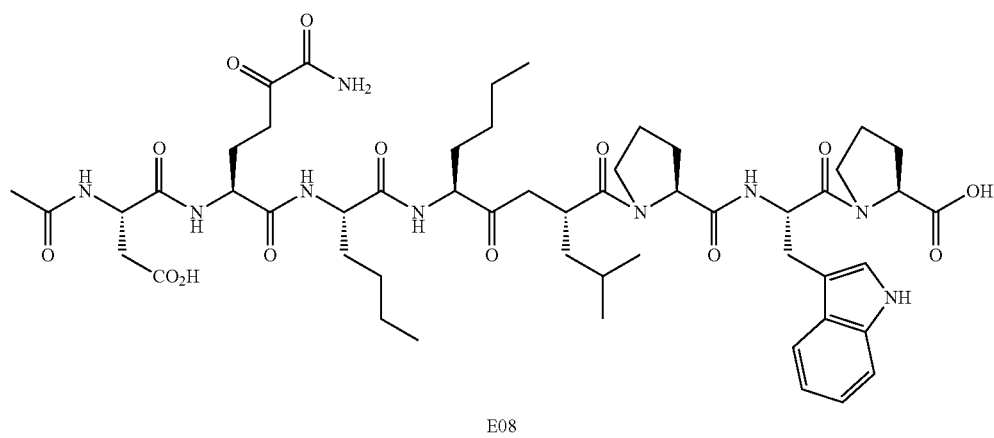
E08
Molecular Weight: 1051.19

Example 9. Preparation of Compound E09
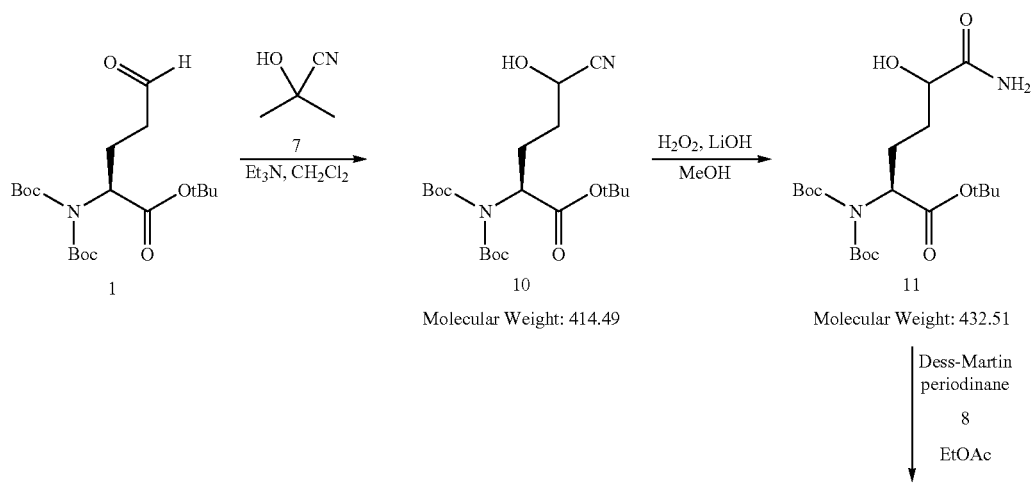
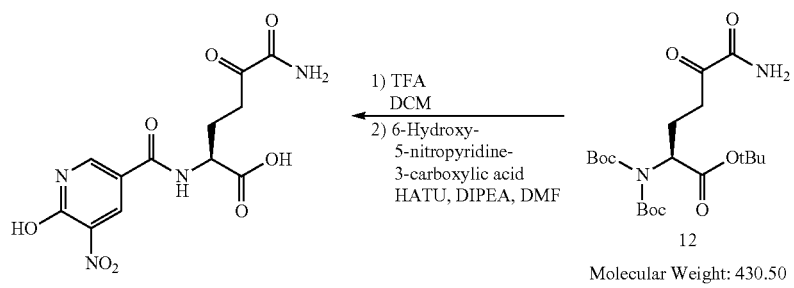
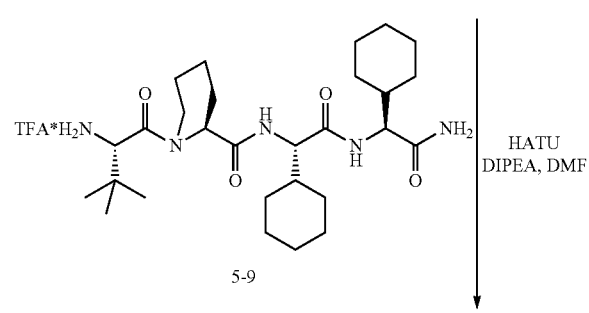

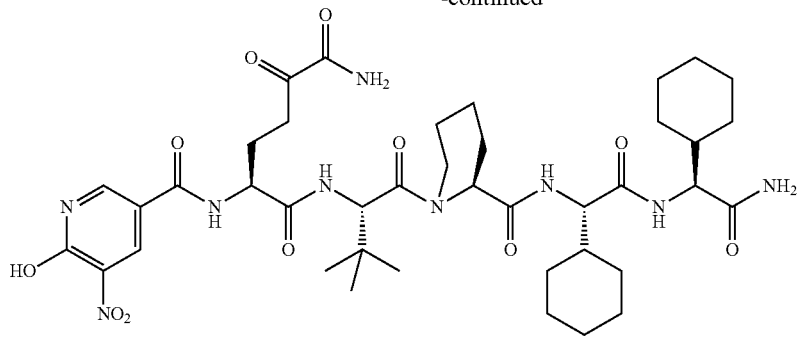

E09

(S)-N[1]-((S)-1-((R)-2-((S)-2-((S)-2-amino-1-cyclohexyl-2-oxoethylamino)-1-cyclohexyl-2-oxoethylcarbamoyl)piperidin-1-yl)-3,3-dimethyl-1-oxobutan-2-yl)-2-(6-hydroxy-5-nitronicotinamido)-5-oxohexanediamide Chemical Formula: $C_{40}H_{59}N_9O_{11}$ Exact Mass: 841.43

Molecular Weight: 841.95

The synthesis of compound E09 was performed according to Example 6, using 6-Hydroxy-5-nitropyridine-3-carboxylic acid (compound 13-4) instead of $Ac_2O$ and (R)—N—((S)-2-((S)-2-amino-1-cyclohexyl-2-oxoethylamino)-1-cyclohexyl-2-oxoethyl)-1-((S)-2-amino-3,3-dimethylbutanoyl)piperidine-2-carboxamide (compound 5-9) instead of 1-(2-chlorophenyl)piperazine (compound 5-6).

Yield: 13 mg, 40% (last step)

ESI-MS: 842.6 $[M+H]^+$

Example 10. Preparation of Compound E10

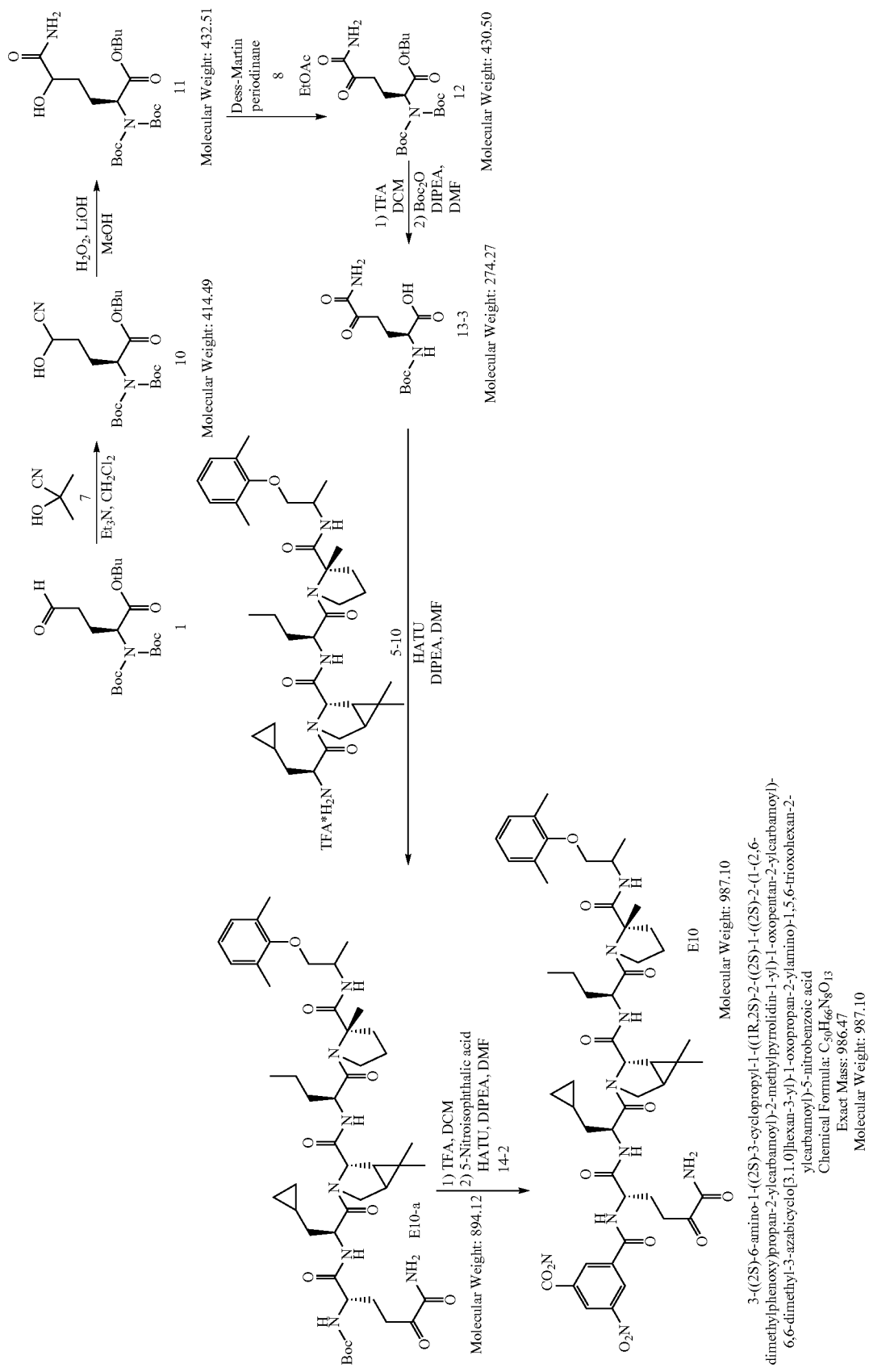

The synthesis of compound E10 was performed according to Example 6, using 5-Nitroisophthalic acid (compound 14-2) instead of Ac₂O (via Boc intermediate) and (1R,2S)-3-((S)-2-amino-3-cyclopropylpropanoyl)-N-((2S)-1-((2S)-2-(1-(2,6-dimethylphenoxy)propan-2-ylcarbamoyl)-2-methylpyrrolidin-1-yl)-1-oxopentan-2-yl)-6,6-dimethyl-3-azabicyclo[3.1.0]hexane-2-carboxamide (compound 5-10) instead of 1-(2-chlorophenyl)piperazine (compound 5-6).

Yield: 6 mg, 27% (last step)
ESI-MS: 987.7 [M+H]$^+$

Example 11. Preparation of Compound E04 by Cynanohydrine Route

Cyanohydrin Route

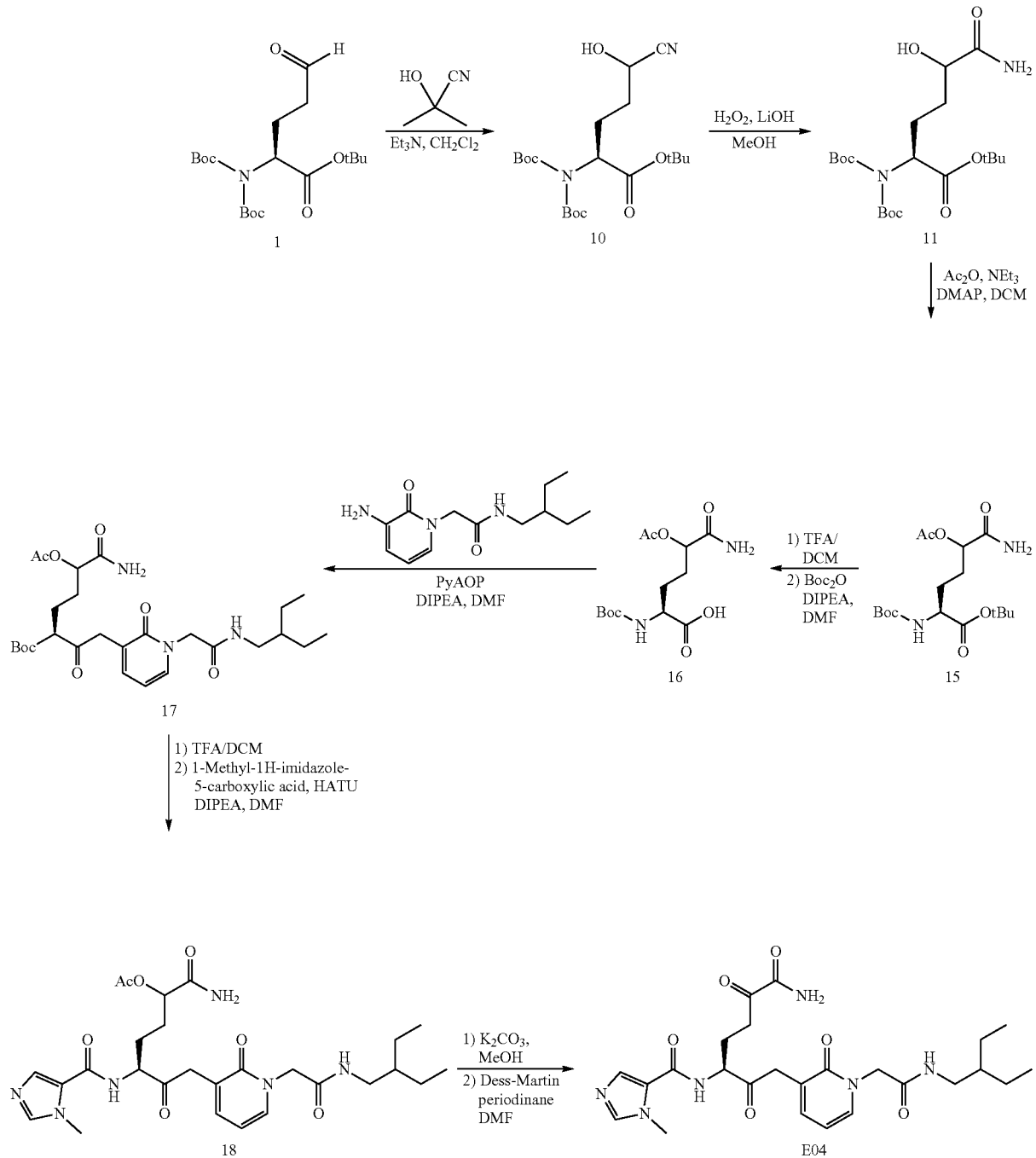

11.1 Preparation of Compound 10

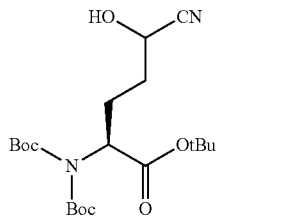

(2S)-tert-butyl 2-(bis(tert-butoxycarbonyl)amino)-
5-cyano-5-hydroxypentanoate
Chemical Formula: $C_{20}H_{34}N_2O_7$
Exact Mass: 414.24
Molecular Weight: 414.49

15.0 g (38.7 mmol) of the aldehyde (S)-tert-butyl 2-(bis(tert-butoxycarbonyl)amino)-5-oxopentanoate 1 were dissolved in 150 ml DCM, 6.42 ml (46.3 mmol) trimethylamine and 7.37 ml (79.9 mmol) acetone cyanohydrin were added and the reaction was stirred at room temperature overnight. The solution was washed twice with each citric acid solution (10%) and brine. The organic phase was dried over $Na_2SO_4$, filtered and the solvent was evaporated. The residue was purified by flash chromatography.

Yield: 16.2 g, >100%

ESI-MS: 437.6 $[M+Na]^+$

11.2 Preparation of Compound 11

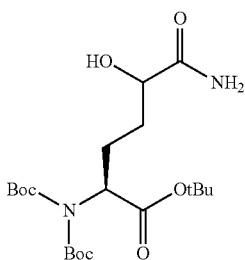

(2S)-tert-butyl 6-amino-2-(bis(tert-butoxycarbonyl)amino)-5-hydroxy-6-oxohexanoate
Chemical Formula: $C_{20}H_{36}N_2O_8$
Exact Mass: 432.25
Molecular Weight: 432.51

16.2 g (~38.6 mmol) of cyanohydrin 10 were dissolved in 95 ml MeOH at 4° C. and 1.91 g (45.5 mmol) lithium hydroxide monohydrate were added, 18.6 ml hydrogen peroxide (35%) were added dropwise and the reaction was stirred at room temperature for 1.5 h before quenching with sodium thiosulfate solution (5%). The aqueous phase was extracted with DCM. The combined organic phases were dried over $Na_2SO_4$, filtered and the solvent was evaporated. The residue was purified by flash chromatography.

Yield: 8.61 g, 52%

ESI-MS: 455.2 $[M+Na]^+$

11.3 Preparation of Compound 15

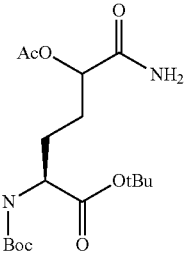

(2S)-tert-butyl 5-acetoxy-6-amino-2-(bis(tert-butoxycarbonyl)amino)-6-oxohexanoate
Chemical Formula: $C_{22}H_{38}N_2O_9$
Exact Mass: 474.26
Molecular Weight: 474.55

8.61 g (19.9 mmol) of hydroxyamide 10 were dissolved in 55 ml DCM, 3.45 ml (24.9 mmol) 1.91 g (45.5 mmol) trimethylamine, 2.12 ml acetic anhydride and 62 mg (0.50 mmol) DMAP were added and the reaction was stirred at room temperature for 3 h. After washing with water and brine, the organic phase was dried over $Na_2SO_4$, filtered and the solvent was evaporated. The product precipitates from MTBE solution by addition of hexane.

Yield: 8.08 g, 86%

ESI-MS: 475.5 $[M+H]^+$

11.4 Preparation of Compound 16

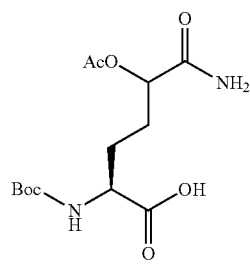

(2S)-5-acetoxy-6-amino-2-(tert-butoxycarbonylamino)-6-oxohexanoic acid
Chemical Formula: $C_{13}H_{22}N_2O_7$
Exact Mass: 318.14
Molecular Weight: 318.32

8.08 g (17.0 mmol) of 15 were dissolved in 140 ml DCM/TFA (1:1) and stirred at room temperature for 3 h. The solvent was evaporated and the residue was dissolved in 40 ml DMF, 5.80 ml (2 eq) DIPEA and 4.55 g (20.4 mmol) di-tert-butyl dicarbonate in 20 ml DMF were added and the reaction was stirred at room temperature overnight. The solvent was evaporated and the residue was dissolved in 80 ml EtOAc. After extraction with $NaHCO_3$ solution (1.05 eq in water), the product precipitates from the aqueous phase by addition of 1.5 eq citric acid.

Yield: 1.64 g, 30

ESI-MS: 319.4 $[M+H]^+$

11.5 Preparation of Compound 17

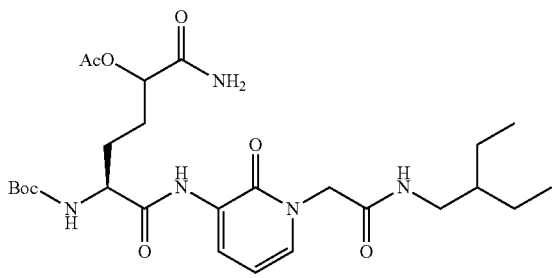

(5S)-1-amino-5-(tert-butoxycarbonylamino)-6-
(1-(2-(2-ethylbutylamino)-2-oxoethyl)-2-oxo-1,2-
dihydropyridin-3-ylamino)-1,6-dioxohexan-2-yl acetate
Chemical Formula: $C_{26}H_{41}N_5O_8$
Exact Mass: 551.30
Molecular Weight: 551.63

1.64 g (5.15 mmol) of 16, 2.68 g (1 eq) PyAOP and 1.29 g (1 eq) 2-(3-amino-2-oxopyridin-1(2H)-yl)-N-(2-ethylbutyl)acetamide were dissolved in 15 ml DMF and 1.75 ml DIPEA and stirred at 45° C. overnight. The solvent was evaporated; the residue was dissolved in EtOAc and washed twice with each citric acid solution (10%). NaHCO$_3$ solution (10%) and brine. The organic phase was dried over Na$_2$SO$_4$, filtered and the solvent was evaporated. The product precipitates from iPrOH solution by addition of MTBE. Yield: 2.71 g, 95%

ESI-MS: 552.4 [M+H]$^+$

11.6 Preparation of Compound 18

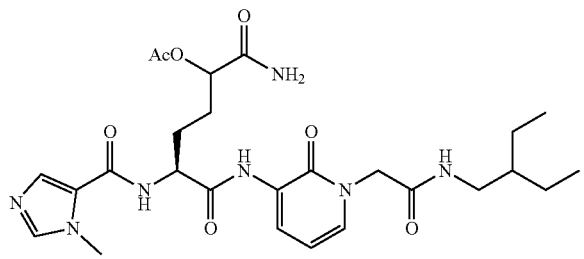

(5S)-1-amino-6-(1-(2-(2-ethylbutylamino)-2-oxoethyl)-2-oxo-1,2-
dihydropyridin-3-ylamino)-5-(1-methyl-1H-imidazole-5-carboxamido)-
1,6-dioxohexan-2-yl acetate
Chemical Formula: $C_{26}H_{37}N_7O_7$
Exact Mass: 559.28
Molecular Weight: 559.61

300 mg (0.54 mmol) of 17 were dissolved in 140 ml DCM/TFA (1:1) and stirred at room temperature for 1 h. The solvent was evaporated and the residue was dissolved in 4 ml DMF, 68.6 mg (1 eq) 1-methyl-1H-imidazole-5-carboxylic acid, 207 mg (1 eq) HATU and 370 µl (4 eq) DIPEA were added and the reaction was stirred at room temperature overnight. The solvent was evaporated and the residue was purified by HPLC.

Yield: 241 mg, 79%

ESI-MS: 560.5 [M+H]$^+$

11.7 Preparation of Compound E04

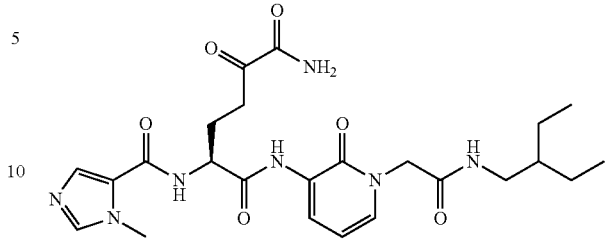

(S)-N$^1$-(1-(2-(2-ethylbutylamino)-2-oxoethyl)-2-oxo-1,2-
dihydropyridin-3-yl)-2-(1-methyl-1H-imidazole-5-
carboxamido)-5-oxohexanediamide
Chemical Formula: $C_{24}H_{33}N_7O_6$
Exact Mass: 515.25
Molecular Weight: 515.56

240 mg (0.43 mmol) of 18 were dissolved in 5 ml MeOH. 89.8 mg (1.5 eq) potassium carbonate were added and the reaction was stirred at room temperature for 1 h. The solution was diluted with DCM and washed with water. The organic phase was dried over Na$_2$SOA, filtered and the solvent was evaporated to yield 88 mg of the hydroxy amide which was used without further purification.

88 mg (0.17 mmol) of the hydroxy amide were dissolved in 2 ml DMF, 115 mg (0.27 mmol, 1.6 eq) Dess-Martin periodinane (DMP) were added and the reaction was stirred at room temperature over 2 h. The precipitate was filtered off and the filtrate was evaporated. The residue was purified by HPLC.

Yield: 59 mg, 67%

ESI-MS: 516.5 [M+H]$^+$

Example 12. Preparation of Compound E11

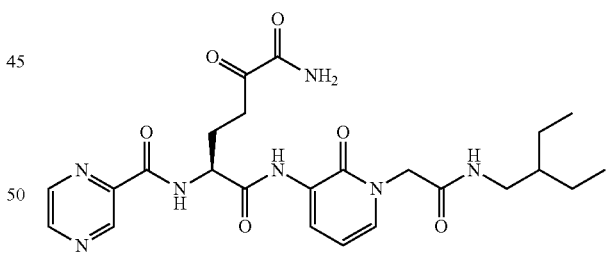

(S)-N$^1$-(1-(2-(2-ethylbutylamino)-2-oxoethyl)-2-oxo-1,2-
dihydropyridin-3-yl)-5-oxo-2-(pyrazine-2-carboxamido)
hexanediamide
Chemical Formula: $C_{24}H_{31}N_7O_6$
Exact Mass: 513.23
Molecular Weight: 513.55

The synthesis of compound E11 was performed according to synthetic method described in Examples 11.6-11.7, using pyrazine-2-carboxylic acid instead of 1-methyl-1H-imidazole-5-carboxylic acid.

Yield: 8 mg, 6% (last step)

ESI-MS: 514.4 [M+H]$^+$

Example 13. Preparation of Compound E12

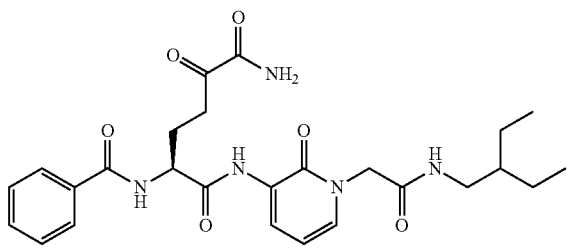

(S)-2-benzamido-$N^1$-(1-(2-(2-ethylbutylamino)-2-oxoethyl)-
2-oxo-1,2-dihydropyridin-3-yl)-5-oxohexanediamide
Chemical Formula: $C_{26}H_{33}N_5O_6$
Exact Mass: 511.24
Molecular Weight: 511.57

The synthesis of compound E12 was performed according to synthetic method described in Examples 11.6-11.7, using benzoic acid instead of 1-methyl-1H-imidazole-5-carboxylic acid. Yield: 52 mg, 37% (last step); ESI-MS: 512.4 [M+H]$^+$

Example 14. Preparation of Compound E13

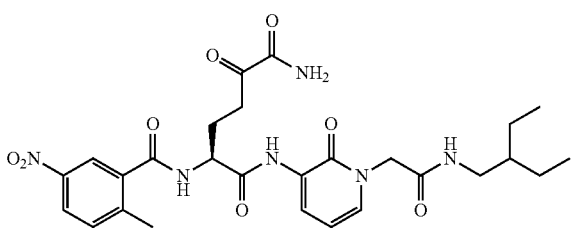

(S)-$N^1$-(1-(2-(2-ethylbutylamino)-2-oxoethyl)-2-oxo-1,2-
dihydropyridin-3-yl)-2-(2-methyl-5-nitrobenzamido)-5-
oxohexanediamide
Chemical Formula: $C_{27}H_{34}N_6O_8$
Exact Mass: 570.24
Molecular Weight: 570.59

The synthesis of compound E13 was performed according to synthetic method described in Examples 11.6-11.7, using 2-methyl-5-nitrobenzoic acid instead of 1-methyl-1H-imidazole-5-carboxylic acid.
Yield: 47 mg, 33% (last step); ESI-MS: 571.4 [M+H]$^+$

Example 15. Preparation of Compound E14

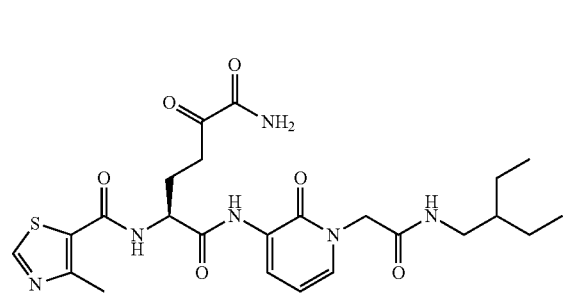

(S)-$N^1$-(1-(2-(2-ethylbutylamino)-2-oxoethyl)-2-oxo-1,2-
dihydropyridin-3-yl)-2-(4-methylthiazole-5-
carboxamido)-5-oxohexanediamide
Chemical Formula: $C_{24}H_{32}N_6O_6S$
Exact Mass: 532.21
Molecular Weight: 532.61

The synthesis of compound E14 was performed according to synthetic method described in Examples 11.6-11.7, using 4-methylthiazole-5-carboxylic acid instead of 1-methyl-1H-imidazole-5-carboxylic acid.
Yield: 18 mg, 25% (last step); ESI-MS: 533.4 [M+H]$^+$

Example 16. Preparation of Compound E15

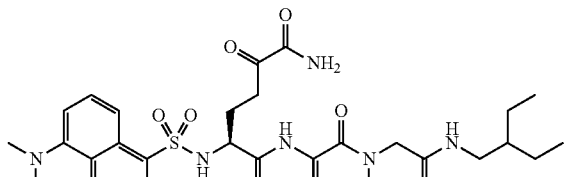

(S)-2-(5-(dimethylamino)naphthalene-1-sulfonamido)-$N^1$-
(1-(2-(2-ethylbutylamino)-2-oxoethyl)-2-oxo-1,2-
dihydropyridin-3-yl)-5-oxohexanediamide
Chemical Formula: $C_{31}H_{40}N_6O_7S$
Exact Mass: 640.27
Molecular Weight: 640.75

The synthesis of compound E15 was performed according to synthetic method described in Examples 11.6-11.7, using dansyl chloride instead of 1-methyl-1H-imidazole-5-carboxylic acid.
Yield: 38 mg, 55% (last step); ESI-MS: 641.4 [M+H]$^+$

Example 17. Preparation of Compound E02

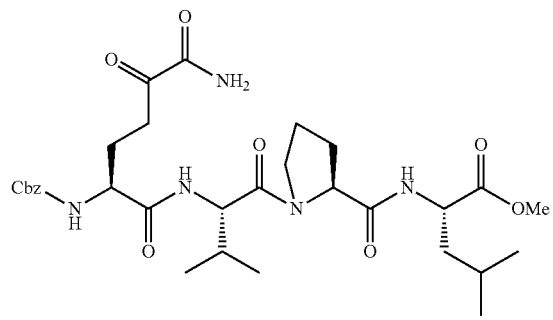

(S)-methyl 2-((S)-1-((S)-2-((S)-6-amino-2-
(benzyloxycarbonylamino)-5,6-dioxohexanamido)-
3-methylbutanoyl)pyrrolidine-2-carboxamido)-4-
methylpentanoate
Chemical Formula: $C_{31}H_{45}N_5O_9$
Exact Mass: 631.32
Molecular Weight: 631.72

Alternatively, the synthesis of compound E02 was performed according to synthetic method described in Examples 11.5-11.7, coupling 16 with the tripeptide H-VPL-OMe and using benzyl chloroformate (Cbz-Cl) instead of 1-methyl-1H-imidazole-5-carboxylic acid.
Yield: 51 mg, 33% (last step); ESI-MS: 632.5 [M+H]$^+$ Example 18. Preparation of Compound E04 by Weinreb Aminde Route
Weinreb Arninde Route
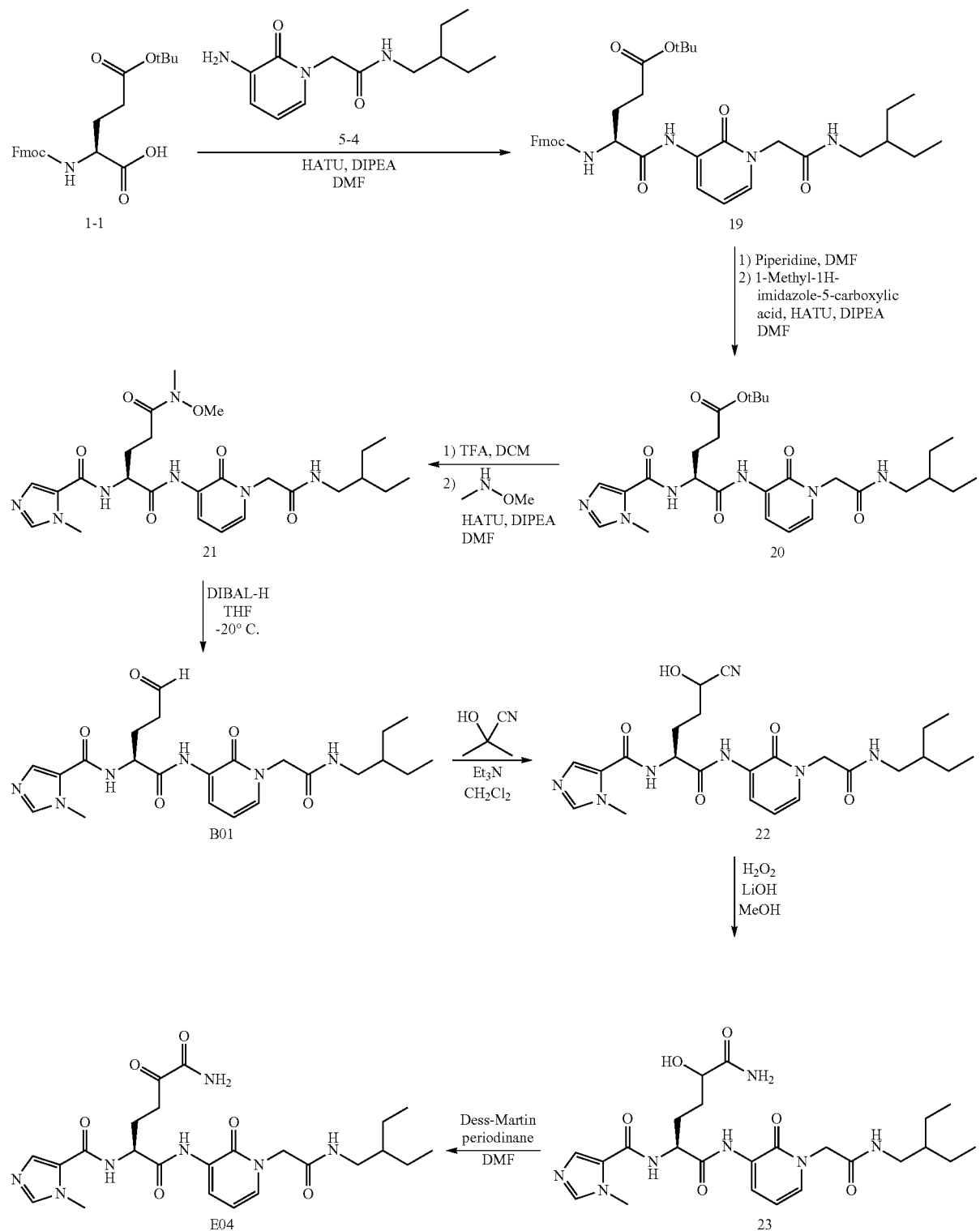

19.1 Preparation of Compound 19

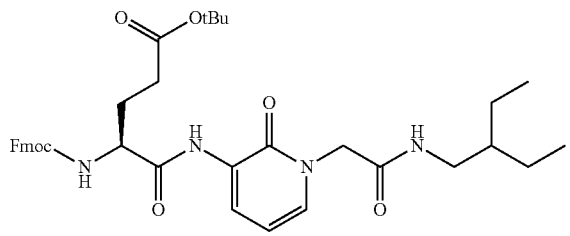

(S)-tert-butyl 4-(((9H-fluoren-9-yl)methoxy)
carbonylamino)-5-(1-(2-(2-ethylbutylamino)-2-
oxoethyl)-2-oxo-1,2-dihydropyridin-3-ylamino)-5-
oxopentanoate
Chemical Formula: $C_{37}H_{46}N_4O_7$
Exact Mass: 658.34
Molecular Weight: 658.78

20.0 g (47.0 mmol) of Fmoc-Glu(OtBu)-OH were dissolved in 100 ml DMF, 11.8 g (1 eq) 2-(3-amino-2-oxopyridin-1(2H)-yl)-N-(2-ethylbutyl)acetamide, 17.9 g (1 eq) HATU and 16.4 ml (2 eq) DIPEA were added and the reaction was stirred at room temperature overnight. The solvent was evaporated; the residue was dissolved in EtOAc and washed twice with each citric acid solution (10%), NaHCO$_3$ solution (10%) and brine. The organic phase was dried over Na$_2$SO$_4$, filtered and concentrated. The product precipitates from EtOAc and was used without further purification.

Yield: 38.3 g, >100%; ESI-MS: 659.4 [M+H]$^+$

19.2 Preparation of Compound 20

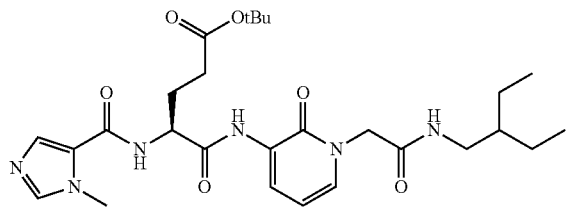

(S)-tert-butyl 5-(1-(2-(2-ethylbutylamino)-2-oxoethyl)-2-
oxo-1,2-dihydropyridin-3-ylamino)-4-(1-methyl-1H-
imidazole-5-carboxamido)-5-oxopentanoate
Chemical Formula: $C_{27}H_{40}N_6O_6$
Exact Mass: 544.30
Molecular Weight: 544.64

38.3 g (=47.0 mmol) of raw 19 were dissolved in 500 ml DMF/Piperidine (5:1) and stirred at room temperature for 3 h. The solvent was evaporated and the product precipitates from diethyl ether (14.3 g, 70%), 5.0 g (11.5 mmol) of the free amine were dissolved in 100 ml DMF, 1.44 g (1 eq) 1-methyl-1H-imidazole-5-carboxylic acid, 4.35 g (1 eq) HATU and 4.0 ml (2 eq) DIPEA were added and the reaction was stirred at room temperature overnight. The solvent was evaporated; the residue was dissolved in EtOAc and washed twice with each citric acid solution (10%), NaHCO$_3$ solution (10%) and brine. The organic phase was dried over Na$_2$SO$_4$, filtered and concentrated. The product precipitates from diethyl ether and was used without further purification.

Yield: 5.66 g, 91%; ESI-MS: 545.5 [M+H]$^+$

19.3 Preparation of Compound 21

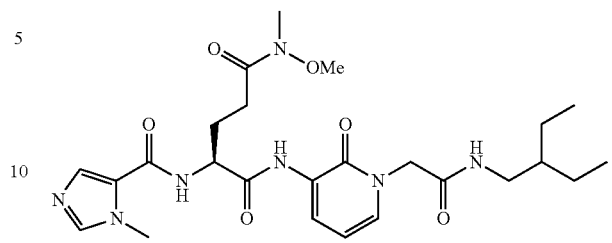

(S)-N$^1$-(1-(2-(2-ethylbutylamino)-2-oxoethyl)-2-oxo-1,2-
dihydropyridin-3-yl)-N$^5$-methoxy-N$^5$-methyl-2-(1-methyl-
1H-imidazole-5-carboxamido)pentanediamide
Chemical Formula: $C_{25}H_{37}N_7O_6$
Exact Mass: 531.28
Molecular Weight: 531.60

3.0 g (5.51 mmol) of 20 were dissolved in 60 ml DCM/TFA (1:1) and stirred at room temperature for 3 h. The solvent was evaporated and the residue was dissolved in 60 ml DMF, 2.09 g (1 eq) HATU, 537 mg (1 eq) N,O-Dimethylhydroxylamine and 1.92 ml (2 eq) DIPEA were added and the reaction was stirred at room temperature overnight. The solvent was evaporated; the residue was dissolved in EtOAc and washed twice with each citric acid solution (10%), NaHCO$_3$ solution (10%) and brine. The organic phase was dried over Na$_2$SO$_4$, filtered and the solvent was evaporated. The Weinreb amide was used without further purification.

Yield: 2.45 g, 84%

ESI-MS: 532.5 [M+H]$^+$

19.4 Preparation of Compound B04

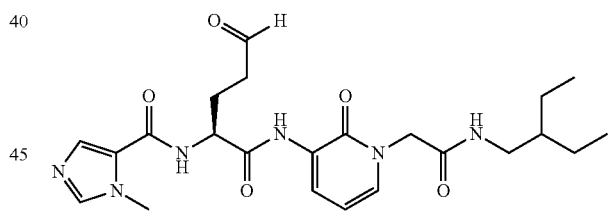

(S)-N-(1-(2-(2-ethylbutylamino)-2-oxoethyl)-2-oxo-
1,2-dihydropyridin-3-ylamino)-1,5-dioxopentan-2-yl)-1-
methyl-1H-imidazole-5-carboxamide
Chemical Formula: $C_{23}H_{32}N_6O_5$
Exact Mass: 472.24
Molecular Weight: 472.54

500 mg (0.94 mmol) of Weinreb amide 9 were dissolved in 10 ml THF. At −20° C., 2.35 ml (3 eq) DIBAL-H (1.2 M in toluene) were added and the reaction was stirred for 30 min before quenching with MeOH. The emulsion was extracted with EtOAc. The combined organic phases were dried over Na$_2$SO$_4$, filtered and the solvent was evaporated and the residue was purified by HPLC.

Yield: 146 mg, 33%

ESI-MS: 473.5 [M+H]$^+$

19.5 Preparation of Compound 22

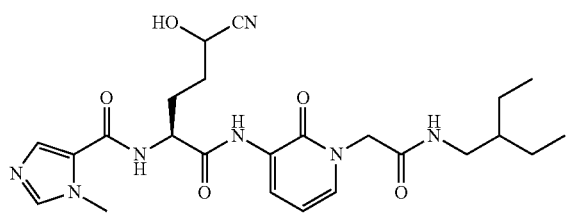

N-((2S)-5-cyano-1-(1-(2-(2-ethylbutylamino)-2-oxoethyl)-2-oxo-1,2-dihydropyridin-3-ylamino)-5-hydroxy-1-oxopentan-2-yl)-1-methyl-1H-imidazole-5-carboxamide
Chemical Formula: $C_{24}H_{33}N_7O_5$
Exact Mass: 499.25
Molecular Weight: 499.56

The synthesis of compound 22 was performed according to 10, using the aldehyde B04 as entry.
Yield: 88 mg, 61%
ESI-MS: 500.4 $[M+H]^+$

Example 19.6 Preparation of Compound 23

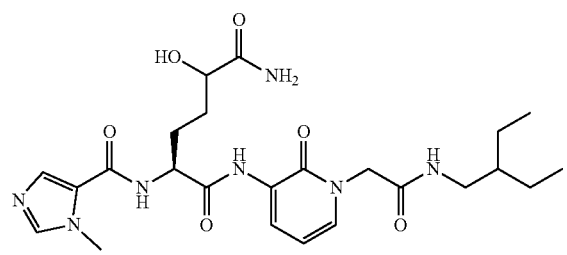

(2S)-N¹-(1-(2-(2-ethylbutylamino)-2-oxoethyl)-2-oxo-1,2-dihydropyridin-3-yl)-5-hydroxy-2-(1-methyl-1H-imidazole-5-carboxamido)hexanediamide
Chemical Formula: $C_{24}H_{35}N_7O_6$
Exact Mass: 517.26
Molecular Weight: 517.58

The synthesis of compound 23 was performed according to 11, using the cyanohydrin 22 as entry.
Yield: 33 mg, 36%
ESI-MS: 518.5 $[M+H]^+$

Example 19.7 Preparation of Compound E04

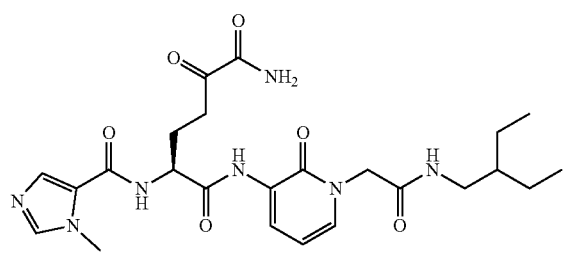

(S)-N¹-(1-(2-(2-ethylbutylamino)-2-oxoethyl)-2-oxo-1,2-dihydropyridin-3-yl)-2-(1-methyl-1H-imidazole-5-carboxamido)-5-oxohexanediamide
Chemical Formula: $C_{24}H_{33}N_7O_6$
Exact Mass: 515.25
Molecular Weight: 515.56

The synthesis of compound E04 was performed according to oxidation method described in Example 1.7 and Example 4, using the hydroxy amide 23 as entry.
Yield: 24 mg, 73%
ESI-MS: 516.4 $[M+H]^+$

Example 19. Preparation of Compound E16 by Passerini Route

Passerini Route

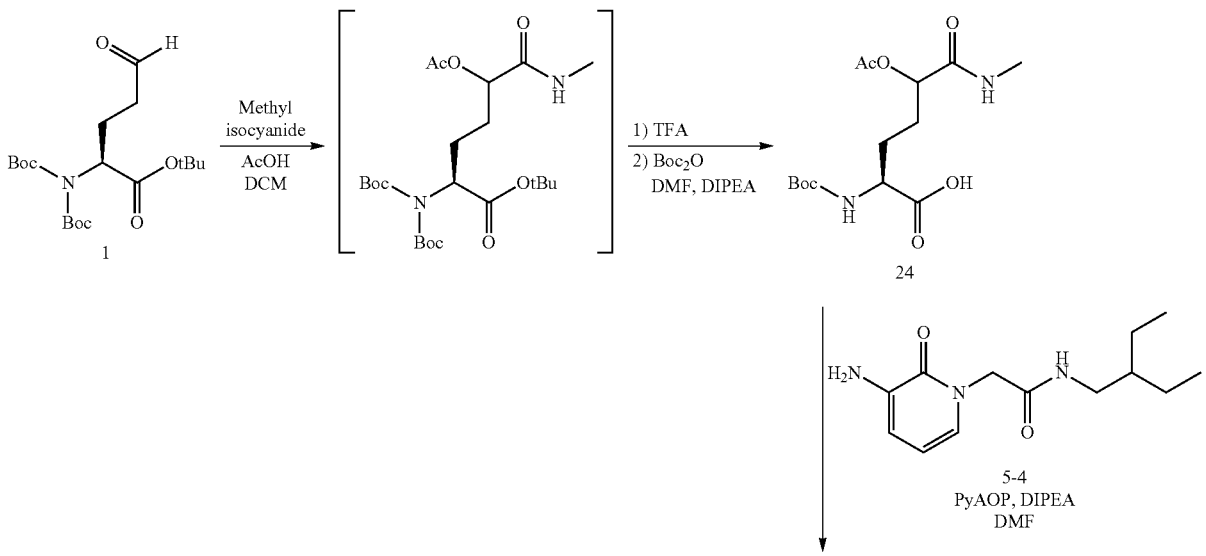

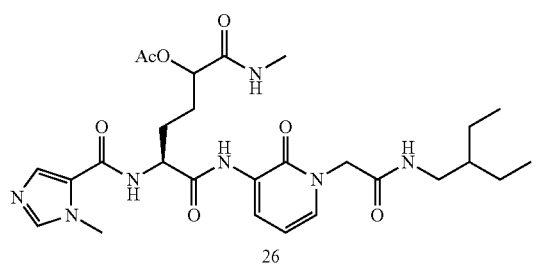

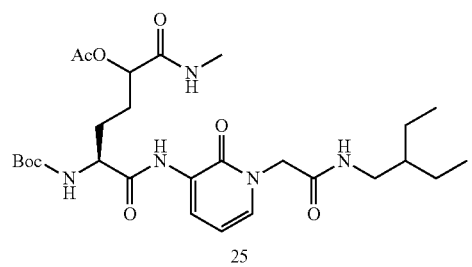

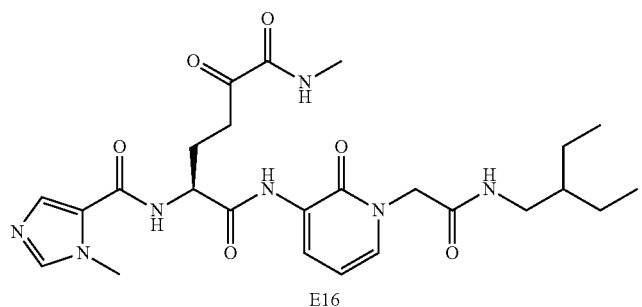

E16

19.1 Preparation of Compound 24

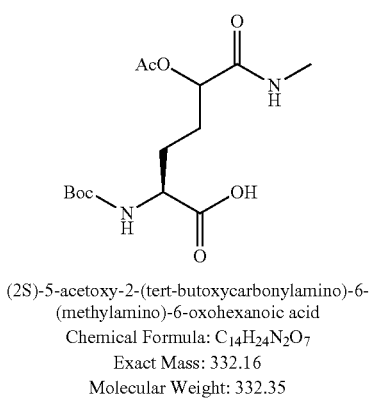 [SMILES: CNC(=O)C(CC[C@H](NC(=O)OC(C)(C)C)C(=O)O)OC(C)=O]

(2S)-5-acetoxy-2-(tert-butoxycarbonylamino)-6-(methylamino)-6-oxohexanoic acid
Chemical Formula: $C_{14}H_{24}N_2O_7$
Exact Mass: 332.16
Molecular Weight: 332.35

15.0 g (38.7 mmol) of the aldehyde (S)-tert-butyl 2-(bis(tert-butoxycarbonyl)amino)-5-oxopentanoate 1 were dissolved in 60 ml DCM. At 0° C. 2.42 ml (1.05 eq) methyl isocyanide and 2.33 ml (1.05 eq) acetic acid were added and the reaction was stirred at room temperature overnight. 75 ml TFA were added and the reaction was stirred for another 3 h. The solvent was evaporated and the residue was dissolved in 40 ml DMF, 13.2 ml (2 eq) DIPEA and 10.4 g (46.6 mmol) di-tert-butyl dicarbonate in 10 ml DMF were added and the reaction was stirred at room temperature overnight. The solvent was evaporated and the residue was dissolved in DCM. After extraction with $NaHCO_3$ solution (1.05 eq in water), 1.5 eq citric acid was added to the aqueous phase, followed by re-extraction with DCM. The organic phase was dried over $Na_2SO_4$, filtered and the solvent was evaporated. The residue was purified by flash chromatography.

Yield: 12.5 g, 95%
ESI-MS: 333.5 [M+H]$^+$

19.2 Preparation of Compound 25

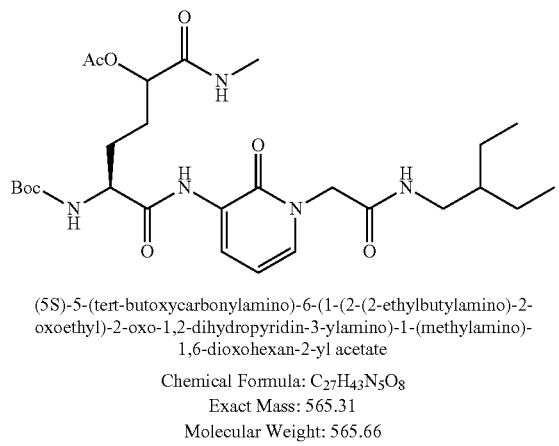 [SMILES: CCC(CC)CNC(=O)Cn1cccc(NC(=O)[C@H](CCC(OC(C)=O)C(=O)NC)NC(=O)OC(C)(C)C)c1=O]

(5S)-5-(tert-butoxycarbonylamino)-6-(1-(2-(2-ethylbutylamino)-2-oxoethyl)-2-oxo-1,2-dihydropyridin-3-ylamino)-1-(methylamino)-1,6-dioxohexan-2-yl acetate
Chemical Formula: $C_{27}H_{43}N_5O_8$
Exact Mass: 565.31
Molecular Weight: 565.66

The synthesis of compound 25 was performed according to 17, using 24 as entry.

Yield: 6.65 g, 32%
ESI-MS: 566.54 [M+H]$^+$

19.3 Preparation of Compound 26

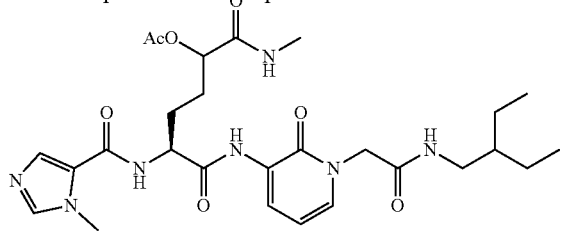

(5S)-6-(1-(2-(2-ethylbutylamino)-2-oxoethyl)-2-oxo-1,2-dihydropyridin-3-ylamino)-5-(1-methyl-1H-imidazole-5-carboxamido)-1-(methylamino)-1,6-dioxohexan-2-yl acetate Chemical Formula: $C_{27}H_{39}N_7O_7$
Exact Mass: 573.29
Molecular Weight: 573.64

The synthesis of compound 26 was performed according to 18, using 25 as entry.
Yield: 4.67 g, 69%
ESI-MS: 574.5 $[M+H]^+$

19.4 Preparation of Compound E16

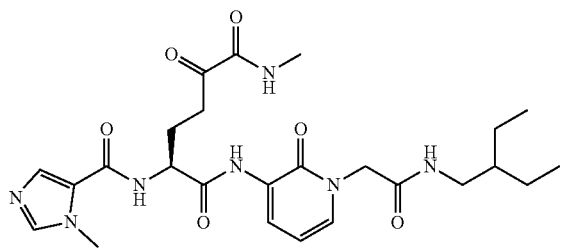

(S)-$N^1$-(1-(2-(2-ethylbutylamino)-2-oxoethyl)-2-oxo-1,2-dihydropyridin-3-yl)-$N^6$-methyl-2-(1-methyl-1H-imidazole-5-carboxamido)-5-oxohexanediamide Chemical Formula: $C_{25}H_{35}N_7O_6$
Exact Mass: 529.26
Molecular Weight: 529.59

The synthesis of compound E16 was performed according to oxidation method described in Example 1.7 and Example 4, using 26 as entry.
Yield: 1.00 g, 31%; ESI-MS: 530.5 $[M+H]^+$

Example 20. Preparation of Compound E17

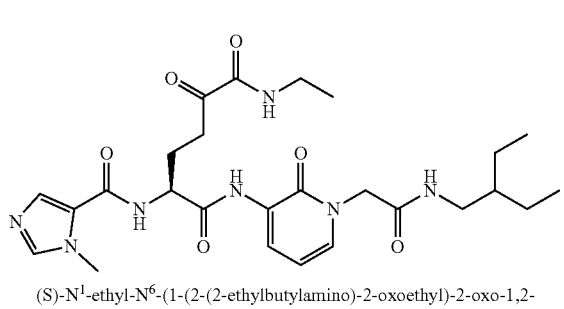

(S)-$N^1$-ethyl-$N^6$-(1-(2-(2-ethylbutylamino)-2-oxoethyl)-2-oxo-1,2-dihydropyridin-3-yl)-5-(1-methyl-1H-imidazole-5-carboxamido)-2-oxohexanediamide Chemical Formula: $C_{26}H_{37}N_7O_6$
Exact Mass: 543.28
Molecular Weight: 543.62

The synthesis of compound E17 was performed according to, synthetic method described in Example 19, using ethyl isocyanide in the Passerini reaction (step 1).
Yield: 148 mg, 44% (last step)
ESI-MS: 544.5 $[M+H]^+$

Example 21. Preparation of Compound E18

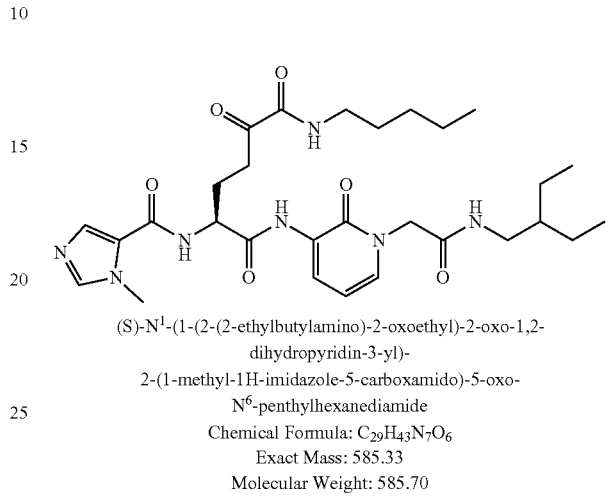

(S)-$N^1$-(1-(2-(2-ethylbutylamino)-2-oxoethyl)-2-oxo-1,2-dihydropyridin-3-yl)-2-(1-methyl-1H-imidazole-5-carboxamido)-5-oxo-$N^6$-penthylhexanediamide Chemical Formula: $C_{29}H_{43}N_7O_6$
Exact Mass: 585.33
Molecular Weight: 585.70

The synthesis of compound E18 was performed according to synthetic method described in Example 19, using pentyl isocyanide in the Passerini reaction (step 1).
Yield: 32 mg, 35% (last step)
ESI-MS: 586.5 $[M+H]^+$

Example 22. Preparation of Compound E19

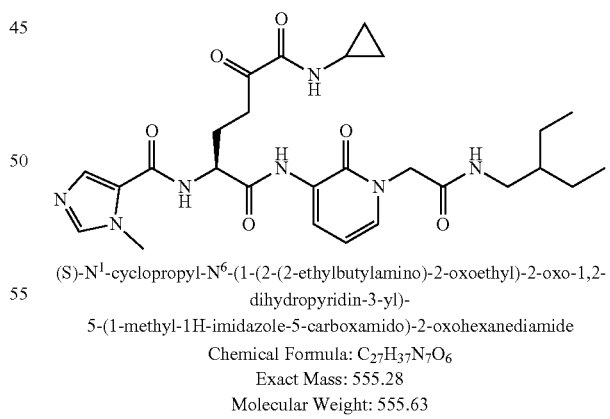

(S)-$N^1$-cyclopropyl-$N^6$-(1-(2-(2-ethylbutylamino)-2-oxoethyl)-2-oxo-1,2-dihydropyridin-3-yl)-5-(1-methyl-1H-imidazole-5-carboxamido)-2-oxohexanediamide Chemical Formula: $C_{27}H_{37}N_7O_6$
Exact Mass: 555.28
Molecular Weight: 555.63

The synthesis of compound E19 was performed according to synthetic method described in Example 19, using cyclopropyl isocyanide in the Passerini reaction (step 1).
Yield: 42 mg, 54% (last step)
ESI-MS: 556.4 $[M+H]^+$

Example 23. Preparation of Compound E20

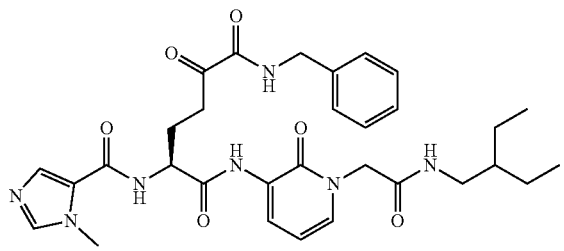

(S)-N¹-benzyl-N⁶-(1-(2-(2-ethylbutylamino)-2-oxoethyl)-2-oxo-1,2-dihydropyridin-3-yl)-5-(1-methyl-1H-imidazole-5-carboxamido)-2-oxohexanediamide Chemical Formula: $C_{31}H_{39}N_7O_6$
Exact Mass: 605.30
Molecular Weight: 605.68

The synthesis of compound E20 was performed according to synthetic method described in Example 19, using benzyl isocyanide in the Passerini reaction (step 1).

Yield: 74 mg, 62% (last step)
ESI-MS: 606.5 [M+H]⁺

Example 24. Preparation of Compound E21

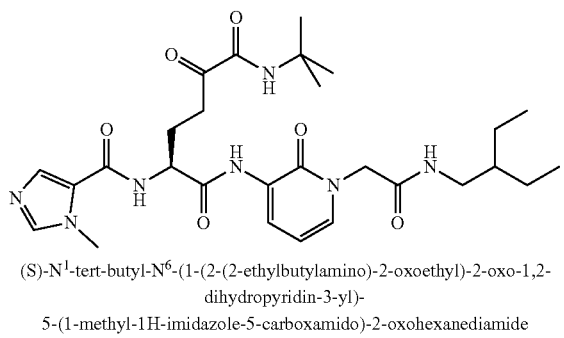

(S)-N¹-tert-butyl-N⁶-(1-(2-(2-ethylbutylamino)-2-oxoethyl)-2-oxo-1,2-dihydropyridin-3-yl)-5-(1-methyl-1H-imidazole-5-carboxamido)-2-oxohexanediamide Chemical Formula: $C_{28}H_{41}N_7O_6$
Exact Mass: 571.31
Molecular Weight: 571.67

The synthesis of compound E21 was performed according to synthetic method described in Example 19, using tert-butyl isocyanide in the Passerini reaction (step 1).

Yield: 40 mg, 51% (last step); ESI-MS: 572.5 [M+H]⁺

Example 25. Preparation of Compound E22

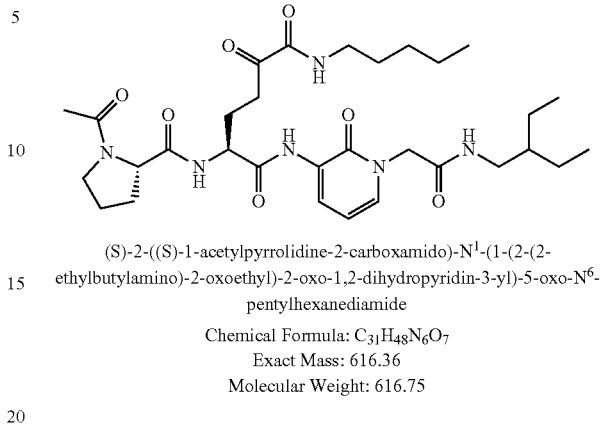

(S)-2-((S)-1-acetylpyrrolidine-2-carboxamido)-N¹-(1-(2-(2-ethylbutylamino)-2-oxoethyl)-2-oxo-1,2-dihydropyridin-3-yl)-5-oxo-N⁶-pentylhexanediamide Chemical Formula: $C_{31}H_{48}N_6O_7$
Exact Mass: 616.36
Molecular Weight: 616.75

The synthesis of compound E22 was performed according to synthetic method described in Example 21 (E18), coupling with acetylproline in step 3.

Yield: 23 mg, 39% (last step); ESI-MS: 617.5 [M+H]⁺

Example 26. Preparation of Compound E23

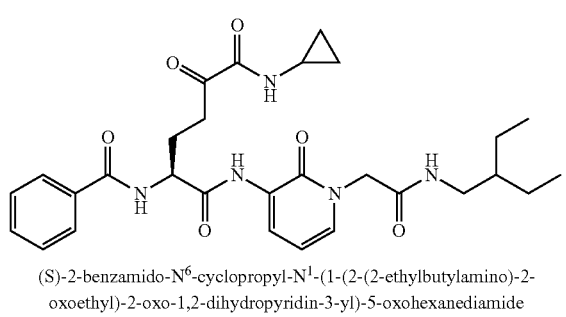

(S)-2-benzamido-N⁶-cyclopropyl-N¹-(1-(2-(2-ethylbutylamino)-2-oxoethyl)-2-oxo-1,2-dihydropyridin-3-yl)-5-oxohexanediamide Chemical Formula: $C_{29}H_{37}N_5O_6$
Exact Mass: 551.27
Molecular Weight: 551.63

The synthesis of compound E23 was performed according to synthetic method described in Example 22 (E19), coupling with benzoic acid in Example 19.3.

Yield: 4 mg, 24% (last step); ESI-MS: 552.4 [M+H]⁺

Example 27. Preparation of Compound E24

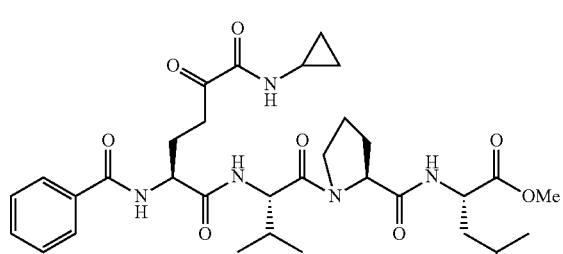

(S)-methyl 2-((S)-1-((S)-2-((S)-2-benzamido-6-(cyclopropylamino)-5,6-dioxohexanamido)-3-methylbutanoyl)pyrrolidine-2-carboxamido)-4-methylpentanoate
Chemical Formula: $C_{33}H_{47}N_5O_8$
Exact Mass: 641.34
Molecular Weight: 641.75

The synthesis of compound E25 was performed according to synthetic method described in Example 26 (E23), coupling with H-VPL-OMe in Example 19.2.
Yield: 14 mg, 30% (last step); ESI-MS: 642.5 [M+H]$^+$

Example 28. Preparation of Compound E25

28.1 Preparation of Compound 32

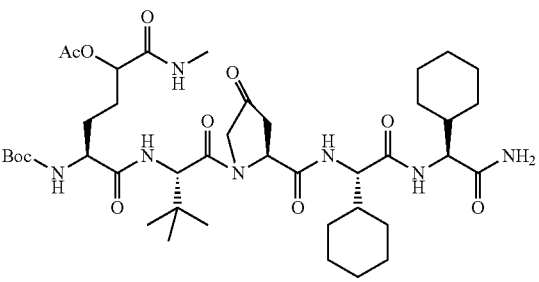

(5S)-6-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-5-(tert-butoxycarbonylamino)-1-(methylamino)-1,6-dioxohexan-2-yl acetate
Chemical Formula: $C_{41}H_{67}N_7O_{11}$
Exact Mass: 833.49
Molecular Weight: 834.01

The synthesis of compound 32 was performed according to 25 by coupling the tetrapeptide (S)—N—((S)-2-((S)-2-amino-1-cyclohexyl-2-oxoethylamino)-1-cyclohexyl-2-oxoethyl)-1-((S)-2-amino-3,3-dimethylbutanoyl)-4-oxopyrrolidine-2-carboxamide with HATU.
Yield: 399 mg, 65%
ESI-MS: 834.7 [M+H]$^+$

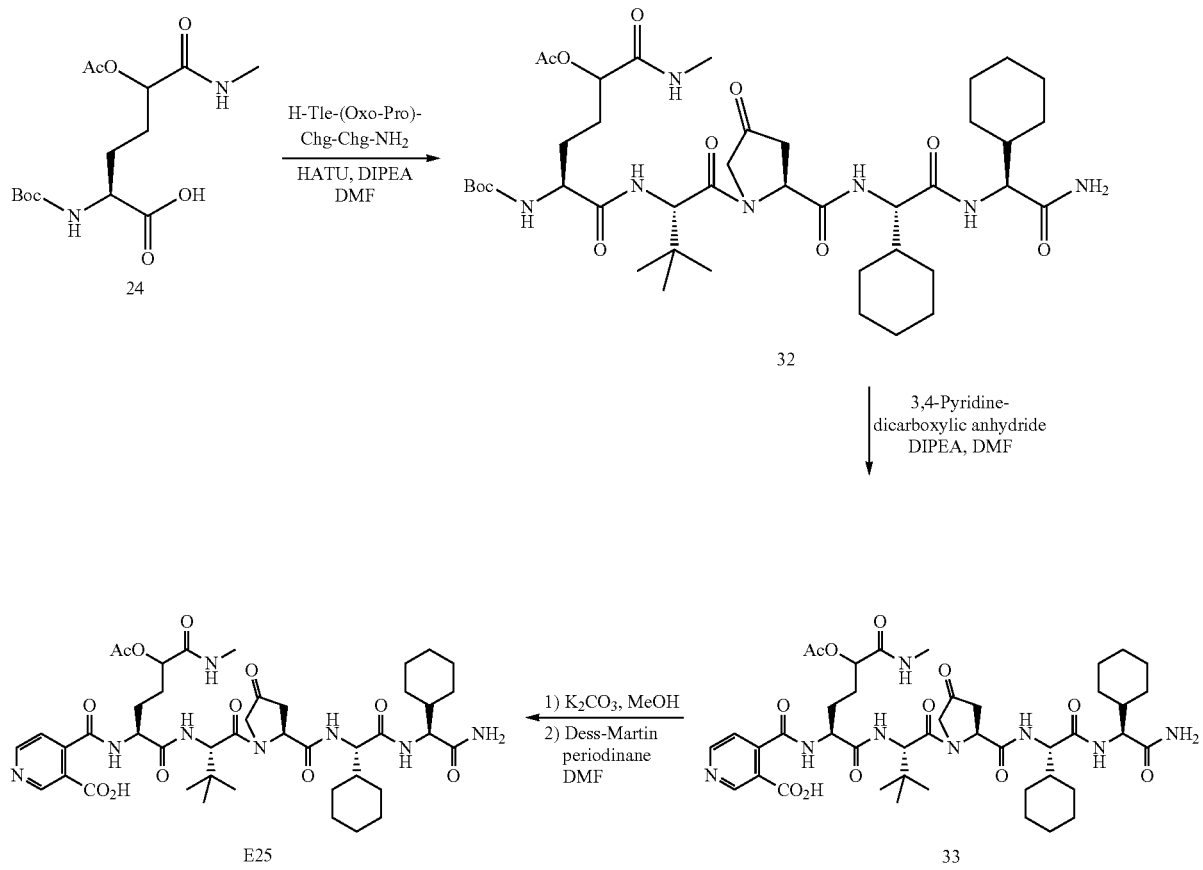

28.2 Preparation of Compound 33

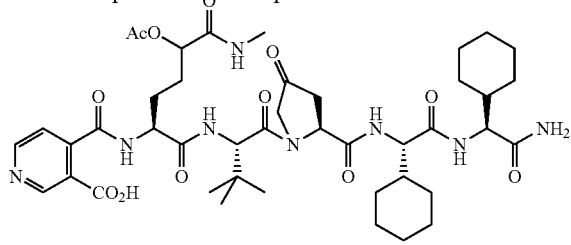

4-((2S)-5-acetoxy-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-6-(methylamino)-1,6-dioxohexan-2-ylcarbamoyl)nicotinic acid
Chemical Formula: $C_{43}H_{62}N_8O_{12}$
Exact Mass: 882.45
Molecular Weight: 883.00

The synthesis of compound 33 was performed according to 26, using 3,4-pyridine-dicarboxylic anhydride as entry.
Yield: 196 mg, 46%
ESI-MS: 883.7 [M+H]$^+$

28.3 Preparation of Compound E25

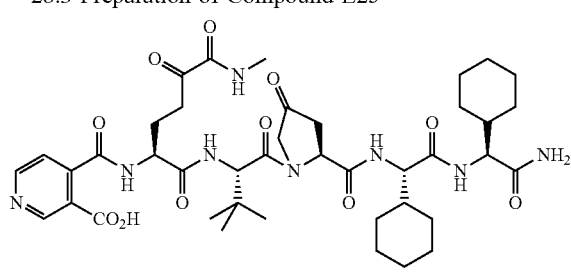

4-((S)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-6-(methylamino)-1,5,6-trioxohexan-2-ylcarbamoyl)nicotinic acid
Chemical Formula: $C_{41}H_{58}N_8O_{11}$
Exact Mass: 838.42
Molecular Weight: 838.95

The synthesis of compound E25 was performed according to oxidation method described in Example 19.4, using 33 as entry.
Yield: 170 mg, 24%

Example 29. Preparation of Compound E26

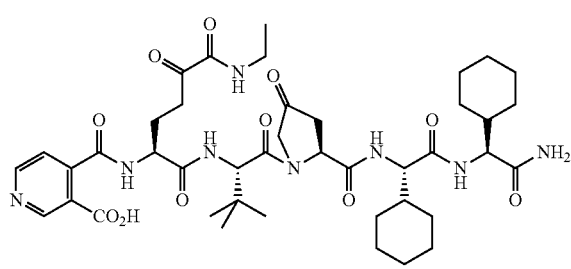

4-((S)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-6-(ethylamino)-1,5,6-trioxohexan-2-ylcarbamoyl)nicotinic acid
Chemical Formula: $C_{42}H_{60}N_8O_{11}$
Exact Mass: 852.44
Molecular Weight: 852.97

The synthesis of compound E26 was performed according to synthetic method described in Example 28, coupling the ethyl analogue with the respective tetrapeptide in step 1.
Yield: 28 mg, 22% (last step)
ESI-MS: 853.7 [M+H]$^+$

Example 30. Preparation of Compound E27

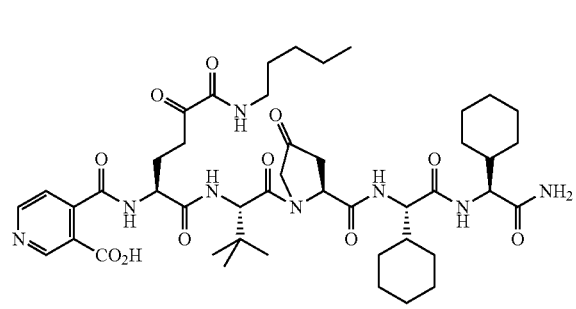

4-((S)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-1,5,6-trioxo-6-(pentylamino)hexan-2-ylcarbamoyl)nicotinic acid
Chemical Formula: $C_{45}H_{66}N_8O_{11}$
Exact Mass: 894.49
Molecular Weight: 895.05

The synthesis of compound E27 was performed according to synthetic method described in Example 28, coupling the pentyl analogue with the respective tetrapeptide in step 1.
Yield: 129 mg, 14% (last step)
ESI-MS: 995.8 [M+H]$^+$

Example 31. Preparation of Compound E28

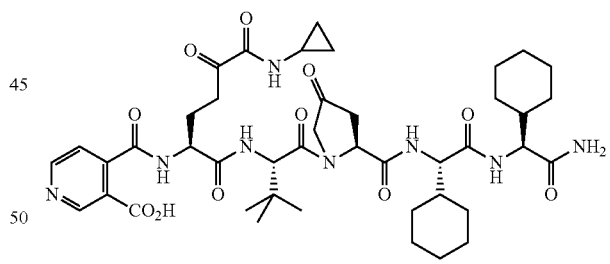

4-((S)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-6-(cyclopropylamino)-1,5,6-trioxohexan-2-ylcarbamoyl)nicotinic acid
Chemical Formula: $C_{43}H_{60}N_8O_{11}$
Exact Mass: 864.44
Molecular Weight: 864.98

The synthesis of compound E28 was performed according to synthetic method described in Example 28, coupling the cyclopropyl analogue with the respective tetrapeptide in step 1.
Yield: 33 mg, 27% (last step)
ESI-MS: 865.7 [M+H]$^+$

Example 32. Preparation of Compound E29

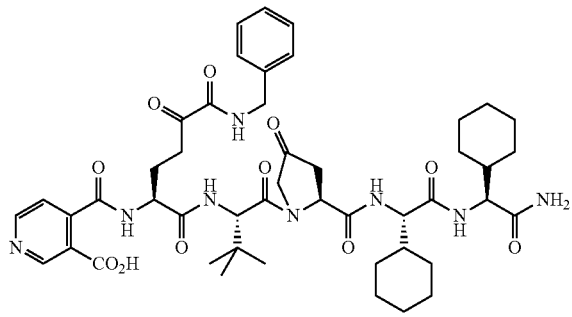

4-((S)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-6-(benzylamino)-1,5,6-trioxohexan-2-ylcarbamoyl)nicotinic acid
Chemical Formula: $C_{47}H_{62}N_8O_{11}$
Exact Mass: 914.45
Molecular Weight: 915.04

The synthesis of compound E29 was performed according to synthetic method described in Example 28, coupling the benzyl analogue with the respective tetrapeptide in step 1.

Yield: 14 mg, 33% (last step)

ESI-MS: 915.7 $[M+H]^+$

Example 33. Preparation of Compound E30

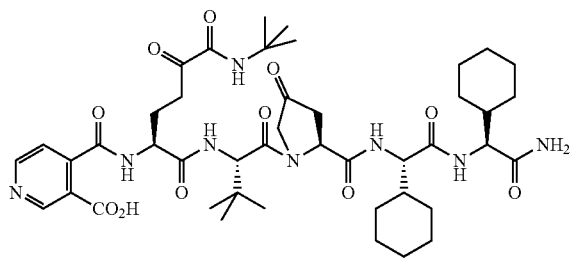

4-((S)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-6-(tert-butylamino)-1,5,6-trioxohexan-2-ylcarbamoyl)nicotinic acid
Chemical Formula: $C_{44}H_{64}N_8O_{11}$
Exact Mass: 880.47
Molecular Weight: 881.03

The synthesis of compound E30 was performed according to synthetic method described in Example 28, coupling the tert-butyl analogue with the respective tetrapeptide in step 1.

Yield: 50 mg, 55% (last step)

ESI-MS: 881.7 $[M+H]^+$

Example 34. Preparation of Compound E31

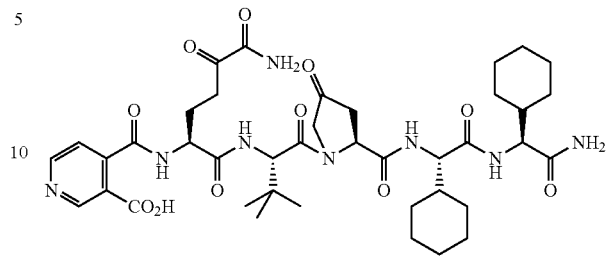

4-((S)-6-amino-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-1,5,6-trioxohexan-2-ylcarbamoyl)nicotinic acid
Chemical Formula: $C_{40}H_{56}N_8O_{11}$
Exact Mass: 824.41
Molecular Weight: 824.92

The synthesis of compound E31 was performed according to synthetic method described in Example 28, coupling 16 with the respective tetrapeptide in step 1.

Yield: 20 mg, 32% (last step)

ESI-MS: 825.6 $[M+H]^+$

Example 35. Preparation of Compound E32

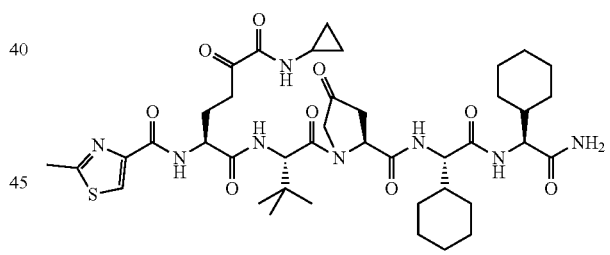

(S)-$N^1$-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-yl)-$N^6$-cyclopropyl-2-(2-methylthiazole-4-carboxamido)-5-oxohexanediamide
Chemical Formula: $C_{41}H_{60}N_8O_9S$
Exact Mass: 840.42
Molecular Weight: 841.03

The synthesis of compound E32 was performed according to synthetic method described in Example 31 coupling with 2-methylthiazole-4-carboxylic acid instead of 1-methyl-1H-imidazole-5-carboxylic acid in step 2.

Yield: 4 mg, 3% (last step)

ESI-MS: 841.7 $[M+H]^+$

Example 36. Preparation of Compound E33

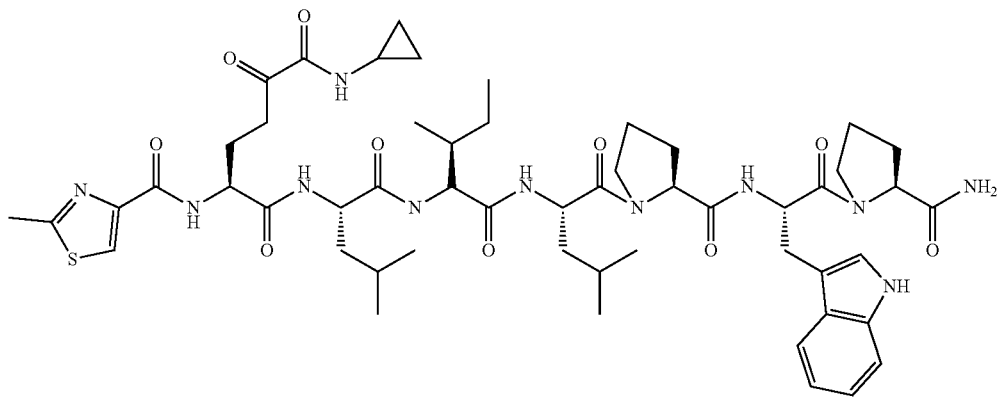

(S)-N¹-((S)-1-((2R,3S)-1-((S)-1-((S)-2-((S)-1-((S)-2-carbamoylpyrrolidin-1-yl)-3-(1H-indol-3-yl)-1-oxopropan-2-ylcarbamoyl)pyrrolidin-1-yl)-4-methyl-1-oxopentan-2-ylamino)-3-methyl-1-oxopentan-2-ylamino)-4-methyl-1-oxopentan-2-yl)-N⁶-cyclopropyl-2-(2-methylthiazole-4-carboxamido)-5-oxohexanediamide
Chemical Formula: $C_{53}H_{75}N_{11}O_{10}S$
Exact Mass: 1057.54
Molecular Weight: 1058.30

The synthesis of compound E33 was performed according to synthetic method described in Example 35, coupling with the hexapeptide H-Leu-Ile-Leu-Pro-Trp-Pro-NH$_2$ in step 1.
Yield: 41 mg, 44% (last step)
ESI-MS: 1058.8 [M+H]⁺

Example 37. Preparation of Compound E34

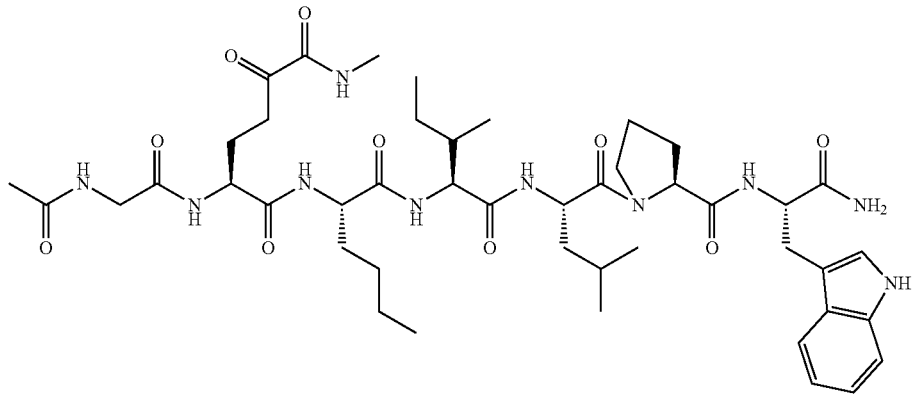

(S)-2-(2-acetamidoacetamido)-N¹-((S)-1-((2S,3S)-1-((S)-1-((S)-2-((S)-1-amino-3-(1H-indol-3-yl)-1-oxopropan-2-ylcarbamoyl)pyrrolidin-1-yl)-4-methyl-1-oxopentan-2-ylamino)-3-methyl-1-oxopentan-2-ylamino)-1-oxohexan-2-yl)-N⁶-methyl-5-oxohexanediamide
Chemical Formula: $C_{45}H_{68}N_{10}O_{10}$
Exact Mass: 908.51
Molecular Weight: 909.08

The synthesis of compound E34 was performed according to E25, coupling with the hexapeptide H-Nle-Ile-Leu-Pro-Trp-Pro-NH$_2$ in step 1 and Ac-Gly-OH in step 2.
Yield: 63 mg, 41% (last step)
ESI-MS: 909.8 [M+H]⁺

Example 38. Preparation of Compound E35

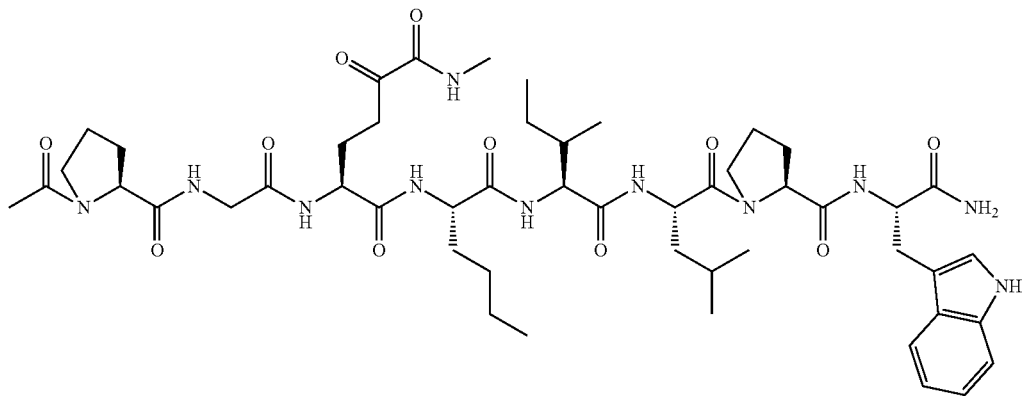

(S)-2-(2-((S)-1-acetylpyrrolidine-2-carboxamido)acetamido)-$N^1$-((S)-1-((2S,3S)-1-((S)-1-((S)-2-((S)-1-amino-3-(1H-indol-3-yl)-1-oxopropan-2-ylcarbamoyl)pyrrolidin-1-yl)-4-methyl-1-oxopentan-2-ylamino)-3-methyl-1-oxopentan-2-ylamino)-1-oxohexan-2-yl)-$N^6$-methyl-5-oxohexanediamide Chemical Formula: $C_{50}H_{75}N_{11}O_{11}$
Exact Mass: 1005.56
Molecular Weight: 1006.20

The synthesis of compound E35 was performed according to E34, coupling with Ac-Pro-Gly-OH in step 2.
Yield: 54 mg, 50% (last step)
ESI-MS: 1006.9 [M+H]$^+$ Example 39. Preparation of Compound E36

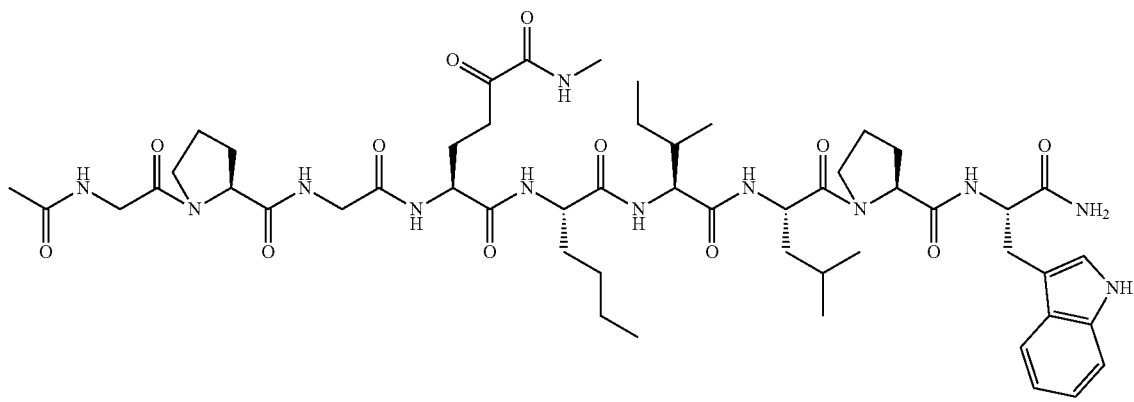

(S)-2-(2-((S)-1-acetamidoacetyl)pyrrolidine-2-carboxamido)acetamido)-$N^1$-((S)-1-((2S,3S)-1-((S)-1-((S)-2-((S)-1-amino-3-(1H-indol-3-yl)-1-oxopropan-2-ylcarbamoyl)pyrrolidin-1-yl)-4-methyl-1-oxopentan-2-ylamino)-3-methyl-1-oxopentan-2-ylamino)-1-oxohexan-2-yl)-$N^6$-methyl-5-oxohexanediamide Chemical Formula: $C_{52}H_{78}N_{12}O_{12}$
Exact Mass: 1062.59
Molecular Weight: 1063.25

The synthesis of compound E36 was performed according to E34, coupling with Ac-Gly-Pro-Gly-OH in step 2.
Yield: 63 mg, 57% (last step)
ESI-MS: 1063.9 [M+H]$^+$

Example 40. Preparation of Compound E37

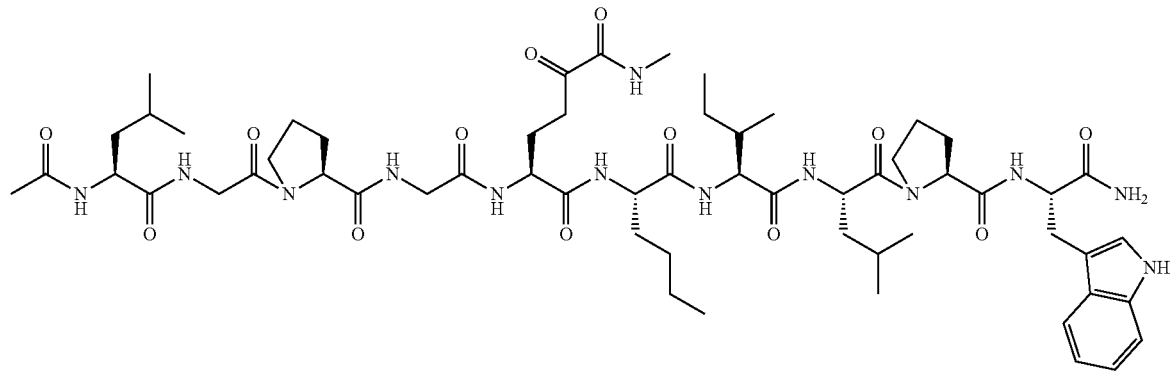

(S)-2-(2-((S)-1-(2-((S)-2-acetamido-4-methylpentanamido)acetyl)pyrrolidine-2-carboxamido)acetamido)-$N^1$-((S)-1-((2S,3S)-1-((S)-1-((S)-2-((S)-1-amino-3-(1H-indol-3-yl)-1-oxopropan-2-ylcarbamoyl)pyrrolidin-1-yl)-4-methyl-1-oxopentan-2-ylamino)-3-methyl-1-oxopentan-2-ylamino)-1-oxohexan-2-yl)-$N^6$-methyl-5-oxohexanediamide
Chemical Formula: $C_{58}H_{89}N_{13}O_{13}$
Exact Mass: 1175.67
Molecular Weight: 1176.41

The synthesis of compound E37 was performed according to E34, coupling with Ac-Leu-Gly-Pro-Gly-OH in step 2.
Yield: 56 mg, 49% (last step)
ESI-MS: 1177.1 [M+H]$^+$

Example 41. Preparation of Compound E38

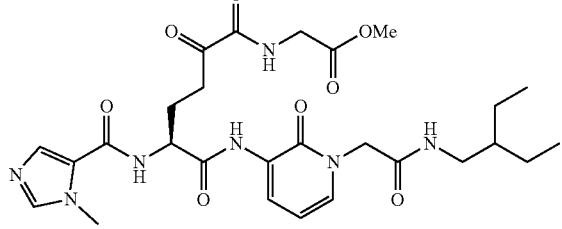

(S)-methyl 2-(6-(1-(2-(2-ethylbutylamino)-2-oxoethyl)-2-oxo-1,2-dihydropyridin-3-ylamino)-5-(1-methyl-1H-imidazole-5-carboxamido)-2,6-dioxohexanamido)acetate
Chemical Formula: $C_{27}H_{37}N_7O_8$
Exact Mass: 587.27
Molecular Weight: 587.62

The synthesis of compound E38 was performed according to E16, using methyl isocyanacetate in the Passerini reaction (step 1).
Yield: 41 mg, 56% (last step)
ESI-MS: 588.4 [M+H]$^+$

Example 42. Preparation of Compound E39

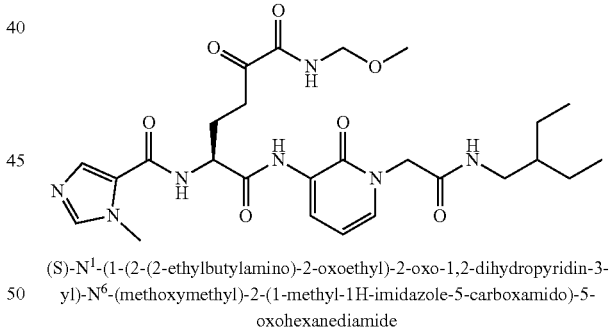

(S)-$N^1$-(1-(2-(2-ethylbutylamino)-2-oxoethyl)-2-oxo-1,2-dihydropyridin-3-yl)-$N^6$-(methoxymethyl)-2-(1-methyl-1H-imidazole-5-carboxamido)-5-oxohexanediamide
Chemical Formula: $C_{26}H_{37}N_7O_7$
Exact Mass: 559.28
Molecular Weight: 559.61

The synthesis of compound E39 was performed according to E16, using isocyano(methoxy)methane in the Passerini reaction (step 1).
Yield: 41 mg, 36% (last step)
ESI-MS: 560.5 [M+H]$^+$

Example 43. Preparation of Compound E40

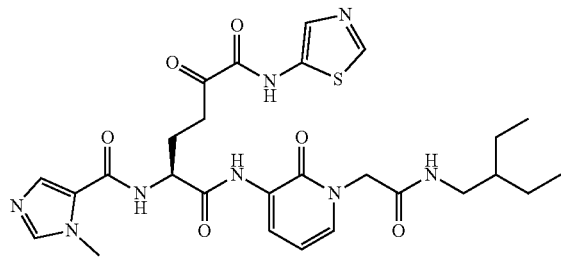

(S)-$N^1$-(1-(2-(2-ethylbutylamino)-2-oxoethyl)-2-oxo-1,2-dihydropyridin-3-yl)-2-(1-methyl-1H-imidazole-5-carboxamido)-5-oxo-$N^6$-(thiazol-5-yl)hexanediamide
Chemical Formula: $C_{27}H_{34}N_8O_6S$
Exact Mass: 598.23
Molecular Weight: 598.67

The synthesis of compound E40 was performed according to E16, using 5-isocyano-1,3-thiazole in the Passerini reaction (step 1).
Yield: 15 mg, 19% (last step)
ESI-MS: 599.4 [M+H]$^+$

Example 44. Preparation of Compound E41

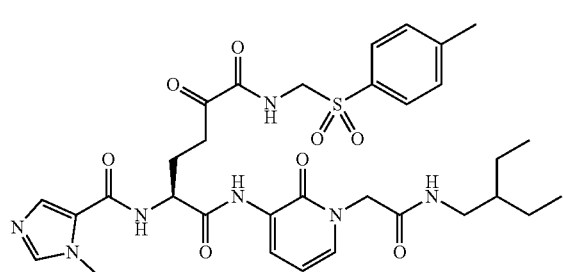

(S)-$N^1$-(1-(2-(2-ethylbutylamino)-2-oxoethyl)-2-oxo-1,2-dihydropyridin-3-yl)-2-(1-methyl-1H-imidazole-5-carboxamido)-5-oxo-$N^6$-(tosylmethyl)hexanediamide
Chemical Formula: $C_{32}H_{41}N_7O_8S$
Exact Mass: 683.27
Molecular Weight: 683.78

The synthesis of compound E41 was performed according to E16, using p-Toluenesulfonylmethyl isocyanide in the Passerini reaction (step 1).
Yield: 26 mg, 41% (last step); ESI-MS: 684.5 [M+H]$^+$

Example 45. Preparation of Compound E42

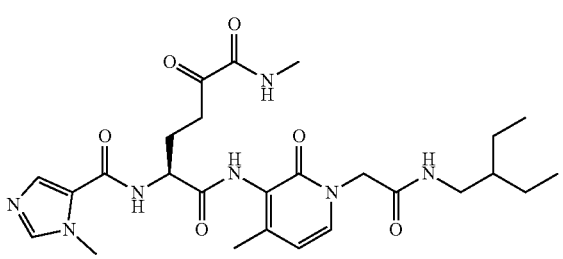

(S)-$N^1$-(1-(2-(2-ethylbutylamino)-2-oxoethyl)-4-methyl-2-oxo-1,2-dihydropyridin-3-yl)-$N^6$-methyl-2-(1-methyl-1H-imidazole-5-carboxamido)-5-oxohexanediamide
Chemical Formula: $C_{26}H_{37}N_7O_6$
Exact Mass: 543.28
Molecular Weight: 543.62

The synthesis of compound E42 was performed according to E16, coupling with 2-(3-amino-4-methyl-2-oxopyridin-1(2H)-yl)-N-(2-ethylbutyl)acetamide in step 3.
Yield: 54 mg, 37% (last step); ESI-MS: 544.5 [M+H]$^+$

Example 46. Preparation of Compound E43

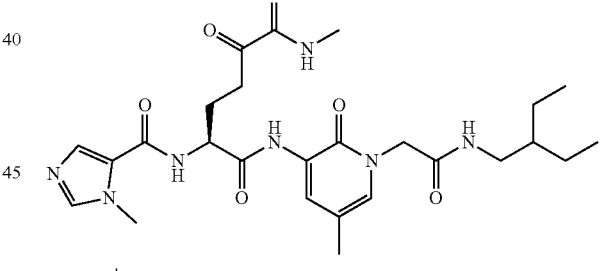

(S)-$N^1$-(1-(2-(2-ethylbutylamino)-2-oxoethyl)-5-methyl-2-oxo-1,2-dihydropyridin-3-yl)-$N^6$-methyl-2-(1-methyl-1H-imidazole-5-carboxamido)-5-oxohexanediamide
Chemical Formula: $C_{26}H_{37}N_7O_6$
Exact Mass: 543.28
Molecular Weight: 543.62

The synthesis of compound E43 was performed according to E16, coupling with 2-(3-amino-5-methyl-2-oxopyridin-1(2H)-yl)-N-(2-ethylbutyl)acetamide in step 3.
Yield: 180 mg, 79% (last step)
ESI-MS: 544.5 [M+H]$^+$

Example 47. Preparation of Compound E44

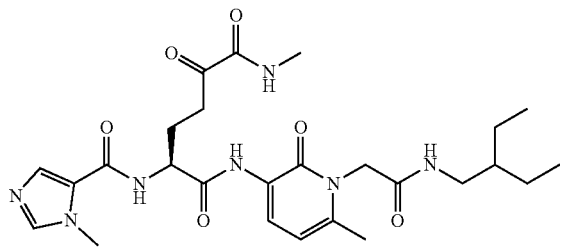

(S)-N¹-(1-(2-(2-ethylbutylamino)-2-oxoethyl)-6-methyl-2-oxo-1,2-dihydropyridin-3-yl)-N⁶-methyl-2-(1-methyl-1H-imidazole-5-carboxamido)-5-oxohexanediamide
Chemical Formula: $C_{26}H_{37}N_7O_6$
Exact Mass: 543.28
Molecular Weight: 543.62

The synthesis of compound E44 was performed according to E16, coupling with 2-(3-amino-6-methyl-2-oxopyridin-1(2H)-yl)-N-(2-ethylbutyl)acetamide in step 3.

Yield: 9 mg, 12% (last step)

ESI-MS: 544.5 [M+H]⁺

Example 48. Preparation of Compound E45

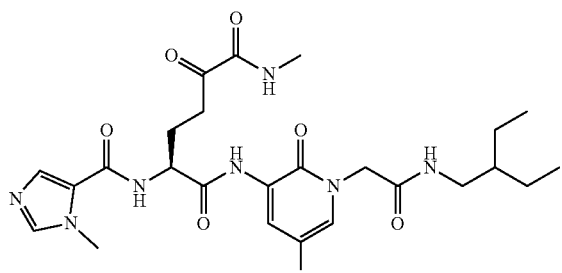

(S)-N¹-(5-chloro-1-(2-(2-ethylbutylamino)-2-oxoethyl)-2-oxo-1,2-dihydropyridin-3-yl)-N⁶-methyl-2-(1-methyl-1H-imidazole-5-carboxamido)-5-oxohexanediamide
Chemical Formula: $C_{25}H_{34}ClN_7O_6$
Exact Mass: 563.23
Molecular Weight: 564.03

The synthesis of compound E45 was performed according to E16, coupling with 2-(3-amino-5-chloro-2-oxopyridin-1(2H)-yl)-N-(2-ethylbutyl)acetamide in step 3.

Yield: 46 mg, 56% (last step)

ESI-MS: 564.4 [M+H]⁺

Example 49. Preparation of Compound E46

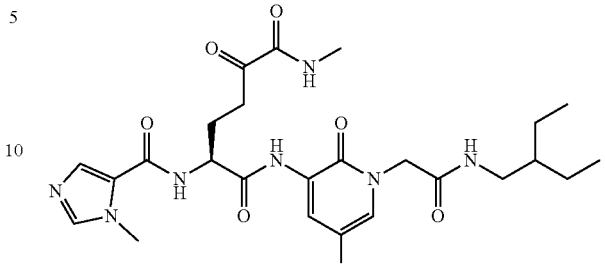

(S)-N¹-(5-bromo-1-(2-(2-ethylbutylamino)-2-oxoethyl)-2-oxo-1,2-dihydropyridin-3-yl)-N⁶-methyl-2-(1-methyl-1H-imidazole-5-carboxamido)-5-oxohexanediamide
Chemical Formula: $C_{25}H_{34}BrN_7O_6$
Exact Mass: 607.18
Molecular Weight: 608.48

The synthesis of compound E46 was performed according to E16, coupling with 2-amino-5-bromo-2-oxopyridin-1(2H)-yl)-N-(2-ethylbutyl)acetamide in step 3.

Yield: 79 mg, 45% (last step)

ESI-MS: 608.4 [M+H]⁺

Example 50. Preparation of Compound E47

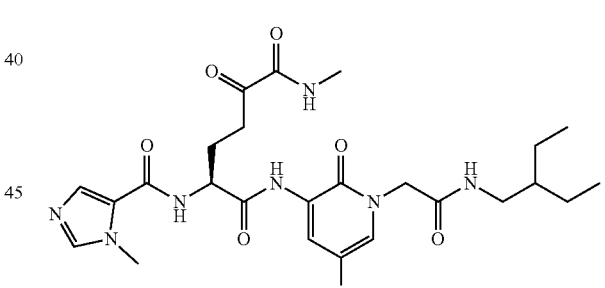

(S)-N¹-(1-(2-(2-ethylbutylamino)-2-oxoethyl)-2-oxo-5-(trifluoromethyl)-1,2-dihydropyridin-3-yl)-N⁶-methyl-2-(1-methyl-1H-imidazole-5-carboxamido)-5-oxohexanediamide
Chemical Formula: $C_{26}H_{34}F_3N_7O_6$
Exact Mass: 597.25
Molecular Weight: 597.59

The synthesis of compound E47 was performed according to E16, coupling with 2-(3-amino-2-oxo-5-(trifluoromethyl)pyridin-1(2H)-yl)-N-(2-ethylbutyl)acetamide in step 3.

Yield: 17 mg, 41% (last step)

ESI-MS: 598.5 [M+H]⁺

Example 51. Preparation of Compound E48

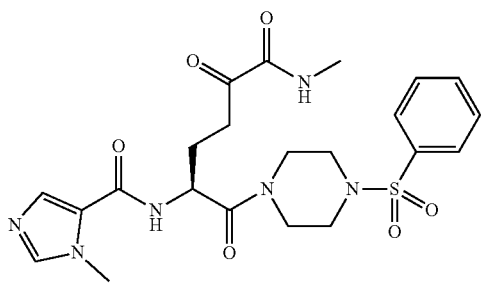

(S)-1-methyl-N-(6-(methylamino)-1,5,6-trioxo-1-(4-(phenylsulfonyl)piperazin-1-yl)hexan-2-yl)-1H-imidazole-5-carboxamide
Chemical Formula: $C_{22}H_{28}N_6O_6S$
Exact Mass: 504.18
Molecular Weight: 504.56

The synthesis of compound E48 was performed according to E16, coupling with 1-benzenesulfonyl-piperazine in step 3.
Yield: 83 mg, 68% (last step); ESI-MS: 505.4 $[M+H]^+$

Example 52. Preparation of Compound E49

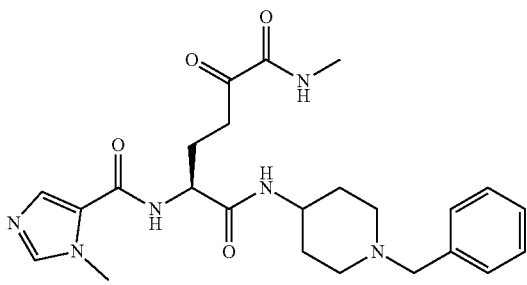

(S)-$N^1$-(1-benzylpiperdin-4-yl)-$N^6$-methyl-2-(1-methyl-1H-imidazole-5-carboxamido)-5-oxohexanediamide
Chemical Formula: $C_{24}H_{32}N_6O_4$
Exact Mass: 468.25
Molecular Weight: 468.55

The synthesis of compound E49 was performed according to E16, coupling with 4-amino-1-benzylpiperidine in step 3.
Yield: 24 mg, 18% (last step)
ESI-MS: 469.5 $[M+H]^+$

Example 53. Preparation of Compound E50

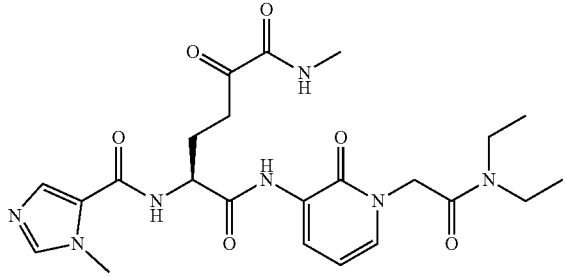

(S)-$N^1$-(1-(2-diethylamino)-2-oxoethyl)-2-oxo-1,2-dihydropyridin-3-yl)-$N^6$-methyl-2-(1-methyl-1H-imidazole-5-carboxamido)-5-oxohexanediamide
Chemical Formula: $C_{23}H_{31}N_7O_6$
Exact Mass: 501.23
Molecular Weight: 501.54

The synthesis of compound E50 was performed according to E16, coupling with 2-(3-amino-2-oxopyridin-1(2H)-yl)-N,N-diethylacetamide in step 3.
Yield: 29 mg, 42% (last step)
ESI-MS: 502.4 $[M+H]^+$

Example 54. Preparation of Compound E51

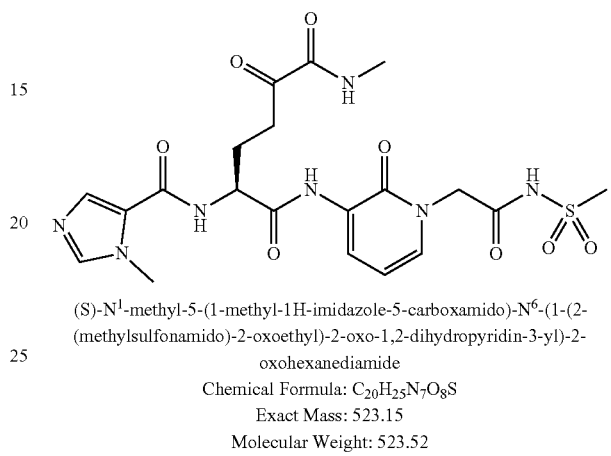

(S)-$N^1$-methyl-5-(1-methyl-1H-imidazole-5-carboxamido)-$N^6$-(1-(2-(methylsulfonamido)-2-oxoethyl)-2-oxo-1,2-dihydropyridin-3-yl)-2-oxohexanediamide
Chemical Formula: $C_{20}H_{25}N_7O_8S$
Exact Mass: 523.15
Molecular Weight: 523.52

The synthesis of compound E51 was performed according to E16, coupling with 2-(3-amino-2-oxopyridin-1(2H)-yl)-N-(methylsulfonyl)acetamide in step 3.
Yield: 39 mg, 49% (last step)
ESI-MS: 524.4 $[M+H]^+$

Example 55. Preparation of Compound E52

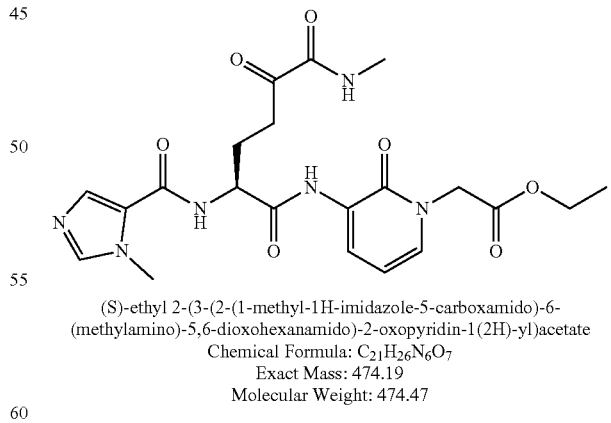

(S)-ethyl 2-(3-(2-(1-methyl-1H-imidazole-5-carboxamido)-6-(methylamino)-5,6-dioxohexanamido)-2-oxopyridin-1(2H)-yl)acetate
Chemical Formula: $C_{21}H_{26}N_6O_7$
Exact Mass: 474.19
Molecular Weight: 474.47

The synthesis of compound E52 was performed according to E16, coupling with ethyl 2-(3-amino-2-oxopyridin-1(2H)-yl)acetate in step 3.
Yield: 12 mg, 19% (last step)
ESI-MS: 475.4 $[M+H]^+$

Example 56. Preparation of Compound E53

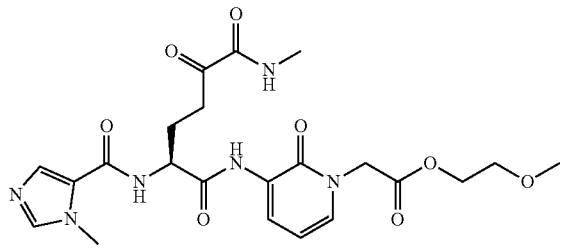

(S)-2-methoxyethyl 2-(3-(2-(1-methyl-1H-imidazole-5-carboxamido)-6-(methylamino)-5,6-dioxohexanamido)-2-oxopyridin-1(2H)-yl)acetate
Chemical Formula: $C_{22}H_{28}N_6O_8$
Exact Mass: 504.20
Molecular Weight: 504.49

The synthesis of compound E53 was performed according to E16, coupling with 2-methoxyethyl 2-(3-amino-2-oxopyridin-1(2H)-yl)acetate in step 3.

Yield: 8 mg, 12% (last step)

ESI-MS: 491.4 [M+H]$^+$

Example 57. Preparation of Compound E54

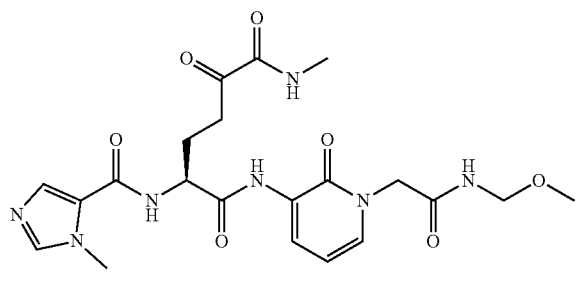

(S)-N$^1$-(1-(2-(methoxymethylamino)-2-oxoethyl)-2-oxo-1,2-dihydropyridin-3-yl)-N$^6$-methyl-2-(1-methyl-1H-imidazole-5-carboxamido)-5-oxohexanediamide
Chemical Formula: $C_{21}H_{27}N_7O_7$
Exact Mass: 489.20
Molecular Weight: 489.48

The synthesis of compound E54 was performed according to E16, coupling with 2-(3-amino-2-oxopyridin-1(2H)-yl)-N-(methoxymethyl)acetamide in step 3.

Yield: 19 mg, 29% (last step)

ESI-MS: 490.4 [M+H]$^+$

Example 58. Preparation of Compound E55

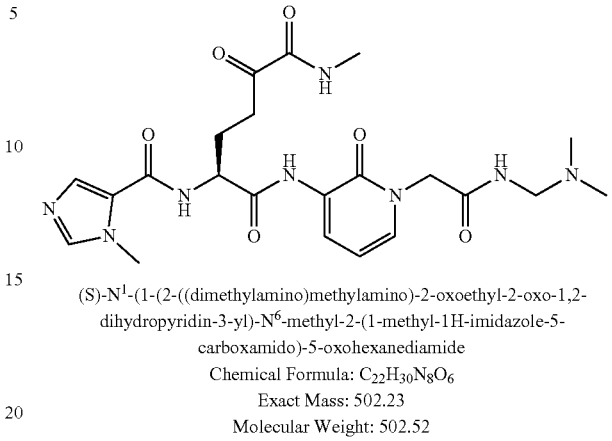

(S)-N$^1$-(1-(2-(((dimethylamino)methylamino)-2-oxoethyl-2-oxo-1,2-dihydropyridin-3-yl)-N$^6$-methyl-2-(1-methyl-1H-imidazole-5-carboxamido)-5-oxohexanediamide
Chemical Formula: $C_{22}H_{30}N_8O_6$
Exact Mass: 502.23
Molecular Weight: 502.52

The synthesis of compound E55 was performed according to E16, coupling with 2-(3-amino-2-oxopyridin-1(2H)-yl)-N-((dimethylamino)methyl)acetamide in step 3.

Yield: 14 mg, 20% (last step); ESI-MS: 503.4 [M+H]$^+$

Example 59. Preparation of Compound E56

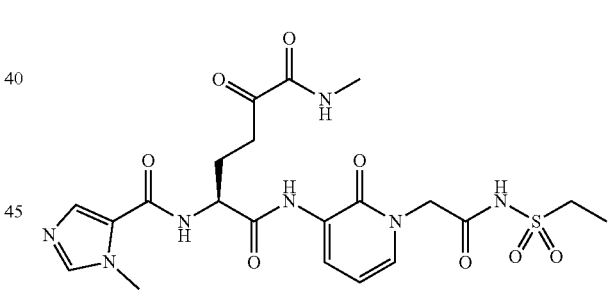

(S)-N$^1$-(1-(2-(ethylsulfonamido)-2-oxoethyl)-2-oxo-1,2-dihydropyridin-3-yl)-N$^6$-methyl-2-(1-methyl-1H-imidazole-5-carboxamido)-5-oxohexanediamide
Chemical Formula: $C_{21}H_{27}N_7O_8S$
Exact Mass: 537.16
Molecular Weight: 537.55

The synthesis of compound E56 was performed according to E16, coupling with 2-(3-amino-2-oxopyridin-1(2H)-yl)-N-(ethylsulfonyl)acetamide in step 3.

Yield: 19 mg, 29% (last step); ESI-MS: 490.4 [M+H]$^+$

Example 60. Preparation of Compound E57

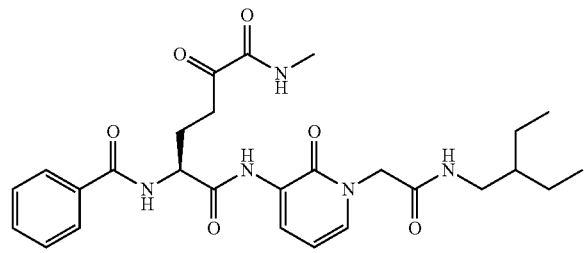

(S)-benzyl 1-(1-(2-(2-ethylbutylamino)-2-oxoethyl)-2-oxo-1,2-dihydropyridin-3-ylamino)-6-(methylamino)-1,5,6-trioxohexan-2-ylcarbamate
Chemical Formula: $C_{28}H_{37}N_5O_7$
Exact Mass: 555.27
Molecular Weight: 555.62

The synthesis of compound E57 was performed according to E16, coupling with benzyl chloroformate in step 4.

Yield: 29 mg, 36% (last step)

ESI-MS: 556.5 [M+H]$^+$

Example 61. Preparation of Compound E58

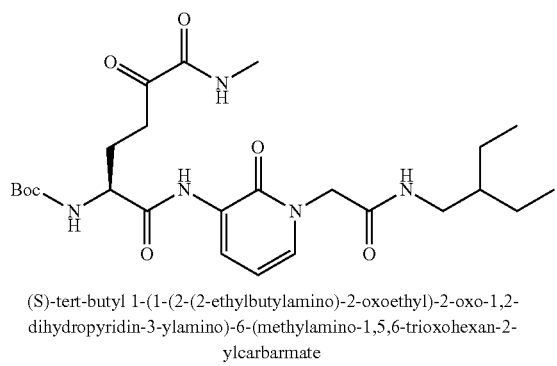

(S)-tert-butyl 1-(1-(2-(2-ethylbutylamino)-2-oxoethyl)-2-oxo-1,2-dihydropyridin-3-ylamino)-6-(methylamino)-1,5,6-trioxohexan-2-ylcarbarmate
Chemical Formula: $C_{25}H_{39}N_5O_7$
Exact Mass: 521.28
Molecular Weight: 521.61

The synthesis of compound E58 was performed according to E16, by cleaving acetyl from compound 25 and subsequent oxidation.

Yield: 16 mg, 59% (last step)

ESI-MS: 522.5 [M+H]$^+$

Example 62. Preparation of Compound E59

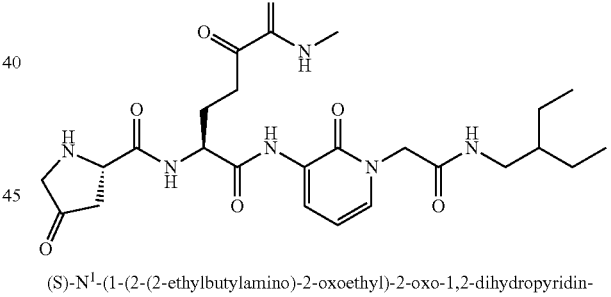

(S)-4-(1-(1-(2-(2-ethylbutylamino)-2-oxoethyl)-2-oxo-1,2-dihydropyridin-3-ylamino)-6-(methylamino)-1,5,6-trioxohexan-2-ylamino)-4-oxobutanoic acid
Chemical Formula: $C_{24}H_{35}N_5O_8$
Exact Mass: 521.25
Molecular Weight: 521.56

The synthesis of compound E59 was performed according to E16, coupling with succinic anhydride in step 4.

Yield: 27 mg, 42% (last step)

ESI-MS: 522.4 [M+H]$^+$

Example 63. Preparation of Compound E60

(S)-N$^1$-(1-(2-(2-ethylbutylamino)-2-oxoethyl)-2-oxo-1,2-dihydropyridin-3-yl)-N$^6$-methyl-5-oxo-2-((S)-4-oxopyrrolidine-2-carboxamido)hexanediamide
Chemical Formula: $C_{25}H_{36}N_6O_7$
Exact Mass: 532.26
Molecular Weight: 532.59

The synthesis of compound E60 was performed according to E16, coupling with N-Boc-4-oxo-L-proline and subsequent cleavage in step 4.

Yield: 14 mg, 41% (last step); ESI-MS: 533.5 [M+H]$^+$

Example 64. Preparation of Compound E61

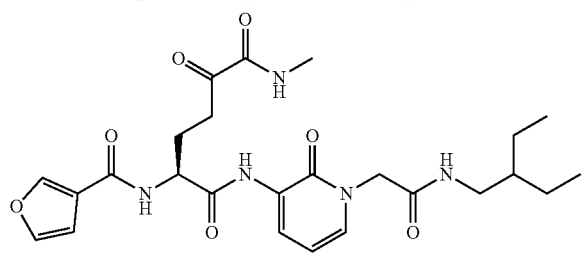

(S)-N$^1$-(1-(2-(2-ethylbutylamino)-2-oxoethyl)-2-oxo-1,2-dihydropyridin-
3-yl)-2-(furan-3-carboxamido)-N$^6$-methyl-5-oxohexanediamide
Chemical Formula: C$_{25}$H$_{33}$N$_5$O$_7$
Exact Mass: 515.24
Molecular Weight: 515.56

The synthesis of compound E61 was performed according to E16, coupling with furan-3-carboxylic acid in step 4.
Yield: 36 mg, 63% (last step); ESI-MS: 516.4 [+H]$^+$

Example 65. Preparation of Compound E62

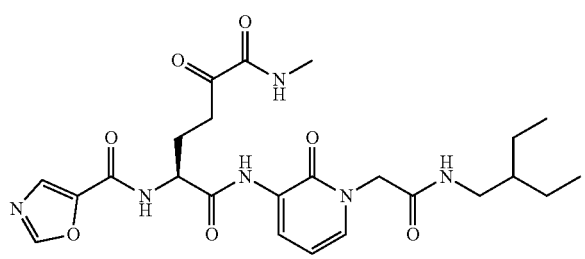

(S)-N$^1$-(1-(2-(2-ethylbutylamino)-2-oxoethyl)-2-oxo-1,2-dihydropyridin-
3-yl)-N$^6$-methyl-2-(oxazole-5-carboxamido)-5-oxohexanediamide
Chemical Formula: C$_{24}$H$_{32}$N$_6$O$_7$
Exact Mass: 516.23
Molecular Weight: 516.55

The synthesis of compound E62 was performed according to E16, coupling with 5-oxazolecarboxylic acid in step 4.
Yield: 15 mg, 33% (last step)
ESI-MS: 517.4 [M+H]$^+$

Example 66. Preparation of Compound E63

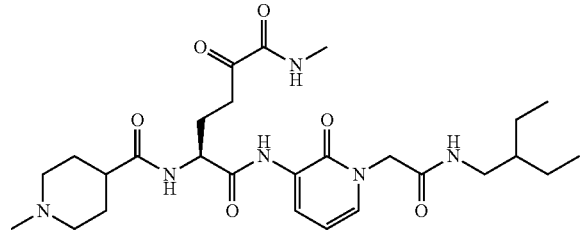

(S)-N$^1$-(1-(2-(2-ethylbutylamino)-2-oxoethyl)-2-oxo-1,2-dihydropyridin-
3-yl)-N$^6$-methyl-2-(1-methylpiperidine-4-carboxamido)-5-
oxohexanediamide
Chemical Formula: C$_{27}$H$_{42}$N$_6$O$_6$
Exact Mass: 546.32
Molecular Weight: 546.66

The synthesis of compound E63 was performed according to E16, coupling with N-methylisonipecotic acid in step 4.
Yield: 9 mg, 21% (last step)
ESI-MS: 547.5 [M+H]$^+$

Example 67. Preparation of Compound E64

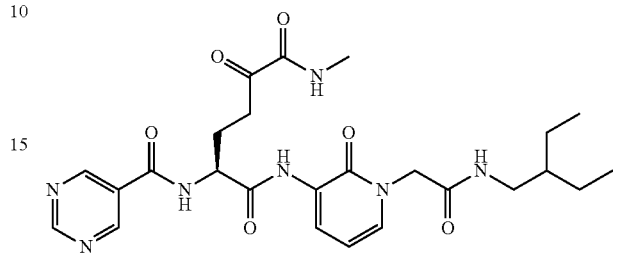

(S)-N$^1$-(1-(2-(2-ethylbutylamino)-2-oxoethyl)-2-oxo-1,2-dihydropyridin-
3-yl)-N$^6$-methyl-5-oxo-2-(pyrimidine-5-carboxamido)hexanediamide
Chemical Formula: C$_{25}$H$_{33}$N$_7$O$_6$
Exact Mass: 527.25
Molecular Weight: 527.57

The synthesis of compound E64 was performed according to E16, coupling with 5-pyrimidinecarboxylic acid in step 4.
Yield: 17 mg, 29% (last step)
ESI-MS: 528.5 [M+H]$^+$

Example 68. Preparation of Compound E65

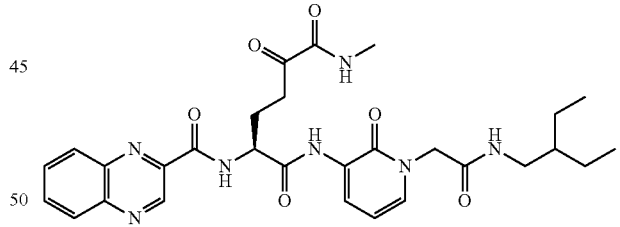

(S)-N$^1$-(1-(2-(2-ethylbutylamino)-2-oxoethyl)-2-oxo-1,2-
dihydropyridin-3-yl)-N$^6$-methyl-5-oxo-2-(quinoxaline-
2-carboxamido)hexanediamide
Chemical Formula: C$_{29}$H$_{35}$N$_7$O$_6$
Exact Mass: 577.26
Molecular Weight: 577.63

The synthesis of compound E65 was performed according to E16, coupling with 2-quinoxalinecarboxylic acid in step 4.
Yield: 6 mg, 13% (last step); ESI-MS: 578.5 [M+H]$^+$

Example 69. Preparation of Compound E66

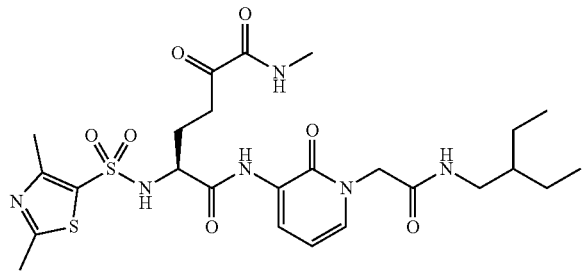

(S)-2-(2,4-dimethylthiazole-5-sulfonamido)-$N^1$-(1-(2-(2-ethylbutylamino)-2-oxoethyl)-2-oxo-1,2-dihydropyridin-3-yl)-$N^6$-methyl-5-oxohexanediamide
Chemical Formula: $C_{25}H_{36}N_6O_7S_2$
Exact Mass: 596.21
Molecular Weight: 596.72

The synthesis of compound E66 was performed according to E16, coupling with 2,4-dimethylthiazole-5-sulfonyl chloride in step 4.

Yield: 26 mg, 61% (last step); ESI-MS: 597.4 $[M+H]^+$

Example 70. Preparation of Compound E67

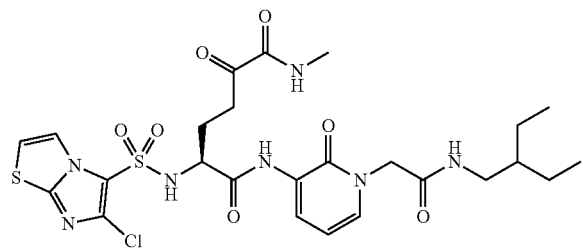

(S)-2-(6-chloroimidazo[2,1-b]thiazole-5-sulfonamido)-$N^1$-(1-(2-(2-ethylbutylamino)-2-oxoethyl)-2-oxo-1,2-dihydropyridin-3-yl)-$N^6$-methyl-5-oxohexanediamide
Chemical Formula: $C_{25}H_{32}ClN_7O_7S_2$
Exact Mass: 641.15
Molecular Weight: 642.15

The synthesis of compound E67 was performed according to E16, coupling with 6-chloroimidazo[2,1-b]thiazole-5-sulfonyl chloride in step 4.

Yield: 16 mg, 25% (last step)
ESI-MS: 642.4 $[M+H]^+$

Example 71. Preparation of Compound E68

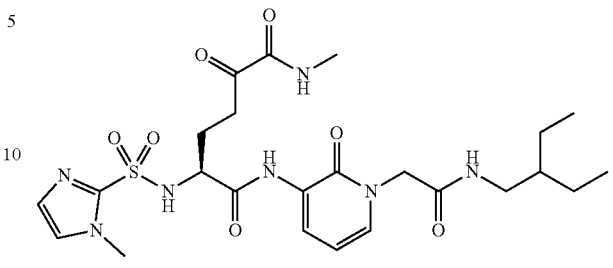

(S)-$N^1$-(1-(2-(2-ethylbutylamino)-2-oxoethyl)-2-oxo-1,2-dihydropyridin-3-yl)-$N^6$-methyl-2-(1-methyl-1H-imidazole-2-sulfonamido)-5-oxohexanediamide
Chemical Formula: $C_{24}H_{35}N_7O_7S$
Exact Mass: 565.23
Molecular Weight: 565.64

The synthesis of compound E68 was performed according to E16, coupling with 1-methyl-1H-imidazole-2-sulfonyl chloride in step 4.

Yield: 11 mg, 19% (last step)
ESI-MS: 566.4 $[M+H]^+$

Example 72. Preparation of Compound E69

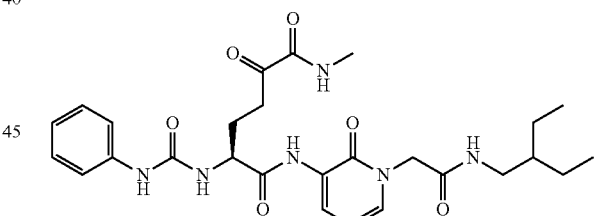

(S)-$N^1$-(1-(2-(2-ethylbutylamino)-2-oxoethyl)-2-oxo-1,2-dihydropyridin-3-yl)-$N^6$-methyl-5-oxo-2-(3-phenylureido)hexanediamide
Chemical Formula: $C_{27}H_{36}N_6O_6$
Exact Mass: 540.27
Molecular Weight: 540.61

The synthesis of compound E69 was performed according to E16, coupling with phenyl isocyanate in step 4.

Yield: 27 mg, 49% (last step)
ESI-MS: 541.5 $[M+H]^+$

Example 73. Preparation of Compound E70

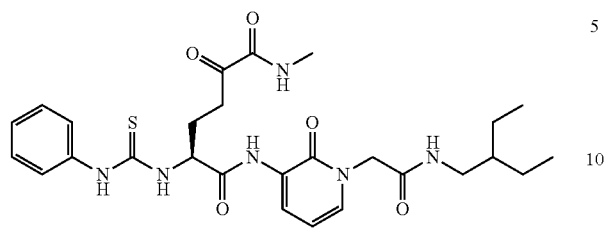

(S)-N$^1$-(1-(2-(2-ethylbutylamino)-2-oxoethyl)-2-oxo-1,2-dihydropyridin-3-yl)-N$^6$-methyl-5-oxo-2-(3-phenylthioureido)hexanediamide
Chemical Formula: C$_{27}$H$_{36}$N$_6$O$_5$S
Exact Mass: 556.25
Molecular Weight: 556.68

The synthesis of compound E70 was performed according to E16, coupling with phenyl isothiocyanate in step 4.
Yield: 21 mg, 36% (last step)
ESI-MS: 557.5 [M+H]$^+$ Example 74. Preparation of Compound E11

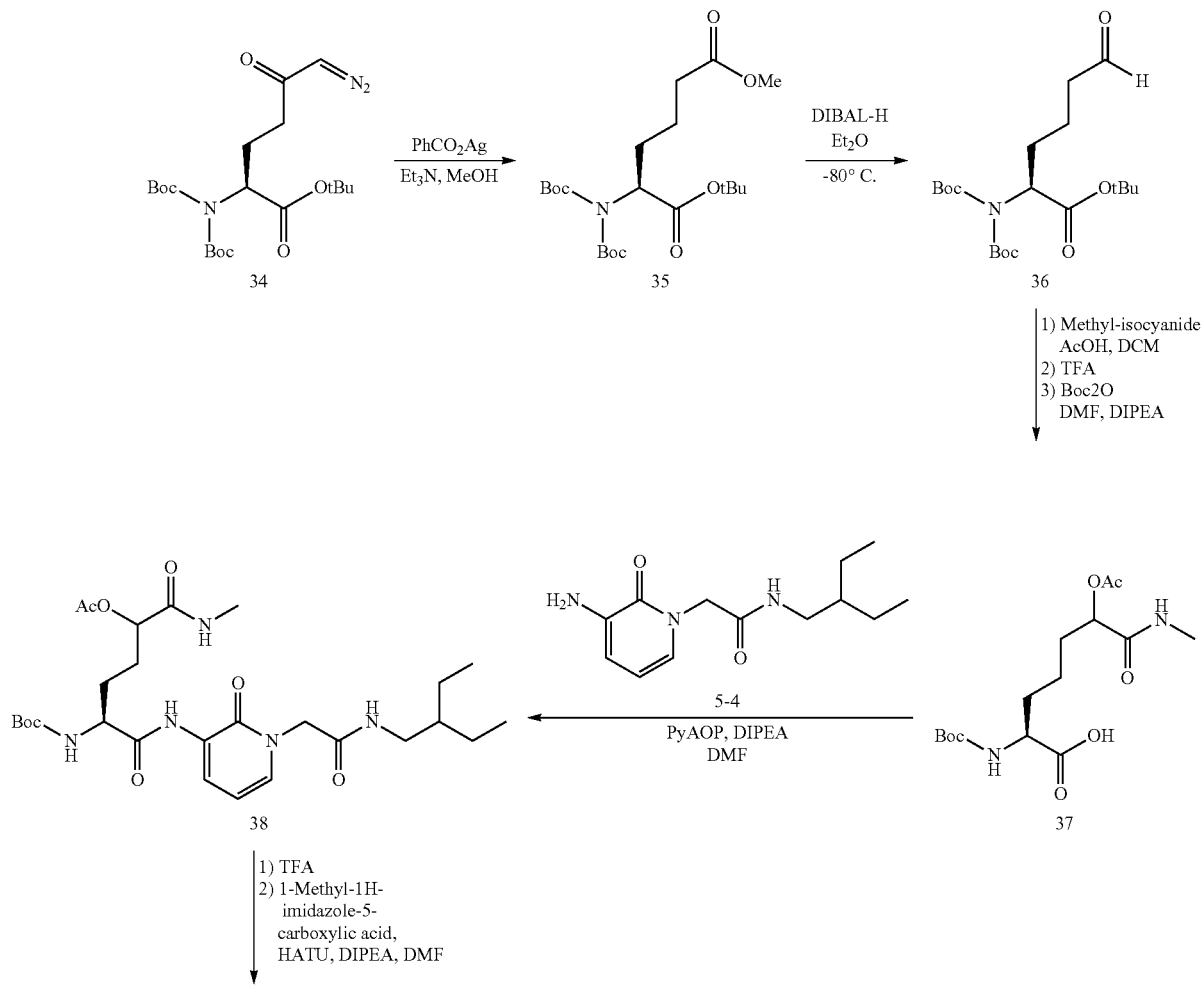

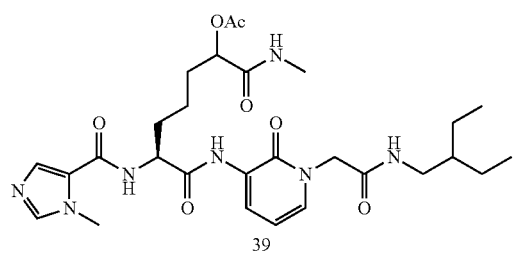
39

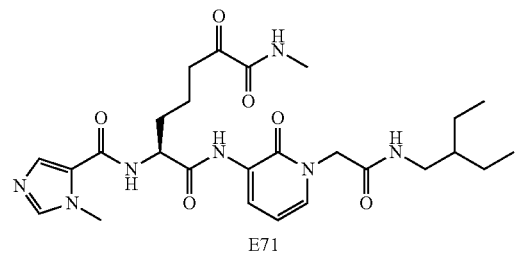
E71

1) K$_2$CO$_3$, MeOH
2) Dess-Martin periodinane DMF

-continued

Preparation of Compound 35

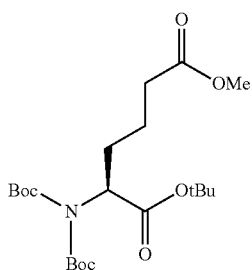

(S)-1-tert-butyl 6-methyl 2-(bis(tert-butoxycarbonyl)amino)hexanedioate
Chemical Formula: C$_{21}$H$_{37}$NO$_8$
Exact Mass: 431.25
Molecular Weight: 431.52

541 mg (1.27 mmol) of (S)-tert-butyl 2-(bis(tert-butoxycarbonyl)amino)-6-diazo-5-oxohexanoate 34 (prepared from Boc2-Glu-OtBu; method described by Pinkas et al. *PLoS Biol.* 2007, 5, e327) were dissolved in 2 ml MeOH. A solution of 16 mg silver benzoate in triethylamine was added dropwise until evolution of nitrogen stopped. The suspension was refluxed for 1 hour, filtered and the solvent was evaporated. The residue was dissolved in diethyl ether and washed twice with each NaHCO$_3$ solution (10%), water and brine. The organic phase was dried over Na$_2$SO$_4$, filtered and the solvent was evaporated. The product was used without further purification.
Yield: 503 mg, 92%
ESI-MS: 885.7 [2M+Na]$^+$
Preparation of Compound 36

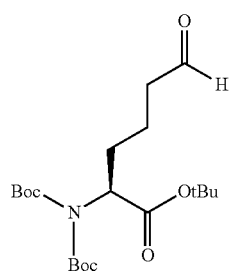

(S)-tert-butyl 2-(bis(tert-butoxycarbonyl)amino)-6-oxohexanoate
Chemical Formula: C$_{20}$H$_{35}$NO$_7$
Exact Mass: 401.24
Molecular Weight: 401.49

854 mg (1.98 mmol) of 35 were dissolved in 10 ml diethyl ether. At −78° C., 2.14 ml (1.3 eq) DIBAL (1.2 M in toluene) were added dropwise and the reaction was stirred for 1 h before being quenched with methanol. The solution was washed with Rochelle salt solution. The organic phase was dried over Na$_2$SO$_4$, filtered and the solvent was evaporated. The product was used without further purification.
Yield: 768 mg, 97%
ESI-MS: 402.5 [M+H]$^+$
Preparation of Compound 37

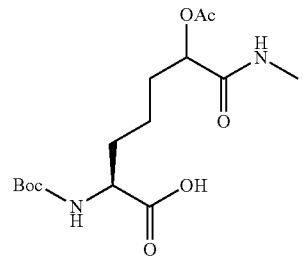

(2S)-6-acetoxy-2-(tert-butoxycarbonylamino)-7-(methylamino)-7-oxoheptanoic acid
Chemical Formula: C$_{15}$H$_{26}$N$_2$O$_7$
Exact Mass: 346.17
Molecular Weight: 346.38

The synthesis of compound 37 was performed according to 24, using aldehyde 36.
Yield: 1.30 g, >100%
ESI-MS: 347.5 [M+H]$^+$
Preparation of Compound 38

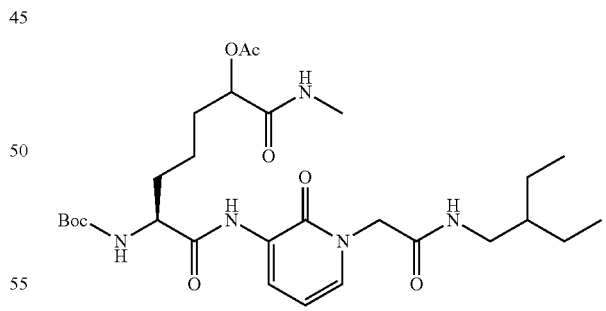

(6S)-6-(tert-butoxycarbonylamino)-7-(1-(2-(2-ethylbutylamino)-2-oxoethyl)-2-oxo-1,2-dihydropyridin-3-ylamino)-1-(methylamino)-1,7-dioxoheptan-2-yl acetate
Chemical Formula: C$_{28}$H$_{45}$N$_5$O$_8$
Exact Mass: 579.33
Molecular Weight: 579.69

Synthesis of compound 38 was performed according to 25, using carboxylic acid 37.
Yield: 580 mg, 52%
ESI-MS: 580.5 [M+H]$^+$

Preparation of Compound 39

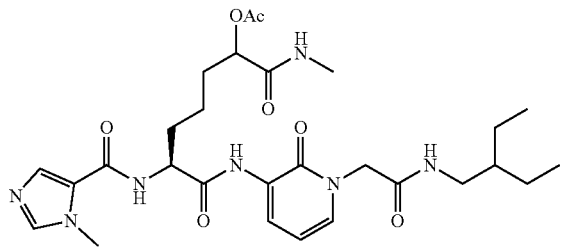

(6S)-7-(1-(2-(2-ethylbutylamino)-2-oxoethyl)-2-oxo-1,2-dihydropyridin-3-ylamino)-6-(1-methyl-1H-imidazole-5-carboxamido)-1-(methylamino)-1,7-dioxoheptan-2-yl acetate
Chemical Formula: $C_{28}H_{41}N_7O_7$
Exact Mass: 587.31
Molecular Weight: 587.67

The synthesis of compound 39 was performed according to 26, using 38 as entry.

Yield: 506 mg, 72%; ESI-MS: 588.5 $[M+H]^+$

Preparation of Compound E71 (n=2)

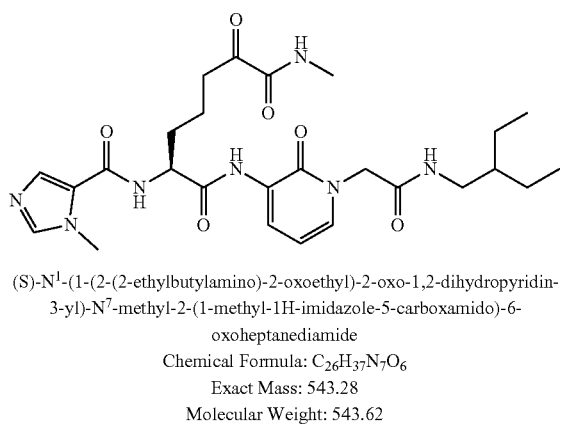 [SMILES: CCC(CC)CNC(=O)Cn1cccc(NC(=O)[C@H](CCCC(=O)C(=O)NC)NC(=O)c2cncn2C)c1=O]

(S)-$N^1$-(1-(2-(2-ethylbutylamino)-2-oxoethyl)-2-oxo-1,2-dihydropyridin-3-yl)-$N^7$-methyl-2-(1-methyl-1H-imidazole-5-carboxamido)-6-oxoheptanediamide
Chemical Formula: $C_{26}H_{37}N_7O_6$
Exact Mass: 543.28
Molecular Weight: 543.62

The synthesis of compound E71 was performed according to E16, using 39 as entry.

Yield: 159 mg. 67%; ESI-MS: 544.5 $[M+H]^+$

Example 75. Preparation of Compound E72 (n=2)

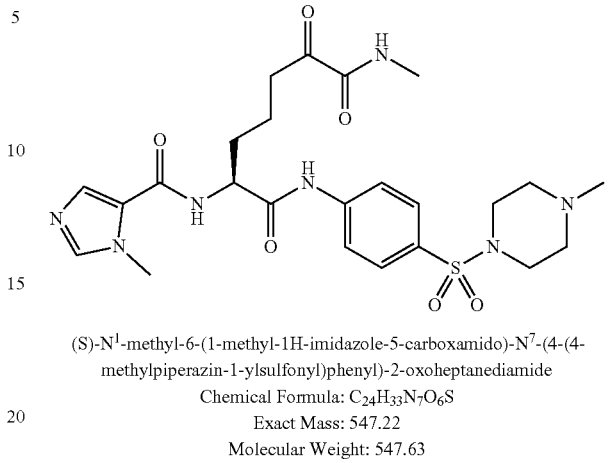

(S)-$N^1$-methyl-6-(1-methyl-1H-imidazole-5-carboxamido)-$N^7$-(4-(4-methylpiperazin-1-ylsulfonyl)phenyl)-2-oxoheptanediamide
Chemical Formula: $C_{24}H_{33}N_7O_6S$
Exact Mass: 547.22
Molecular Weight: 547.63

The synthesis of compound E72 was performed according to E71, coupling with 4-(4-methylpiperazin-1-ylsulfonyl)aniline in step 4.

Yield: 23 mg, 30%; ESI-MS: 548.4 $[M+H]^+$

Example 76. Preparation of Compound E73 (n=3)

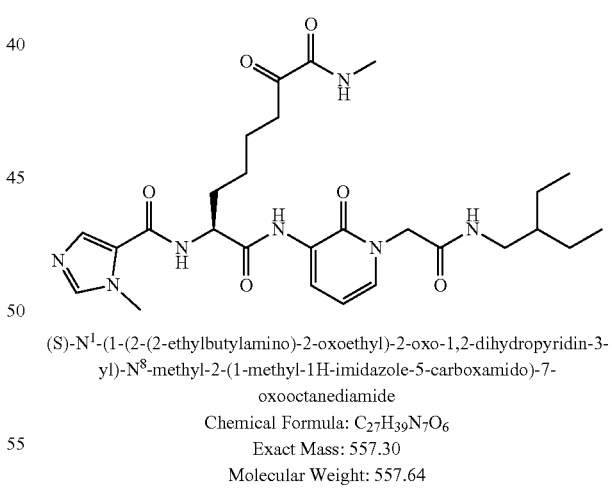

(S)-$N^1$-(1-(2-(2-ethylbutylamino)-2-oxoethyl)-2-oxo-1,2-dihydropyridin-3-yl)-$N^8$-methyl-2-(1-methyl-1H-imidazole-5-carboxamido)-7-oxooctanediamide
Chemical Formula: $C_{27}H_{39}N_7O_6$
Exact Mass: 557.30
Molecular Weight: 557.64

The synthesis of compound E73 was performed according to E71, using (S)-tert-butyl 2-(bis(tert-butoxycarbonyl)amino)-7-diazo-6-oxoheptanoate (prepared from Boc2-Aad-OtBu; method described by Pinkas et al. *PLoS Biol.* 2007, 5, e327) in step 1.

Yield: 41 mg, 56% (last step)

ESI-MS: 558.5 $[M+H]^+$

Example 77. Preparation of Diketone E74 According to the Weinreb Route

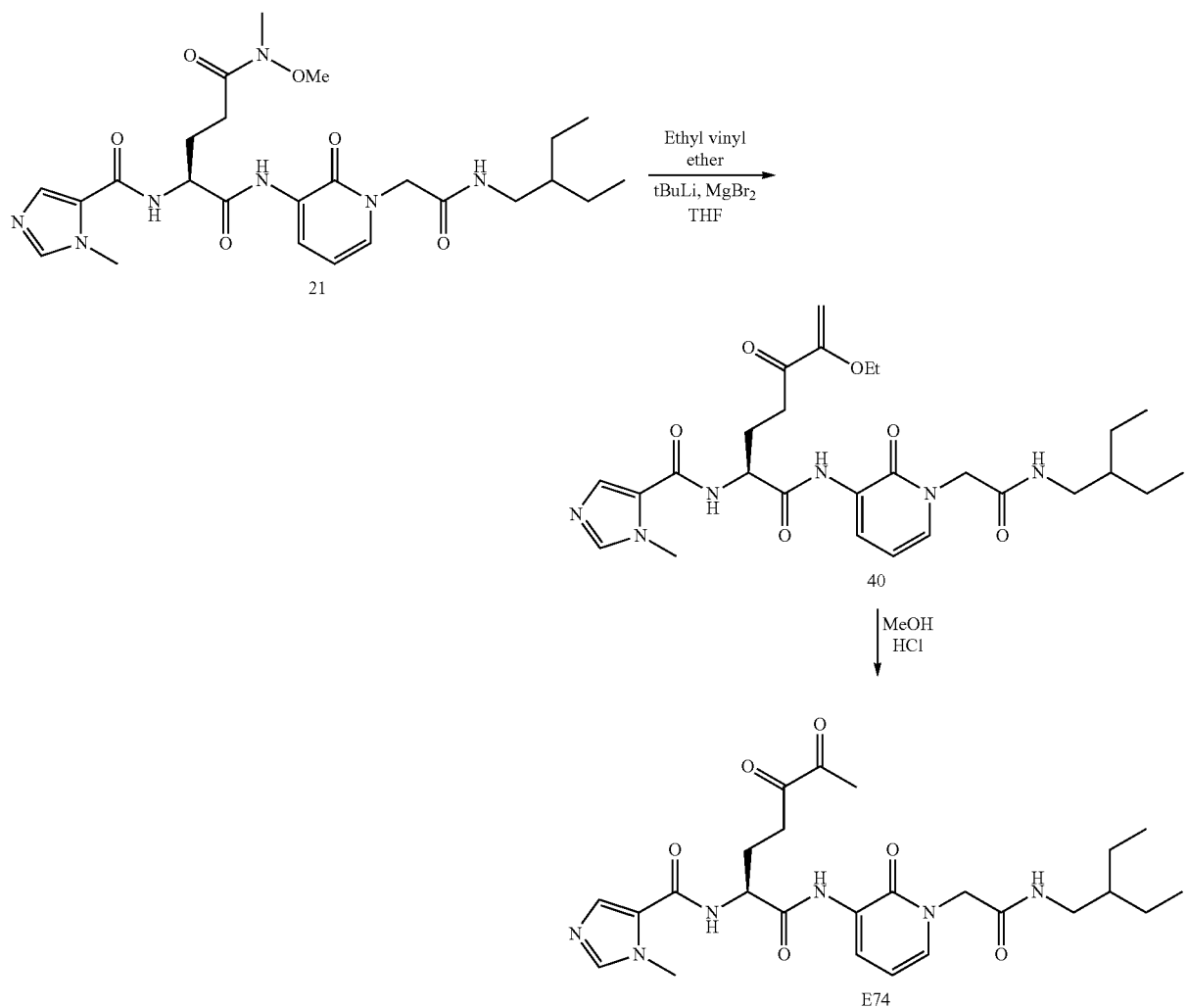

Preparation of Compound 40

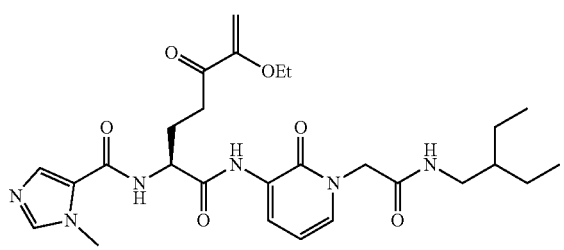

(S)-N-(6-ethoxy-1-(1-(2-(2-ethylbutylamino)-2-oxoethyl)-2-oxo-1,2-dihydropyridin-3-ylamino)-1,5-dioxohept-6-en-2-yl)-1-methyl-1H-imidazole-5-carboxamide
Chemical Formula: $C_{27}H_{38}N_6O_6$
Exact Mass: 542.29
Molecular Weight: 542.63

To a solution of 57 µl (0.58 mmol) ethyl vinyl ether in 2.4 ml THF, 299 µl (0.57 mmol) tert-butyllithium (1.9 M in pentane) were added at −78° C. After warming to 0° C. (2 h), 142 mg (0.54 mmol) magnesium bromide etherate were added at −30° C. After warming to 0° C. (15 min), 58 mg (0.11 mmol) of Weinreb amide 21 in THF (0.3 ml) were added and the reaction was stirred at room temperature overnight. The solution was washed with NH$_4$Cl solution and extracted with diethyl ether. The organic phase was dried over Na$_2$SO$_4$, filtered and the solvent was evaporated. The residue was purified by flash chromatography.

Yield: 41 mg, 69%
ESI-MS: 543.5 [M+H]$^+$

Preparation of Compound E74

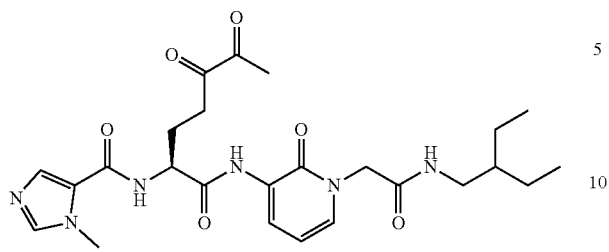

(S)-N-(1-(1-(2-(2-ethylbutylamino)-2-oxoethyl)-2-oxo-1,2-dihydropyridin-3-ylamino)-1,5,6-trioxoheptan-2-yl)-1-methyl-1H-imidazole-5-carboxamide
Chemical Formula: $C_{25}H_{34}N_6O_6$
Exact Mass: 514.25
Molecular Weight: 514.57

To a solution of 41 mg (0.08 mmol) 40 in MeOH (5 ml), HCl conc. (500 µl) were added and stirred for 24 h. The solvent was evaporated and the residue was purified by HPLC.

Yield: 21 mg, 54%

ESI-MS: 515.4 [M+H]$^+$

Example 77. Preparation of Diketone E75 According to Corey-Seebach

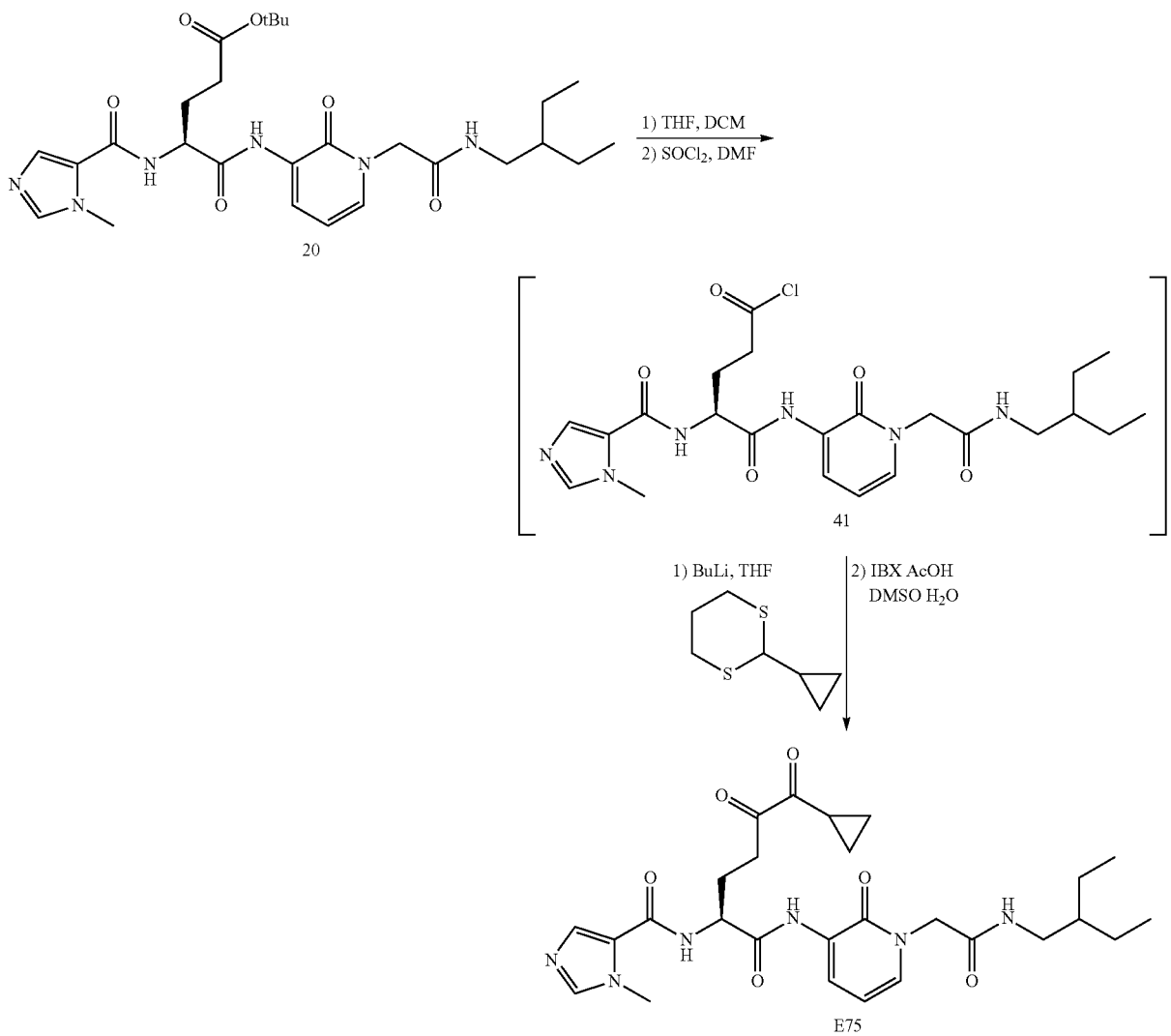

Preparation of Compound E75

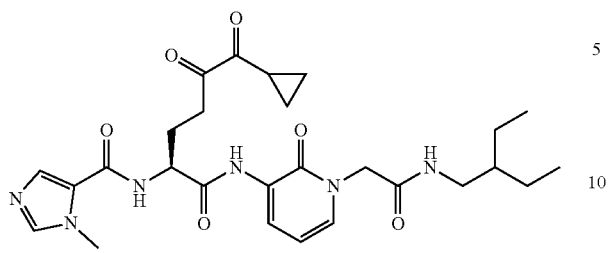

(S)-N-(6-cyclopropyl-1-(1-(2-(2-ethylbutylamino)-2-oxoethyl)-2-oxo-1,2-dihydropyridin-3-ylamino)-1,5,6-trioxohexan-2-yl)-1-methyl-1H-imidazole-5-carboxamide
Chemical Formula: $C_{27}H_{36}N_6O_6$
Exact Mass: 540.27
Molecular Weight: 540.61

205 mg (0.38 mmol) of tert-butyl ester 20 were dissolved in 4 ml DCM/TFA (1:1) and stirred at room temperature for 3 h. The solvent was evaporated and the residue was dissolved in 1 ml thionyl chloride and 50 μl DMF, After stirring at room temperature for 2 h, the solvent was evaporated.

61 mg (0.38 mmol) 2-cyclopropyl-1,3-dithiane were dissolved in 1 ml THF and 25 μl n-Butyllithium (1.6 M in hexane, 1.05 eq) were added at −30° C. A solution of the intermediate acyl chloride 41 in THF was added and the reaction was stirred at room temperature for 24 h. The solution was washed with $NH_4Cl$ solution and extracted with ethyl acetate. The organic phase was dried over $Na_2SO_4$, filtered and the solvent was evaporated.

The residue was dissolved in 2 ml water/DMSO (1:9, 1 mol % acetic acid) with 213 mg 2-iodoxybenzoic acid (IBX, 2 eq) and stirred for 1 h at 25° C. Saturated $Na_2S_2O_3$ solution was added and the suspension was extracted with EtOAc. The organic phase was washed with saturated $NaHCO_3$ solution and brine, dried over $Na_2SO_4$, filtered and the solvent was evaporated. The residue was purified by HPLC.
Yield: 13 mg, 23%
ESI-MS: 541.5 $[M+H]^+$ Example 78. Preparation of Compound E76

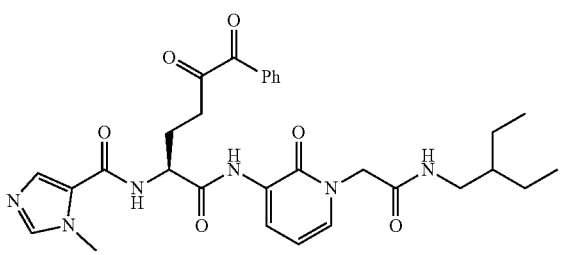

(S)-N-(1-(1-(2-(2-ethylbutylamino)-2-oxoethyl)-2-oxo-1,2-dihydropyridin-3-ylamino)-1,5,6-trioxo-6-phenylhexan-2-yl)-1-methyl-1H-imidazole-5-carboxamide
Chemical Formula: $C_{30}H_{36}N_6O_6$
Exact Mass: 576.27
Molecular Weight: 576.64

The synthesis of compound E76 was performed according to E75, using 2-phenyl-1,3-dithiane in sub-step 3.
Yield: 41 mg, 56% (last step)
ESI-MS: 558.5 $[M+H]^+$ Example 79. Preparation of α-Ketoester E77

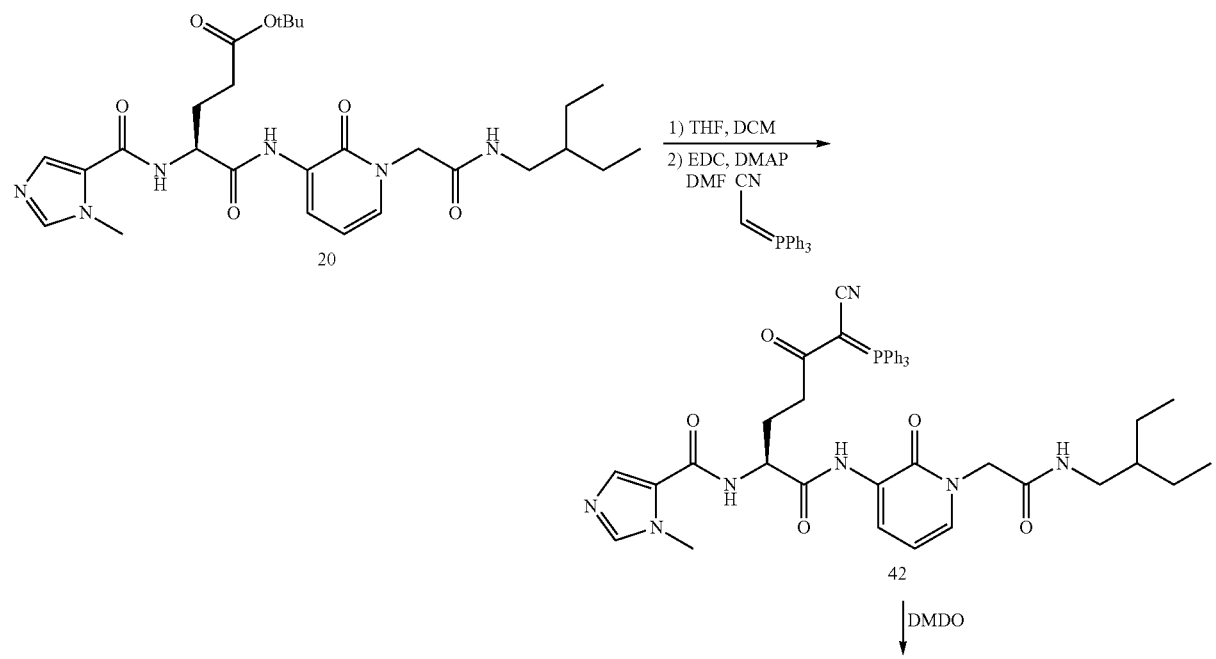

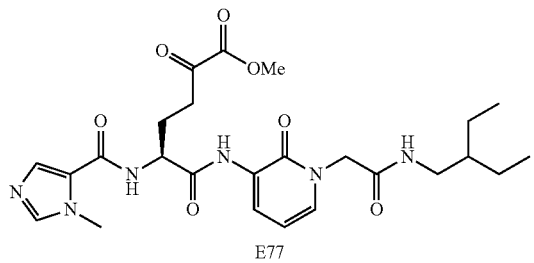

E77

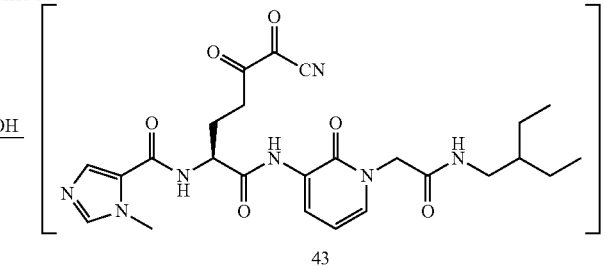

43

Preparation of Compound 42

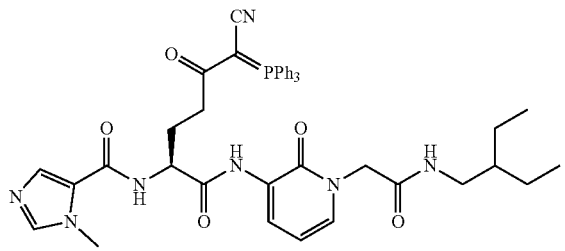

(S, E)-N-(6-cyano-1-(1-(2-(2-ethylbutylamino)-2-oxoethyl)-2-oxo-1,2-dihydropyridin-3-ylamino)-6-(triphenylphosphinylidene)-1,5-dioxohexan-2-yl)-1-methyl-1H-imidazole-5-carboxamide
Chemical Formula: $C_{43}H_{46}N_7O_5P$
Exact Mass: 771.33
Molecular Weight: 771.84

557 mg (1.02 mmol) of 20 were dissolved in 6 ml DCM/TFA (1:1) and stirred at room temperature for 3 h. The solvent was evaporated and the residue was dissolved in 5 ml DMF, 294 mg 1-Ethyl-3-(3-dimethylaminopropyl)carbodiimide (EDC.HCl, 1.5 eq), 12.5 mg DMAP (0.1 eq) and 1.92 ml (2 eq) DIPEA were added, followed by 339 mg (cyanomethylene)triphenylphosphorane (1.1 eq) and the reaction was stirred at room temperature overnight. The solvent was evaporated and the residue was purified by HPLC.

Yield: 96 mg, 12%
ESI-MS: 772.6 [M+H]$^+$
Preparation of Compound E77

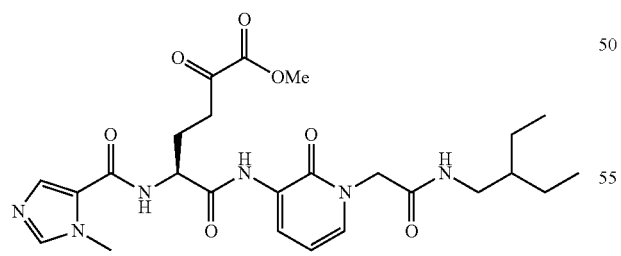

(S)-methyl 6-(1-(2-(2-ethylbutylamino)-2-oxoethyl)-2-oxo-1,2-dihydropyridin-3-ylamino)-5-(1-methyl-1H-imidazole-5-carboxamido)-2,6-dioxohexanoate
Chemical Formula: $C_{25}H_{34}N_5O_7$
Exact Mass: 530.25
Molecular Weight: 530.57

96 mg (0.12 mmol) of α-keto-cyanophosphorane 42 were dissolved in MeOH (2 ml) and DMDO (freshly prepared according to Taber et al. *Org. Synth.* 2013, 90, 350-357) (2 eq, dimethyldioxirane in acetone) was added dropwise at room temperature and the reaction was stirred at room temperature for 1 h. The solvent was evaporated and the residue was purified by HPLC.

Yield: 22 mg, 35%
ESI-MS: 531.5 [M+H]$^+$

Example 80. Preparation of Compound E78

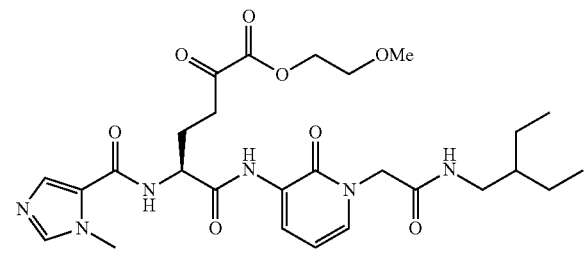

(S)-2-methoxyethyl 6-(1-(2-(2-ethylbutylamino)-2-oxoethyl)-2-oxo-1,2-dihydropyridin-3-ylamino)-5-(1-methyl-1H-imidazole-5-carboxamido)-2,6-dioxohexanoate
Chemical Formula: $C_{27}H_{38}N_6O_8$
Exact Mass: 574.28
Molecular Weight: 574.63

The synthesis of compound E78 was performed according to E77 from intermediate 43 by performing in ethylene glycol monomethyl ether.

Yield: 15 mg, 23%
ESI-MS: 575.5 [M+H]$^+$

Example 81. Preparation of Compound E79

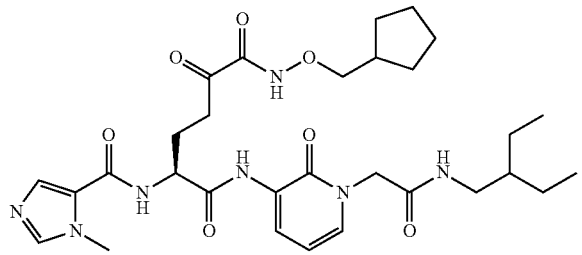

(S)-N$^1$-(cyclopentylmethoxy)-N$^6$-(1-(2-(2-ethylbutylamino)-2-oxoethyl)-2-oxo-1,2-dihydropyridin-3-yl)-5-(1-methyl-1H-imidazole-5-carboxamido)-2-oxohexanediamide
Chemical Formula: C$_{30}$H$_{43}$N$_7$O$_7$
Exact Mass: 613.32
Molecular Weight: 613.71

The synthesis of compound E79 was performed according to E77 from intermediate 43 by performing in cyclopentanemethanol.

Yield: 26 mg, 38%
ESI-MS: 614.5 [M+H]$^+$

Example 82. Preparation of Compound E80 (Via Corey-Seebach)

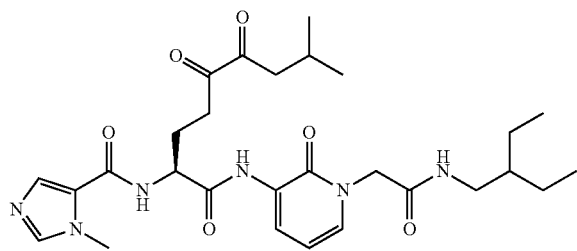

(S)-N-(1-(1-(2-(2-ethylbutylamino)-2-oxoethyl)-2-oxo-1,2-dihydropyridin-3-ylamino)-8-methyl-1,5,6-trioxononan-2-yl)-1-methyl-1H-imidazole-5-carboxamide
Chemical Formula: C$_{28}$H$_{40}$N$_6$O$_6$
Exact Mass: 556.30
Molecular Weight: 556.65

The synthesis of compound E80 was performed according to E75, using 2-isobutyl-1,3-dithiane in sub-step 3.

Yield: 26 mg, 36% (last step)
ESI-MS: 557.5 [M+H]$^+$

Example 83. Preparation of Compound E81 (Via Corey-Seebach)

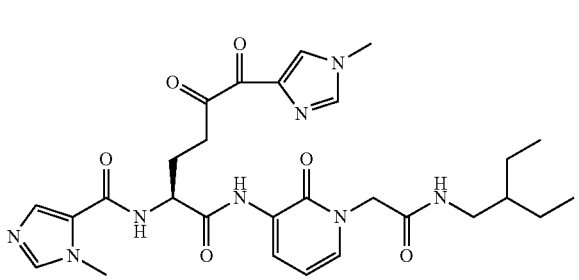

(S)-N-(1-(1-(2-(2-ethylbutylamino)-2-oxoethyl)-2-oxo-1,2-dihydropyridin-3-ylamino)-6-(1-methyl-1H-imidazol-4-yl)-1,5,6-trioxohexan-2-yl)-1-methyl-1H-imidazole-5-carboxamide
Chemical Formula: C$_{28}$H$_{36}$N$_8$O$_6$
Exact Mass: 580.28
Molecular Weight: 580.64

The synthesis of compound E81 was performed according to E75, using 4-(1,3-dithian-2-yl)-1-methyl-1H-imidazole in sub-step 3.

Yield: 12 mg, 28% (last step)
ESI-MS: 581.5 [M+H]$^+$

Example 84. Preparation of Compound E82 (Via Passerini Route)

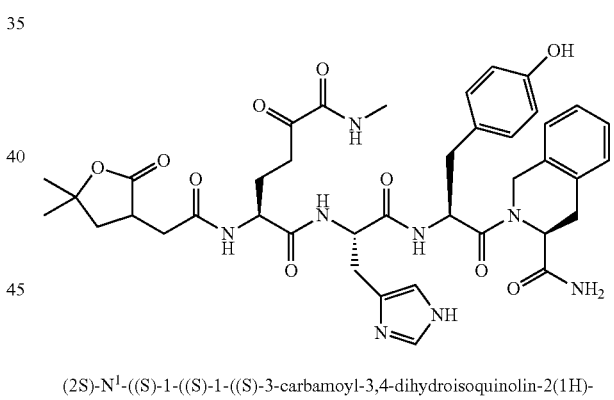

(2S)-N$^1$-((S)-1-((S)-1-((S)-3-carbamoyl-3,4-dihydroisoquinolin-2(1H)-yl)-3-(4-hydroxyphenyl)-1-oxopropan-2-ylamino)-3-(1H-imidazol-4-yl)-1-oxopropan-2-yl)-2-(2-(5,5-dimethyl-2-oxotetrahydrofuran-3yl)acetamido)-N$^6$-methyl-5-oxohexanediamide
Chemical Formula: C$_{40}$H$_{48}$N$_8$O$_{10}$
Exact Mass: 800.35
Molecular Weight: 800.86

The synthesis of compound E82 was performed according to E16, coupling with (S)-2-((S)-2-((S)-2-amino-3-(1H-imidazol-4-yl)propanamido)-3-(4-hydroxyphenyl)propanoyl)-1,2,3,4-tetrahydroisoguinoline-3-carboxamide in step 3 and (5,5-dimethyl-2-oxotetrahydro-3-furanyl)acetic acid in step 4.

Yield: 19 mg, 35% (last step)
ESI-MS: 801.6 [M+H]$^+$

Example 85. Preparation of Compound E83 (Via Passerini Route)

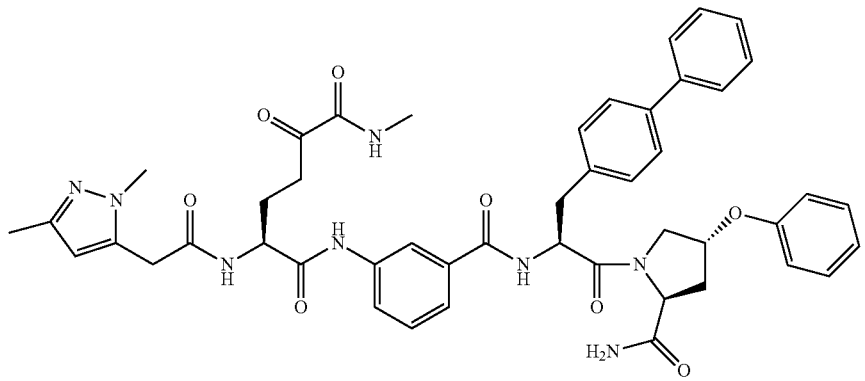

(S)-N$^1$-(3-((S)-3-(biphenyl-4-yl)-1-((2S,4R)-2-carbamoyl-4-phenoxypyrrolidin-1-yl)-1-oxopropan-2-ylcarbamoyl)phenyl)-2-(2-(1,3-dimethyl-1H-pyrazol-5-yl)acetamido)-N$^6$-methyl-5-oxohexanediamide Chemical Formula: C$_{47}$H$_{50}$N$_8$O$_8$
Exact Mass: 854.38
Molecular Weight: 854.95

The synthesis of compound E83 was performed according to E16, coupling with (2S,4R)-14(S)-2-(3-aminobenzamido)-3-(biphenyl-4-yl)propanoyl)-4-phenoxyl)pyrrolidine-2-carboxamide in step 3 and 1,3-dimethyl-1H-pyrazole-5-acetic acid in step 4.
Yield: 8 mg, 19% (last step)
ESI-MS: 855.6 [M+H]$^+$

Example 86. Preparation of Compound E84 (Via Passerini Route)

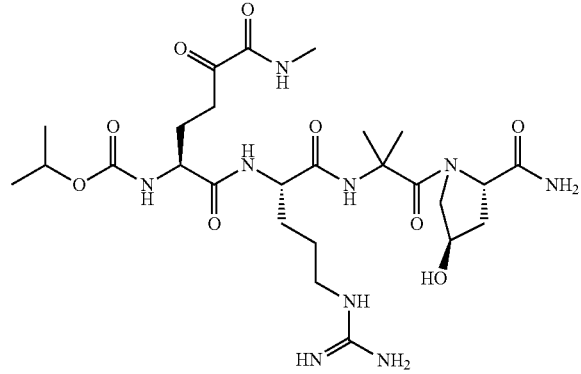

isopropyl (S)-1-((S)-1-(1-((2S,4R)-2-carbamoyl-4-hydroxypyrrolidin-1-yl)-2-methyl-1-oxopropan-2-ylamino)-5-guanidino-1-oxopentan-2-ylamino)-6-(methylamino)-1,5,6-trioxohexan-2-ylcarbamate Chemical Formula: C$_{26}$H$_{45}$N$_9$O$_9$
Exact Mass: 627.33
Molecular Weight: 627.69

The synthesis of compound E84 was performed according to E16, coupling with (2S,4R)-1-(2-((S)-2-amino-5-guanidinopentanamido)-2-methylpropanoyl)-4-hydroxypyrrolidine-2-carboxamide in step 3 and propan-2-yl carbonochloridate in step 4.

Yield: 28 mg, 31% (last step)
ESI-MS: 628.5 [M+H]$^+$

Compounds for Determination of Cell Toxicity
Preparation of Compound Z006 ("Z-DON")

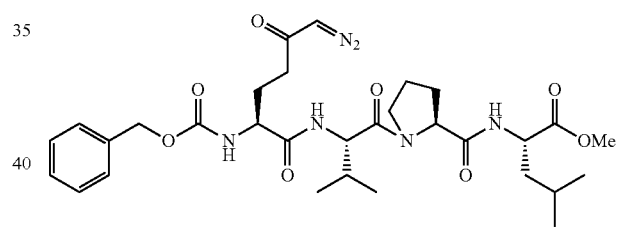

The synthesis of compound Z006 was performed according to Pinkas et al. (*PLoS Biol.* 2007, 5, e327.) using Z-Glu-Val-Pro-Leu-OMe as entry.

Preparation of Compound Z007

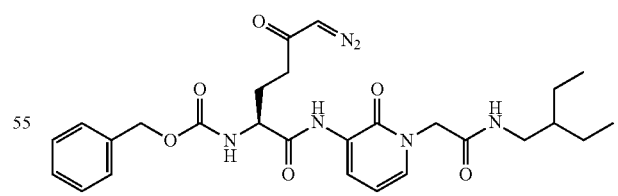

The synthesis of compound Z007 was performed according to Pinkas et al. (*PLoS Biol* 2007, 5, e327.) using (S)-4-(benzyloxycarbonylamino)-5-(1-(2-(2-ethylbutylamino)-2-oxoethyl)-2-oxo-1,2-dihydropyridin-3-ylamino)-5-oxopentanoic acid as entry.

Preparation of Compound DON06

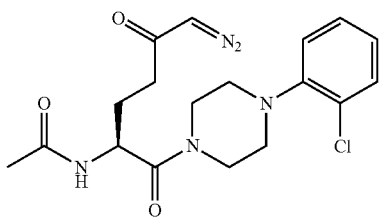

The synthesis of compound DON06 was performed according to Pinkas et al. (*PLoS Biol.* 2007, 5, e327.) using (S)-4-acetamido-5-(4-(2-chlorophenyl)piperazin-1-0)-5-oxopentanoic acid as entry.

DON07

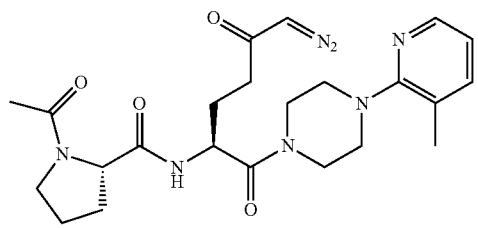

The synthesis of compound DON07 was performed according to Pinkas et al. (*PLoS Biol.* 2007, 5, e327.) using (S)-4-((S)-1-acetylpyrrolidine-2-carboxamido)-5-(4-(3-methylpyridin-2-yl)piperazin-1-yl)-5-oxopentanoic acid as entry.

BIOLOGICAL EXAMPLES

Example B-1. Inhibitory Effect of the Compounds According to the Invention

Method for Inhibition Studies of Rec. Human Tissue Transglutaminase (rhTG2)

250 µg lyophilized His-tagged recombinant human tissue transglutaminase ($His_6$-rhTG2, Zedira product 1022) is reconstituted in $H_2O$ (volume depends on original volume before lyophilization) resulting in a buffer containing 10 mM Tris-HCl, 150 mM NaCl, 1 mM EDTA, 5 mM DTT, 189 mg/ml maltodextrin, pH=8.1. The rhTG2 stock solution is diluted in buffer (50 mM Tris-HCl, 7.5 mM $CaCl_2$, 150 mM NaCl, pH=7.4) to give a working solution of 100 U/ml (based on the amine-incorporation activity measured using T036, described below).

A 10 mM inhibitor stock solution is prepared in DMSO, and from this stock solution a serial 1:2-fold dilution series is prepared, also in DMSO. Each of these initial dilutions is subsequently diluted 1:50-fold with buffer (50 mM Tris-HCl, 7.5 mM $CaCl_2$, 150 mM NaCl, pH=7.4) to yield the final working dilutions containing 2% (v/v) DMSO. 15 µl of inhibitor working dilution are added per well of a 96 well microtiter plate. As control, 15 µl of a 2% (v/v) DMSO solution prepared using the buffer mentioned above are added per well.

600 µl of $His_6$-rhTG2 working solution are added to 11.4 ml assay buffer (50 mM Iris-HCl, 7.5 mM $CaCl_2$, 150 mM NaCl, 5 mM DTI, 13.4 mM glycine methylester, 50 µM Abz-APE(CAD-DNP)QEA-OH, (Zedira product A102; patent No.: EP 1781807B1), pH=7.4). From this master-mix solution, 285 µl are added per well containing the inhibitor. Increase in fluorescence is measured using $\lambda_{ex}$=313 nm and $\lambda_{em}$=418 nm at 37° C. for 20 min. A slope of the increase in fluorescence between 10 and 20 min is calculated for determination of the $IC_{50}$ value (inhibitor concentration at which 50% of the initial TG2 activity is blocked).

Method for Inhibition Studies of Rec. Human Coagulation Factor XIII (Plasma Transglutaminase, rhFXIII-A)

50 µg lyophilized His-tagged recombinant human factor XIII A-subunit ($His_6$-rhFXIII, Zedira product 1027) is reconstituted in $H_2O$ (volume depends on original volume before lyophilization) resulting in a buffer containing 20 mM Tris-HCl, 150 mM NaCl, 1 mM EDTA, 1 mM DTT, 189 mg/ml maltodextrin, pH=7.5. The rhFXIII stock solution is diluted in buffer (50 mM Tris-HCl, 7.5 mM $CaCl_2$, 150 mM NaCl, pH=7.4) to give a working solution of 59 U/ml (based on the amine-incorporation activity measured using transglutaminase activity assay #1036 (Zedira GmbH), described below).

A 10 mM inhibitor stock solution is prepared in DMSO, and from this a serial 1:2-fold dilution series is prepared also in DMSO. Each of the initial dilutions is subsequently diluted 1:50-fold with buffer (50 mM Tris-HCl, 7.5 mM $CaCl_2$, 150 mM NaCl, pH=7.4) to yield the final working dilutions containing 2% (v/v) DMSO.

15 µl of inhibitor working dilution are added per well of a 96 well microtiter plate. As control, 15 µl of a 2% (v/v) DMSO solution prepared using the buffer mentioned above are added per well.

480 µl of $His_6$-rhFXIII working solution and 120 µl human alpha thrombin (0.5 NIH units/µl) are added to 10.8 ml assay buffer (50 mM Tris-HCl, 7.5 mM $CaCl_2$, 150 mM NaCl, 5 mM DTT, 13.4 mM glycine methylester, 50 µM Abz-NE(CAD-DNP)EQVSPLILLK-OH, (Zedira product A101; patent No.: EP 1781807B1), pH=7.4). From this master-mix solution, 285 µl are added per well containing the inhibitor. Increase in fluorescence is measured using $\lambda_{ex}$=313 nm and $\lambda_{em}$=418 nm at 37° C. for 35 min. A slope of the increase in fluorescence between 20 and 30 min is calculated for determination of the $IC_{50}$ value (inhibitor concentration at which 50% of the initial FXIII activity is blocked).

This assay was also used to determine selectivity of inhibitors preferentially blocking FXIIIa by using TG2 instead of FXIII.

Selectivity Assay (General Transglutaminase Assay; T036)

For the determination of selectivity of inhibitors against different transglutaminases, the incorporation of dansylcadaverine into dimethyicasein (Zedira product 1036, Lorand et al., Anal Biochem, 1971, 44:221-31) was measured using recombinant human transglutaminase 1 (Zedira Product T009), transglutaminase 2 (Zedira Product T022), transglutaminase 3 (Zedira Product T012), transglutaminase 6 (Zedira Product T021), and plasma transglutaminase (rhFXIII, Zedira Product T027).

The different transglutaminases are diluted in buffer (50 mM Tris-HCl, 7.5 mM $CaCl_2$, 150 mM NaCl, pH=7.4) to the respective working concentrations.

A 10 mM inhibitor stock solution is prepared in DMSO, and from this a serial 1:2-fold dilution series is prepared also in DMSO. Each of the initial dilutions is subsequently diluted 1:50-fold with buffer (50 mM Tris-HCl, 7.5 mM $CaCl_2$, 150 mM NaCl, pH=7.4) to yield the final working dilutions containing 2% (v/v) DMSO.

15 µl of inhibitor working dilution are added per well of a 96 well microtiter plate. As control, 15 µl of a 2% (v/v) DMSO solution prepared using the buffer mentioned above are added per well.

Immediately before starting the assay, 600 µl transglutaminase working solution are added to 11.4 ml assay buffer (50 mM Tris-HCl, 10 mM $CaCl_2$, 10 mM glutathione, 2.5% glycerol, 16.7 µM dansylcadaverine, 4 µM N,N-dimethyl-casein, 200 mM NaCl, pH=8.0). 285 µl of this reaction mix are added per well containing the inhibitor. Increase in fluorescence is measured using $\lambda_{ex}$=330 nm and $\lambda_{em}$=500 nm at 37° C. for 30 min. A slope of the increase in fluorescence between 20 and 30 min is calculated for determination of the $IC_{50}$ value (inhibitor concentration at which 50% of the initial activity is blocked).

Analysis of enzymatic activity is performed by calculation of the slope of an increase in fluorescence intensity. $IC_{50}$ values are calculated by plotting the enzymatic activity (as percentage from control containing 2% DMSO instead of inhibitor) against the inhibitor concentration. $IC_{50}$ is defined as the inhibitor concentration blocking 50%) of initial enzyme activity.

The inhibitory activity of the inventive compounds in regard to tissue transglutaminase (TG2) and FXIII-A is shown in the following table using $IC_{50}$-values.

TABLE 1

TG2 inhibitors, selectivity with respect to FXIII

| compound | $IC_{50}$ TG2 [nM] | $IC_{50}$ FXIII [nM] |
|---|---|---|
| E01 | 600 | >100,000 |
| E02 | 70 | >100,000 |
| E03 | 750 | >100,000 |
| E04 | 100 | >100,000 |
| E05 | 150 | >100,000 |
| E06 | 100 | >100,000 |
| E07 | 100 | >100,000 |
| E16 | 50 | >100,000 |

TABLE 2

TG2 inhibitors

| compound | $IC_{50}$ TG2 [nM] |
|---|---|
| E11 | 450 |
| E12 | 950 |
| E13 | 700 |
| E14 | 250 |
| E15 | 6,000 |
| E17 | 100 |
| E18 | 125 |
| E19 | 350 |
| E20 | 600 |
| E21 | 5,000 |
| E38 | 700 |
| E39 | 135 |
| E40 | 500 |
| E41 | 1,450 |
| E22 | 85 |
| E23 | 1,100 |
| E24 | 550 |
| E42 | 1,600 |
| E43 | 60 |
| E44 | 80 |
| E45 | 75 |
| E46 | 95 |
| E47 | 80 |
| E50 | 300 |

TABLE 2-continued

TG2 inhibitors

| compound | $IC_{50}$ TG2 [nM] |
|---|---|
| E51 | 760 |
| E52 | 500 |
| E53 | 750 |
| E54 | 550 |
| E55 | 200 |
| E56 | 850 |
| E57 | 230 |
| E58 | 280 |
| E59 | 625 |
| E60 | 60 |
| E61 | 80 |
| E62 | 70 |
| E63 | 80 |
| E64 | 95 |
| E65 | 65 |
| E66 | 120 |
| E67 | 150 |
| E68 | 150 |
| E69 | 275 |
| E70 | 265 |
| E71 | 6,000 |
| E72 | 6,300 |
| E73 | 6,300 |
| E74 | 125 |
| E75 | 135 |
| E76 | 550 |
| E77 | 200 |
| E78 | 400 |
| E80 | 135 |
| E81 | 740 |
| E84 | 960 |
| E82 | 1,350 |
| E83 | 2,000 |
| E79 | 530 |

TABLE 3

FXIII inhibitors, selectivity with respect to TG2

| compound | $IC_{50}$ FXIII [nM] | $IC_{50}$ TG2 [nM] |
|---|---|---|
| E08 | 150 | 100 |
| E09 | 150 | 100 |
| E10 | 150 | 100 |
| E25 | 50 | 5,500 |
| E26 | 320 | 10,800 |
| E27 | 60 | 7,800 |
| E28 | 275 | 20,000 |
| E29 | 850 | >20,000 |
| E30 | 2,900 | >20,000 |
| E31 | 5,000 | >20,000 |
| E32 | 2,650 | 1,000 |
| E33 | 16,000 | 11,500 |
| E34 | 2,450 | 200 |
| E35 | 1,950 | 525 |
| E36 | 3,100 | 800 |
| E37 | 2,500 | 390 |

Example B-2. Determination of Cytotoxicity of Transglutaminase Inhibitors

The following cell lines are used for determination of cytotoxicity:
  CaCo2 (human colon carcinoma cell line)
  Huh7 (human liver carcinoma cell line).

Cells are cultivated in DMEM/10% FCS at 37° C. and 5% $CO_2$ in a 96 well plate with an initial seeding density of $2 \times 10^4$ cells/well.

Transglutaminase inhibitors are added to the cells with final concentrations from 0.1 µM to 1 mM one hour after seeding. The different inhibitor dilutions are prepared in DMSO, resulting in a final concentration of 1% (v/v) DMSO in every well (2 µl inhibitor in 200 µl cell culture medium). Cycloheximide (2.5 µg/ml) and Camptothecin (0.2 µg/ml) are used as control compounds. All measurements are performed in triplicates.

Cytotoxicity of transglutaminase inhibitors is evaluated with two different assays:

Determination of proliferation using Cell Proliferation ELISA, BrdU (Roche, Cat. No. 11647229001).

After 24 h of incubation with inhibitors or controls, BrdU is added to the cells. After further incubation for 18 h, the cells are fixed and cellular DNA becomes denatured. A monoclonal antibody (conjugated with peroxidase) raised against BrdU is added to the wells and binds to BrdU which is incorporated into the DNA. Substrate solution is added and absorbance at 450 nm is recorded. Further analysis is performed according to the manufacturer's protocol.

Determination of metabolic activity using EZ4U-Assay (Biomedica, Cat. No. BI-5000).

After 48 h of incubation with inhibitors or controls, the tetrazolium substrate is added to the cells. Substrate turnover by the cells is measured over two hours at 450 nm (using 630 nm was reference wavelength).

Cytotoxicity of inhibitor pairs characterized by the same backbone, but either a reversible (alpha ketoamide) or irreversible (diazooxonorleucine) warhead are given in table 4. For the compounds with diazooxonorleucine-warhead, reduced cell proliferation and metabolic activity at concentrations from 100 µM to 500 µM (depending on the cell type) have been found. In sharp contrast, the reversible inhibitors showed no impact on both parameters up to the highest concentrations measured (1 mM). In order to demonstrate this effect, we compared the commercial available irreversible acting inhibitor Z006 (Z-DON-VPL-OMe, "Z-DON", Zedira) carrying a 6-diazo-5-oxo-norleucine warhead with the reversible inhibitor E02. The peptidic backbone is the same, the warhead (α-ketoamide) and the mode-of-action (irreversible vs. reversible) is different. While Z006 is cytotoxic at 125 µM the novel compound E02 shows no influence on cell proliferation or metabolic activity up to 1 mM (highest concentration measured).

TABLE 4

Cytotoxicity concentrations (>10% deviation from negative control) of tissue transglutaminase blockers with identical backbone but reversibly (alpha ketoamide) or irreversibly (diazooxonorleucine) reacting warhead in cell proliferation assays (BrdU) and metabolic activity assays (EZ4U).

| Compound | BrdU | | EZ4U | |
|---|---|---|---|---|
| | Caco2 | Huh-7 | Caoo2 | Huh-7 |
| Z006 | 250 µM | 125 µM | 500 µM | 125 µM |
| E02 | >1 mM | >1 mM | >1 mM | >1 mM |
| Z007 | 250 µM | 125 µM | 500 µM | 125 µM |
| E57 | >1 mM | >1 mM | >1 mM | >1 mM |
| DON06 | 125 µM | 100 µM | 250 µM | 100 µM |
| E06 | >1 mM | >1 mM | >1 mM | >1 mM |
| DON07 | 100 µM | 100 µM | 250 µM | 100 µM |
| E07 | >1 mM | >1 mM | >1 mM | >1 mM |

Example B-3. Antifibrotic Effect on Renal Cells

Fibrosis is a hallmark in diabetic nephropathy and chronic kidney diseases. Proximal tubular epithelial cells show increased TG2 activity and increased extracellular matrix proteins (ECM) accumulation under hyperglycemic conditions. ECM accumulation is a hall mark of fibrosis. In order to demonstrate the antifibrotic effect of reversible transglutaminase inhibitors, compounds E06 and E22 were tested on proximal tubular epithelial cells cultured under normal versus hyperglycemic conditions. TG2-activity and ECM-accumulation was measured. Rattus norvegicus kidney derived cell line NRK52E was grown at 37° C. in a humidified atmosphere at 5% (v/v) $CO_2$ in DMEM (Dulbecco's modified Eagle's medium) containing 100 µg/mL streptomycin, 100 units/ml penicillin, 20 mM glutamine, and 10% (v/v) fetal calf serum. For simulation of normal physiological conditions 6 mM D-glucose were added to the medium, while addition of 24 mM and 36 mM D-glucose simulated hyperglycemic conditions. Reversible TG2 inhibitor E06 in the concentrations indicated in FIG. 1A was added at the time of plating to the medium. Reversible TG2 inhibitor E22 in the concentrations indicated in FIG. 2A was added at the time of plating to the medium.

TG2-activity was determined in cell homogenates. Therefore, cells were removed from plates with trypsin (2 mg/mL)-EDTA (2 mM) solution, centrifuged, washed with PBS and finally stored in sucrose (0.32 mM)-Tris (5 mM)-EDTA (1 mM)-buffer pH7.2, containing 1 µl/mL protease inhibitor (Halt™ Protease and Phosphatase Inhibitor Cocktail, EDTA-free, ThermoFisher, #1861279). Equal amounts of cells were homogenized by sonication.

TG2-activity was measured using the TG2-selective Tissue Transglutaminase Pico-Assay Kit (#M003, Zedira, Darmstadt, Germany) according to the manufacturer's instructions. One unit is defined as the amount of enzyme, which causes the formation of 1.0 µmole of hydroxamate per minute by catalysing the reaction between Z-Gln-Gly-OH and hydroxylamine at pH 6.0 at 37° C.

For the determination of extracellular matrix proteins (ECM) deposition, cells grown in 10 cm Petri-dishes were removed with 1 mL sodium deoxycholate (0.1%)-EDTA (2 mM)-solution. ECM proteins remaining on the plate were solubilized by digestion with trypsin (0.2 mg/mL)-EDTA (2 mM) solution. The resulting solution was concentrated by speed-vac. Protein concentration was determined using the DC-protein-assay (BioRad, #5000111).

Intracellular TG2 is increased in NRK52E-cells at hyperglycemic concentrations of 24 and 36 mM glucose (FIG. 1A, 0 µM E06). With increasing concentrations of E06 the TG2 activity determined in the cell homogenates decreases (FIG. 1A, 10-100 µM E06). Production of extracellular matrix protein increases at hyperglycemic concentrations (FIG. 1B, 0 µM E06). The increase of ECM was reduced in a dose dependent manner by the addition of E06 to the culture medium.

Figure 2:
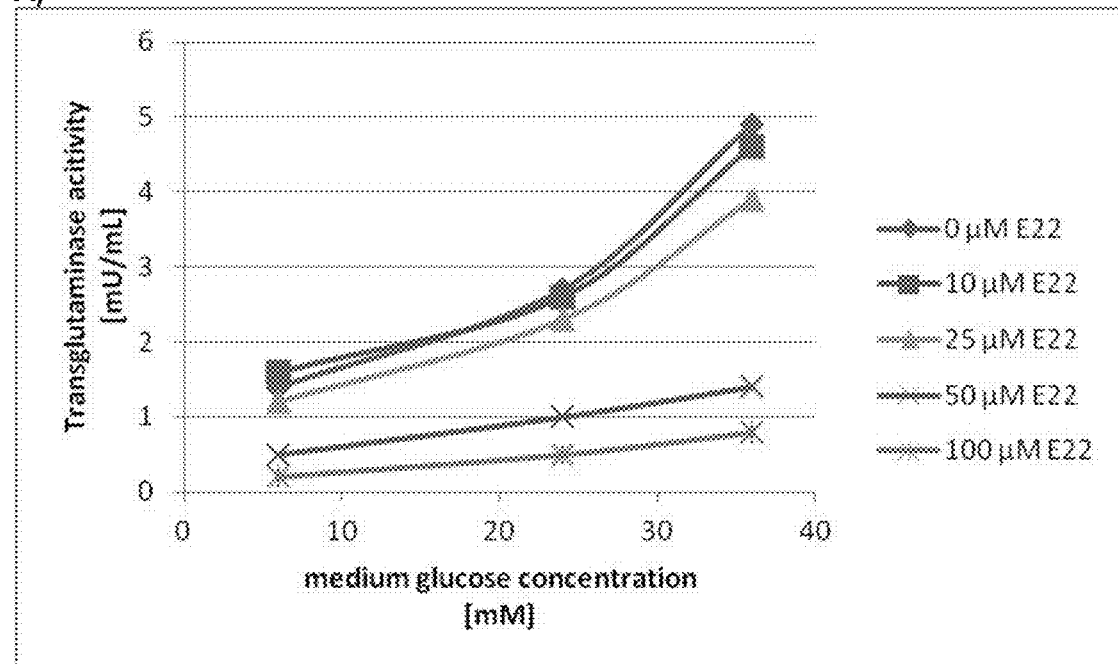
FIG. 2
A) Transglutaminase activity of homogenates from NRK52E-cell grown at physiological (6 mM) and hyperglycemic glucose concentrations (24 mM and 36 mM) in the presence of compound E22.
B) Extracellular matrix protein deposition from NRK52E-cell grown at physiological and hyperglycemic glucose concentrations in the presence of compound E22.
Figure 2:
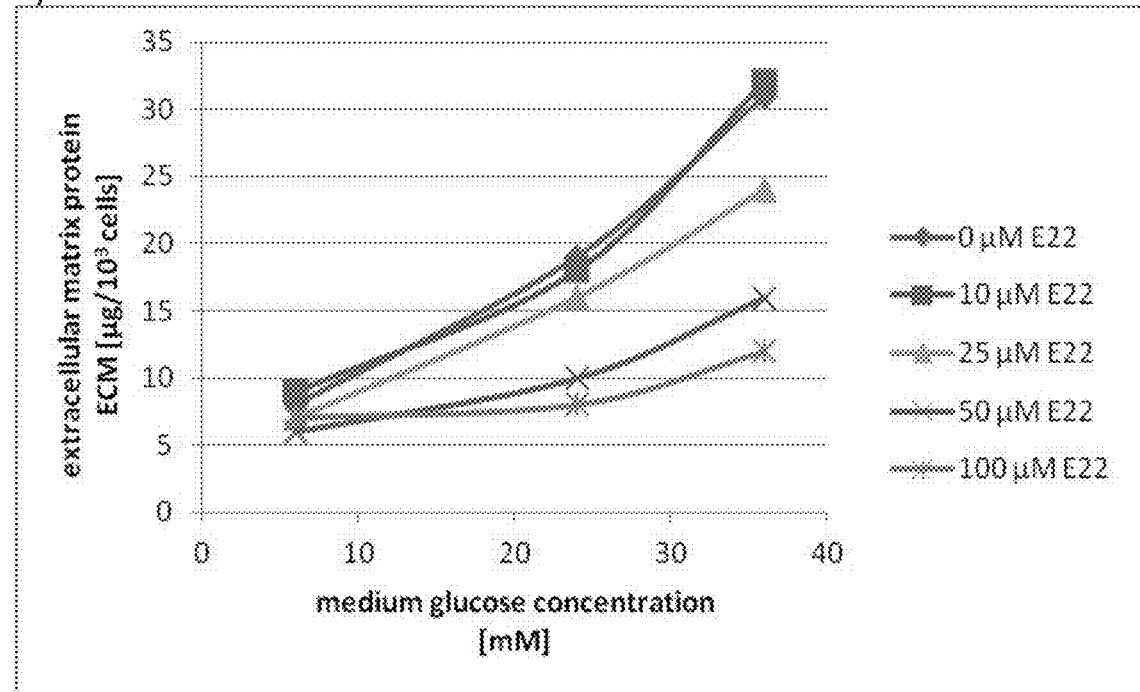

Intracellular TG2 is increased in NRK52E-cells at hyperglycemic concentrations of 24 and 36 mM glucose (FIG. 2A, 0 µM E22). With increasing concentrations of E22 the TG2 activity determined in the cell homogenates decreases (FIG. 2A, 10-100 µM E22). Production of extracellular matrix protein increases at hyperglycemic concentrations (FIG. 2B, 0 µM E22). The increase of ECM was reduced in a dose dependent manner by the addition of E22 to the culture medium.

In summary these results show, that tissue transglutaminase inhibition using reversible tissue transglutaminase blocker E06 and E22 reduce transglutaminase activity and reduces ECM accumulation. These data indicate that E06 and E22 have an antifibrotic effect in proximal tubular epithelial cells.

Example B-4. Thromboelastometry (TEM)

Thromboelastometry is a visco-elastic method for the assessment of blood coagulation. In whole blood parameters like clotting time (CT), clot formation time (CFT), maximum clot firmness (MCF) and lysis index at 60 min ($LI_{60}$) were obtained using the ROTEM® delta device according to the manufacturer.

The potency of selected compounds (serial dilution covering 6.25 µM to 50 µM final concentration) in the presence of 0.02 µg/ml tissue plasminogen activator (t-PA, Zedira product P016) were investigated. Briefly, 20 µL star-TEM® (0.2 mol/l $CaCl_2$), 20 µL r ex-TEM® (recombinant tissue factor, phospholipids, heparin inhibitor), 10 µL inhibitor stock solution (1.8-0.23 mM), combined with 10 µL t-PA stock solution (0.72 µg/ml) to yield concentrations of 0.9-0.11 mM in 18% DMSO/PBS with 0.36 µg/ml t-PA and 300 µL fresh citrated whole blood (human, from healthy consenting donors) were mixed in a disposable cuvette. As control the inhibitor stock solution was replaced by 36% DMSO/0.36 µg/ml t-PA in PBS.

(Lang T, von Depka M. Possibilities and limitations of thrombelastometry/-graphy. *Hamostaseologie*. 2006; 26:S20-529.)

Figure 3:
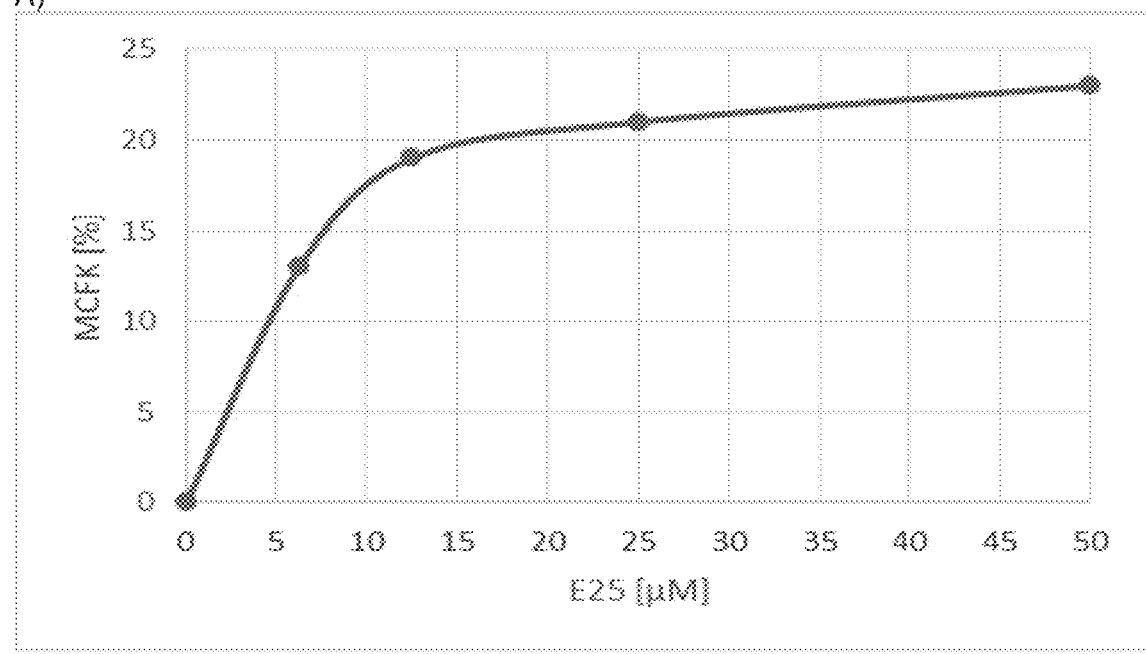
FIG. 3
A) Dose dependent influence of compound E25 on the reduction of maximum clot firmness (MCF) compared to control (K).
B) Dose dependent influence of compound E25 on the clot lysis at 60 minutes ($LI_{60}$) in the presence of 0.02% t-PA.
Figure 3:
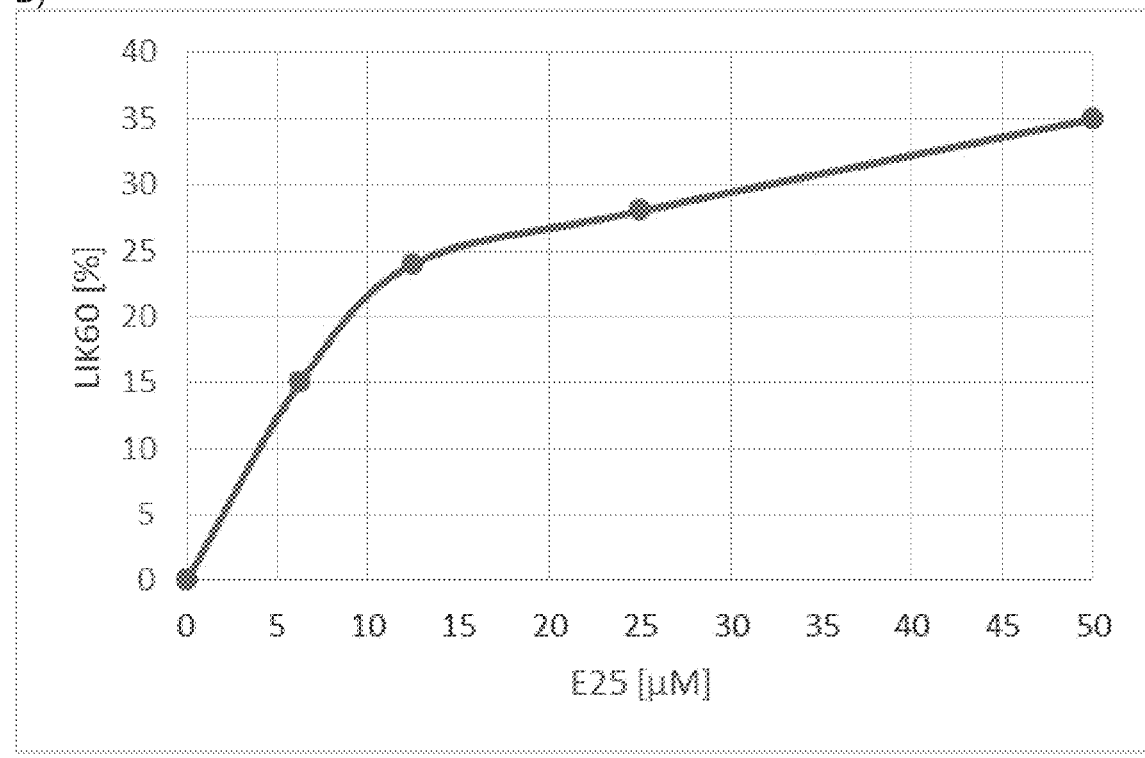
Figure 4:
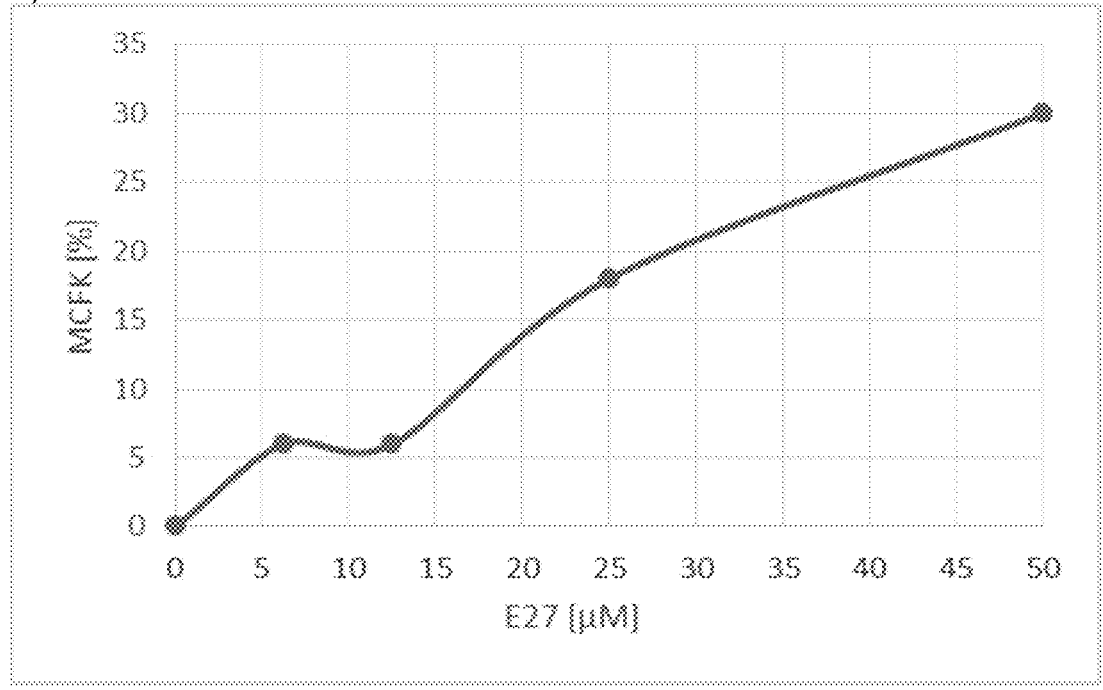
FIG. 4
A) Dose dependent influence of compound E27 on the reduction of maximum clot firmness (MCF) compared to control (K).
B) Dose dependent influence of compound E27 on the clot lysis at 60 minutes ($LI_{60}$) in the presence of 0.02% t-PA.
Figure 4:
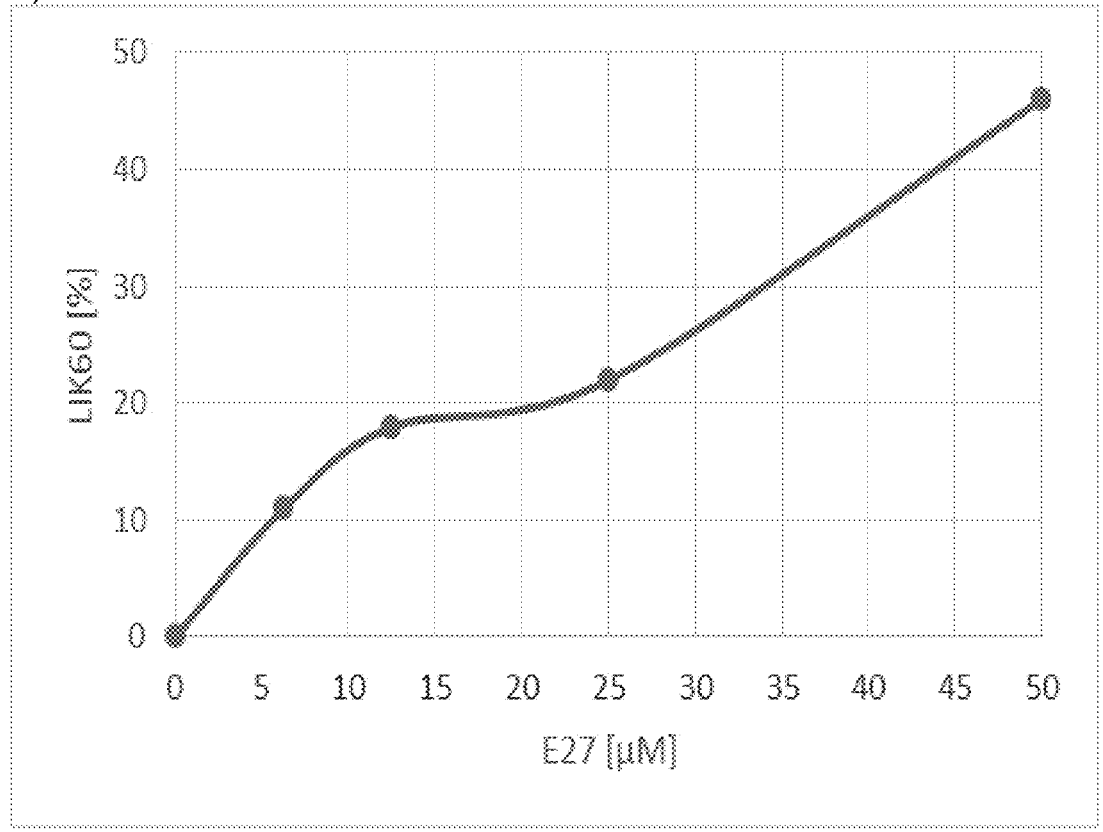

The results of dose dependent influence of compounds E25 and E27 on TEM parameters are presented respectively in FIGS. 3A)/3B) and FIGS. 4A)/4B).

FIG. 3A) and FIG. 4A) show dose dependent influence of compounds E25 and E27 on the reduction of maximum clot firmness (MCF) compared to control (K).

FIG. 3B) and FIG. 4B) show dose dependent influence of compounds E25 and E27 on the clot lysis at 60 minutes ($LI_{60}$) in the presence of 0.02% t-PA.

Example B-5, Investigation of the Reversible Mode of Inhibition of α-Keto Compounds In order to investigate the reversibility of α-ketoamides as TG2-inhibitors, the inhibitor was removed stepwise using Vivaspin® centriufugal concentrators (VS2022, Sartorius Stedim) while the molecular weight of the TG2 prevents passing the ultrafiltration membrane. Briefly, recombinant human tissue transglutaminase (Zedira, T002) was incubated with the inhibitor E16 at 1.6 µM. The transglutaminase activity was determined using the casein/dansylcadaverine assay (Zedira, T036). Subsequently, buffer was added to dilute the inhibitor within the reaction mixture as shown in table 5. After concentration using the Vivaspin centrifugal concentrators to the original volume, the procedure was repeated twice to obtain 1:100 and 1:1,000 dilution. The activity rises with increasing dilution indicating that the inhibitor binds in equilibrium to TG2. Once the concentration of the inhibitor is decreased the ratio of non-inhibited transglutaminase rises and consequently the activity increases. As a control, the same experiment was performed using REF1. REF1 irreversibly binds to the active site cysteine of TG2 thereby blocking its activity.

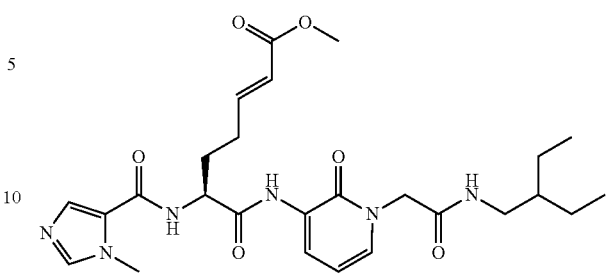

REF1

As expected, we could not find any rebound of activity. Conclusively, the oi-keto compounds claimed provide a reversible mode of inhibition.

TABLE 5

| inhibitor [1.6 µM] | Activity after inhibition | Recovery of activity by dilution of inhibitor (constant TG2 concentration) | | |
|---|---|---|---|---|
| | | 1:10 | 1:100 | 1:1,000 |
| E16 | 0% | 15% | 61% | 100% |
| REF1 | 0% | 0% | 0% | 0% |

Example B-6, Blocking of Neurite Outgrowth

The irreversible-reversible inhibitor pair Z007 and E57 was further compared using a neurite outgrowth assay (Merck, #NS220) with mouse neuroblastoma cell line N1E-115. Laminin-coated Millicell® 12-well inserts were placed in a 12 well plate containing 1.2 mL differentiation medium (Merck, NS002). Then, 300 µL of a $10^6$ N1E-115-cells/mL suspension were added. Differentiation medium contained 0 µM, 75 µM and 150 µM Nocadazole as positive controls, and 100 µM, 250 µM and 500 µM of inhibitors 2007 or E57. Nocodazole interferes with the polymerization of microtubules resulting in an antineoplastic effect.

For neurite extension the plates were incubated at 37° C. for 48 hours. Then the insert was transferred to a new 12 well plate with 1,200 µL of PBS per plate and finally to a plate with 400 µL of −20° C. methanol per well, where the cells were fixed for 20 min at room temperature. After rinsing with PBS, the insert was stained with Neurite Staining Solution for 20 min. After rinsing the inserts in PBS cell bodies were carefully swabbed off and inserts were washed again in PBS. Inserts were then transferred into 15 mL tubes and 100 µL Neurite Stain Extraction Buffer were added to the top of the inserts. After 5 min incubation at ambient temperature, tubes were centrifuged for 1 min at 1,200 rpm. Finally 75 µL extraction buffer were removed and the absorbance was determined at 590 nm.

Figure 5:
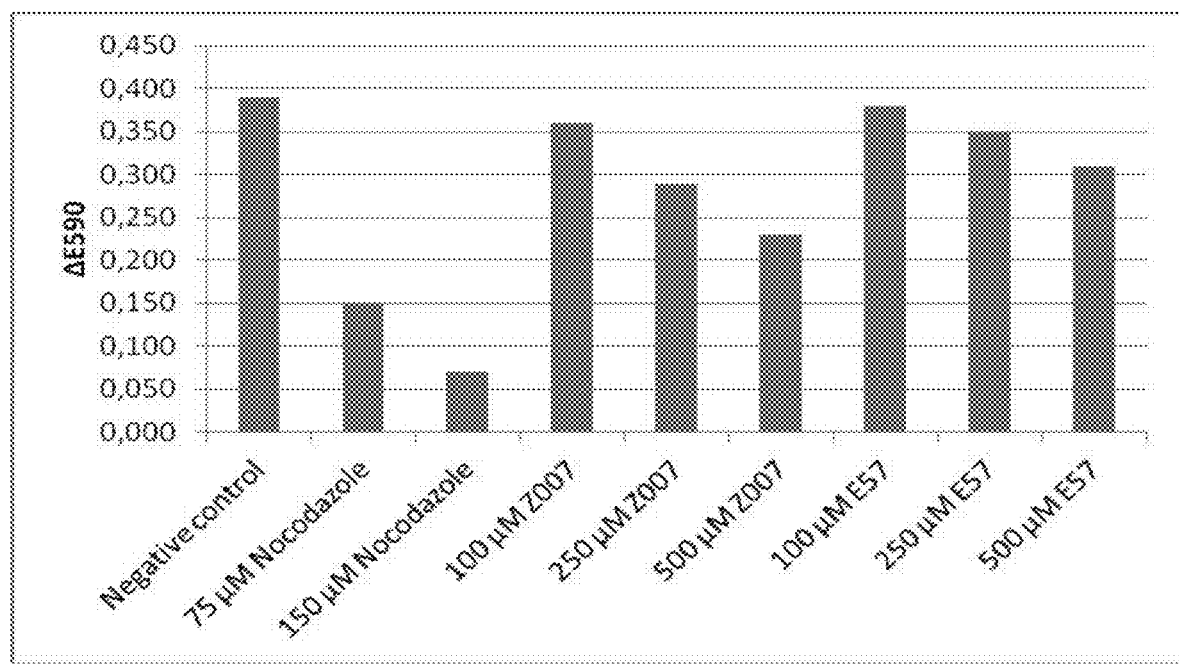
FIG. 5
Determination of neurite outgrowth reduction by antineoplastic agent nocodazole, irreversible TG2 blocker ZED1537 and reversible TG2-blocker N01. Extinction values determined for the stained neurite extract are shown.

The results are summarized in FIG. 5. The irreversible TG2-blocker Z007 reduced neurite outgrowth in a dose dependent manner. At 500 µM, a moderate 36% reduction was observed. For reversible TG2-inhibitor E57 also a dose dependent, but even milder impact, on neurite outgrowth could be determined. At 500 µM the reduction of neurite outgrowth was 18%.

Example B-7 Effect of TG2-Inhibition in a Cellular System of Huntingtin Producing Cells Insoluble protein aggregates composed of the protein huntingtin (htt) are a hallmark of Chorea Huntington. Htt is characterized by polyglutamine (polyQ)-expansions, triggering aggregation and serving as substrate for transglutaminase catalyzed cross-linking.

N2a cells (mouse neuroblastoma cell line) transfected with Htt-exon1-97Q were grown in Dulbecco's modified Eagle's medium (DMEM) supplemented with 10% fetal calf serum, 1 mM glutamine, 100 µg/mL streptomycin, and 100 U/mL penicillin in a humidified incubator with 5% $CO_2$ at 37° C.

For preparation of SDS-soluble and formic acid soluble extracts, cells were harvested in 0.5 mL cold PBS, centrifugated, resuspended in 70 mM Tris-HCl pH 6.8, 1.5% SDS, 20% glycerol and lysed through sonication. DTT was added to a final concentration of 50 mM and the sample was boiled for 10 min in a ThermoMixer® at 1000 rpm, followed by centrifugation for 1 h at 14,000 rpm. The supernatant was transferred to a new tube and was stored at 4° C. before coating of microtiter plates.

For solubilization of the SDS-insoluble proteins in the remaining pellet, 10 µl formic acid were added and mixed by pipetting 10 times up and down, followed by incubation at 37° C. for 40 min at 1,000 rpm in a ThermoMixer®. Formic acid was then removed in a SpeedVac™ concentrator at 30° C. under vacuum. The resulting protein pellet was dissolved in 70 mM Tris-HCl pH 6.8, 1.5% SDS, 20% glycerol. The sample was boiled for 10 min, and stored at 4° C. before coating of microtiter plates.

SDS-soluble and formic acid soluble extracts were used subsequently for coating of 96-well micro-titer-plates. Therefore, 100 µL of the cell extracts were added in each well and incubated over night at 4° C. After washing with Tris-buffered saline, 0.1% Tween 20, plates were blocked with 150 µL 1%-BSA-solution in PBS for 60 min at 37° C. After washing, 100 µL detection antibody was added and incubated for 60 min at ambient temperature. This solution was removed, the plates washed again intensively and secondary antibody was applied (goat anti-mouse IgG-HRP-conjugate) for a further 30 minutes at ambient temperature. The plates were intensively washed and 100 µL substrate solution (TMB-$H_2O_2$) was added. After incubation for 60 min at room temperature the reaction was stopped by the addition of 0.2 M sulfuric acid. Extinction was measured at 450 nm in a plate reader device.

In order to analyze the effect of E22 on huntingtin aggregation and cross-linking, Htt-exon1-97Q transfected N2a-cells were grown in presence of 150 or 300 µM TG2-blacker E22. SDS-soluble and formic acid soluble extracts were generated and huntingtin and cross-links (iso-peptide bonds) were determined in an ELISA-format as described above.

Figure 6:
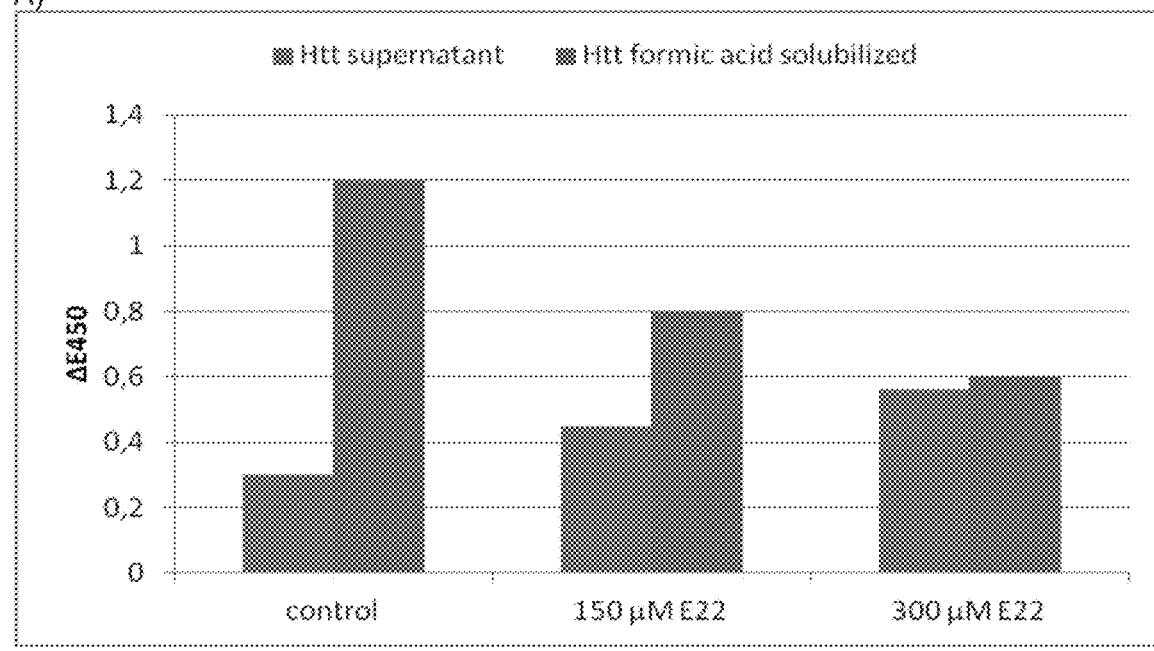
FIG. 6
A) Detection of huntingtin (htt) in an ELISA-Assay. Microtiter plate wells were coated with SDS-soluble and formic acid solubilized extracts of Htt-exon1-97Q transfected N2a-cells grown in the presence of 150 and 300 µM TG2-inhibitor E22. Anti-Htt-antibody $1C_2$ (1:250, Millipore, MAB1574) was used as detection antibody, followed by a conventional ELISA-protocol.
Figure 6:
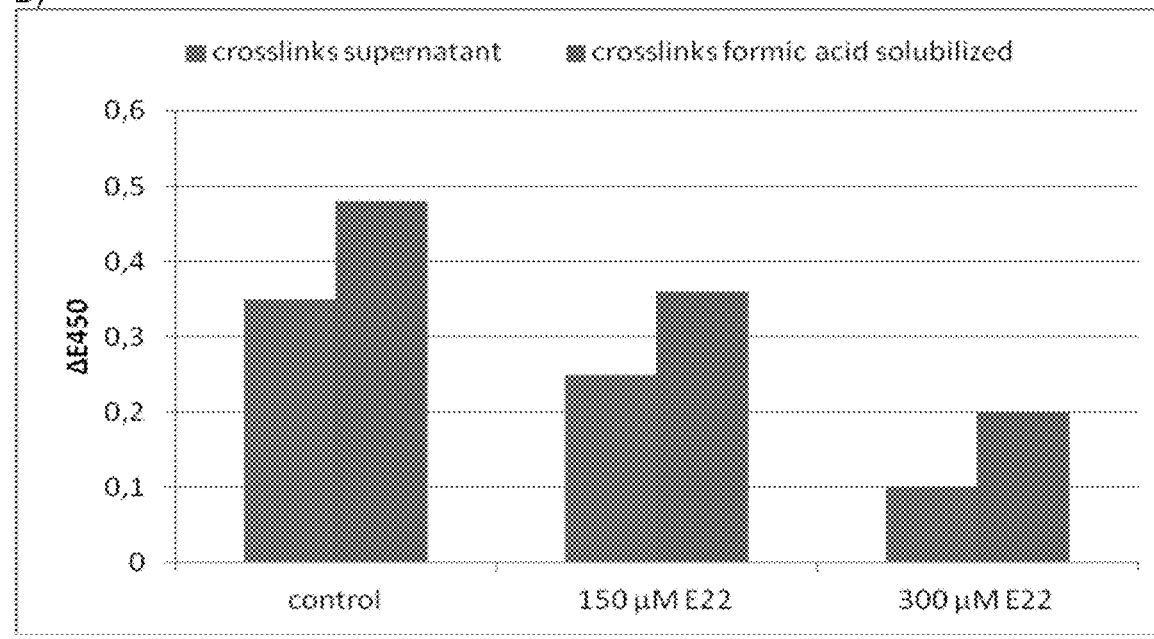

The results are summarized in FIGS. 6A and 6B. The amount of SDS-soluble htt increases along with higher E22-concentrations. Concomitantly, the mount of formic acid soluble htt decreases.

In the soluble extract as well as in the formic acid soluble extract the amount of cross-links decreases dose dependently.

Taken together, E22 reduces protein cross-linking in a dose dependent manner. The increasing amount of htt protein in the SDS-soluble fraction may be explained by reduced enzymatic cross-linking of htt, which keeps the protein soluble, because concomitantly htt-protein is reduced in the formic acid soluble fraction.

The observed htt-aggregation reducing effect of TG2-blocker E22 supports the potential of reversible acting transglutaminase blockers for treatment of neurodegenerative disorders characterized by cross-linked insoluble protein aggregates.

Example B-13. Antifibrotic Effect on Lung Epithelial Cells

Extracellular matrix deposition is a hallmark in pulmonary fibrosis. The BEAS-2B cell line is derived from normal human bronchial epithelium. In order to demonstrate the antifibrotic effect of reversible transglutaminase inhibitors, compound E22 was tested on BEAS-2B cells stimulated with lipopolysaccharides (LPS).

BEAS-2B cells were grown at 37° C. and 5% $CO_2$ in 25 mM HEPES-buffered M199-medium (Merck, Darmstadt) containing 10% FBS, 100 mg/ml streptomycin, 2 mM glutamine, 100 U/ml penicillin (supplemented with 2.5 mg/ml apotransferrin, 20 ng/ml human epidermal growth factor (EGF), 2.5 mg/ml insulin, and 0.361 mg/ml hydrocortisone). For the induction of airway fibrosis by epithelial-to-mesenchymal transition (EMT), cells were seeded at 80% confluence on six-well plates. After one day cultivation 4 µg/mL LPS as well as 0 µM, 100 µM or 200 µM E22 were added and then incubated for further 72 h.

Subsequently, cells were harvested and TG2-activity as well as ECM-deposition was measured as described above for the demonstration of the antifibrotic effect in renal cells.

Figure 7:
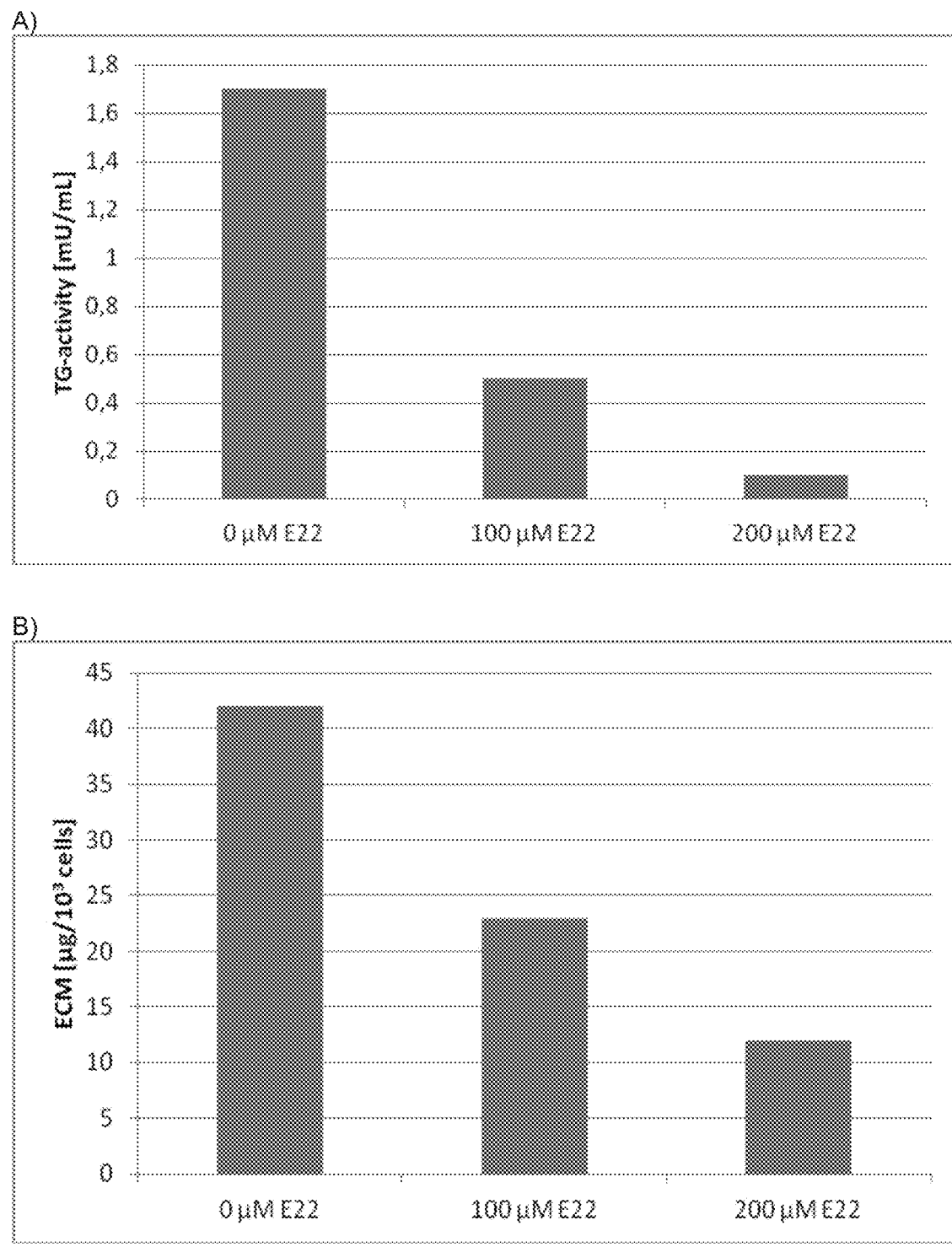

Transglutaminase activity measured in LPS-stimulated BEAS-2B-cells showed dose dependent reduction upon addition of increasing amounts of E22 to the culture medium (FIG. 7A).

In parallel, the deposition of ECM-proteins was significantly reduced, also in a dose dependent manner (FIG. 7B). Taken together, these data indicate an antifibrotic effect of E22 in pulmonary epithelial cells.

Example B-9. Antifibrotic Effect on Hepatic Stellate Cells

Liver fibrosis is characterized by the formation of scar tissue as a response to liver damage. Activated hepatic stellate cells (HSC) are the major cell type in liver fibrosis, deposing extracellular matrix protein, essentially collagens, in the space of Disse (perisinusoidal space). Hepatic fibrosis is the result of inflammation as a response to liver injury. Inflammation is characterized by HSC activation to a myofibroblast-like phenotype.

LX-2 Human Hepatic Stellate Cell Line

Human hepatic stellate cell line LX-2 was cultured on standard plastic 6 well plates in Dulbecco's Modified Eagle's Medium containing 100 µg/mL streptomycin, 100 units/ml penicillin, 2 mM glutamine, and 10% (v/v) fetal calf serum. E22 was added to a concentration of 0 µM, 100 µM and 200 µM. Cells were grown at 37° C. and 5% $CO_2$ humidified atmosphere. Medium was exchanged every two days. After 12 days cells were harvested and analyzed for TG2-activity and extracellular matrix deposition as described above for the demonstration of the antifibrotic effect on renal cells.

Figure 8:
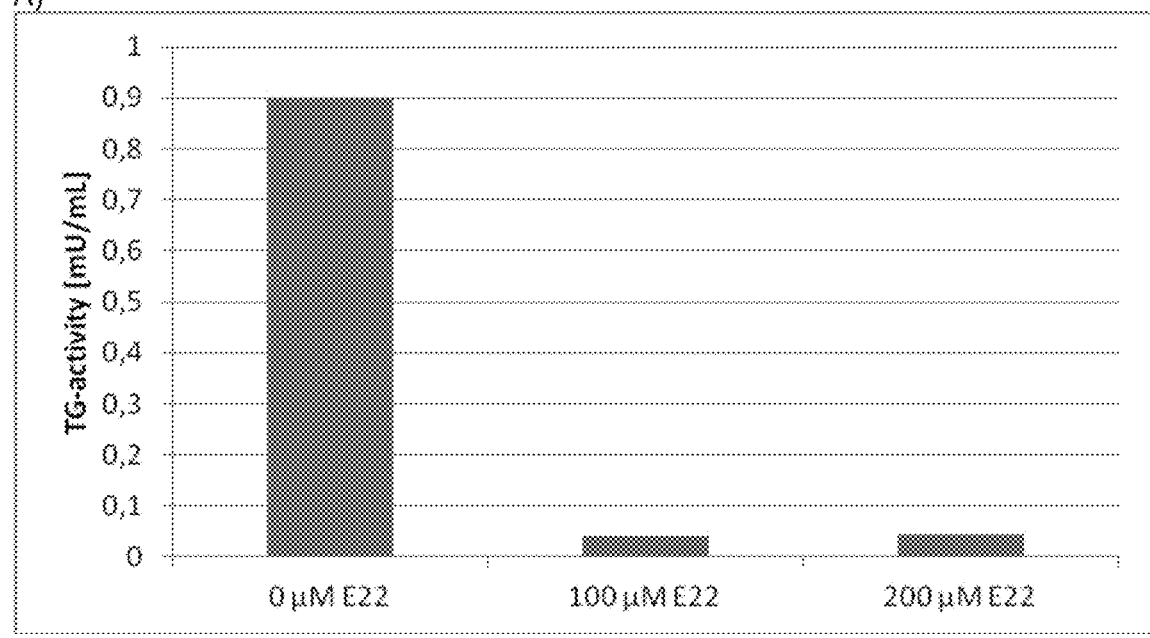
Figure 8:
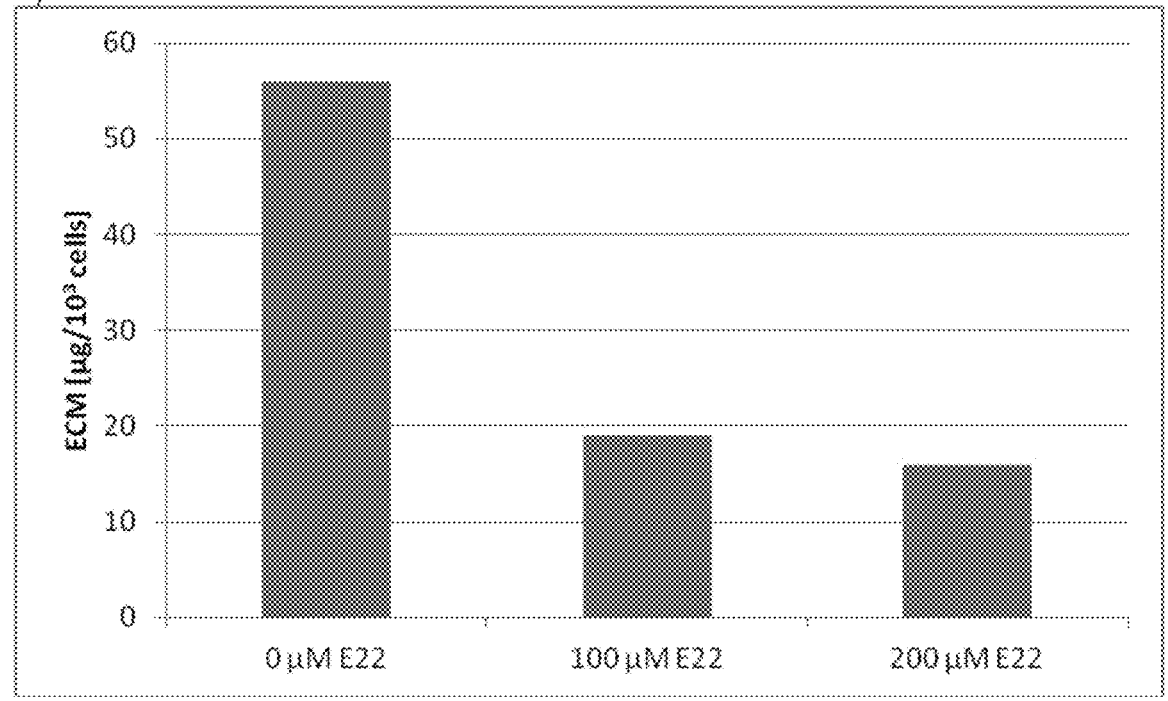

Transglutaminase activity was reduced to <5% of the inhibitor free control already at 100 µM reversible transglutaminase-inhibitor E22 in the culture medium (FIG. 8A). The extracellular matrix deposition on the plates was reduced to about 30% of control at both E22 concentrations.

This observation shows that TG2-inhibition of HSCs reduces deposition of extracellular matrix proteins. TG2-inhibition may therefore provide an antifibrotic effect on liver fibrosis.

In parallel, the deposition of ECM-proteins was significantly reduced, also in a dose dependent manner (FIG. 8B). Taken together, these data indicate an antifibrotic effect of E22 in hepatic stellate cells.

What is claimed is:

1. A compound of the general formula (I):

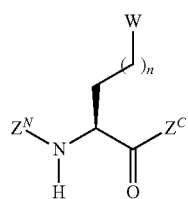
(I)

wherein n is an integer selected from 1, 2 or 3;

W represents

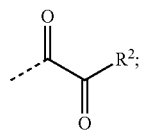

$R^2$ represents —$R^1$, —$OR^1$, —$NH_2$, —$NH(R^1)$, —$NH(OR^1)$, —$N(R^1)(R^3)$;

$R^1$ and $R^3$ represent independently of each other —$CH_3$, —$CH_2CH_3$, —$CH_2CH_2CH_3$, —$CH(CH_3)_2$, —$CH_2CH_2CH_2CH_3$, —$CH_2CH_2CH_2CH_2CH_3$, —$CH_2CH_2CH_2CH_2CH_2CH_3$, —$CH_2CH_2CH_2CH_2CH_2CH_2CH_3$, —$CH_2CH(CH_3)_2$, —$CH(CH_3)CH_2CH_3$, —$CH(C_2H_5)_2$, —$CH_2CH(C_2H_5)_2$, —$C(CH_3)_3$, —$CH_2$—$C(CH_3)_3$, -cyclo-$C_3H_5$, -cyclo-$C_4H_7$, -cyclo-$C_5H_9$, -cyclo-$C_6H_{11}$, —$CH_2$-cyclo-$C_3H_5$, —$CH_2$-cyclo-$C_4H_7$, —$CH_2$-cyclo-$C_5H_9$, —$CH_2$-cyclo-$C_6H_{11}$, -Ph, —$CH_2$-Ph, —$CH_2OCH_3$, —$CH_2OCH_2CH_3$, —$CH_2CH_2OCH_3$, —$CH_2CH_2OCH_2CH_3$, —$CH_2CO_2CH_3$, —$CH_2CO_2CH_2CH_3$, —$CH_2CH_2NHCH_3$, —$CH_2CH_2N(CH_3)_2$, —$CH_2S(O)_2$-(4-methyl-phenyl),

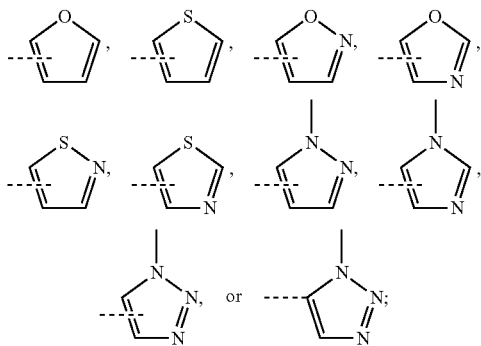

or

—$N(R^1)(R^3)$ forms

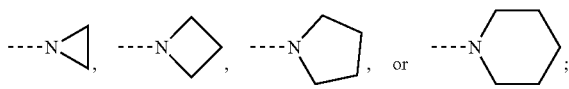

$Z^N$ represents $E^N$-, or $E^N$-$AS^{N1}$;

$Z^C$ represents -$E^C$, -$AS^{C1}$-$E^C$, -$AS^{C1}$-$AS^{C2}$-$E^C$, -$AS^{C1}$-$AS^{C2}$-$AS^{C3}$-$E^C$, or -$AS^{C1}$-$AS^{C2}$-$AS^{C3}$-$AS^{C4}$-$E^C$;

$AS^{N1}$ is selected from the group consisting of:

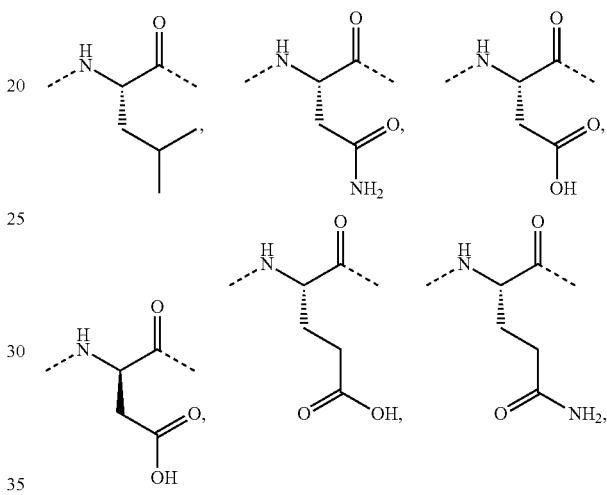

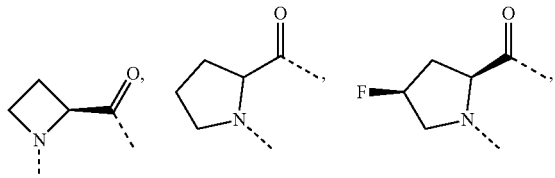

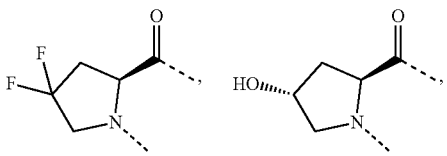

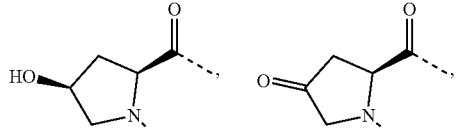

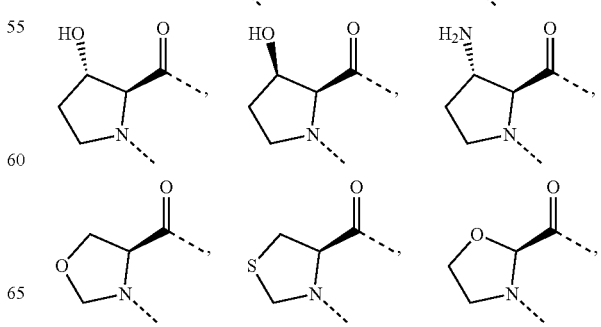

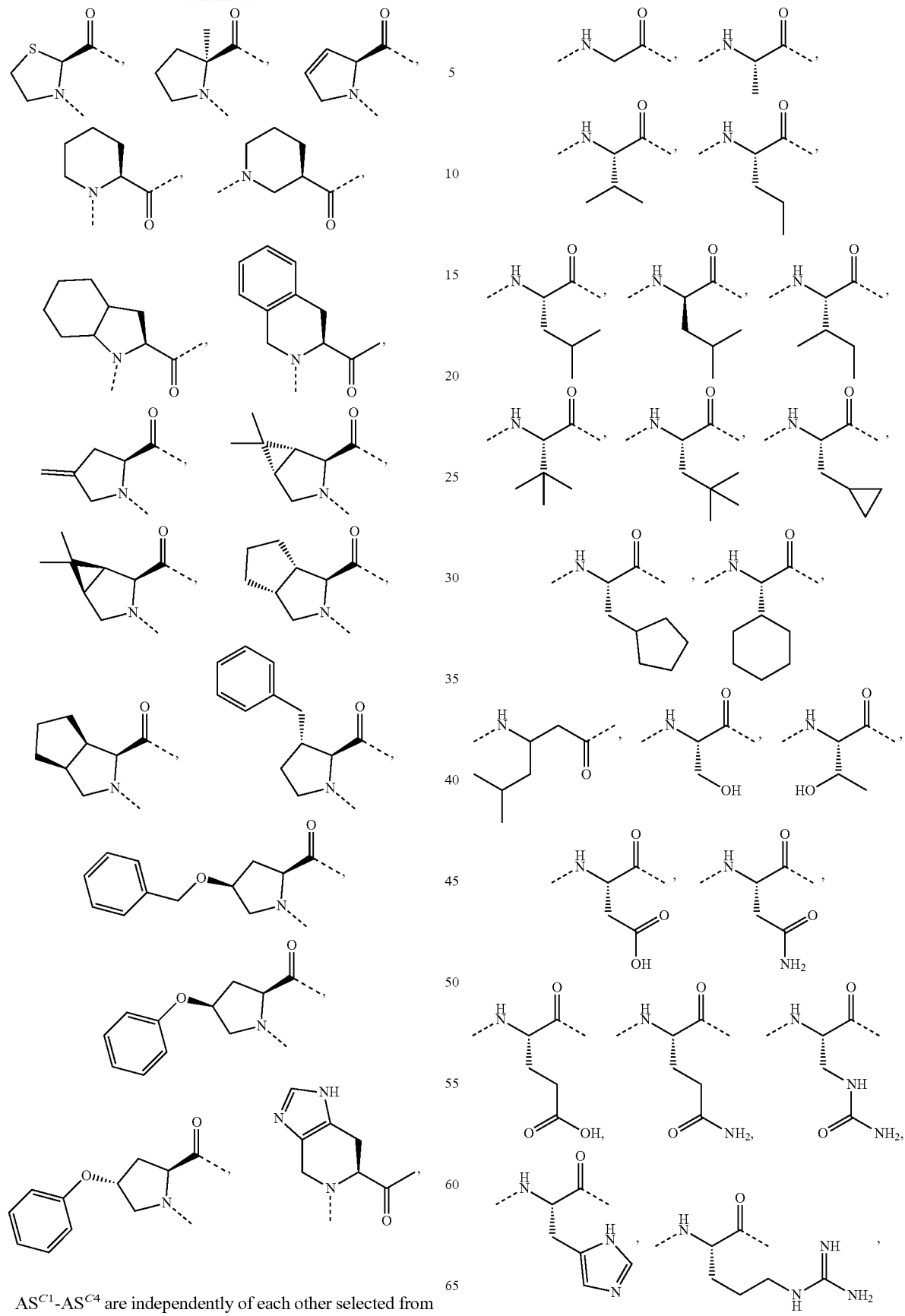
AS$^{C1}$-AS$^{C4}$ are independently of each other selected from the group consisting of:

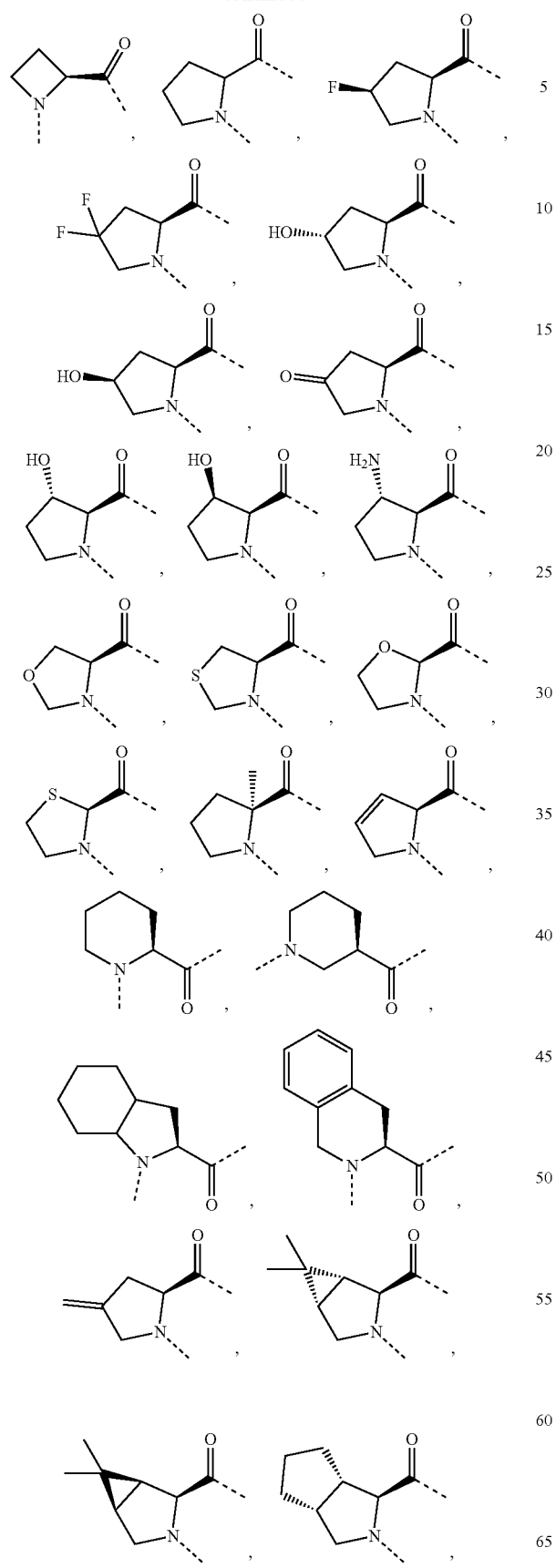
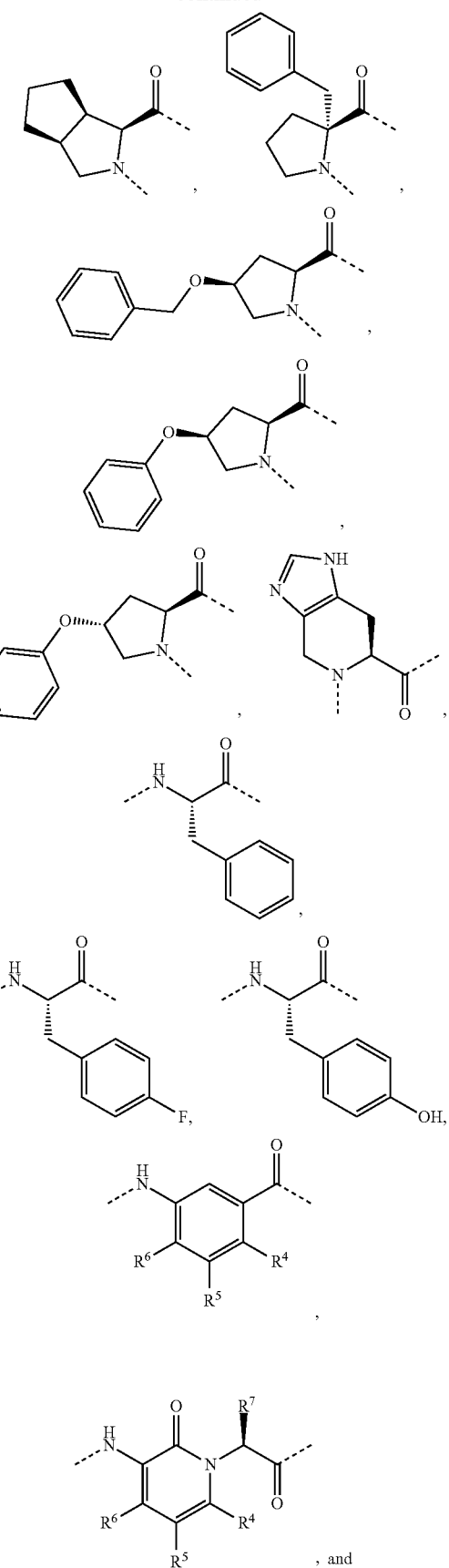
, and

235

-continued

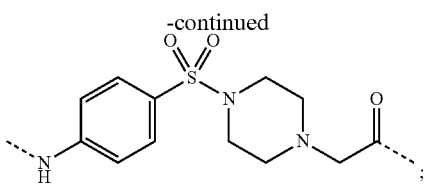

$E^C$ is selected from C terminal groups consisting of: —OR$^8$, —NR$^9$R$^{10}$, —NHSO$_2$R$^{11}$, —O-L$_1$-R$^8$, —O-L$_1$-O—R$^8$, —NH-L$_1$-O—R$^8$, —NH-L$_1$-NR$^9$R$^{10}$, —NHSO$_2$-L$_1$-R$^{11}$,

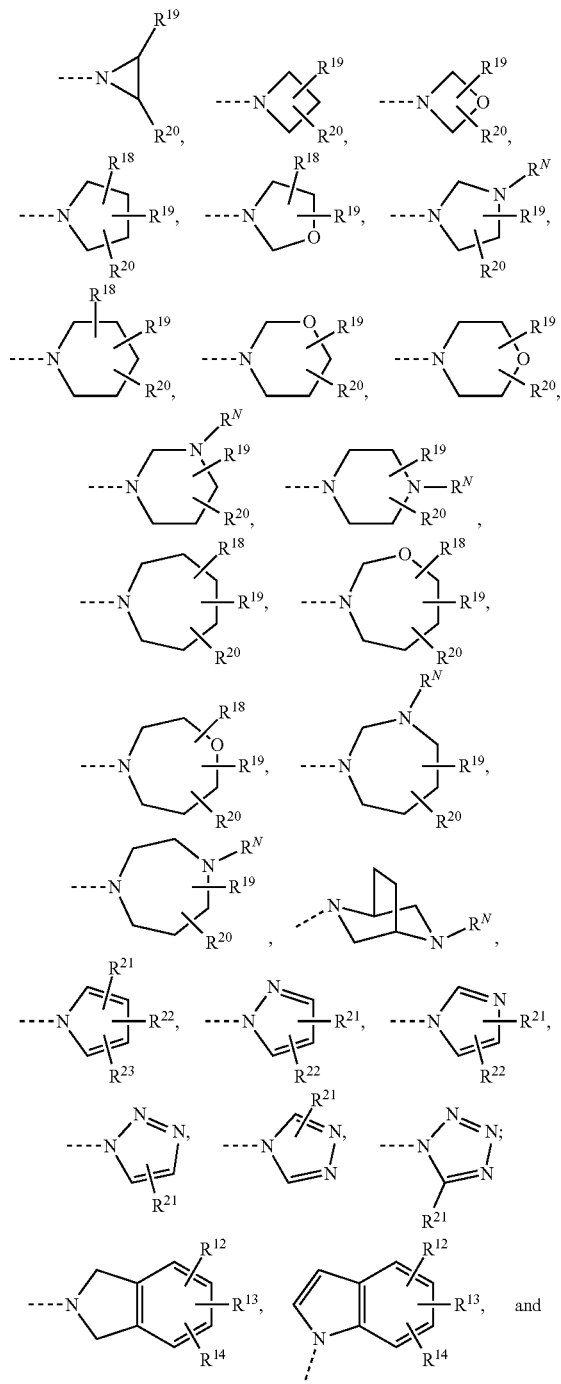

236

-continued

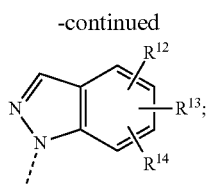

$E^N$ is selected from N terminal groups consisting of: —H, —COCF$_3$, —CH$_3$, —C$_2$H$_5$, —C$_3$H$_7$, —CH(CH$_3$)$_2$, —CH(C$_2$H$_5$)$_2$, —C$_4$H$_9$, —C$_5$H$_{11}$, —C$_6$H$_{13}$, —CH$_2$—CH(CH$_3$)$_2$, —CH$_2$—CH(C$_2$H$_5$)$_2$, —CH(CH$_3$)—C$_2$H$_5$, —C(CH$_3$)$_3$, —CH$_2$—C(CH$_3$)$_3$, -cyclo-C$_3$H$_5$, -cyclo-C$_4$H$_7$, -cyclo-C$_5$H$_9$, -cyclo-C$_6$H$_{11}$, —CH$_2$-cyclo-C$_3$H$_5$, —CH$_2$-cyclo-C$_4$H$_7$, —CH$_2$-cyclo-C$_5$H$_9$, —CH$_2$-cyclo-C$_6$H$_{11}$, -Ph, —CH$_2$-Ph, —CH$_2$F, —CHF$_2$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$CH$_2$Br, —CH$_2$—CH$_2$I, —CH$_2$—CH═CH$_2$, —CH$_2$—C≡CH, —CHO, —COCH$_3$, —COC$_2$H$_5$, —COC$_3$H$_7$, —COCH(CH$_3$)$_2$, —COCH(C$_2$H$_5$)$_2$, —COC$_4$H$_9$, —COC$_5$H$_{11}$, —COC$_6$H$_{13}$, —COCH$_2$—CH(CH$_3$)$_2$, —COCH$_2$—CH(C$_2$H$_5$)$_2$, —COCH(CH$_3$)—C$_2$H$_5$, —COC(CH$_3$)$_3$, —COCH$_2$—C(CH$_3$)$_3$, —CO-cyclo-C$_3$H$_5$, —CO-cyclo-C$_4$H$_7$, —CO-cyclo-C$_5$H$_9$, —CO-cyclo-C$_6$H$_{11}$, —COCH$_2$-cyclo-C$_3$H$_5$, —COCH$_2$-cyclo-C$_4$H$_7$, —COCH$_2$-cyclo-C$_5$H$_9$, —COCH$_2$-cyclo-C$_6$H$_{11}$, —COPh, —COCH$_2$-Ph, —COOCH$_3$, —COOC$_2$H$_5$, —COOC$_3$H$_7$, —COOCH(CH$_3$)$_2$, —COOCH(C$_2$H$_5$)$_2$, —COOC$_4$H$_9$, —COOC$_5$H$_{11}$, —COOC$_6$H$_{13}$, —COOCH$_2$—CH(CH$_3$)$_2$, —COOCH$_2$—CH(C$_2$H$_5$)$_2$, —COOCH(CH$_3$)—C$_2$H$_5$, —COOC(CH$_3$)$_3$, —COOCH$_2$—C(CH$_3$)$_3$, —COO-cyclo-C$_3$H$_5$, —COO-cyclo-C$_4$H$_7$, —COO-cyclo-C$_5$H$_9$, —COO-cyclo-C$_6$H$_{11}$, —COOCH$_2$-cyclo-C$_3$H$_5$, —COOCH$_2$-cyclo-C$_4$H$_7$, —COOCH$_2$-cyclo-C$_5$H$_9$, —COOCH$_2$-cyclo-C$_6$H$_{11}$, —COOPh, —COOCH$_2$-Ph,

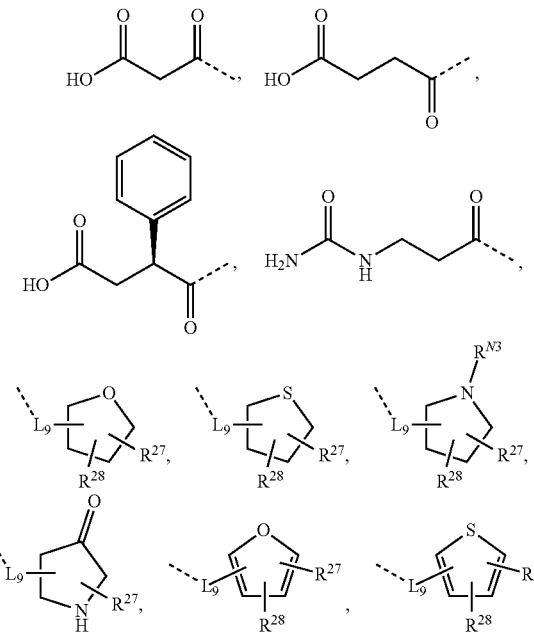

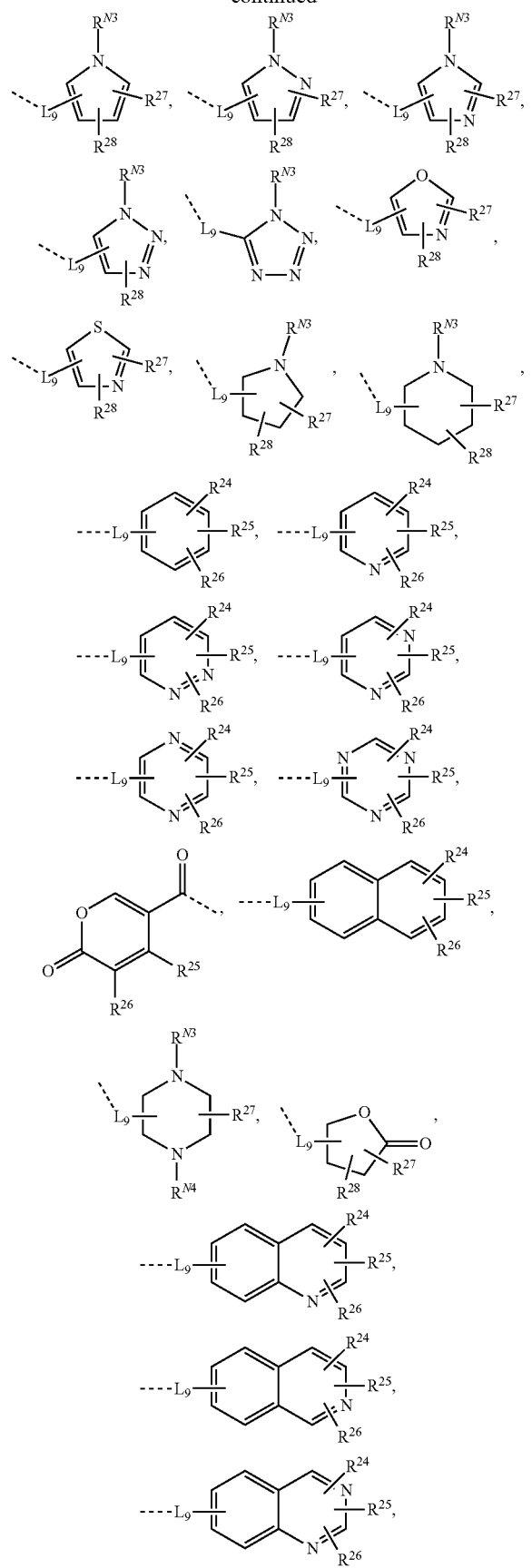

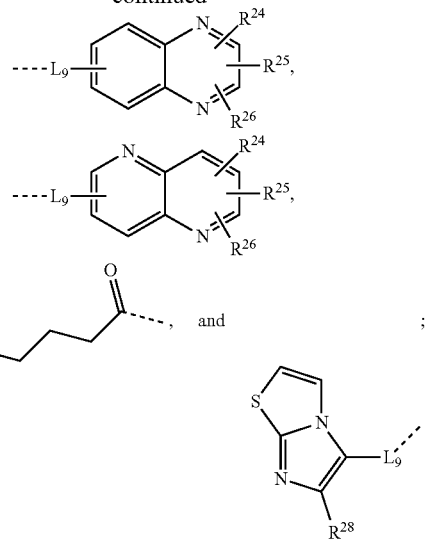

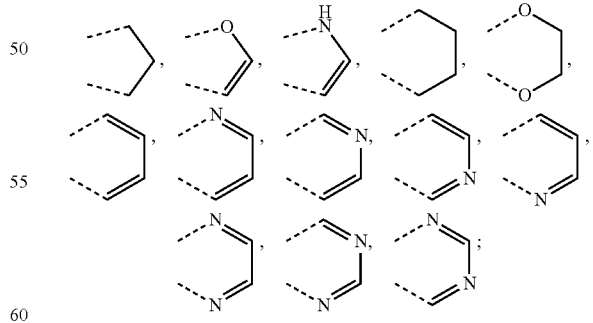

with proviso that when $Z^N$ is $E^N$ and $Z^C$ is $E^C$, then $E^C$ is not —$OR^8$ and/or $E^N$ is not —H, $R^4$, $R^5$ and $R^6$ represent independently of each other: —H, —F, —Cl, —Br, —I, —$CH_3$, —$CH_2CH_3$, —$CH(CH_3)_2$, -cyclo-$C_3H_5$, —$OCH_3$, —$OCH_2CH_3$, —$OCH(CH_3)_2$, —O-cyclo-$C_3H_5$, —$CF_3$, —$CF_2CF_3$, —$OCHF_2$, —$OCF_3$, —$OCF_2CF_3$, —OH, —CN, —CHO, —$COCH_3$, —$COCH_2CH_3$, —$COCH(CH_3)_2$, —$COCH_2F$, —$COCH_2Cl$, —$COCF_3$, —$COCCl_3$, —$CO_2H$, —$CO_2H$, —$CO_2Me$, —$CO_2CH_2CH_3$, —$CO_2CH(CH_3)_2$, —$OCOCH_3$, —$OCOCH_2CH_3$, —$OCOCH(CH_3)_2$, —$OCOCF_3$, —$OCOCCl_3$, —$NH_2$, —$NHCH_3$, —$N(CH_3)_2$, —$NHCH_2CH_3$, —NHCH$(CH_3)_2$, —$N(CH_2CH_3)_2$, —NH-cyclo-$C_3H_5$, —$NHCOCH_3$, —$NHCOCF_3$, —$NHSO_2CH_3$, —$NHSO_2CF_3$, —$SCH_3$, —$SCH_2CH_3$, —$SCH(CH_3)_2$, —S-cyclo-$C_3H_5$, —$SOCH_3$, —$SOCF_3$, —$SO_2CH_3$, —$SO_2CF_3$, —$SO_2NH_2$, —$SO_2NHCH_3$, —$SO_2N(CH_3)_2$, —$SO_2NHCH_2CH_3$, —$SO_2NHCH(CH_3)_2$, —$SO_2NH$-cyclo-$C_3H_5$, —$SO_2N(CH_2CH_3)_2$, or $R^4$ and $R^5$ or $R^5$ and $R^6$ form together the following five or six rings:

$R^7$ represents —H, —$CH_2CO_2H$, —$CH_2CH_2CO_2H$, —$CH_2CH_2CH_2CO_2H$, —$CH_2CONH_2$, —$CH_2CH_2CONH_2$, or —$CH_2NHCONH_2$;

$R^8$, $R^9$, $R^{10}$ and $R^{11}$ represent independently of each other: —H, —$CH_3$, —$CH_2CH_3$, —$CH_2CH_2CH_3$, —CH$(CH_3)_2$, —$CH(C_2H_5)_2$, —$CH_2CH(CH_3)_2$, —$CH_2$—CH $(C_2H_5)_2$, $-C_4H_9$, $-C_5H_{11}$, $-C_6H_{13}$, $-CH(CH_3)-$
$C_2H_5$, $-C(CH_3)_3$, $-CH_2-C(CH_3)_3$,

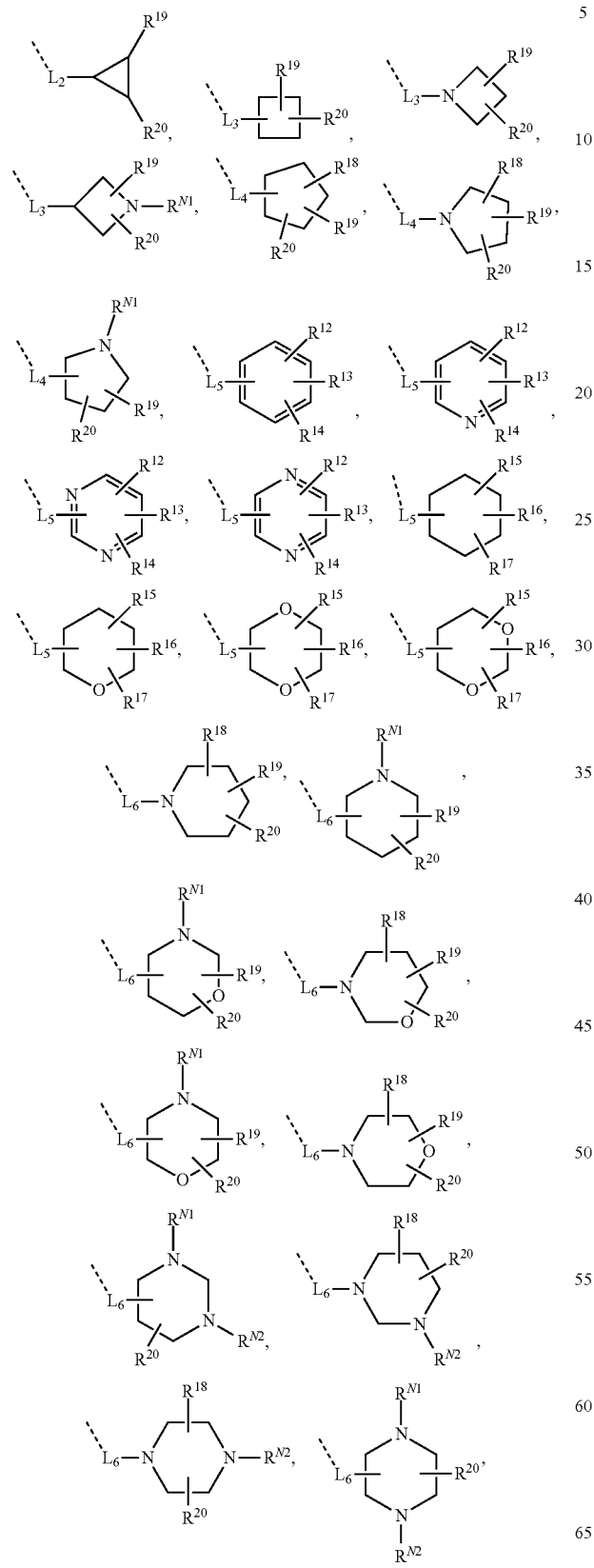

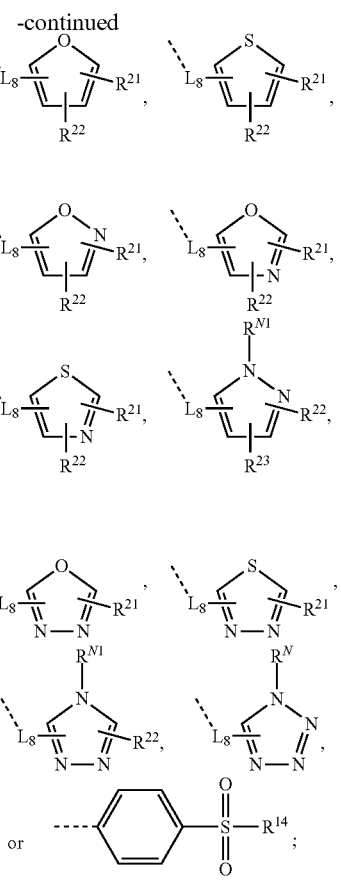

$R^{12}$-$R^{29}$ represents independently of each other —H, —F, —Cl, —Br, —I, —OH, —CN, —NO$_2$, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, -cyclo-C$_3$H$_5$, —CH$_2$-cyclo-C$_3$H$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —OCH$_3$, —OC$_2$H$_5$, —OC$_3$H$_7$, —OCH(CH$_3$)$_2$, —OC(CH$_3$)$_3$, —OC$_4$H$_9$, —OCHF$_2$, —OCF$_3$, —OCH$_2$CF$_3$, —OC$_2$F$_5$, —OCH$_2$OCH$_3$, —O-cyclo-C$_3$H$_5$, —OCH$_2$-cyclo-C$_3$H$_5$, —O—C$_2$H$_4$-cyclo-C$_3$H$_5$, —CHO, —COCH$_3$, —COCF$_3$, —COC$_2$H$_5$, —COC$_3$H$_7$, —COCH(CH$_3$)$_2$, —COC(CH$_3$)$_3$, —COOH, —COOCH$_3$, —COOC$_2$H$_5$, —COOC$_3$H$_7$, —COOCH(CH$_3$)$_2$, —COOC(CH$_3$)$_3$, —OOC—CH$_3$, —OOC—CF$_3$, —OOC—C$_2$H$_5$, —OOC—C$_3$H$_7$, —OOC—CH(CH$_3$)$_2$, —OOC—C(CH$_3$)$_3$, —NH$_2$, —NHCH$_3$, —NHC$_2$H$_5$, —NHC$_3$H$_7$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N[CH(CH$_3$)$_2$]$_2$, —N[C(CH$_3$)$_3$]$_2$, —NHCOCH$_3$, —NHCOCF$_3$, —NHCOC$_2$H$_5$, —NHCOC$_3$H$_7$, —NHCOCH(CH$_3$)$_2$, —NHCOC(CH$_3$)$_3$, —CONH$_2$, —CONHCH$_3$, —CONHC$_2$H$_5$, —CONHC$_3$H$_7$, —CONHCH(CH$_3$)$_2$, —CONH-cyclo-C$_3$H$_5$, —CONHC(CH$_3$)$_3$, —CON(CH$_3$)$_2$, —CON(C$_2$H$_5$)$_2$, —CON(C$_3$H$_7$)$_2$, —CON[CH(CH$_3$)$_2$]$_2$, —CON[C(CH$_3$)$_3$]$_2$, —SO$_2$NH$_2$, —SO$_2$NHCH$_3$, —SO$_2$NHC$_2$H$_5$, —SO$_2$NHC$_3$H$_7$, —SO$_2$NHCH(CH$_3$)$_2$, —SO$_2$NH-cyclo-C$_3$H$_5$, —SO$_2$NHC(CH$_3$)$_3$, —SO$_2$N(CH$_3$)$_2$, —SO$_2$N(C$_2$H$_5$)$_2$, —SO$_2$N(C$_3$H$_7$)$_2$, —SO$_2$N[CH(CH$_3$)$_2$]$_2$, —SO$_2$N[C (CH$_3$)$_3$]$_2$, —NHSO$_2$CH$_3$, —NHSO$_2$CF$_3$, —NHSO$_2$C$_2$H$_5$, —NHSO$_2$C$_3$H$_7$, —NHSO$_2$CH(CH$_3$)$_2$, —NHSO$_2$C(CH$_3$)$_3$, —CH═CH$_2$, —CH$_2$—CH═CH$_2$, —C(CH$_3$)═CH$_2$, —CH═CH—CH$_3$, —C≡CH, —C≡C—CH$_3$, —CH$_2$—C≡CH, -Ph, —O-Ph, or —O—CH$_2$-Ph,

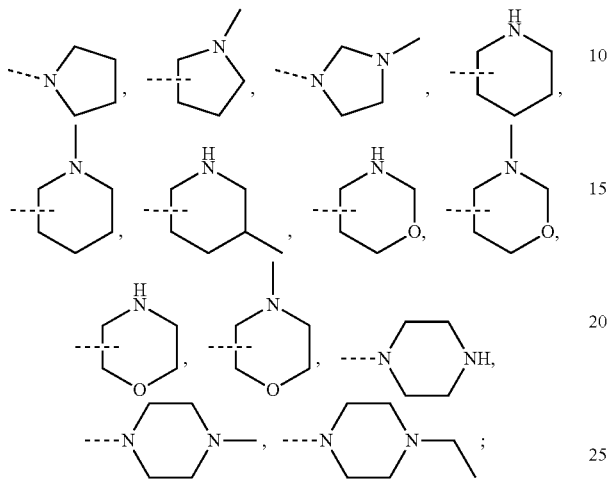

or R$^{12}$ and R$^{13}$, R$^{13}$ and R$^{14}$, R$^{24}$ and R$^{25}$, R$^{25}$ and R$^{26}$, R$^{27}$ and R$^{28}$, R$^{28}$ and R$^{29}$ can form together the following five or six rings, when R$^{12}$-R$^{14}$, R$^{24}$-R$^{29}$ are substituted at six-membered ring;

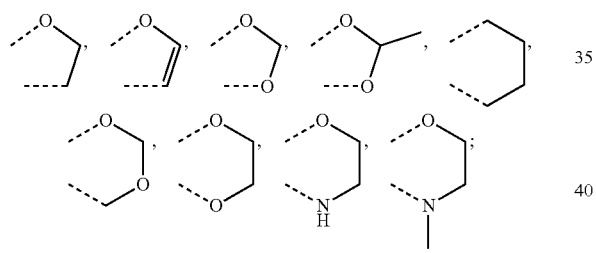

R$^N$, represents independently of each other —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, -cyclo-C$_3$H$_5$, —CH$_2$-cyclo-C$_3$H$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —CH$_2$—CH═CH$_2$, —CH$_2$—C≡CH, —CHO, —COCH$_3$, —COC$_2$H$_5$, —COC$_3$H$_7$, —COCH(CH$_3$)$_2$, —COC(CH$_3$)$_3$, —COOCH$_3$, —COOC$_2$H$_5$, —COOC$_3$H$_7$, —COOCH(CH$_3$)$_2$, —COOC(CH$_3$)$_3$,

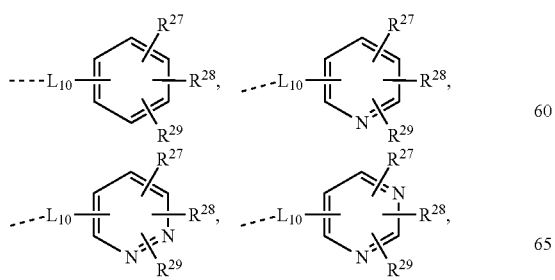

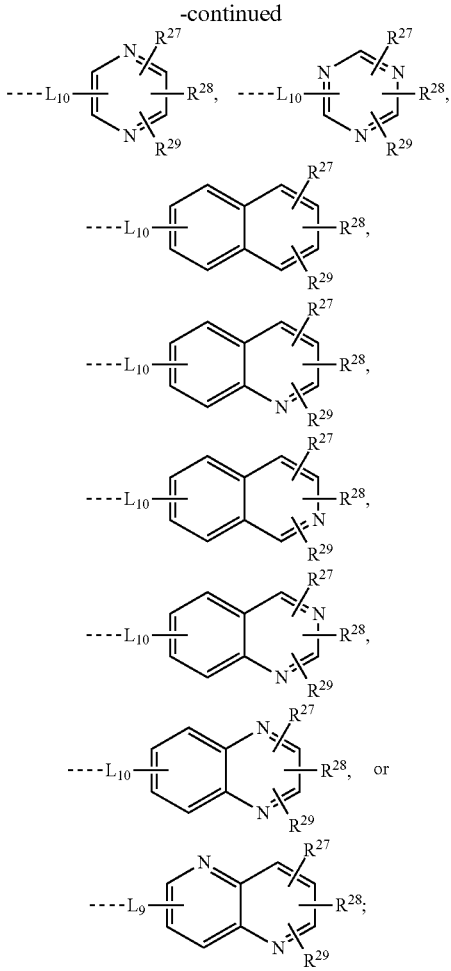

R$^{N1}$-R$^{N4}$ represent independently of each other —H, —CH$_3$, —C$_2$H$_5$, —C$_3$H$_7$, —CH(CH$_3$)$_2$, —C$_4$H$_9$, —CH$_2$—CH(CH$_3$)$_2$, —CH(CH$_3$)—C$_2$H$_5$, —C(CH$_3$)$_3$, -cyclo-C$_3$H$_5$, —CH$_2$-cyclo-C$_3$H$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$Cl, —CH$_2$—CH$_2$Br, —CH$_2$—CH$_2$I, —CH$_2$—CH═CH$_2$, —CH$_2$—C≡CH, —CH$_2$Ph, —CHO, —COCH$_3$, —COC$_2$H$_5$, —COC$_3$H$_7$, —COCH(CH$_3$)$_2$, —COC(CH$_3$)$_3$, —COOCH$_3$, —COOC$_2$H$_5$, —COOC$_3$H$_7$, —COOCH(CH$_3$)$_2$, —COOC(CH$_3$)$_3$, or —COOCH$_2$Ph;

L$^1$-L$^8$ represent independently of each other a covalent bond, —CH$_2$—, —CH(CH$_3$)—, —CH(CH$_3$)$_2$—, —CO—, —SO—, —SO$_2$—,

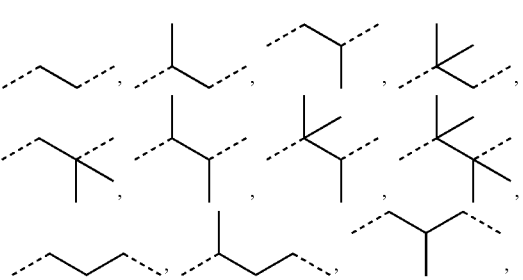

-continued

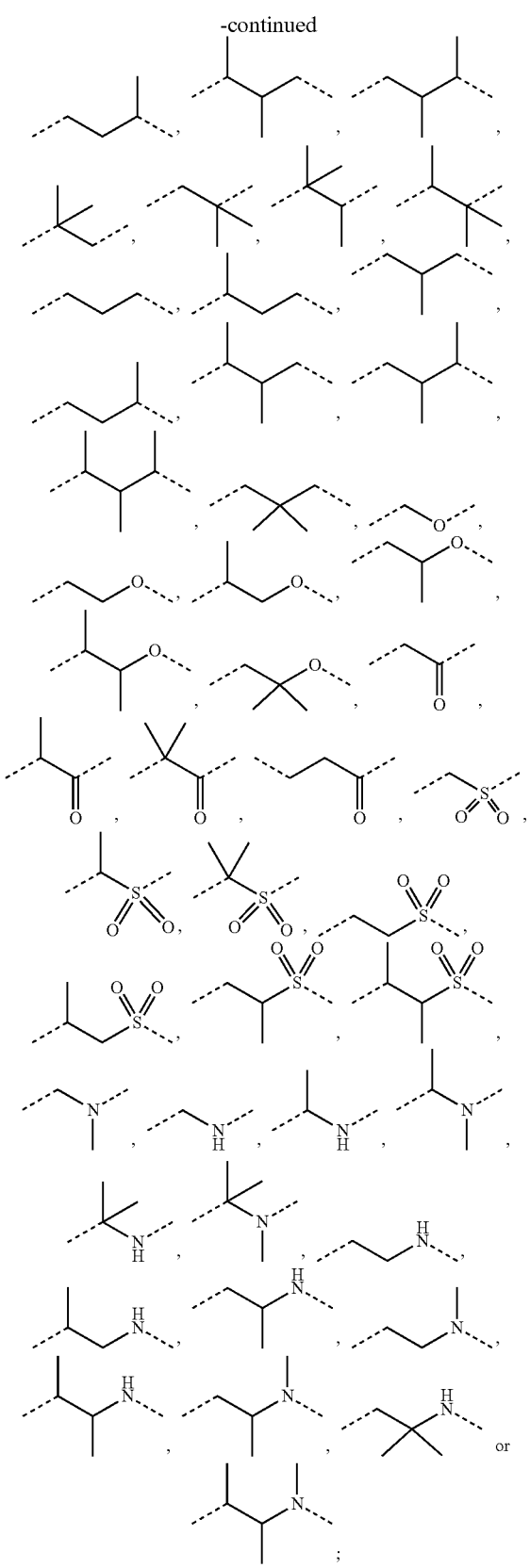

L⁹ and L¹⁰ are independently of each other: a covalent bond, —CH₂—, —CH₂CH₂—, —CO—, —CH₂CO—, —COCH₂—, —CO—CH=CH—, —COO—, —O—, CO—, —CH₂CO₂—, —CO₂CH₂—, —CONH—, —NHCO—, —CH₂CONH—, —CONHCH₂—, —CSNH—, —NHCS—, —SO₂—, —SO₂CH₂—, —SO₂NH—, or —SO₂NHCH₂—;

or diastereomer, enantiomer, mixture of diastereomers, mixture of enantiomer, racemates, solvates, hydrates, or pharmaceutically acceptable salts thereof.

2. The compound according to claim 1 having any one of the formulae (II-1)-(II-3):

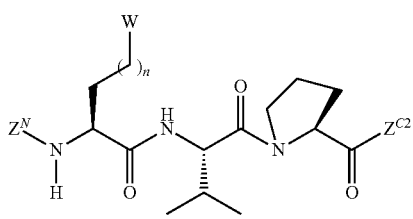

(II-1)

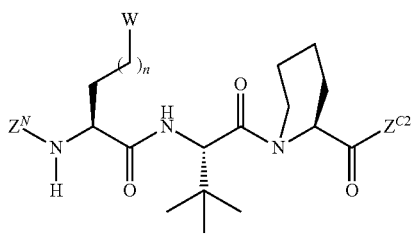

(II-2)

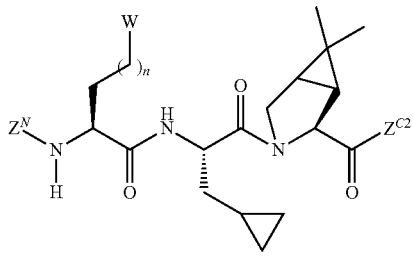

(II-3)

wherein $Z^{C2}$ represents -$E^C$, -$AS^{C3}$-$E^C$, or -$AS^{C3}$-$AS^{C4}$-$E^C$;

$Z^N$ represents $E^N$-, or $E^N$-$AS^{N1}$;

and $E^C$, $E^N$, n, $AS^{C3}$-$AS^{C4}$, $AS^{N1}$, and W have the same meanings as defined in claim 1.

3. The compound according to claim 1 having any one of the formulae (III-1)-(III-3):

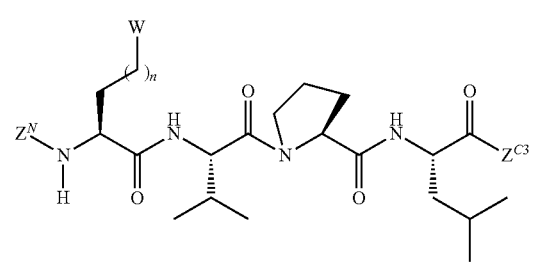

(III-1)

-continued (III-2)

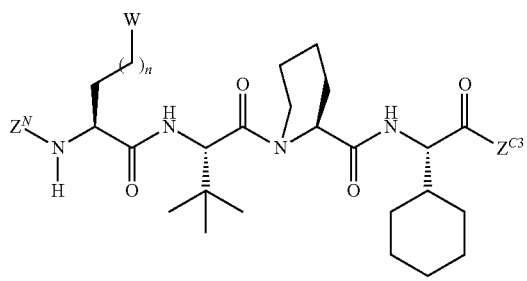

(III-3)

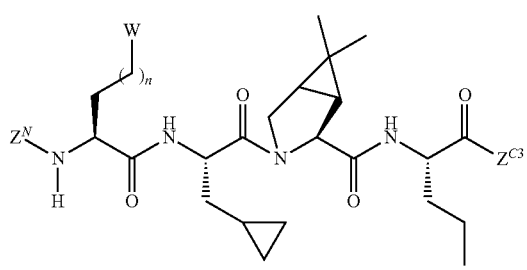

wherein $Z^{C3}$ represents -$E^C$, or -$AS^{C4}$-$E^C$;

$Z^N$ represents $E^N$-, or $E^N$-$AS^{N1}$;

and $E^C$, $E^N$, n, $AS^{C4}$, $AS^{N1}$, and W have the same meanings as defined in claim 1.

4. The compound according to claim 1 having any one of the formulae (VI-1)-(VI-3):

(VI-1)

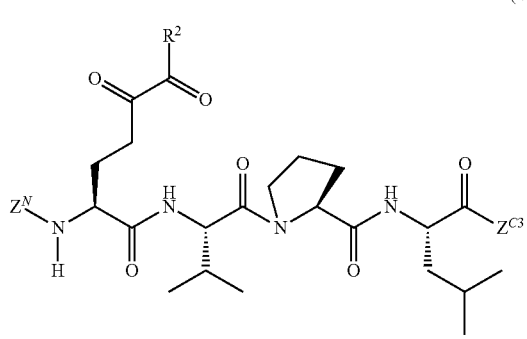

(VI-2)

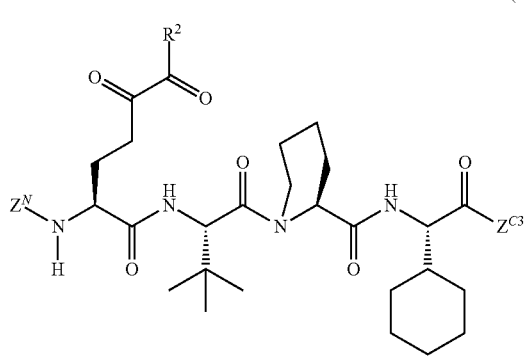

-continued (VI-3)

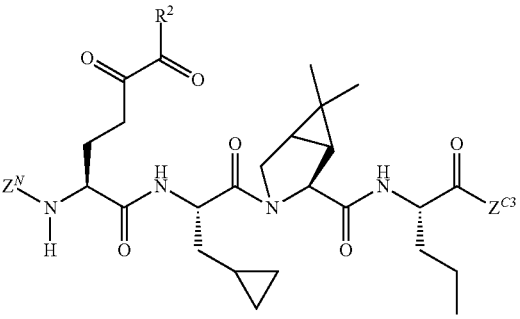

wherein $Z^N$ represents $E^N$-, or $E^N$-$AS^{N1}$-, $Z^{C3}$ represents -$E^C$, or -$AS^{C4}$-$E^C$;

$R^2$ represents —OCH$_3$, —NH$_2$, —NHCH$_3$, —NHCH$_2$CH$_3$, —NHCH$_2$CH$_2$CH$_3$, —NHCH$_2$CH$_2$CH$_2$CH$_3$, —NHCH$_2$CH$_2$CH$_2$CH$_2$CH$_3$, —NH-cyclo-C$_3$H$_5$, or —NHCH$_2$Ph; and $AS^{C4}$, $AS^{N1}$, $E^C$, and $E^N$ have the same meanings as defined in claim 1.

5. The Compound according to claim 1 having the formula (VII-4):

(VII-4)

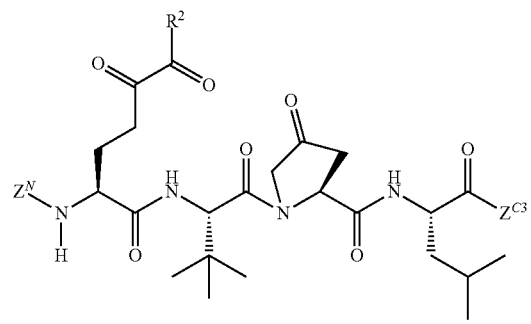

wherein $R^2$ represents —OCH$_3$, —NH$_2$, —NHCH$_3$, —NHCH$_2$CH$_3$, —NHCH$_2$CH$_2$CH$_3$, —NHCH$_2$CH$_2$CH$_2$CH$_3$, —NHCH$_2$CH$_2$CH$_2$CH$_2$CH$_3$, —NH-cyclo-C$_3$H$_5$, or —NHCH$_2$Ph; and $Z^N$ represents $E^N$-, $Z^{C3}$ represents -$E^C$, or -$AS^{C4}$-$E^C$;

$AS^{C4}$, $E^C$, and $E^N$ have the same meanings as defined in claim 1.

6. The compounds according to claim 1 of the formula (IX):

(IX)

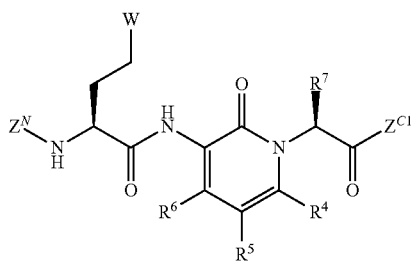

wherein $Z^{C1}$ represents -$E^C$, or -$AS^{C2}$-$E^C$;

$AS^{C2}$, $E^C$, $R^4$-$R^7$, W and $Z^N$ have the same meaning as defined in claim 1.

7. The compound according to claim 6 having the formula (XI-3):

(XI-3)

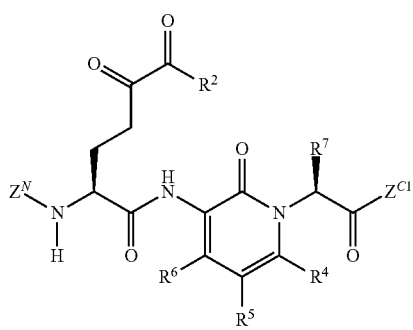

wherein $Z^{C1}$ represents -$E^C$;

$Z^N$ represents $E^N$- or $E^N$-$AS^{N1}$;

$R^2$ represents —$CH_3$, —$CH_2CH_3$, —$CH(CH_3)_2$, -cyclo-$C_3H_5$, -Ph, —$OCH_3$, —$OCH_2CH_3$, —$NH_2$, —$NHCH_3$, —$N(CH_3)_2$, —NH-cyclo-$C_3H_5$, —NH—$CH_2$Ph, —$NC(CH_3)_3$, —NH—$C_5H_{11}$, —$NHCH_2OCH_3$, —$NHCH_2CH_2OCH_3$, —$NHCH_2CO_2OCH_3$, —NH—$OCH_2$-cyclo-$C_5H_9$; and $R^4$, $R^5$ and $R^6$ represent independently of each other: —H, —F, —Cl, —Br, —I, —$CH_3$, —$CH_2CH_3$, —$CH(CH_3)_2$, -cyclo-$C_3H_5$, —$OCH_3$, —$CF_3$, —$OCF_3$, —OH, —CN, —$COCH_3$, —$CO_2$H, —$CO_2$Me, —$OCOCH_3$, —$NH_2$, —$NHCH_3$, —$N(CH_3)_2$, —$NHCOCH_3$, —$NHCOCF_3$, —$NHSO_2CH_3$, —$NHSO_2CF_3$, —$SCH_3$, —$SO_2CH_3$, —$SO_2CF_3$, —$SO_2NH_2$, —$SO_2NHCH_3$, or —$SO_2N(CH_3)_2$, $R^7$ represents —H or —$CH_2CH_2CO_2H$; and $AS^{N1}$, $E^C$, and $E^N$ have the same meanings as defined in claim 1.

8. The compound according to claim 1 having the formula (XIII):

(XIII)

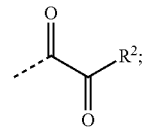

wherein n is an integer selected from 1, 2 or 3;

W represents

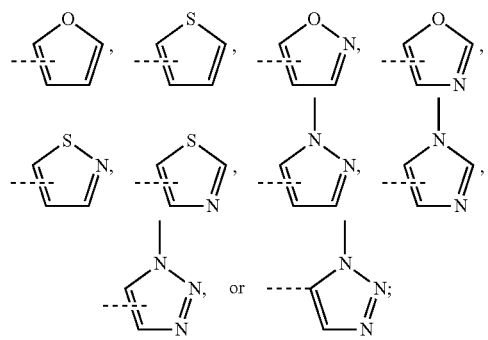

$R^2$ represents —$R^1$, —$OR^1$, —$NH_2$, —$NH(R^1)$, —$N(R^1)(R^3)$;

$R^1$ and $R^3$ represent independently of each other —$CH_3$, —$CH_2CH_3$, —$CH_2CH_2CH_3$, —$CH(CH_3)_2$, —$CH_2CH_2CH_2CH_3$, —$CH_2CH_2CH_2CH_2CH_3$, —$CH_2CH_2CH_2CH_2CH_2CH_3$, —$CH_2CH_2CH_2CH_2CH_2CH_2CH_3$, —$CH_2CH(CH_3)_2$, —$CH(CH_3)CH_2CH_3$, —$CH(C_2H_5)_2$, —$CH_2CH(C_2H_5)_2$, —$C(CH_3)_3$, —$CH_2$—$C(CH_3)_3$, -cyclo -$C_3H_5$, -cyclo-$C_4H_7$, -cyclo-$C_5H_9$, -cyclo-$C_6H_{11}$, —$CH_2$-cyclo-$C_3H_5$, —$CH_2$-cyclo-$C_4H_7$, —$CH_2$-cyclo-$C_5H_9$, —$CH_2$-cyclo-$C_6H_{11}$, -Ph, —$CH_2$-Ph, —$CH_2OCH_3$, —$CH_2OCH_2CH_3$, —$CH_2CH_2OCH_3$, —$CH_2CH_2OCH_2CH_3$, —$CH_2CO_2CH_3$, —$CH_2CO_2CH_2CH_3$, —$CH_2CH_2NHCH_3$, —$CH_2CH_2N(CH_3)_2$, —$CH_2S(O)_2$-(4-methyl-phenyl),

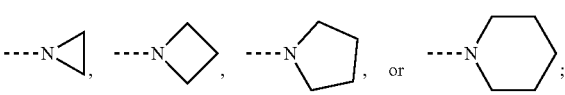

or

—$N(R^1)(R^3)$ forms

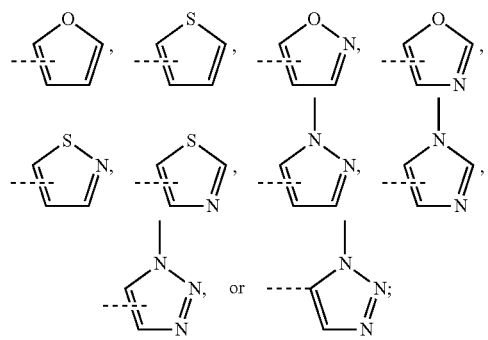

$R^{19}$-$R^{20}$ represents independently of each other —H, —F, —Cl, —Br, —I, —OH, —CN, —$NO_2$, —$CH_3$, —$C_2H_5$, —$C_3H_7$, —$CH(CH_3)_2$, —$C_4H_9$, —$CH_2$—CH$(CH_3)_2$, —$CH(CH_3)$—$C_2H_5$, —$C(CH_3)_3$, -cyclo-$C_3H_5$, —$CH_2$-cyclo-$C_3H_5$, —$CH_2F$, —$CHF_2$, —$CF_3$, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, —OCH₃, —OC₂H₅, —OC₃H₇, —OCH(CH₃)₂, —OC(CH₃)₃, —OC₄H₉, —OCHF₂, —OCF₃, —OCH₂CF₃, —OC₂F₅, —OCH₂OCH₃, —O-cyclo-C₃H₅, —OCH₂-cyclo-C₃H₅, —O—C₂H₄-cyclo-C₃H₅, —CHO, —COCH₃, —COCF₃, —COC₂H₅, —COC₃H₇, —COCH(CH₃)₂, —COC(CH₃)₃, —COOH, —COOCH₃, —COOC₂H₅, —COOC₃H₇, —COOCH(CH₃)₂, —COOC(CH₃)₃, —OOC—CH₃, —OOC—CF₃, —OOC—C₂H₅, —OOC—C₃H₇, —CCC—CH(CH₃)₂, —OOC—C(CH₃)₃, —NH₂, —NHCH₃, —NHC₂H₅, —NHC₃H₇, —NHCH(CH₃)₂, —NHC(CH₃)₃, —N(CH₃)₂, —N(C₂H₅)₂, —N(C₃H₇)₂, —N[CH(CH₃)₂]₂, —N[C(CH₃)₃]₂, —NHCOCH₃, —NHCOCF₃, —NHCOC₂H₅, —NHCOC₃H₇, —NHCOCH(CH₃)₂, —NHCOC(CH₃)₃, —CONH₂, —CONHCH₃, —CONHC₂H₅, —CONHC₃H₇, —CONHCH(CH₃)₂, —CONH-cyclo-C₃H₅, —CONHC(CH₃)₃, —CON(CH₃)₂, —CON(C₂H₅)₂, —CON(C₃H₇)₂, —CON[CH(CH₃)₂]₂, —CON[C(CH₃)₃]₂, —SO₂NH₂, —SO₂NHCH₃, —SO₂NHC₂H₅, —SO₂NHC₃H₇, —SO₂NHCH(CH₃)₂, —SO₂NH-cyclo-C₃H₅, —SO₂NHC(CH₃)₃, —SO₂N(CH₃)₂, —SO₂N(C₂H₅)₂, —SO₂N(C₃H₇)₂, —SO₂N[CH(CH₃)₂]₂, —SO₂N[C(CH₃)₃]₂, —NHSO₂CH₃, —NHSO₂CF₃, —NHSO₂C₂H₅, —NHSO₂C₃H₇, —NHSO₂CH(CH₃)₂, —NHSO₂C(CH₃)₃, —CH=CH₂, —CH₂—CH=CH₂, —C(CH₃)=CH₂, —CH=CH—CH₃, —C≡CH, —C≡C—CH₃, and —CH₂—C≡CH;

$E^N$ is selected from N terminal groups consisting of:
—H, —COCH₃, —COCF₃, —CH₃, —C₂H₅, —C₃H₇, —CH(CH₃)₂, —C₄H₉, —CH₂—CH(CH₃)₂, —CH(CH₃)—C₂H₅, —C(CH₃)₃, -cyclo-C₃H₅, —CH₂-cyclo-C₃H₅, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, —CH₂—CH=CH₂, —CH₂—C≡CH, —CHO, —COCH₃, —COC₂H₅, —COC₃H₇, —COCH(CH₃)₂, —COC(CH₃)₃, —COOCH₃, —COOC₂H₅, —COOC₃H₇, —COOCH(CH₃)₂, —COOC(CH₃)₃,

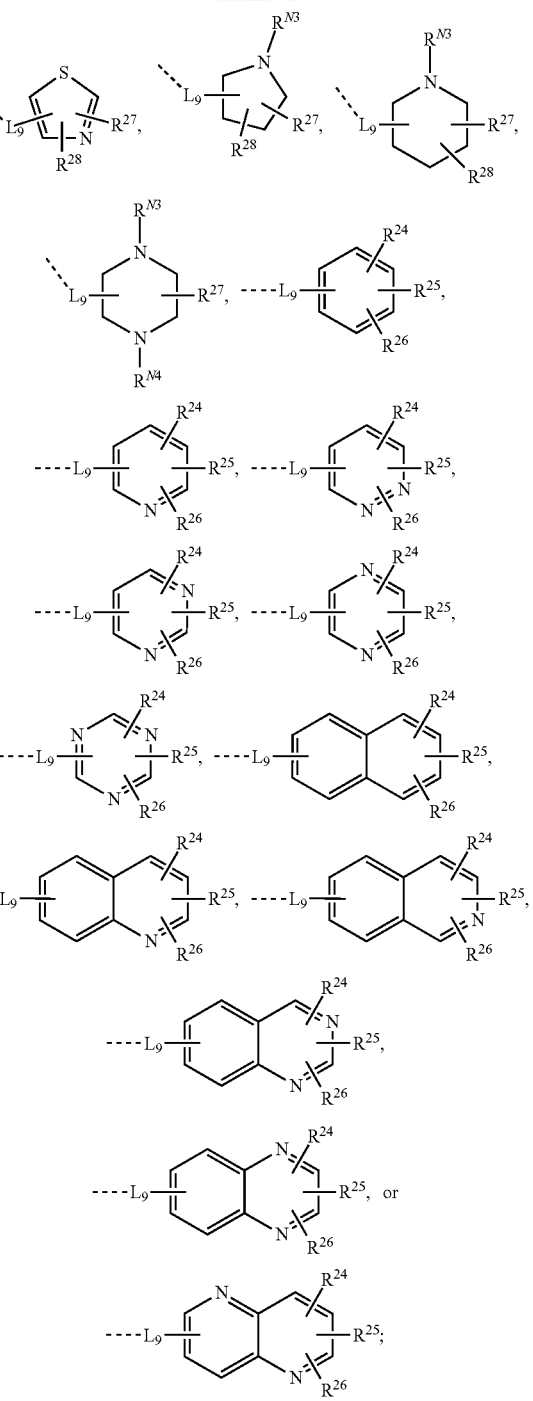

$R^N$, represents independently of each other —H, —CH₃, —C₂H₅, —C₃H₇, —CH(CH₃)₂, —C₄H₉, —CH₂—CH(CH₃)₂, —CH(CH₃)—C₂H₅, —C(CH₃)₃, -cyclo-C₃H₅, —CH₂-cyclo-C₃H₅, —CH₂F, —CHF₂, —CF₃, —CH₂Cl, —CH₂Br, —CH₂I, —CH₂—CH₂F, —CH₂—CHF₂, —CH₂—CF₃, —CH₂—CH₂Cl, —CH₂—CH₂Br, —CH₂—CH₂I, —CH₂—CH=CH₂, —CH₂—C≡CH, —CHO, —COCH₃, —OOC₂H₅, —OOC₃H₇, —COCH(CH₃)₂, —COC(CH₃)₃, —COOCH₃, —COOC₂H₅, —COOC₃H₇, —COOCH(CH₃)₂, —COOC(CH₃)₃,

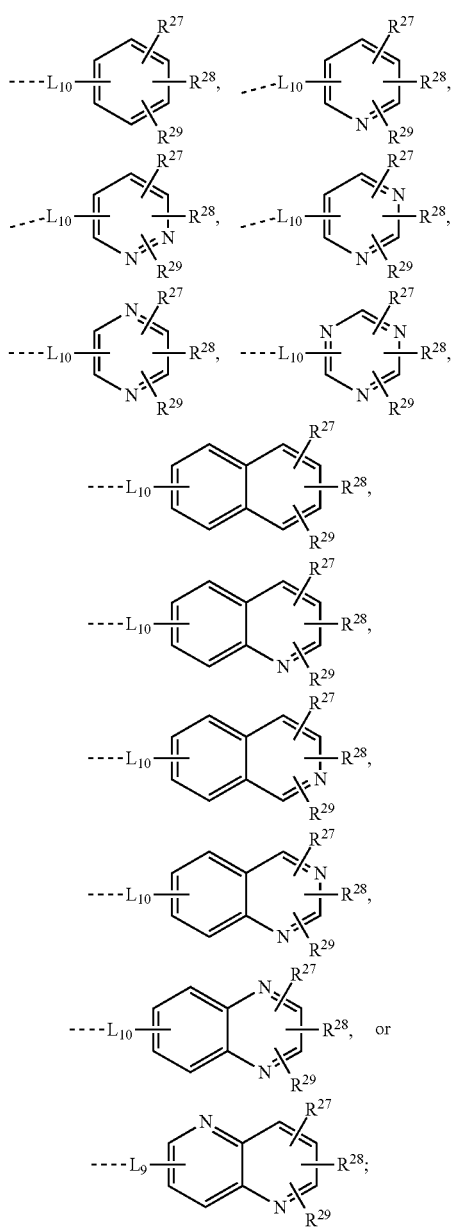

$R^{27}$-$R^{29}$ represents independently of each other —H, —F, —Cl, —Br, —I, —OH, —CN, —NO$_2$, —CH$_3$, —C$_2$H$_5$, —C$_3$H$_7$, —CH(CH$_3$)$_2$, —C$_4$H$_9$, —CH$_2$—CH (CH$_3$)$_2$, —CH(CH$_3$)—C$_2$H$_5$, —C(CH$_3$)$_3$, -cyclo-C$_3$H$_5$, —CH$_2$-cyclo-C$_3$H$_5$, —CH$_2$F, —CHF$_2$, —CF$_3$, —CH$_2$Cl, —CH$_2$Br, —CH$_2$I, —CH$_2$—CH$_2$F, —CH$_2$—CHF$_2$, —CH$_2$—CF$_3$, —CH$_2$—CH$_2$O, —CH$_2$—CH$_2$Br, —CH$_2$—CH$_2$I, —OCH$_3$, —OC$_2$H$_5$, —OC$_3$H$_7$, —OCH(CH$_3$)$_2$, —OC(CH$_3$)$_3$, —OC$_4$H$_9$, —OCHF$_2$, —OCF$_3$, —OCH$_2$CF$_3$, —OC$_2$F$_5$, —OCH$_2$OCH$_3$, —O-cyclo-C$_3$H$_5$, —OCH$_2$-cyclo-C$_3$H$_5$, —O—C$_2$H$_4$-cyclo-C$_3$H$_5$, —CHO, —COCH$_3$, —COCF$_3$, —COC$_2$H$_5$, —COC$_3$H$_7$, —COCH(CH$_3$)$_2$, —COC(CH$_3$)$_3$, —COOH, —COOCH$_3$, —COOC$_2$H$_5$, —COOC$_3$H$_7$, —COOCH(CH$_3$)$_2$, —COOC(CH$_3$)$_3$, —OOC—CH$_3$, —OOC—CF$_3$, —OOC—C$_2$H$_5$, —OOC—C$_3$H$_7$, —OOC—CH(CH$_3$)$_2$, —OOC—C(CH$_3$)$_3$, —NH$_2$, —NHCH$_3$, —NHC$_2$H$_5$, —NHC$_3$H$_7$, —NHCH(CH$_3$)$_2$, —NHC(CH$_3$)$_3$, —N(CH$_3$)$_2$, —N(C$_2$H$_5$)$_2$, —N(C$_3$H$_7$)$_2$, —N[CH(CH$_3$)$_2$]$_2$, —N[C(CH$_3$)$_3$]$_2$, —NHCOCH$_3$, —NHCOCF$_3$, —NHCOC$_2$H$_5$, —NHCOC$_3$H$_7$, —NHCOCH(CH$_3$)$_2$, —NHCOC(CH$_3$)$_3$, —CONH$_2$, —CONHCH$_3$, —CONHC$_2$H$_5$, —CONHC$_3$H$_7$, —CONHCH(CH$_3$)$_2$, —CONH-cyclo-C$_3$H$_5$, —CONHC(CH$_3$)$_3$, —CON(CH$_3$)$_2$, —CON(C$_2$H$_5$)$_2$, —CON(C$_3$H$_7$)$_2$, —CON[CH(CH$_3$)$_2$]$_2$, —CON[C(CH$_3$)$_3$]$_2$, —SO$_2$NH$_2$, —SO$_2$NHCH$_3$, —SO$_2$NHC$_2$H$_5$, —SO$_2$NHC$_3$H$_7$, —SO$_2$NHCH(CH$_3$)$_2$, —SO$_2$NH-cyclo-C$_3$H$_5$, —SO$_2$NHC(CH$_3$)$_3$, —SO$_2$N(CH$_3$)$_2$, —SO$_2$N(C$_2$H$_5$)$_2$, —SO$_2$N(C$_3$H$_7$)$_2$, —SO$_2$N[CH(CH$_3$)$_2$]$_2$, —SO$_2$N[C(CH$_3$)$_3$]$_2$, —NHSO$_2$CH$_3$, —NHSO$_2$CF$_3$, —NHSO$_2$C$_2$H$_5$, —NHSO$_2$C$_3$H$_7$, —NHSO$_2$CH(CH$_3$)$_2$, —NHSO$_2$C(CH$_3$)$_3$, —CH=CH$_2$, —CH$_2$—CH=CH$_2$, —C(CH$_3$)=CH$_2$, —CH=CH—CH$_3$, —C≡CH, —C≡C—CH$_3$, —CH$_2$C≡CH, -Ph, —O-Ph, or —O—CH$_2$-Ph,

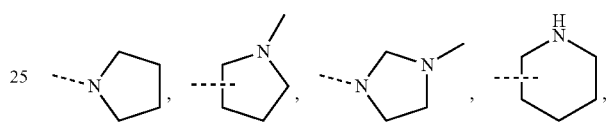

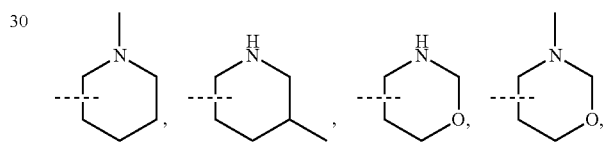

or $R^{24}$ and $R^{25}$, $R^{25}$ and $R^{26}$, $R^{27}$ and $R^{28}$, $R^{28}$ and $R^{29}$ can form together the following five or six rings, when $R^{24}$-$R^{29}$ are substituted at six-membered ring;

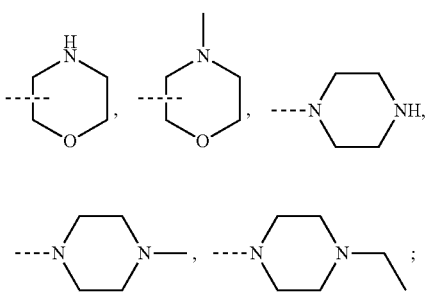

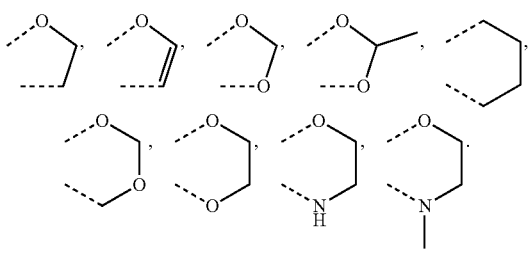

9. The compound according to claim 8 having the formula (XIV-1)

(XIV-1)

wherein n, W, $E^N$ and $R^{27}$-$R^{29}$ have the same meanings as defined claim 8.

10. The compound according to claim 1 selected from the group consisting of:
- (S)-methyl 2-((S)-1-((S)-2-((S)-2-acetamido-6-amino-5,6-dioxohexanamido)-3-methylbutanoyl)pyrrolidine-2-carboxamido)-4-methylpentanoate (E01),
- (S)-methyl 2-((S)-1-((S)-2-((S)-6-amino-2-(benzyloxycarbonylamino)-5,6-dioxo-hexanamido)-3-methylbutanoyl)pyrrolidine-2-carboxamido)-4-methylpentanoate (E02),
- (S)—N1-(1-(2-(2-ethylbutylamino)-2-oxoethyl)-2-oxo-1,2-dihydropyridin-3-yl)-2-(1-methyl-1H-imidazole-5-carboxamido)-5-oxohexanediamide (E04),
- (S)-2-(2-bromo-4-methylthiazole-5-carboxamido)-N1-(1-(2-(isopentylamino)-2-oxoethyl)-2-oxo-1,2-dihydropyridin-3-yl)-5-oxohexanediamide (E05),
- (S)-5-acetamido-6-(4-(2-chlorophenyl)piperazin-1-yl)-2,6-dioxohexanamide (E06),
- (S)-1-acetyl-N—((S)-6-amino-1-(4-(3-methylpyridin-2-yl)piperazin-1-yl)-1,5,6-trioxohexan-2-yl)pyrrolidine-2-carboxamide (E07),
- (S)—N1-((S)-1-((R)-2-((S)-2-((S)-2-amino-1-cyclohexyl-2-oxoethylamino)-1-cyclohexyl-2-oxoethylcarbamoyl)piperidin-1-yl)-3,3-dimethyl-1-oxobutan-2-yl)-2-(6-hydroxy-5-nitronicotinamido)-5-oxohexanediamide (E09),
- 3-((2S)-6-amino-1-((2S)-3-cyclopropyl-1-((1R,2S)-2-((2S)-1-((2S)-2-(1-(2,6-dimethylphenoxy)propan-2-ylcarbamoyl)-2-methylpyrrolidin-1-yl)-1-oxopentan-2-ylcarbamoyl)-6,6-dimethyl-3-azabicyclo[3.1.0]hexan-3-yl)-1-oxopropan-2-ylamino)-1,5,6-trioxonexan-2-ylcarbamoyl)-5-nitrobenzoic acid (E10),
- (S)—N1-(1-(2-(2-ethylbutylamino)-2-oxoethyl)-2-oxo-1,2-dihydropyridin-3-yl)-5-oxo-2-(pyrazine-2-carboxamido)hexanediamide (E11),
- (S)-2-benzamido-N1-(1-(2-(2-ethylbutylamino)-2-oxoethyl)-2-oxo-1,2-dihydropyridin-3-yl)-5-oxonexanediamide (E12),
- (S)—N1-(1-(2-(2-ethylbutylamino)-2-oxoethyl)-2-oxo-1,2-dihydropyridin-3-yl)-2-(2-ethyl-5-nitrobenzamido)-5-oxohexanediamide (E13),
- (S)—N1-(1-(2-(2-ethylbutylamino)-2-oxoethyl)-2-oxo-1,2-dihydropyridin-3-yl)-2-(4-methylthiazole-5-carboxamido)-5-oxohexanediamide (E14),
- (S)-2-(5-(dimethylamino)naphthalene-1-sulfonamido)-N1-(1-(2-(2-ethylbutylamino)-2-oxoethyl)-2-oxo-1,2-dihydropyridin-3-yl)-5-oxonexanediamide (E15),
- (S)—N1-(1-(2-(2-ethylbutylamino)-2-oxoethyl)-2-oxo-1,2-dihydropyridin-3-yl)-N6-methyl-2-(1-methyl-1H-imidazole-5-carboxamido)-5-oxohexanediamide (E16),
- (S)—N1-ethyl-N6-(1-(2-(2-ethylbutylamino)-2-oxoethyl)-2-oxo-1,2-dihydropyridin-3-yl)-5-(1-methyl-1H-imidazole-5-carboxamido)-2-oxonexanediamide (E17),
- (S)—N1-(1-(2-(2-ethylbutylamino)-2-oxoethyl)-2-oxo-1,2-dihydropyridin-3-yl)-2-(1-methyl-1H-imidazole-5-carboxamido)-5-oxo-N6-pentylhexanediamide (E18),
- (S)—N1-cyclopropyl-N6-(1-(2-(2-ethylbutylamino)-2-oxoethyl)-2-oxo-1,2-dihydropyridin-3-yl)-5-(1-methyl-1H-imidazole-5-carboxamido)-2-oxonexanediamide (E19),
- (S)—N1-benzyl-N6-(1-(2-(2-ethylbutylamino)-2-oxoethyl)-2-oxo-1,2-dihydropyridin-3-yl)-5-(1-methyl-1H-imidazole-5-carboxamido)-2-oxonexanediamide (E20),
- (S)—N1-tert-butyl-N6-(1-(2-(2-ethylbutylamino)-2-oxoethyl)-2-oxo-1,2-dihydropyridin-3-yl)-5-(1-methyl-1H-imidazole-5-carboxamido)-2-oxonexanediamide (E21),
- (S)-2-((S)-1-acetylpyrrolidine-2-carboxamido)-N1-(1-(2-(2-ethylbutylamino)-2-oxoethyl)-2-oxo-1,2-dihydropyridin-3-yl)-5-oxo-N6-pentylhexanediamide (E22),
- (S)-2-benzamido-N6-cyclopropyl-N1-(1-(2-(2-ethylbutylamino)-2-oxoethyl)-2-oxo-1,2-dihydropyridin-3-yl)-5-oxonexanediamide (E23),
- (S)-methyl 2-((S)-1-((S)-2-((S)-2-benzamido-6-(cyclopropylamino)-5,6-dioxonexan-amido)-3-methylbutanoyl)pyrrolidine-2-carboxamido)-4-methylpentanoate (E24),
- 4-((S)-1-((S)-1-((S)-2-((S)-2-((S)-2-amino-1-cyclonexyl-2-oxoethylamino)-1-cyclonexyl-2-oxoethylcarbamoyl)-4-oxopyrrolidin-1-yl)-3,3-dimethyl-1-oxobutan-2-ylamino)-6-(methylamino)-1,5,6-trioxohexan-2-ylcarbamoyl)nicotinic acid (E25),
- 4-((S)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-6-(ethylamino)-1,5,6-trioxohexan-2-ylcarbamoyl)nicotinic acid (E26),
- 4-((S)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-6-1,5,6-trioxo-6-(pentylamino)hexan-2-ylcarbamoyl)nicotinic acid (E27),
- 4-((S)-1-((S)-1-((S)-2-((S)-2-((S)-2-amino-1-cyclohexyl-2-oxoethylamino)-1-cyclo-hexyl-2-oxoethylcarbamoyl)-4-oxopyrrolidin-1-yl)-3,3-dimethyl-1-oxobutan-2-yl-amino)-6-(cyclopropylamino)-1,5,6-trioxohexan-2-ylcarbamoyl)nicotinic acid (E28),
- 4-((S)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-6-(benzylamino)-1,5,6-trioxohexan-2-ylcarbamoyl)nicotinic acid (E29),
- 4-((S)-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-6-(tert-butylamino)-1,5,6-trioxohexan-2-ylcarbamoyl)nicotinic acid (E30),
- 4-((S)-6-amino-1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-ylamino)-1,5,6-trioxohexan-2-ylcarbamoyl)nicotinic acid (E31),
- (S)—N1-((S)-1-((S)-2-((S)-2-((S)-2-amino-1-cyclohexyl-2-oxoethylamino)-1-cyclohexyl-2-oxoethylcarbamoyl)-4-oxopyrrolidin-1-yl)-3,3-dimethyl-1-oxobutan-2-yl)-N6-cyclopropyl-2-(2-methylthiazole-4-carboxamido)-5-oxohexanediamide (E32), (S)-methyl 2-(6-(1-(2-(2-ethylbutylamino)-2-oxoethyl)-2-oxo-1,2-dihydropyridin-3-ylamino)-5-(1-methyl-1H-imidazole-5-carboxamido)-2,6-dioxohexanamido)acetat (E38), (S)—N1-(1-(2-(2-ethylbutylamino)-2-oxoethyl)-2-oxo-1,2-dihydropyridin-3-yl)-N6-(methoxymethyl)-2-(1-methyl-1H-imidazole-5-carboxamido)-5-oxohexanediamide (E39), (S)—N1-(1-(2-(2-ethylbutylamino)-2-oxoethyl)-2-oxo-1,2-dihydropyridin-3-yl)-2-(1-methyl-1H-imidazole-5-carboxamido)-5-oxo-N6-(thiazol-5-yl)hexanediamide (E40), (S)—N1-(1-(2-(2-ethylbutylamino)-2-oxoethyl)-2-oxo-1,2-dihydropyridin-3-yl)-2-(1-methyl-1H-imidazole-5-carboxamido)-5-oxo-N6-(tosylmethyl)hexanediamide (E41), (S)—N1-(1-(2-(2-ethylbutylamino)-2-oxoethyl)-4-methyl-2-oxo-1,2-dihydropyridin-3-yl)-N6-methyl-2-(1-methyl-1H-imidazole-5-carboxamido)-5-oxohexanediamide (E42), (S)—N1-(1-(2-(2-ethylbutylamino)-2-oxoethyl)-5-methyl-2-oxo-1,2-dihydropyridin-yl)-N6-methyl-2-(1-methyl-1H-imidazole-5-carboxamido)-5-oxohexanediamide (E43), (S)—N1-(1-(2-(2-ethylbutylamino)-2-oxoethyl)-6-methyl-2-oxo-1,2-dihydropyridin-3-yl)-N6-methyl-2-(1-methyl-1H-imidazole-5-carboxamido)-5-oxohexanediamide (E44), (S)—N1-(5-chloro-1-(2-(2-ethylbutylamino)-2-oxoethyl)-2-oxo-1,2-dihydropyridin -yl)-N6-methyl-2-(1-methyl-1H-imidazole-5-carboxamido)-5-oxohexanediamide (E45), (S)—N1-(5-bromo-1-(2-(2-ethylbutylamino)-2-oxoethyl)-2-oxo-1,2-dihydropyridin-3-yl)-N6-methyl-2-(1-methyl-1H-imidazole-5-carboxamido)-5-oxohexanediamide (E46), (S)—N1-(1-(2-(2-ethylbutylamino)-2-oxoethyl)-2-oxo-5-(trifluoromethyl)-1,2-dihydropyridin-3-yl)-N6-methyl-2-(1-methyl-1H-imidazole-5-carboxamido)-5-oxohexanediamide (E47), (S)-1-methyl-N-(6-(methylamino)-1,5,6-trioxo-1-(4-(phenylsulfonyl)piperazin-1-yl)hexan-2-yl)-1H-imidazole-5-carboxamide (E48), (S)—N1-(1-benzylpiperidin-4-yl)-N6-methyl-2-(1-methyl-1H-imidazole-5-carboxamido)-5-oxohexanediamide (E49), (S)—N1-(1-(2-(diethylamino)-2-oxoethyl)-2-oxo-1,2-dihydropyridin-3-yl)-N6-methyl-2-(1-methyl-1H-imidazole-5-carboxamido)-5-oxohexanediamide (E50), (S)—N1-methyl-5-(1-methyl-1H-imidazole-5-carboxamido)-N6-(1-(2-(methylsulfonamido)-2-oxoethyl)-2-oxo-1,2-dihydropyridin-3-yl)-2-oxohexanediamide (E51), (S)-ethyl 2-(3-(2-(1-methyl-1H-imidazole-5-carboxamido)-6-(methylamino)-5,6-dioxohexanamido)-2-oxopyridin-1(2H)-yl)acetate (E52), (S)-2-methoxyethyl 2-(3-(2-(1-methyl-1H-imidazole-5-carboxamido)-6-(methylamino)-5,6-dioxohexanamido)-2-oxopyridin-1(2H)-yl)acetate (E53), (S)—N1-(1-(2-(methoxymethylamino)-2-oxoethyl)-2-oxo-1,2-dihydropyridin-3-yl)-N6-methyl-2-(1-methyl-1H-imidazole-5-carboxamido)-5-oxohexanediamide (E54), (S)—N1-(1-(2-((dimethylamino)methylamino)-2-oxoethyl)-2-oxo-1,2-dihydropyridin-3-yl)-N6-methyl-2-(1-methyl-1H-imidazole-5-carboxamido)-5-oxohexanediamide (E55), (S)—N1-(1-(2-(ethylsulfonamido)-2-oxoethyl)-2-oxo-1,2-dihydropyridin-3-yl)-N6-methyl-2-(1-methyl-1H-imidazole-5-carboxamido)-5-oxohexanediamide (E56), (S)-benzyl 1-(1-(2-(2-ethylbutylamino)-2-oxoethyl)-2-oxo-1,2-dihydropyridin-3-ylamino)-6-(methylamino)-1,5,6-trioxohexan-2-ylcarbamate (E57), (S)-tert-butyl 1-(1-(2-(2-ethylbutylamino)-2-oxoethyl)-2-oxo-1,2-dihydropyridin-3-ylamino)-6-(methylamino)-1,5,6-trioxohexan-2-ylcarbamate (E58), (S)-4-(1-(1-(2-(2-ethylbutylamino)-2-oxoethyl)-2-oxo-1,2-dihydropyridin-3-ylamino)-6-(methylamino)-1,5,6-trioxohexan-2-ylamino)-4-oxobutanoic acid (E59), (S)—N1-(1-(2-(2-ethylbutylamino)-2-oxoethyl)-2-oxo-1,2-dihydropyridin-3-yl)-N6-methyl-5-oxo-2-((S)-4-oxopyrrolidine-2-carboxamido)hexanediamide (E60), (S)—N1-(1-(2-(2-ethylbutylamino)-2-oxoethyl)-2-oxo-1,2-dihydropyridin-3-yl)-2-(furan-3-carboxamido)-N6-methyl-5-oxohexanediamide (E61), (S)—N1-(1-(2-(2-ethylbutylamino)-2-oxoethyl)-2-oxo-1,2-dihydropyridin-3-yl)-N6-methyl-2-(oxazole-5-carboxamido)-5-oxohexanediamide (E62), (S)—N1-(1-(2-(2-ethylbutylamino)-2-oxoethyl)-2-oxo-1,2-dihydropyridin-3-yl)-N6-methyl-2-(1-methylpiperidine-4-carboxamido)-5-oxohexanediamide (E63), (S)—N1-(1-(2-(2-ethylbutylamino)-2-oxoethyl)-2-oxo-1,2-dihydropyridin-3-yl)-N6-methyl-5-oxo-2-(pyrimidine-5-carboxamido)hexanediamide (E64), (S)—N1-(1-(2-(2-ethylbutylamino)-2-oxoethyl)-2-oxo-1,2-dihydropyridin-3-yl)-N6-methyl-5-oxo-2-(quinoxaline-2-carboxamido)hexanediamide (E65), (S)-2-(2,4-dimethylthiazole-5-sulfonamido)-N1-(1-(2-(2-ethylbutylamino)-2-oxoethyl)-26 oxo-1,2-dihydropyridin-3-yl)-N6-methyl-5-oxohexanediamide (E66), (S)-2-(6-chloroimidazo[2,1-b]thiazole-5-sulfonamido)-N1-(1-(2-(2-ethylbutylamino)-2-oxoethyl)-2-oxo-1,2-dihydropyridin-3-yl)-N6-methyl-5-oxohexanediamide (E67), (S)—N1-(1-(2-(2-ethylbutylamino)-2-oxoethyl)-2-oxo-1,2-dihydropyridin-3-yl)-N6-methyl-2-(1-methyl-1H-imidazole-2-sulfonamido)-5-oxohexanediamide (E68), (S)—N1-(1-(2-(2-ethylbutylamino)-2-oxoethyl)-2-oxo-1,2-dihydropyridin-3-yl)-N6-methyl-5-oxo-2-(3-phenylureido)hexanediamide (E69), (S)—N1-(1-(2-(2-ethylbutylamino)-2-oxoethyl)-2-oxo-1,2-dihydropyridin-3-yl)-N6-methyl-5-oxo-2-(3-phenylthioureido)hexanediamide (E70), (S)—N1-(1-(2-(2-ethylbutylamino)-2-oxoethyl)-2-oxo-1,2-dihydropyridin-3-yl)-N7-methyl-2-(1-methyl-1H-imidazole-5-carboxamido)-6-oxoheptanediamide (E71), (S)—N1-methyl-6-(1-methyl-1H-imidazole-5-carboxamido)-N7-(4-(4-methylpiperazin-1-ylsulfonyl)phenyl)-2-oxoheptanediamide (E72), (S)—N1-(1-(2-(2-ethylbutylamino)-2-oxoethyl)-2-oxo-1,2-dihydropyridin-3-yl)-N8-methyl-2-(1-methyl-1H-imidazole-5-carboxamido)-7-oxooctanediamide (E73), (S)—N-(1-(1-(2-(2-ethylbutylamino)-2-oxoethyl)-2-oxo-1,2-dihydropyridin-3-ylamino)-1,5,6-trioxoheptan-2-yl)-1-methyl-1H-imidazole-5-carboxamide (E74), (S)—N-(6-cyclopropyl-1-(1-(2-(2-ethylbutylamino)-2-oxoethyl)-2-oxo-1,2-dihydropyridin-3-ylamino)-1,5,6-trioxohexan-2-yl)-1-methyl-1H-imidazole-5-carboxamide (E75), (S)—N-(1-(1-(2-(2-ethylbutylamino)-2-oxoethyl)-2-oxo-1,2-dihydropyridin-3-ylamino)-1,5,6-trioxo-6-phenylhexan-2-yl)-1-methyl-1H-imidazole-5-carboxamide (E76), (S)-methyl 6-(1-(2-(2-ethylbutylamino)-2-oxoethyl)-2-oxo-1,2-dihydropyridin-3-ylamino)-5-(1-methyl-1H-imidazole-5-carboxamido)-2,6-dioxohexanoate (E77), (S)-2-methoxyethyl 6-(1-(2-(2-ethylbutylamino)-2-oxoethyl)-2-oxo-1,2-dihydropyridin-3-ylamino)-5-(1-methyl-1H-imidazole-5-carboxamido)-2,6-dioxohexanoate (E78), (S)—N1-(cyclopentylmethoxy)-N6-(1-(2-(2-ethylbutylamino)-2-oxoethyl)-2-oxo-1,2-di-hydropyridin-3-yl)-5-(1-methyl-1H-imidazole-5-carboxamido)-2-oxohexanediamide (E79), (S)—N-(1-(1-(2-(2-ethylbutylamino)-2-oxoethyl)-2-oxo-1,2-dihydropyridin-3-ylamino)-8-methyl-1,5,6-trioxononan-2-yl)-1-methyl-1H-imidazole-5-carboxamide (E80), (S)—N-(1-(1-(2-(2-ethylbutylamino)-2-oxoethyl)-2-oxo-1,2-dihydropyridin-3-ylamino)-6-(1-methyl-1H-imidazol-4-yl)-1,5,6-trioxohexan-2-yl)-1-methyl-1H-imidazole-5-carboxamide (E81), (2S)—N1-((S)-1-((S)-1-((S)-3-carbamoyl-3,4-dihydroisoquinolin-2(1H)-yl)-3-(4-hydroxy-phenyl)-1-oxopropan-2-ylamino)-3-(1H-imidazol-4-yl)-1-oxopropan-2-yl)-2-(2-(5,5-dimethyl-2-oxotetrahydrofuran-3-yl)acetamido)-N6-methyl-5-oxohexanediamide (E82), (S)—N1-(3-((S)-3-(biphenyl-4-yl)-1-((2S,4R)-2-carbamoyl-4-phenoxypyrrolidin-1-yl)-1-oxopropan-2-ylcarbamoyl)phenyl)-2-(2-(1,3-dimethyl-1H-pyrazol-5-yl)acetamido)-N6-methyl-5-oxohexanediamide (E83), and isopropyl (S)-1-((S)-1-(1-((2S,4R)-2-carbamoyl-4-hydroxypyrrolidin-1-yl)-2-methyl-1-oxopropan-2-ylamino)-5-guanidino-1-oxopentan-2-ylamino)-6-(methylamino)-1,5,6-trioxohexan-2-ylcarbamate (E84).

11. A method for producing a compound according to claim 1 comprising:

Step (0): providing a protected amino acid having a chemical warhead;

Step 1C: deprotecting an amino protecting group $PG^2$ and a carboxyl protecting group $PG^3$;

Step 1C':

(a) performing coupling reaction of a resulting compound of Step 1C with a corresponding C-terminal amino acid building block $H_2AS^{Ci}$-$OPG^4$;

(b) deprotecting the protecting group $PG^4$;

(c) repeating the steps (a) and (b) i times, wherein i is 1-8

Step 2C: performing coupling reaction with a C-terminal building block $E^C$-H;

Step 3C: deprotecting an amino protecting group $PG^1$;

Step 4C: performing coupling reaction with a N-terminal building block $E^N$-$AG^1$;

to produce the compound of the formula (I).

12. The method according to claim 11 further comprising the Step 3C' between the step 3B and the step 4C:

Step 3C':

(d) performing coupling reaction of a resulting compound of Step 3C with a corresponding N-terminal amino acid building block $(PG^5)HAS^{Nj}$-OH;

(e) deprotecting the protecting group $PG^5$;

(f) repeating the steps (a) and (b) j times, wherein j is 1-4.

13. A method for producing a compound according to claim 1 comprising:

Step (0): providing a protected amino acid (1C') having a chemical warhead precursor (W');

Step 1D: performing coupling reaction of the protected amino acid (1C') with a C-terminal peptide building block (C-P) or a C-terminal building block ($E^C$-H) to obtain a compound 1 D-1 or 1 D-2;

Step 2D: deprotecting an amino protecting group $PG^1$; to obtain a compound 2D-1 or 2D-2;

Step 3D: performing coupling reaction of the compound 2D-1 or 2D-2 with a N-terminal peptide building block (N-P) or a N-terminal building block ($E^N$-H);

to obtain a compound 3D-1, 3D-2, 3D-3, or 3D-4;

Step 4D: converting the chemical warhead precursor (W') of the compound 3D-1, 3D-2, 3D-3, or 3D-4 to a chemical precursor (W)

to produce a compound 4D-1, 4D-2, 4D-3, or 4D-4 as compound of the formula (I).

* * * * *